(12) United States Patent
Xiao et al.

(10) Patent No.: US 11,566,223 B2
(45) Date of Patent: *Jan. 31, 2023

(54) CHIMERIC ANTIGEN RECEPTOR CELL PREPARATION AND USES THEREOF

(71) Applicant: Innovative Cellular Therapeutics Holdings, Ltd., Rockville, MD (US)

(72) Inventors: Lei Xiao, Rockville, MD (US); Chengfei Pu, Shanghai (CN); Zhiyuan Cao, Shanghai (CN); Zhao Wu, Shanghai (CN)

(73) Assignee: Innovative Cellular Therapeutics Holdings, Ltd., Rockville, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/992,833

(22) Filed: May 30, 2018

(65) Prior Publication Data
US 2018/0346876 A1    Dec. 6, 2018

Related U.S. Application Data

(60) Provisional application No. 62/640,523, filed on Mar. 8, 2018, provisional application No. 62/598,024, filed on Dec. 13, 2017, provisional application No. 62/527,140, filed on Jun. 30, 2017, provisional application No. 62/527,649, filed on Jun. 30, 2017, provisional application No. 62/513,781, filed on Jun. 1, 2017.

(51) Int. Cl.
| | |
|---|---|
| *C12N 5/0783* | (2010.01) |
| *C12N 15/63* | (2006.01) |
| *A61K 35/17* | (2015.01) |
| *C07K 14/725* | (2006.01) |
| *C07K 14/705* | (2006.01) |
| *A61P 35/00* | (2006.01) |
| *A61K 39/395* | (2006.01) |
| *C07K 14/075* | (2006.01) |
| *A61K 48/00* | (2006.01) |
| *C07K 14/525* | (2006.01) |
| *C07K 14/71* | (2006.01) |
| *C07K 16/30* | (2006.01) |
| *C12N 15/85* | (2006.01) |
| *A61K 39/00* | (2006.01) |
| *C12N 9/12* | (2006.01) |
| *C07K 16/28* | (2006.01) |

(52) U.S. Cl.
CPC ........... *C12N 5/0638* (2013.01); *A61K 35/17* (2013.01); *A61K 39/0011* (2013.01); *A61K 39/39558* (2013.01); *A61K 48/005* (2013.01); *A61P 35/00* (2018.01); *C07K 14/075* (2013.01); *C07K 14/525* (2013.01); *C07K 14/7051* (2013.01); *C07K 14/70517* (2013.01); *C07K 14/71* (2013.01); *C07K 16/2803* (2013.01); *C07K 16/30* (2013.01); *C12N 5/0636* (2013.01); *C12N 5/0646* (2013.01); *C12N 9/1276* (2013.01); *C12N 15/85* (2013.01); *C12Y 207/07049* (2013.01); *A61K 2039/505* (2013.01); *A61K 2039/5156* (2013.01); *A61K 2039/5158* (2013.01); *A61K 2039/585* (2013.01); *C07K 2317/53* (2013.01); *C07K 2317/622* (2013.01); *C07K 2317/732* (2013.01); *C07K 2317/76* (2013.01); *C07K 2317/80* (2013.01); *C07K 2319/03* (2013.01); *C07K 2319/33* (2013.01); *C12N 2510/00* (2013.01); *C12N 2740/16043* (2013.01)

(58) Field of Classification Search
None
See application file for complete search history.

(56) References Cited

U.S. PATENT DOCUMENTS

| | | | |
|---|---|---|---|
| 8,906,682 B2 | 12/2014 | June et al. | |
| 9,868,774 B2 * | 1/2018 | Orentas | A61P 35/00 |
| 2008/0131962 A1 | 6/2008 | Miller | |
| 2016/0185861 A1 | 6/2016 | Bedoya et al. | |
| 2017/0137783 A1 * | 5/2017 | Bedoya | C07K 14/705 |
| 2019/0000878 A1 | 1/2019 | Xiao et al. | |
| 2019/0136186 A1 * | 5/2019 | Germeroth | A61P 31/00 |

FOREIGN PATENT DOCUMENTS

| | | |
|---|---|---|
| CN | 101215577 A | 7/2008 |
| CN | 106166313 A | 11/2016 |
| CN | 106755023 A | 5/2017 |
| JP | 2005505299 A | 2/2005 |
| JP | 2012525825 A | 10/2012 |

(Continued)

OTHER PUBLICATIONS

Oliveira et al., A CD19/Fc Fusion Protein for Detection of anti-CD19 Chimeric Antigen Receptors. J Transl Med. Jan. 29, 2013;11:23 (Year: 2013).*

(Continued)

*Primary Examiner* — Arthur S Leonard
(74) *Attorney, Agent, or Firm* — Lee & Hayes, P.C.

(57) ABSTRACT

Embodiments described herein relate to compositions including genetically modified CAR cells and uses thereof for treating cancer. Some embodiments of the present disclosure relate to compositions and methods for T cell response enhancement and/or CAR cell preparation. For example, a method may include obtaining cells comprising a CAR and culturing the cells in the presence of an agent that is recognized by the extracellular domain of the CAR.

21 Claims, 49 Drawing Sheets
Specification includes a Sequence Listing.

(56) References Cited

FOREIGN PATENT DOCUMENTS

| | | | |
|---|---|---|---|
| JP | 2016525888 A | 9/2016 | |
| JP | 2016534995 A | 11/2016 | |
| JP | 2017060422 A | 3/2017 | |
| JP | WO2017078176 A1 | 9/2018 | |
| WO | 2003089630 A1 | 10/2003 | |
| WO | WO2013074916 A1 | 5/2013 | |
| WO | WO-2014191128 A1 * | 12/2014 | ........... C12N 5/0637 |
| WO | WO2016109410 A2 | 7/2016 | |
| WO | WO2017015427 A1 | 1/2017 | |
| WO | WO2017059796 A1 | 4/2017 | |
| WO | WO2017068421 A1 | 4/2017 | |
| WO | WO2017068425 A1 | 4/2017 | |

OTHER PUBLICATIONS

Milone et al., Chimeric Receptors Containing CD137 Signal Transduction Domains Mediate Enhanced Survival of T Cells and Increased Antileukemic Efficacy In Vivo. Molecular Therapy vol. 17 No. 8, 1453-1464 Aug. 2009 (Year: 2009).*

Mahon et al., Vectors bicistronically linking a gene of interest to the SV40 large T antigen in combination with the SV40 origin of replication enhance transient protein expression and luciferase reporter activity. Biotechniques. Aug. 2011; 51(2): 119-128. (Year: 2011).*

Bai et al., Enhancement of the in vivo persistence and antitumor efficacy of CD19 chimeric antigen receptor T cells through the delivery of modified TERT mRNA.. Cell Discovery (2015) 1, 15040 (Year: 2015).*

Roth et al., Telomerase levels control the lifespan of human T lymphocytes (Blood, 2003, 102:849-857) (Year: 2003).*

Rufer et al., Transfer of the human telomerase reverse transcriptase (TERT) gene into T lymphocytes results in extension of replicative potential. Blood. 2001;98:597-603 (Year: 2001).*

Ye et al., Controlling T cell senescence in the tumor microenvironment for tumor immunotherapy. OncoImmunology 4:3, e994398; Mar. 2015 (Year: 2015).*

Anderson et al., Transduction with human telomerase reverse transcriptase immortalizes a rhesus macaque CD8+ T cell clone with maintenance of surface marker phenotype and function. AIDS Res Hum Retroviruses. Mar. 2007;23(3):456-65 (Year: 2007).*

Gattinoni et al., "A human memory T-cell subset with stem cell-like properties," Apr. 2012, Nat Med., 17(10):1290-1297.

International search report and written opinion of International Application No. PCT/CN2018/088914 dated Sep. 6, 2018, 10 pages.

Translation of Kakarot Discussion on serveral technical issues in CAR-T research, WeChat public No. Cytocare (internet) 15, Mar. 2016, 7 pages.

Levine et al., "Global Manufacturing of CAR T Cell Therapy" Mar. 2017, Molecular Therapy—Methods & Clinical Development, vol. 4, 92-101.

Lombardo et al., "Gene editing in human stem cells using zinc finger nucleases and integrase-defective lentiviral vector delivery," Nov. 2007, Nature Biotechnology, 25(11):1298-1306.

Morton et al., "Establishment of human tumor xenografts in immunodeficient mice," Feb. 2007, Nature Protocols, 2(2):247-250.

Song et al., "Loss of TGF-beta Adapter beta2SP Activates Notch Signaling and SOX9 Expression in Esophageal Adenocarcinoma," Mar. 2013, Cancer Reserch, 73(7): 2159-2169.

Umov et al., "Highly efficient endogenous human gene correction using designed zinc-finger nucleases," Jun. 2005, Nature 435(7042):646-651.

U.S. Appl. No. 15/992,833, filed May 30, 2018, US-2018-0346876-A1, Pending.

U.S. Appl. No. 16/023,310, filed Jun. 29, 2018, US-2019-0000878-A1, Pending.

Translated Japanese Office Action dated Feb. 16, 2021 for Japanese Patent Application No. 2019-565882, a counterpart of U.S. Appl. No. 15/992,833, 8 pages.

Takenouchi et al., "Frontiers in Veterinary Science", Aug. 21, 2017, vol. 4, Article 132, 9 pgs.

Canadian Office Action dated Nov. 19, 2020 for Canadian Patent Application No. 3,065,126, a counterpart of U.S. Appl. No. 15/992,833, 4 pages.

Extended European Search Report dated Feb. 9, 2021 for European Patent Application No. 15/992,833, counterpart of U.S. Appl. No. 15/992,833, 8 pages.

Xu et al., "Closely related T-memory stem cells correlate with in vivo expansion of CAR.CD19-T cells and are preserved by IL-7 and IL-15," Jun. 2014, Blood, 123(24): 3750-3759.

European Office Action dated Nov. 5, 2021 for European Patent Application No. 15/992,833, a foreign counterpart to U.S. Appl. No. 15/992,833, 7 pages.

Japanese Office Action dated Sep. 21, 2021 for Japanese Patent Application No. 2019-565882, a foreign counterpart to U.S. Appl. No. 15/992,833, 5 pages.

Tackenouchi et al., "Immortalization and Characterization of Porcine Macrophages that had been Transduced with Lentiviral Vectors Encoding the SV40 Large T Antigen and Porcine Telomerase Reverse Trascriptase," Aug. 2017. Frontiers in Vetrinary Science, 4: 132. 9 pages.

Japanese Office Action dated Apr. 26, 2022 for Japanese Patent Application No. 2019-565882, a foreign counterpart to U.S. Appl. No. 15/992,833, 6 pages.

Canadian Office Action dated Nov. 16, 2021 for Canadian Patent Application No. 3065126, a foreign counterpart to U.S. Appl. No. 15/992,833, 3 pages.

* cited by examiner

FIG. 2

| | Day 1 | Day 22 | Expansion Fold At day 22 | Copy/per cell At day 22 | CAR+ cell number At day 22 | CAR+ ratio At day 22 |
|---|---|---|---|---|---|---|
| aCD3/CD28,IL2 | 2x10^5 cells | 10.15x10^7 cells | 507.5 | 8.4/cell | 1.56x10^6 | 1.54% |
| aCD3/CD28,IL2, soluble CD19 | 2x10^5 cells | 6.44x10^7 cells | 322 | 13.3/cell | 6.35x10^6 | 9.92% |

Gated by CAR+ cells:
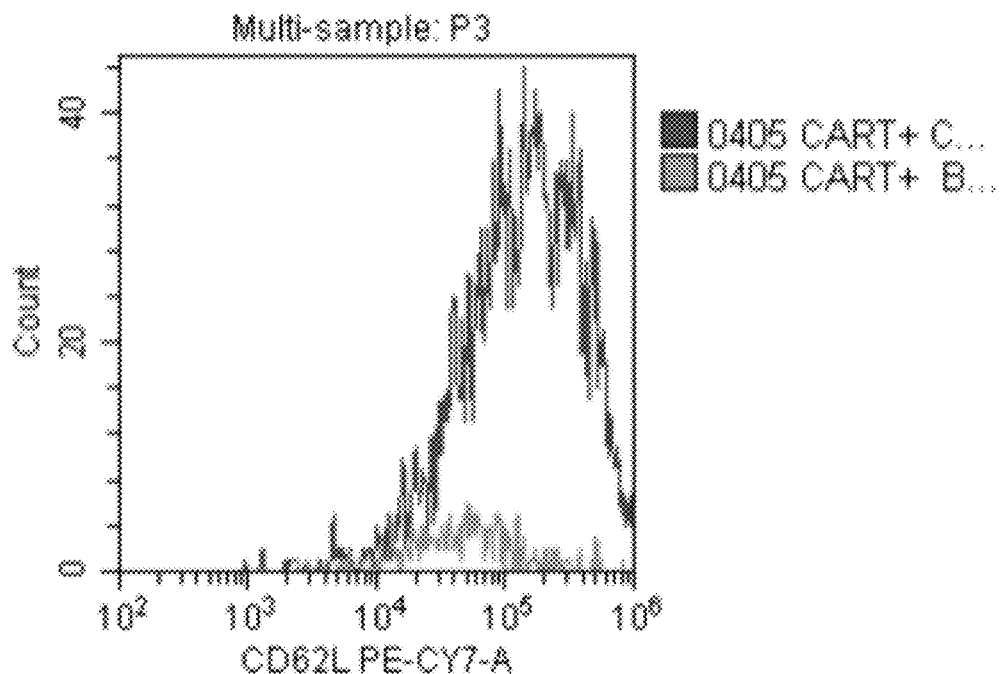
Gated by CAR- cells:
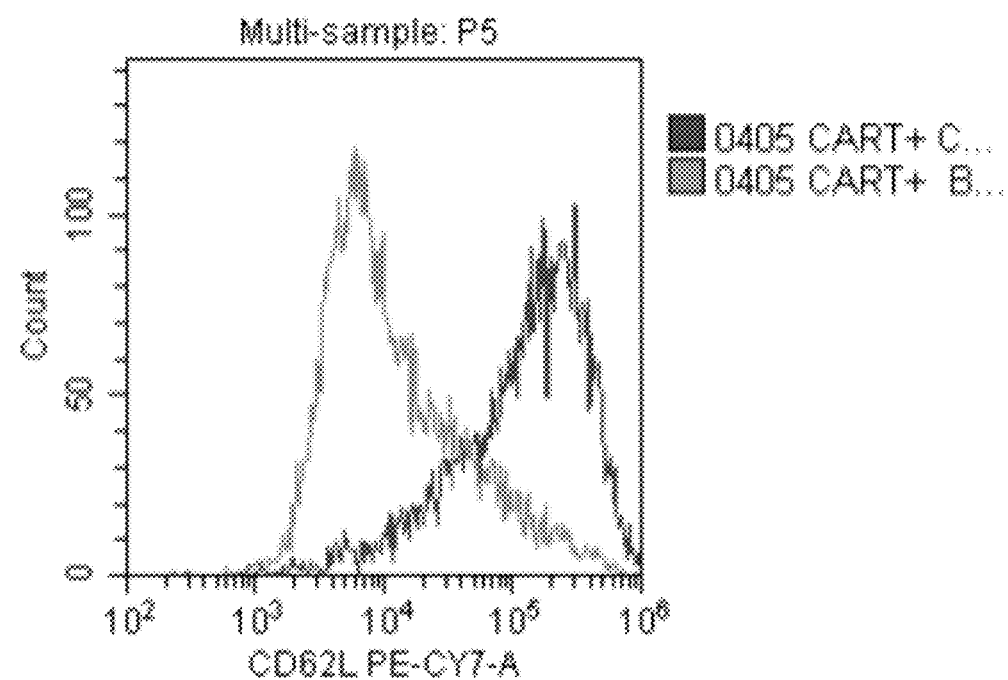
FIG. 5

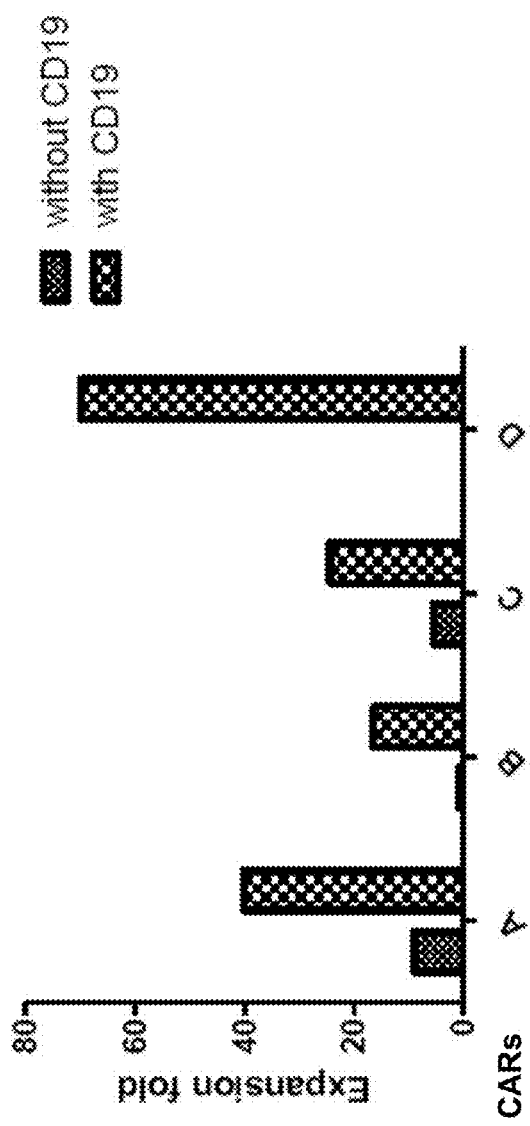
FIG. 13

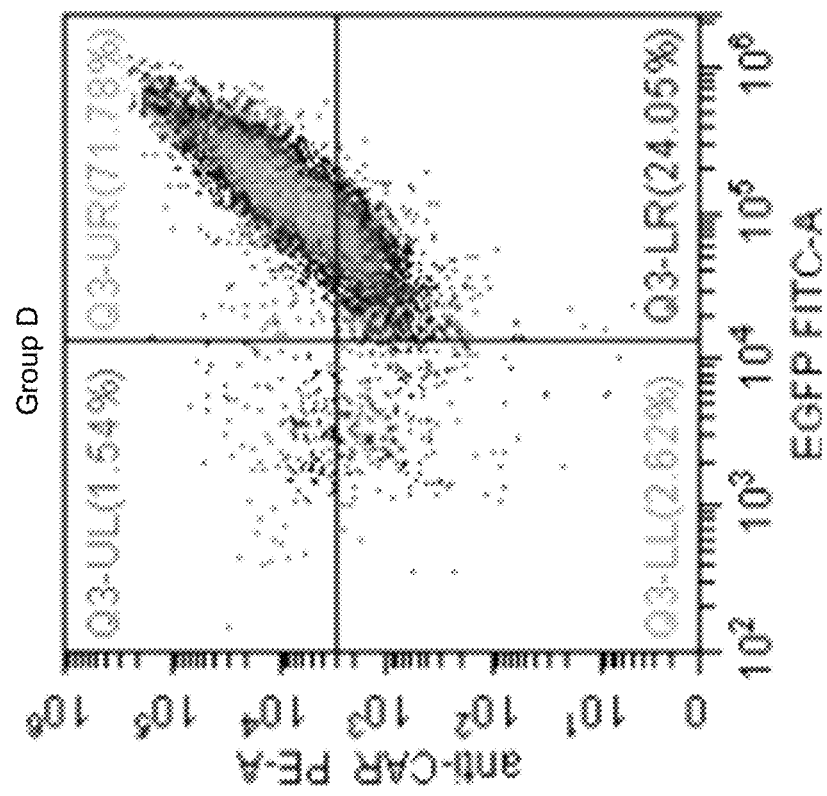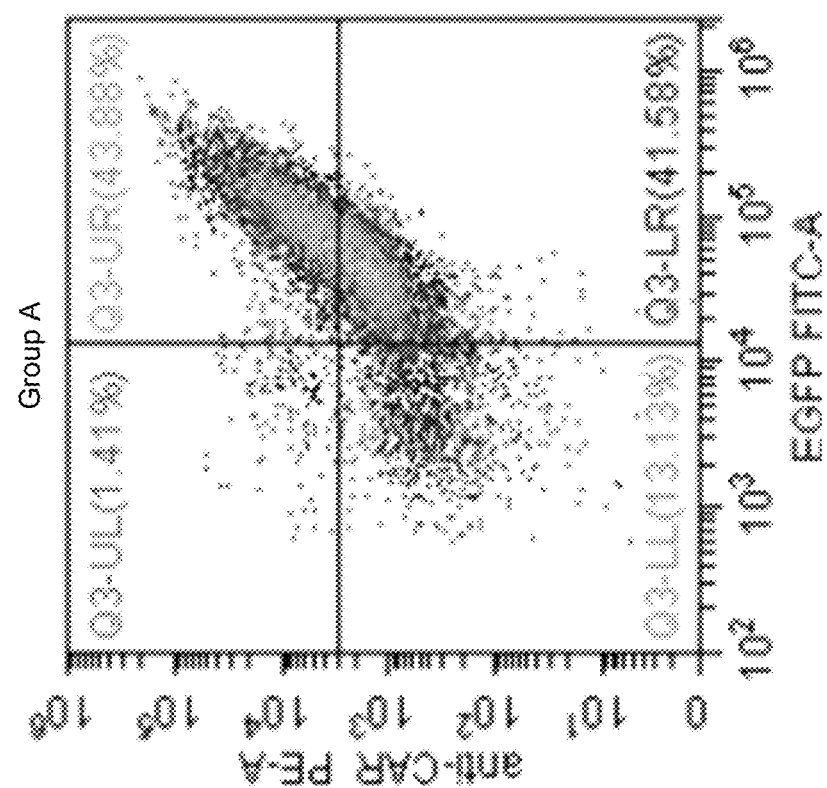
FIG. 20

Activation by soluble CD19 protein

| | | | | | | |
|---|---|---|---|---|---|---|
| RK562 | 1 | 1 | - | - | - | - |
| RK19 | - | - | 1 | 1 | 1 | 1 |
| D+ | - | 10 | - | 1 | 1 | 10 |

24h cytotoxicity

FIG. 21

| Ef1a | TK | IRES | rtTA | TRE | hTERT |

1. ef1a-TK-IRES-rtTA-TRE-hTERT

| Ef1a | TK | IRES | rtTA | TRE | SV40t |

2. ef1a-TK-IRES-rtTA-TRE-SV40t

| Ef1a | hTERT |

3. ef1a-hTERT

| Ef1a | SV40t |

4. ef1a-SV40t

| Ef1a | SP | VL/VH | Linker | VH/VL | Hinge | 4-1BB | CD3 zeta |

5. CAR

| Ef1a | rtTA | TRE | hTERT |

6. ef1a-rtTa-TRE-hTERT

FIG. 23

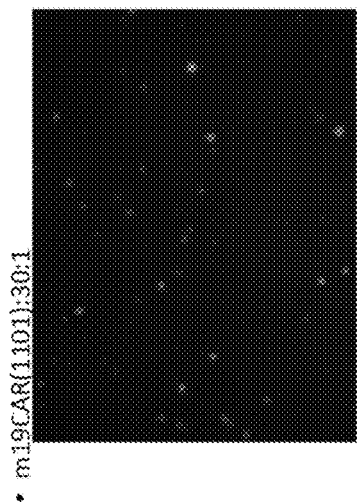
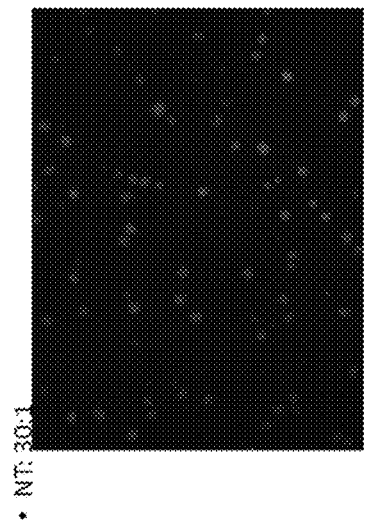
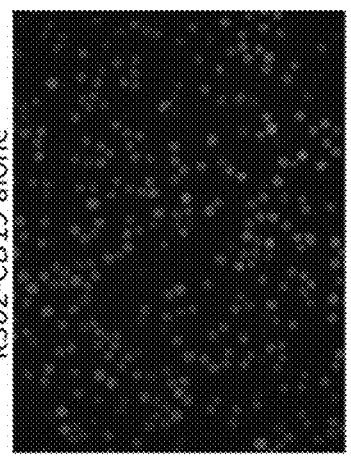
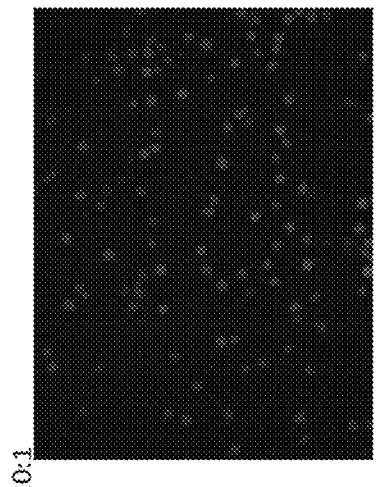
FIG. 24

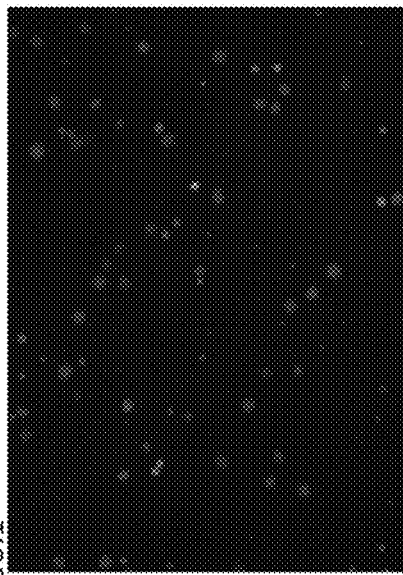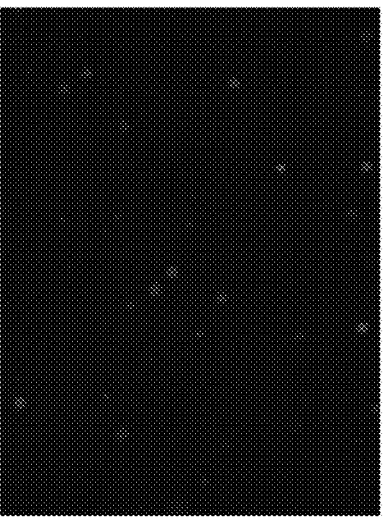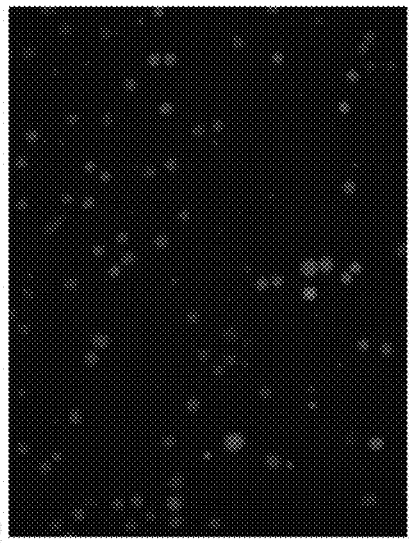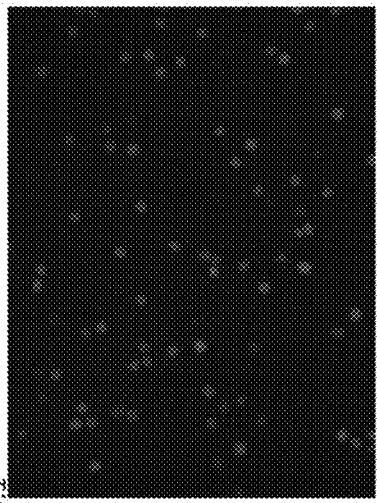
FIG. 25

SV40:
- CD8A 402.987
- CD8B 152.932 hTERT:
- CD8A 963.769
- CD8B 216.291

TNF:
NT: 77.9
SV40: 0
hTERT: 0

0.0008%

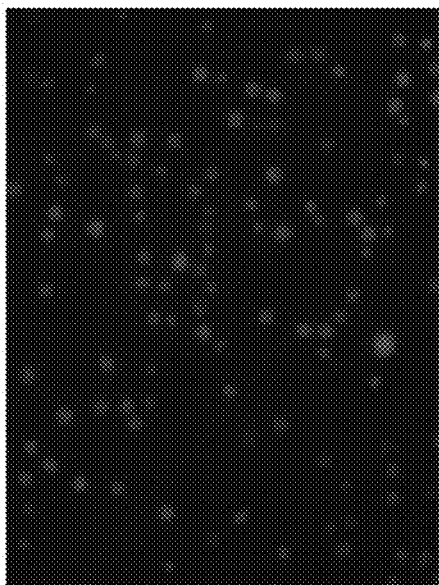
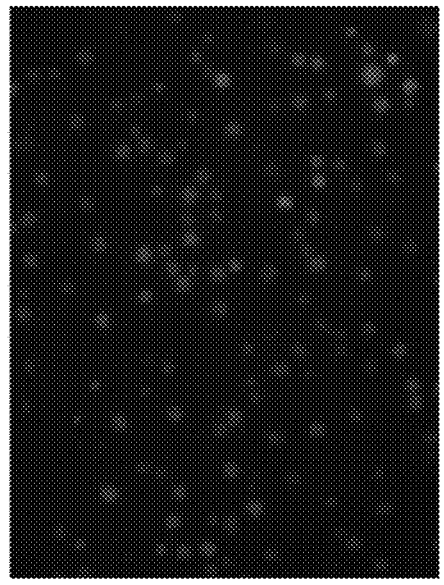
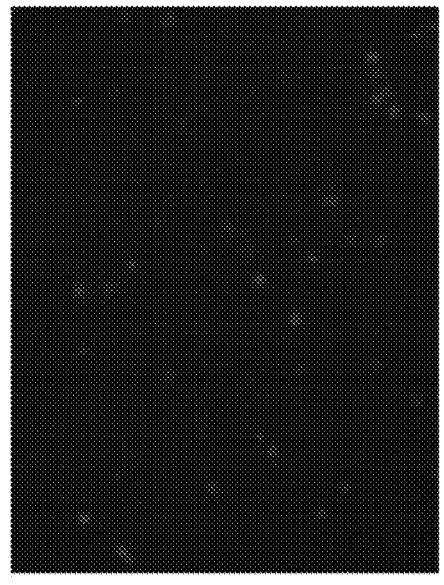
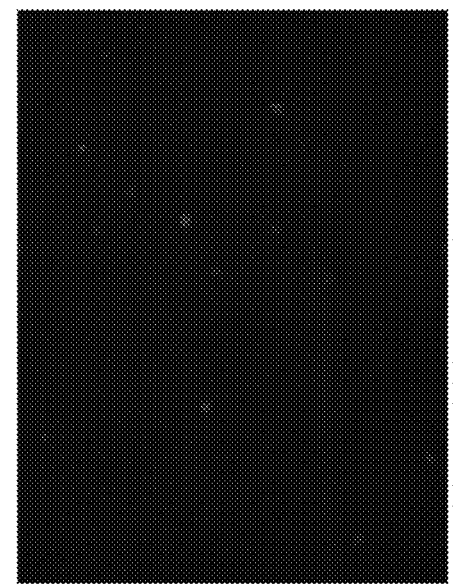
FIG. 39

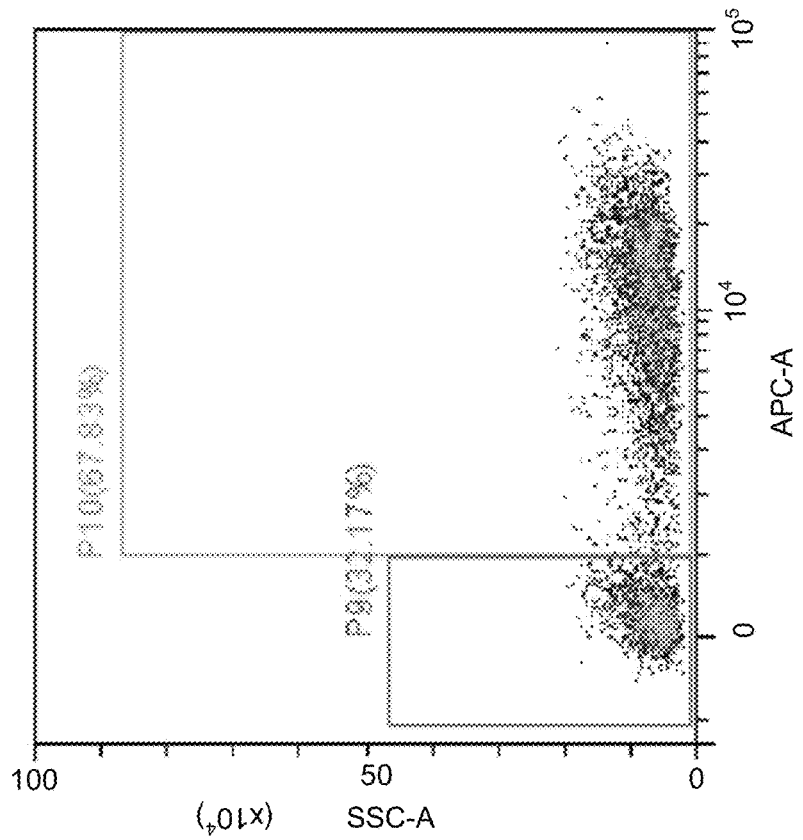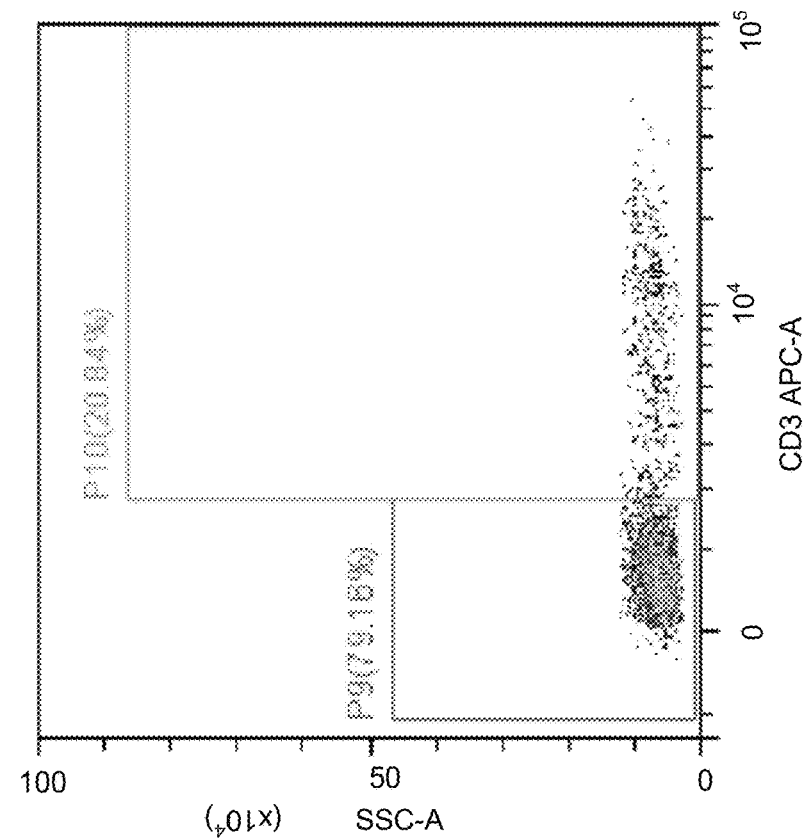
FIG. 40

CHIMERIC ANTIGEN RECEPTOR CELL PREPARATION AND USES THEREOF

CROSS REFERENCE TO RELATED PATENT APPLICATIONS

This application claims the benefit of U.S. Provisional Patent Application No. 62/640,523, filed on Mar. 8, 2018, entitled "Lymphocyte cell line and uses thereof", U.S. Provisional Patent Application No. 62/598,024, filed on Dec. 13, 2017, entitled "Chimeric Antigen Receptor Cell Preparation and Uses thereof", U.S. Provisional Patent Application No. 62/527,649, filed on Jun. 30, 2017, entitled "Chimeric Antigen Receptor Cell Preparation and Uses thereof", U.S. Provisional Patent Application No. 62/527,140, filed on Jun. 30, 2017, entitled "Modified lymphocyte cell line and uses thereof," and U.S. Provisional Patent Application No. 62/513,781 filed on Jun. 1, 2017, entitled "Lymphocyte cell line and uses thereof", which are hereby incorporated by reference in their entirety.

SEQUENCE LISTING INFORMATION

A computer readable textfile, entitled Chimeric Antigen Receptor Cell Preparation and Uses thereof "1071-0029US Sequence Listing.txt," created on or about May 3, 2018, with a file size of about 24.5 KB, contains the sequence listing for this application and is hereby incorporated by reference in its entirety.

TECHNICAL FIELD

The present disclosure relates to modified cells, in particular to compositions including the modified cells and uses thereof for treating diseases and conditions.

BACKGROUND

Scientists developed chimeric antigen receptors (CARs) for expression on T cells more than 25 years ago. The chimeric antigen receptor (CAR) technology combines an antigen recognition domain of a specific antibody with an intracellular domain of a T cell receptor (TCR). T cells genetically modified with a CAR to target certain malignant tumors have demonstrated favorable clinical outcomes. During CAR T cell therapy, physicians draw patients' blood and harvest their cytotoxic T cells. The cells are then re-engineered in a lab, so they can learn how to attack each patient's particular cancer. The patients are usually treated with chemotherapy before the CAR T cell therapy or during the CAR T cell therapy to wipe out some of their existing immune cells. However, chemotherapy may cause the patients' T cells to drop significantly. While most patients will recover and their immune cells will reach pre-chemo levels in nine months, some patients may not be able to generate enough T cells for continuous CAR T cell therapy. This puts the lives of these patients at risk. Further, as for CAR T therapy, long-term maintenance of CAR T cells in patient bodies is important for the prognosis of patients in the treatment of tumors. For example, if long-term presence of CAR T cells can be maintained, this technology may effectively reduce tumor recurrence.

SUMMARY

Embodiments described herein relate to compositions including genetically modified CAR cells and uses thereof for treating diseases and conditions.

Some embodiments of the present disclosure relate to a method comprising: providing a cell; introducing a nucleic acid sequence encoding a CAR and a nucleic acid sequence encoding hTERT, SV40LT, or a combination thereof, into the cell; and culturing the cell in the presence of an agent that is recognized by the extracellular domain of the CAR, thereby producing a modified CAR cell.

In some embodiments, integration of the nucleic acid sequence encoding hTERT, the nucleic acid encoding SV40LT, or a combination thereof includes genomic integration of the nucleic acid sequence encoding hTERT, a nucleic acid encoding SV40LT, or a combination thereof and constitutive expression of hTERT, SV40LT, or a combination thereof. In some embodiments, expression of hTERT, SV40LT, or a combination thereof, is regulated by an inducible expression system. In some embodiments, the method may further include introducing a nucleic acid sequence encoding a suicide gene into the cell and culturing the CAR cell comprising the suicide gene and the nucleic acid encoding CAR with a nucleoside analogue in a manner permitting expression of the suicide gene to render the nucleoside analogue cytotoxic. In some embodiments, the cell is a T cell or a natural killer (NK) cell.

In some embodiments, the CAR comprises an extracellular domain, a transmembrane domain, and an intracellular domain. In some embodiments, the intracellular domain comprises a costimulatory signaling domain that includes an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

In some embodiments, the agent is a regulatory compound that binds an extracellular component of the CAR and mediates a response by the cells, a ligand that binds the extracellular domain of the CAR, an antigen that the extracellular domain of the CAR binds, or the extracellular domain of an antigen that the extracellular domain of the CAR binds. In some embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

In some embodiments, the agent is an antibody that binds the extracellular domain of the CAR. In some embodiments, the antibody is a human IgG antibody and/or binds a Fab fragment of a human IgG. In some embodiments, the regulatory compound comprises an extracellular domain of at least one of CD19, FZD10, TSHR, PRLR, Muc 17, GUCY2C, CD207, CD3, CD5, or CD4. In some embodiments, the regulatory compound comprises at least one of amino acid sequences: SEQ IDs: 41-47. In some embodiments, the regulatory compound binds at least one of amino acid sequences: SEQ IDs: 21 and 48-53. In some embodiments, the CAR cells comprise at least one of SEQ ID Nos: 38, 35, 39, and 40.

In some embodiments, the CAR cells cultured in the presence of the agent exhibit about a 1.5 to 2 fold increase in cell growth as compared to the CAR cells cultured in the absence of the agent. In some embodiments, the CAR cells cultured in the presence of the agent exhibit about a 1.5 to 3 fold increase in cell growth as compared to the CAR cells cultured in the absence of the agent. In some embodiments, the CAR cells cultured in the presence of the agent exhibit about a 2 fold increase in cell growth as compared to the CAR cells cultured in the absence of the agent. In some embodiments, the cell density of the CAR cells in the culture medium is at least about 25×104 cells/ml of the cell culture medium. In some embodiments, the cell density of the CAR cells in the culture medium is less than about 200×104 cells/ml of the cell culture medium. In some embodiments, the cell density of the CAR cells in the cell culture medium is between about 50×104 to about 200×104 cells/ml of the cell culture medium. In some embodiments, the cell density of the CAR cells in the cell culture medium is between about 50×104 to about 100×104 cells/ml of cell culture medium.

In some embodiments, the CAR cells are sensitive to a tetracycline from the cell culture medium. In some embodiments, the CAR cells comprise a third nucleic acid sequence encoding a reverse tetracycline transactivator (rtTA). In some embodiments, expression of hTERT or SV40LT is regulated by the rtTA, such that hTERT or SV40LT is expressed in the presence of tetracycline. In some embodiments, a concentration of tetracycline in the cell culture medium is not less than about 2 µg/ml. In some embodiments, the tetracycline is selected from the group consisting of tetracycline, demeclocycline, meclocycline, doxycycline, lymecycline, methacycline, minocycline, oxytetracycline, rolitetracycline, and chlortetracycline. In some embodiments, the tetracycline is doxycycline.

In some embodiments, the CAR cells comprise a fourth nucleic acid sequence encoding a suicide gene, such that when the CAR cells are cultured in the presence of a nucleoside analogue in a manner permitting expression of the suicide gene, to render the nucleoside analogue cytotoxic to the CAR cells. In some embodiments, the suicide gene is selected from the group consisting of thymidine kinase of herpes simplex virus, thymidine kinase of varicella zoster virus, and bacterial cytosine deaminase. In some embodiments, the suicide gene is thymidine kinase of herpes simplex virus. In some embodiments, the nucleoside analogue is selected from the group consisting of ganciclovir, acyclovir, buciclovir, famciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5-dideoxyuridine, idoxuridine, AZT, AIU, dideoxycytidine, and AraC. In some embodiments, the nucleoside analogue is ganciclovir.

Some embodiments relate to an isolated cell obtained using the method described herein. Some embodiments relate to a composition comprising a population of the isolated cells. Some embodiments relate to a method of enhancing T cell response in a subject and/or treating a tumor of the subject, the method comprising: administering an effective amount of the composition described herein.

Some embodiments relate to a modified cell comprising a nucleic acid sequence encoding hTERT, a nucleic acid encoding SV40LT, or a combination thereof, wherein integration of the nucleic acid sequence encoding hTERT, a nucleic acid encoding SV40LT, or a combination thereof includes genomic integration of the nucleic acid sequence encoding hTERT, the nucleic acid encoding SV40LT, or a combination thereof and constitutive expression of hTERT, SV40LT, or a combination thereof.

In some embodiments, the modified cell is a T cell and further comprising a nucleic acid sequence encoding a CAR, and the modified cell is capable of inhibiting a cell expressing the antigen that the CAR recognizes. In some embodiments, the nucleic acid encoding CAR and the nucleic acid encoding hTERT, a nucleic acid encoding SV40LT, or a combination thereof is expressed as gene products that are separate polypeptides.

In some embodiments, expression of the nucleic acid sequence encoding hTERT, the nucleic acid encoding SV40LT, or a combination thereof, is regulated by an inducible expression system. In some embodiments, the inducible expression system is a rtTA-TRE system, which increases or activates the expression of SV40LT gene or hTERT gene, or a combination thereof. In some embodiments, the modified cell comprises a nucleic acid sequence encoding a suicide gene. In some embodiments, the modified cell is a T cell or an NK cell. In some embodiments, the suicide gene is an HSV-TK system. In some embodiments, the modified cell is a proliferable T cell. In some embodiments, the CAR comprises an extracellular domain, a transmembrane domain, and an intracellular domain, and the extracellular domain binds a tumor antigen. In some embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ES0-1, PSC1, folate receptor-α, CD44v7/8, 8H9, NCAM, VEGF receptors, 5T4, Fetal AchR, NKG2D ligands, CD44v6, TEM1, or TEM8. In some embodiments, the intracellular domain comprises a costimulatory signaling domain that includes an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In some embodiments, the intracellular domain comprises a CD3 zeta signaling domain. In some embodiments, the TCR gene of the T cell is disrupted such that expression of the endogenous TCR is reduced. In some embodiments, a targeting vector associated with the TCR gene is integrated into the genome of the T cell such that the expression of the endogenous TCR is eliminated. In some embodiments, the CD4 gene of the T cell is disrupted such that expression of the endogenous CD4 is reduced. In some embodiments, an antigen binding domain of the CAR binds a molecule on the surface of an HIV. In some embodiments, hTERT has a sequence of SEQ ID NO: 6, and SV40LT has a sequence of SEQ ID NO: 7.

Some embodiments relate to a method of generating a CAR T cell, the method comprising: proliferating a T cell by transferring one or more nucleic acid sequences to the T cell to obtain proliferable T cells; and introducing a nucleic acid sequence encoding a CAR into the proliferated T cells to obtain CAR T cells, the CAR comprising an extracellular domain, a transmembrane domain, and an intracellular domain.

In some embodiments, the proliferated T cells are any of the modified T cell described herein. In some embodiments, the one or more nucleic acid sequences comprise Tet-inducible HPV16-E6/E7 expression system. In some embodiments, the T cell is a primary T cell extracted from a subject. In some embodiments, the T cell is a T cell having decreased immunogenicity as compared to a corresponding wild-type T cell in response to a T cell transfusion. Some embodiments relate to a method of treating a disease or condition, the method comprising: administering to the human patient a pharmaceutical composition comprising the modified cells described herein. In some embodiments, the disease or condition is AIDS, and the pharmaceutical composition comprises cells including a CAR with an antigen binding domain that binds a molecule on the surface of the HIV. In some embodiments, the disease or condition is cancer, and the pharmaceutical composition comprises modified cells including a CAR with an antigen binding domain of the CAR binds a molecule on a cancer cell, and the number of endogenous TCR on the cells is reduced. In some embodiments, the nucleic acid encoding the CAR is integrated into the genome of the T cell.

Some embodiments relate to a CAR T cell comprising: a nucleic acid sequence encoding a CAR that comprises an extracellular domain, a transmembrane domain, and an intracellular domain comprising a CD3-zeta signaling domain and a signaling domain of a costimulatory molecule, wherein the TCR gene of the T cell is disrupted such that expression of the TCR is reduced or eliminated. In some embodiments, the CAR T cell comprises a modified T cell described herein.

Some embodiments relate to a CAR T cell comprising: a nucleic acid sequence encoding a CAR that comprises an extracellular domain, a transmembrane domain, and an intracellular domain comprising a CD3-zeta signaling domain and a signaling domain of a costimulatory molecule, wherein the CD4 gene of the T cell is disrupted such that expression of the endogenous CD4 is reduced. In some embodiments, an antigen binding domain of the CAR binds a molecule on the surface of the HIV. In some embodiments, the CAR-T cell comprises a modified T cell described herein.

Some embodiments relate to a method of producing conditionally proliferable T cells, the method comprising: transferring one or more nucleic acid sequences to the T cells to obtain proliferable T cells, wherein the one or more nucleic acid sequences encode a peptide such that expression of the peptide causes the T cells to become proliferable T cells, and the peptide is regulated by an inducible expression system, an inducible suicide system, or a combination thereof. In some embodiments, the peptide is hTERT, SV40LT, or a combination thereof. In some embodiments, the inducible expression system is the rtTA-TRE system. In some embodiments, the inducible suicide system is an HSV-TK system or an inducible caspase-9 system.

Some embodiments relate to a method of treating a disease or condition, the method comprising: preparing conditionally proliferable T cells using the method described herein; culturing the conditionally proliferable T cells with a medium containing tetracycline or doxycycline; culturing the conditionally proliferable T cell with a medium without any the tetracycline or doxycycline; obtaining T cells of which the expression of SV40LT gene or hTERT gene is reduced; and administering to a subject in need thereof, a pharmaceutical composition comprising the T cells.

Some embodiments relate to a pharmaceutical composition including proliferable T cells obtained using the method described herein for use in the treatment of a disease or condition comprising: preparing conditionally proliferable T cells using the method described herein; culturing the conditionally proliferable T cells with a medium containing tetracycline or doxycycline; culturing the conditionally proliferable T cell with a medium without any tetracycline or doxycycline; obtaining T cells of which the expression of SV40LT gene or hTERT gene is reduced; and administering to a subject a pharmaceutical composition comprising the T cells. In some embodiments, the method may further include administering ganciclovir to the subject in response to a certain predetermined condition.

Some embodiments relate to a population of T cells comprising the modified cells, wherein an endogenous gene associated with a biosynthesis or transportation pathway of the TCR gene of the modified cell is disrupted such that expression of the endogenous TCR is reduced.

Some embodiments relate to a population of T cells comprising the modified cells, wherein an endogenous gene associated with a biosynthesis or transportation pathway of the PD-1 gene of the modified cell is disrupted such that expression of the endogenous TCR is reduced. In some embodiments, the modified cell comprises a nucleic acid sequence that encodes a truncated PD-1 that reduces an inhibitory effect of programmed death ligand 1 (PD-L1) on a human T cell.

Some embodiments relate to a method comprising: providing cells comprising a CAR, and culturing the cells in the presence of an agent that the extracellular domain of the CAR recognizes to obtain CAR cells.

Some embodiments relate to a method for in vitro CAR cell preparation, the method comprising: providing cells; introducing a nucleic acid sequence encoding a CAR into the cells to obtain CAR cells; and culturing the CAR cells in the presence of an agent that an extracellular domain of the CAR recognizes to obtain CAR cells.

Some embodiments relate to a method for enriching cells expressing a CAR, the method comprising: providing cells; introducing a nucleic acid sequence encoding a CAR into the cells to obtain cells expressing the CAR (CAR cells) and cells not expressing the CAR; and culturing the CAR cells in the presence of an agent that binds an extracellular domain of the CAR to enrich the cells expressing the CAR.

Some embodiments relate to a method for in vitro CAR cell preparation, the method comprising the following steps in the following order: (a) introducing a nucleic acid sequence encoding a CAR into cells to obtain CAR cells; (b) culturing the CAR cells using a first medium for a predetermined time; and (c) culturing the CAR cells using a second medium, wherein the first medium does not contain an agent, the second medium contains the agent, and the agent binds an extracellular domain of the CAR.

In some embodiments, the agent is a regulatory compound that binds the extracellular domain of the CAR and mediates a response by the cells. In some embodiments, the regulatory compound is a ligand for the extracellular domain of the CAR or an antigen that the extracellular domain of the CAR binds. In some embodiments, the agent is the extracellular domain of an antigen that the extracellular domain of the CAR binds. In some embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CDS, B-Cell Maturation Antigen (BCMA), or CD4. In some embodiments, the regulatory compound is an antibody that binds the extracellular domain of the CAR binds. In some embodiments, the antibody is a human IgG antibody and/or binds a Fab fragment of a human IgG. In some embodiments, the regulatory compound comprises an extracellular domain of at least one of CD19, FZD10, TSHR, PRLR, Muc 17, GUCY2C, CD207, CD3, CDS, or CD4. In some embodiments, the regulatory compound comprises at least one of amino acid sequences: SEQ IDs: 41-47 and 61-63. In some embodiments, the regulatory compound binds at least one of amino acid sequences: SEQ IDs: 55, 21, 48, 49, 40, 51-53, and 56-60. In some embodiments, the regulatory compound comprises at least one of GCC, B7-H4, Prostate specific membrane antigen (PSMA), Carcinoembryonic Antigen (CEA), IL13Ralpha, her-2, CD19, CD20, CD22, CD123, NY-ES0-1, HIV-I Gag, Lewis Y antigen, Mart-I, gp100, tyrosinase, WT-I, hTERT, MUC16, mesothelin, MIC-A, MIC-B, estrogen, progesterone, RON, or one or more members of the ULBP/RAETI family.

In some embodiments, the costimulatory molecule of CAR comprises at least one of CD27, CD28, 4-IBB, OX40, CD30, CD40, PD-L ICOS, lymphocyte function-associated antigen-I (LFA-1), CD2, CD7, LIGHT, NKG2C, or B7-H3. In some embodiments, the CAR comprises an extracellular domain, a transmembrane domain, and an intracellular domain comprising a CD3-zeta signaling domain and a signaling domain of a costimulatory molecule. In some embodiments, the cells are an NK cell or a T cell, or a combination thereof. In some embodiments, the regulatory compound is a soluble antigen generated by a eukaryotic system or a bacterial expression system.

In some embodiments, after culturing the CAR cells with an agent, a ratio of an amount of the agent and the number of CAR cells is 1:50 to 1:5 (µg/104 cell), 1:500 to 1:5 (µg/104 cell), or 1:5000 to 10:5 (µg/104 cell). In some embodiments, culturing the cells comprises culturing the cells using a culture medium comprising at least one of anti-CD3 beads, anti-CD28 beads, and IL2. In some embodiments, after culturing the CAR cells with an agent, a ratio of an amount of the agent and the number of CAR cells is 1:50 to 1:5 (µg/104 cell). In some embodiments, the number of copies of CAR on the CAR cells cultured in the presence of the agent is greater than the number when the CAR cells are cultured without the agent. In some embodiments, a ratio of the number of cells expressing the CAR and the number of cells not expressing the CAR when cultured in the presence of the agent is greater than the ratio when the cells are cultured without the agent. In some embodiments, culturing the CAR cells in the presence of the agent comprises: culturing the CAR cells in the presence of the agent for a predetermined period of time, or culturing the CAR cells in the presence of the agent for at least 10, 11, 12, 13, 14, 15, 16, 17, 18, 19, 20, 21, 22, 23, 24, 25, 26, 27, 28, 29, or 30 days. In some embodiments, the predetermined period of time is from 7-100 days. In some embodiments, the number of the CAR cells producing a phenotype of memory T cells, when cultured in the presence of an agent is greater than the number when the CAR cells are cultured without the agent. In some embodiments, the amount of a cytokine produced by the CAR cells, when cultured in the presence of the agent, is greater than the amount of the cytokine produced by CAR cells when the CAR cells are cultured without the agent.

In some embodiments, the CAR cells are derived from a healthy donor and have a reduced expression of endogenous TCR gene and/or HLA I. In some embodiments, the CAR cells are derived from a healthy donor and elicit no graft-versus-host disease (GVHD) response or a reduced GVHD response in a human recipient as compared to the GVHD response elicited by a primary human T-cell isolated from the same human donor and having no reduced expression of the endogenous TCR gene and/or HLA I, or that the expression of the endogenous TCR gene and/or HLA I is not disrupted and the endogenous TCR gene and/or HLA I are expressed as normal. In some embodiments, the CAR T cell is a T cell comprising a nucleic acid sequence encoding hTERT, a nucleic acid encoding SV40LT, or a combination thereof.

In some embodiments, the CAR cells comprise a nucleic acid sequence encoding hTERT and a nucleic acid encoding SV40LT. In some embodiments, expression of hTERT is regulated by an inducible expression system. In some embodiments, expression of SV40LT gene is regulated by an inducible expression system. In some embodiments, the inducible expression system is rtTA-TRE, which increases or activates the expression of the SV40LT gene, the hTERT gene, or a combination thereof. In some embodiments, the CAR cell comprises a nucleic acid sequence encoding a suicide gene. In some embodiments, the suicide gene is an HSV-TK system.

Some embodiments relate to an isolated cell obtained by the method above.

Some embodiments relate to a pharmaceutical composition comprising the isolated cells obtained by the method above.

Some embodiments relate to a method for stimulating an anti-tumor immune response in a subject, the method comprising administering to a subject in need thereof an effective amount of the pharmaceutical composition. Some embodiments relate to a pharmaceutical composition for use in the treatment of cancer comprising administering to a subject in need thereof, an effective amount of the pharmaceutical composition. In some embodiments, a spacer domain of the CAR comprises an amino acid sequence of SEQ ID NO.: 68 or 69. In some embodiments, a transmembrane domain of the CAR comprises an amino acid sequence of SEQ ID NO.: 72 or 75 and a spacer domain of the CAR comprises an amino acid sequence of SEQ ID NO.: 68.

Some embodiments relate to a method comprising: administering an effective amount of T cells comprising a CAR to the subject in need thereof to provide a T cell response, and administering an effective amount of presenting cells expressing a soluble agent that the extracellular domain of the CAR recognizes.

Some embodiments relate to a method of enhancing T cell response in a subject, the method comprising: administering an effective amount of T cell comprising a CAR to the subject to provide a T cell response; and administering an effective amount of presenting cells expressing a soluble agent that an extracellular domain of the CAR recognizes to enhance the T cell response in the subject. In some embodiments, the enhancing T cell response in the subject comprises selectively enhancing proliferation of T cells comprising the CAR.

Some embodiments relate to a method of enhancing treatment of a condition of a subject using CAR cells. In some embodiments, the method comprises administrating to the subject a population of cells that express an agent and a population of CAR cells. In other embodiments, the method comprises administering to the subject a vaccine derived from the agent and a population of CAR cells. The CAR cells comprise a nucleic acid sequence that encodes a CAR, and an extracellular domain of the CAR recognizes the agent.

Some embodiments relate to a method of enhancing proliferation of CAR cells in a subject having a disease. The method comprises: preparing cells comprising a CAR; administering an effective amount of the CAR cells to the subject; introducing into cells, a nucleic acid sequence encoding an agent that an extracellular domain of the CAR recognizes to obtain modified cells, and administering an effective amount of the modified cells to the subject.

In some embodiments, the agent is a ligand for the extracellular domain of the CAR. In some embodiments, the agent is an antigen that the extracellular domain of the CAR binds, and the agent comprises an extracellular domain of at least one of Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, or CD4. In some embodiments, the agent comprises at least one of amino acid sequences: SEQ IDs: 41-47 and 61-63. In some embodiments, the agent binds at least one of amino acid sequences: SEQ IDs: 55, 21, 48, 49, 40, 51-53, and 56-60. In some embodiments, the agent comprises at least one of GCC, B7-H4, Prostate specific membrane antigen (PSMA), Carcinoembryonic Antigen (CEA), IL13Ralpha, her-2, CD19, CD20, CD22, CD123, NY-ES0-1, HIV-I Gag, Lewis Y antigen, Mart-I, gp100, tyrosinase, WT-I, hTERT, MUC16, mesothelin, MIC-A, MIC-B, estrogen, progesterone, RON, or one or more members of the ULBP/RAETI family. In some embodiments, the costimulatory molecule of CAR comprises at least one of CD27, CD28, 4-1BB, OX40, CD30, CD40, PD-L ICOS, lymphocyte function-associated antigen-I (LFA-1), CD2, CD7, LIGHT, NKG2C, or B7-H3. In some embodiments, the CAR comprises the extracellular domain, a transmembrane domain, and an intracellular domain comprising a CD3-zeta signaling domain and a signaling domain of a costimulatory molecule. In some embodiments, the agent is expressed by the cells, and the expression of the agent is regulated by an inducible expression system. In some embodiments, the CAR cells are cultured with cells that express the agent, and the agent is expressed by the cells, and the expression of the agent is regulated by an inducible suicide gene expression system. In some embodiments, the cells are modified cells that have reduced immunogenicity for an allogeneic CAR therapy, as compared to a wild-type cell. In some embodiments, the agent is a soluble antigen such that the antigen is released by the cells that express the agent. In some embodiments, the cells that express the agent are attenuated to be viable and replication incompetent. In some embodiments, the cells that express the agent are attenuated to be viable and replication incompetent by gamma irradiation or chemical inactivation. In some embodiments, the cells that express the agent or the isolated modified cells are obtained from peripheral blood mononuclear cells (PBMC) of the subject. In some embodiments, the cells that express the agent are T cells of the subject. In some embodiments, the cells that express the agent are T cells that are formulated as a vaccine. In some embodiments, the cells that express the agent are attenuated tumor cells. In some embodiments, a spacer domain of the CAR comprises an amino acid sequence of SEQ ID NO.: 68 or 69. In some embodiments, the transmembrane domain of the CAR comprises an amino acid sequence of SEQ ID NO.: 72 or 75, and the spacer domain of the CAR comprises an amino acid sequence of SEQ ID NO.: 68.

Some embodiments relate to an isolated nucleic acid sequence encoding a CAR comprising an extracellular domain, a spacer domain, a transmembrane domain, and an intracellular domain. The extracellular domain of the CAR binds a tumor antigen, and the spacer domain comprises an amino acid sequence of SEQ ID NO.: 67 or 68.

Some embodiments relate to an isolated nucleic acid sequence encoding a CAR comprising an extracellular domain, a spacer domain, a transmembrane domain, and an intracellular domain. The extracellular domain of the CAR binds a tumor antigen; the spacer domain comprises an amino acid sequence of SEQ ID NO.: 69; and the transmembrane domain comprises an amino acid sequence of SEQ ID NO.: 73 or 74.

In some embodiments, the antigen binding domain of the CAR comprises an antibody, a ligand, or an antigen-binding fragment thereof. In some embodiments, the antigen-binding fragment comprises a Fab or a scFv. In some embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ES0-1, PSC1, folate receptor-α, CD44v7/8, 8H9, NCAM, VEGF receptors, 5T4, Fetal AchR, NKG2D ligands, CD44v6, TEM1, or TEM8. In some embodiments, the intracellular domain of the CAR comprises a costimulatory signaling domain that includes an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In some embodiments, the intracellular domain of the CAR comprises a CD3 zeta signaling domain.

Some embodiments relate to a vector comprising the isolated nucleic acid sequence described above.

Some embodiments relate to a cell comprising the isolated nucleic acid sequence described above.

Some embodiments relate to a composition comprising a population of T cells which comprises the isolated nucleic acid sequence described above.

Some embodiments relate to a method for stimulating an anti-tumor immune response or treating a condition in a subject. The method comprises administrating to the subject an effective amount of a pharmaceutical composition comprising a population of human T cells which comprises the isolated nucleic acid sequence described above.

Some embodiments relate to a method comprising: providing cells comprising the isolated nucleic acid sequence described above and culturing the cells in the presence of an agent that the extracellular domain of the CAR recognizes.

Some embodiments relate to a method for in vitro CAR cell preparation. The method comprises: providing cells; introducing any one of the isolated nucleic acid sequence described above into the cells to obtain CAR cells; and culturing the CAR cells in the presence of an agent that the extracellular domain of the CAR recognizes.

Some embodiments relate to a method for enriching cells expressing a CAR. The method comprises: providing cells; introducing any one of the isolated nucleic acid sequence described above into the cells to obtain cells expressing a CAR (CAR cells) and cells that do not express the CAR; and culturing the CAR cells in the presence of an agent that binds the extracellular domain of the CAR to enrich the cells expressing the CAR.

In some embodiments, the agent is a ligand for the extracellular domain of the CAR. In some embodiments, the agent is an antigen that the extracellular domain of the CAR binds. In some embodiments, the agent is the extracellular domain of an antigen. In some embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, or CD4. In some embodiments, the agent is an antibody that binds the extracellular domain of the CAR. In some embodiments, the antibody is a human IgG antibody. In some embodiments, the antibody binds a Fab fragment of a human IgG. In some embodiments, the agent comprises an extracellular domain of at least one of CD19, FZD10, TSHR, PRLR, Muc 17, GUCY2C, CD207, CD3, CD5, or CD4. In some embodiments, the agent comprises at least one of amino acid sequences: SEQ IDs: 22 and 34. In some embodiments, the agent binds at least one of amino acid sequences: SEQ IDs: 55, 21, 48, 49, 40, and 50-60. In some embodiments, the agent activates the CAR and/or causes a co-stimulatory response of the cells. In some embodiments, the cells that express the antigen are an NK cell or a T cell, or a combination thereof.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIG. 2 shows a table with various parameters for comparison of T cells cultured with or without an antigen.

FIG. 5 shows the results of flow cytometry analysis indicating CD19 stimulates and/or induces CAR T cells to produce the phenotype of memory cells. The analysis results indicate that CD19 stabilizes the state of cells. 402 and 406 of FIG. 4 indicate levels of cell debris of cells cultured with and without CD19, respectively. 404 and 408 of FIG. 4 indicate proportions of cell debris with respect to the cells cultured with and without CD19, respectively.

FIG. 13 shows various constructs of CARs and expansion results of T cells having the CARs. T cells with various contracts of CARs were cultured for a predetermined time, respectively. Flow cytometric analysis of the cultured T cells was performed on day 1 and day 15; cell expansion ratios were measured. A histogram is showing expansion folds of CAR T cells cultured with or without CD19 extracellular domain.

FIG. 20 shows flow cytometric analysis of CAR expression levels on CAR T cells in two groups, as indicated in FIG. 13. The CAR T cells were cultured CD19 extracellular domain for 17 days.

FIG. 21 shows flow cytometric analysis of a killing assay on CAR T cells.

FIG. 23 shows schematic diagrams for a plurality of DNA constructs.

FIG. 24 shows fluorescence photographs of the killing effect of T cells.

FIG. 25 shows fluorescence photographs of the killing effect of T cells.

FIG. 31 shows a graph of multiple immortalized single-cell sequencing assays.

FIG. 36 shows that 35.725 ng/ml was used in the control and the experiment. The starting cells were cultured in 200 w cell density of 50 w/ml.

FIG. 39 shows dual-switch CART cell killing assay results.

FIG. 40 shows the results of cell killing analysis.

FIGS. 26 and 27 are results of killing analysis (knock out the result of cd3 of primary t cell). After knocking out and transfecting CAR and hTERT, a universal CAR T was made. The flow chart: 32.17% of the left is cd3 knock cd3-cell and 79.16% too. The sequencing peak map can be seen from the obvious set of peaks to prove the knocked out.

DETAILED DESCRIPTION

Figure 1:
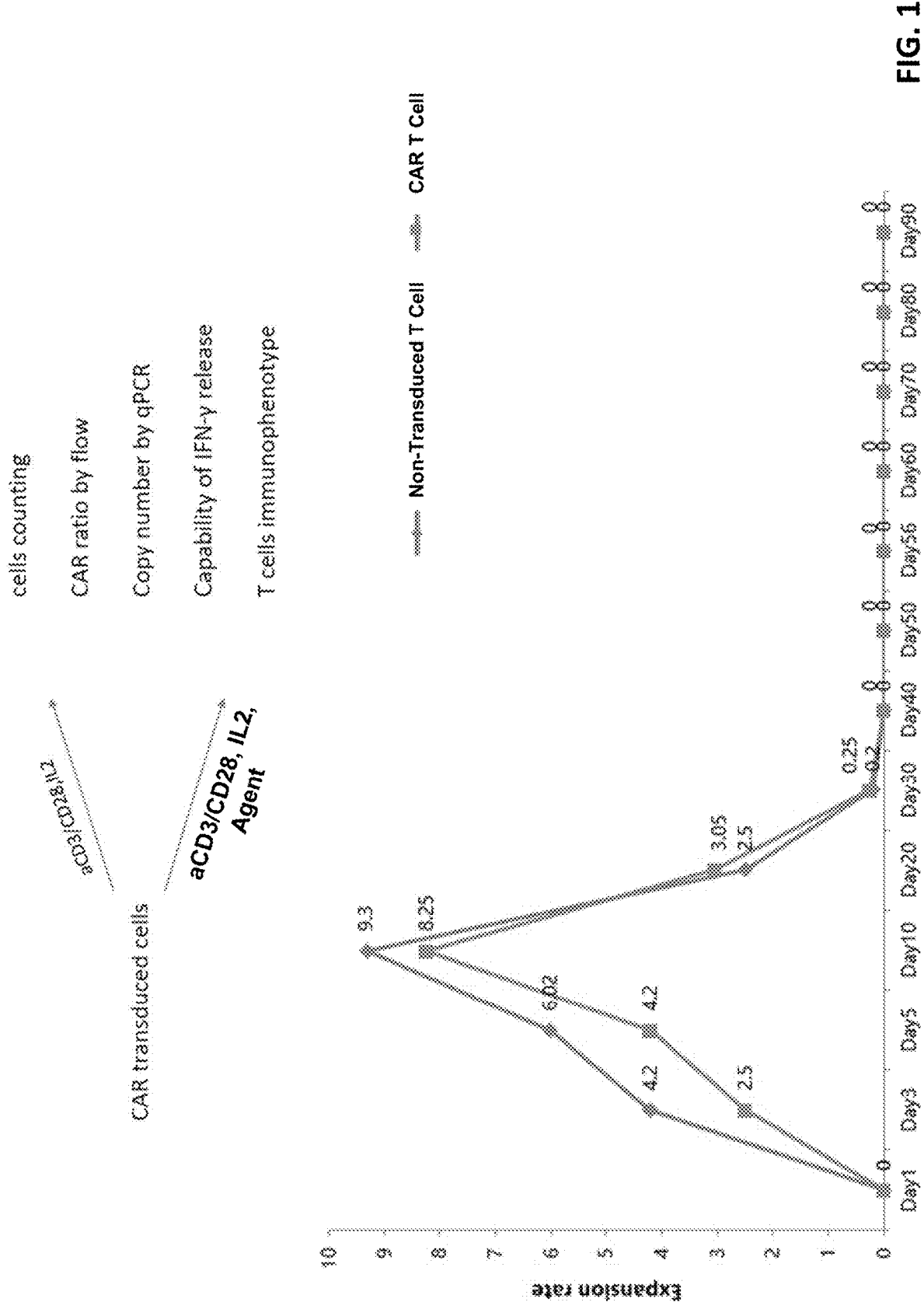
FIG. 1 shows a schematic diagram illustrating culturing T cells with or without an antigen and a histogram showing results of cell expansion of non-transduced T cells and CAR T cells using a media without an agent in accordance with the embodiments of the present disclosure.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies, monoclonal antibodies, Fv, Fab and F(ab)2, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab' F(ab')2, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute the amino acid residues for antigen binding and confer antigen binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. κ and λ light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody, or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be a related or unrelated or recipient subject, but the donor subject has immune system markers which are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" as used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any elements listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand," refers to a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules. The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to a naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide including expression control sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially frr from components that normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In some embodiments, the cells are cultured in vitro. In other embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), intrasternal injection, or infusion techniques.

The terms "patient," "subject," and "individual," and the like are used interchangeably herein, and refer to any human, animal, or living organism, amenable to the methods described herein. In certain non-limiting embodiments, the patient, subject, or individual is a human or animal. In some embodiments, the term "subject" is intended to include living organisms in which an immune response can be elicited (e.g., mammals). Examples of subjects include humans, and animals such as dogs, cats, mice, rats, and transgenic species thereof.

A subject in need of treatment or in need thereof includes a subject having a disease, condition, or disorder that needs to be treated. A subject in need thereof also includes a subject that needs treatment for prevention of a disease, condition, or disorder.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double-stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

"Polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In some embodiments, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a particular second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-$\beta$, and/or reorganization of cytoskeletal structures.

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex.

The term "stimulatory ligand" refers to a ligand that when present on an antigen presenting cell (e.g., an APC, a dendritic cell, a B-cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

A "vector" is a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate transfer of nucleic acid into cells, such as, for example, polylysine compounds, liposomes, and the like. Examples of viral vectors include, adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The present disclosure relates to isolated nucleic acid sequences, vectors including the isolated nucleic acid sequences, modified cells, and methods of treating cancer using these cells.

Some aspects of the present disclosure relate to a surprising discovery that uses of an agent for culturing CAR cell in vitro may enhance efficacy of CAR cells and/or efficiency of CAR cell preparation, achieve long-term in vitro maintenance of CAR cells, and/or induce CAR T cells to produce phenotypes of memory T cells. In these instances, the CAR expressed by the CAR cell recognizes and/or binds the agent. In some embodiments, the agent is a regulatory compound that binds an extracellular component of the CAR and/or activates signaling pathways of the CAR to thereof stimulate T cells expressing the CAR. For example, the regulatory compound may bind the CAR of the T cells and mediates a response by the T cells, including activation, initiation of an immune response, and/or proliferation.

Some aspects of the present disclosure relate to the modified T cells/CAR T cells that can grow numerous times (i.e., proliferable cells or longevity cells). Such proliferable cells remain functions of normal T cells/CAR T cells such as cell therapy functions. In some embodiments, a dual switch may be designed to regulate the growth of proliferable T cells/CAR T cells. Embodiments herein design a mechanism that includes one or two control switches. The first switch includes rtTA-TRE-hTERT/SV40LT. rtTA-TRE is a eukaryotic cell-induced expression of regulatory genes. By adding tetracycline to induce expression of hTERT (human telomerase reverse transcriptase) or SV40LT (SV40 large T antigen), phenotypes of immortalization may be produced. The second regulatory switch is EF1a-TK. TK gene is a suicide gene. In the case of adding ganciclovir, this agent will make the suicide gene exercise function to regulate the cell itself to die. In some embodiments, CAR T cells with one or two control switches may make the CAR T cells survive longer and retain relevant biological functions, while remaining effective and safe. Further, T cells may be generated using, in addition to lentiviruses, various other methods, which are included in the present invention, such as a knock-in method to insert the genome into another and uses of other vectors (e.g., retroviral vectors).

Embodiments of the present disclosure relate to compositions and methods for treating conditions using Chimeric Antigen Receptor (CAR) cells. The term "Chimeric Antigen Receptor" or alternatively a "CAR" refers to a recombinant polypeptide construct comprising at least an extracellular antigen binding domain, a transmembrane domain and an intracellular signaling domain (e.g., cytoplasmic domain). In some embodiments, the domains in the CAR polypeptide construct are in the same polypeptide chain (e.g., comprising a chimeric fusion protein) or not contiguous with each other (e.g., in different polypeptide chains).

In some embodiments, the intracellular signaling domain may include a functional signaling domain derived from a stimulatory molecule and/or a co-stimulatory molecule as described above. In certain embodiments, the intracellular signaling domain includes a functional signaling domain derived from a primary signaling domain (e.g., a primary signaling domain of CD3-zeta). In other embodiments, the intracellular signaling domain further includes one or more functional signaling domains derived from at least one co-stimulatory molecule. The co-stimulatory signaling region refers to a portion of the CAR including the intracellular domain of a co-stimulatory molecule. Co-stimulatory molecules are cell surface molecules other than antigens receptors or their ligands that are required for an efficient response of lymphocytes to antigen.

Between the extracellular domain and the transmembrane domain of the CAR, there may be incorporated a spacer domain (i.e., a hinge domain). As used herein, the term "spacer domain" refers to any oligo- or polypeptide that functions to link the transmembrane domain to, either the extracellular domain or, the cytoplasmic domain in the polypeptide chain. A spacer domain may include up to 300 amino acids, preferably 10 to 100 amino acids, and most preferably 25 to 50 amino acids.

The extracellular domain of a CAR may include an antigen binding domain (e.g., a scFv, a single domain antibody, or TCR (e.g., a TCR alpha binding domain or TCR beta binding domain)) that targets a specific tumor marker (e.g., a tumor antigen). Tumor antigens are proteins that are produced by tumor cells that elicit an immune response, particularly T cell mediated immune responses. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, and mesothelin. For example, if the tumor antigen is CD19, then the CAR thereof may be referred as CD19 CAR, and the corresponding CAR cell may be referred as CD19 CAR cell (e.g., CD19 CAR T cell).

In some embodiments, the extracellular ligand-binding domain comprises a scFv comprising the light chain variable (VL) region and the heavy chain variable (VH) region of a target antigen-specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)3 (SEQ ID: 76), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can, in turn, be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In some embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by the tumor. In some embodiments, the binding element of the CAR may include any antigen binding moiety that when bound to its cognate antigen, affects a tumor cell such that the tumor cell fails to grow, or is promoted to die or diminish.

In some embodiments relate to a genetically modified cell. In some embodiments, the modified cell may include a nucleic acid sequence encoding hTERT, a nucleic acid encoding SV40LT, or a combination thereof. In certain embodiments, the modified cell may include a first nucleic acid sequence encoding hTERT and/or a second nucleic acid sequence encoding SV40LT. For example, the nucleic acid sequence encoding hTERT has a sequence of SEQ ID NO: 6, and the nucleic acid sequence encoding SV40LT has a sequence of SEQ ID NO: 7.

In some embodiments, the modified cell is a T cell or an NK cell. In certain embodiments, the modified cell is a proliferable T cell. Proliferable cells refer to genetically modified cells having higher proliferation capacity than that of wild type cells. Several techniques may be implemented to obtain the proliferable cells. For example, hTERT, SV40LT, and/or other genes may be transferred to a cell to obtain a proliferable cell. In some embodiments, mRNA encoding constructs (e.g., hTERT and/or SV40LT) may be injected into cells to achieve transient gene expression in these cells. In other embodiments, vectors encoding constructs (e.g., hTERT and/or SV40LT) may be introduced into cells to obtain proliferable cells. For example, at least a portion of a vector may be integrated into the genome of the cells. In these instances, the integration of the nucleic acid sequence encoding hTERT, a nucleic acid encoding SV40LT, or a combination thereof may include genomic integration of the nucleic acid sequence encoding hTERT, a nucleic acid encoding SV40LT, or a combination thereof and constitutive expression of hTERT, SV40LT, or a combination thereof.

Some embodiments relate to a multi-step control of ability of proliferation, as described above. For example, a eukaryotic cell-induced expression system may be used to regulate the proliferation ability of T cells. By continuing to add "tetracycline" to these cells, hTERT and/or SV40LT can be expressed; however, if provision of tetracycline is terminated, hTERT and/or SV40LT may not be expressed. Accordingly, this proliferation may be terminated. In some embodiments, Ef1α and TK suicide gene may be used to regulate the proliferation ability. Since TK suicide gene function is an agent-sensitive gene, cells transferred with the system may die in the presence of the agent. Therefore, proliferation ability of T cells may be regulated in a safe and effective way.

In some embodiments, the expression of the nucleic acid sequence encoding hTERT, a nucleic acid encoding SV40LT, or a combination thereof, is regulated by an inducible expression system. For example, the inducible expression system is rTTA-TRE, which increases or activates the expression of SV40LT gene, hTERT gene, or a combination thereof. An inducible expression system allows for a temporal and spatial controlled activation and/or expression of genes. For example, Tetracycline-Controlled Transcriptional Activation is a method of inducible gene expression where transcription is reversibly turned on or off in the presence of the antibiotic tetracycline or one of its derivatives (e.g., doxycycline). For example, an inducible suicide gene expression system allows for a temporal and spatial controlled activation and/or expression of a suicide gene, which causes a cell to kill itself through apoptosis.

In some embodiments, the modified cell may include a nucleic acid sequence encoding a suicide gene. For example, the suicide gene is an HSV-TK system.

In some embodiments, the modified cell may include a nucleic acid sequence encoding a CAR. For example, the CAR may include an extracellular domain, a transmembrane domain, and an intracellular domain, and the extracellular domain binds a tumor antigen. In certain embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, or TEM8. In certain embodiments, the intracellular domain comprises a costimulatory signaling domain that may include an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. For example, the intracellular domain may include a CD3 zeta signaling domain. In certain embodiments, the nucleic acid encoding CAR, the nucleic acid encoding nhTERT, the nucleic acid encoding SV40LT, or a combination thereof is expressed as gene products that are separate polypeptides.

In some embodiments, the TCR gene of the T cell is disrupted such that expression of the endogenous TCR is reduced. In certain embodiments, a targeting vector associated with the TCR gene is integrated into the genome of the T cell such that the expression of the endogenous TCR is eliminated.

In some embodiments, the CD4 gene of the T cell is disrupted such that expression of the endogenous CD4 is reduced. In certain embodiments, an antigen binding domain of the CAR binds a molecule on the surface of HIV.

Some embodiments relate to a method for preparing the modified cell having a CAR (CAR cell). In some embodiments, the method may include providing a cell; and introducing a nucleic acid sequence encoding a CAR and a nucleic acid sequence encoding hTERT, SV40LT, or a combination thereof, into the cell. In some embodiments, the integration of the nucleic acid sequence encoding hTERT, a nucleic acid encoding SV40LT, or a combination thereof includes genomic integration of the nucleic acid sequence encoding hTERT, a nucleic acid encoding SV40LT, or a combination thereof and constitutive expression of hTERT, SV40LT, or a combination thereof. In some embodiments, the expression of the nucleic acid sequence encoding hTERT, SV40LT, or a combination thereof, is regulated by an inducible expression system. In some embodiments, the method may further include culturing the CAR cell in the presence of an agent that the extracellular domain of the CAR recognizes.

In some embodiments, the method may further include introducing a nucleic acid sequence encoding a suicide gene into the cell. In certain embodiments, the agent is a regulatory compound that binds an extracellular component of the CAR and mediates a response by the cells. For example, the regulatory compound is a ligand for the extracellular domain of the CAR or an antigen that extracellular domain of the CAR binds. In certain embodiments, the agent is the extracellular domain of an antigen that the extracellular domain of the CAR binds. For example, antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4. In certain embodiments, the agent is an antibody that binds the extracellular domain of the CAR. For example, the antibody is a human IgG antibody and/or binds a Fab fragment of a human IgG. In certain embodiments, the regulatory compound comprises an extracellular domain of at least one of CD19, FZD10, TSHR, PRLR, Muc 17, GUCY2C, CD207, CD3, CD5, or CD4. In some instances, the regulatory compound comprises at least one of amino acid SEQ IDs: 41-47. In some instances, the regulatory compound binds at least one of amino acid sequences: SEQ IDs: 21 and 48-B3. In some instances, the CAR cell may include at least one sequence of SEQ ID Nos: 38, 35, 39, and 40.

In some embodiments, the CAR cell exhibits about a 1.5 to 2 fold increase in cell growth as compared to the CAR cells cultured without the agent. In certain embodiments, the CAR cells exhibit about a 1.5 to 3 fold increase in cell growth as compared to the CAR cells cultured without the agent. In certain embodiments, the CAR cells exhibit about a 2 fold increase in cell growth as compared to the CAR cells cultured without the agent.

In some embodiments, the cell density of the CAR cells in the culture medium is at least 25 cells/ml of cell culture medium. In certain embodiments, the cell density of the CAR cells is less than 200×104 cells/ml of cell culture medium. In certain embodiments, the cell density of the CAR cells is between 50×104 to 200 cells/ml of cell culture medium. In certain embodiments, the cell density of the CAR cells between 50×104 to 100×104 cells/ml of cell culture medium.

In some embodiments, the CAR cells are sensitive to tetracycline in the cell culture medium. For example, the CAR cells comprise a third nucleic acid sequence encoding a reverse tetracycline transactivator (rtTA). In certain embodiments, the expression of hTERT, SV40LT is regulated by the rtTA such that hTERT, SV40LT is expressed in the presence of tetracycline. For example, the tetracycline is selected from the group of tetracycline, demeclocycline, meclocycline, doxycycline, lymecycline, methacycline, minocycline, oxytetracycline, rolitetracycline, and chlortetracycline. In specific embodiments, the tetracycline is doxycycline. In certain embodiments, a concentration of tetracycline in the cell culture medium is not less than 2 µg/ml.

In some embodiments, the CAR cell may include a fourth nucleic acid sequence encoding a suicide gene such that the CAR cells are cultured with a nucleoside analogue in a manner permitting expression of the suicide gene to render nucleoside analogue cytotoxic. For example, the suicide gene is selected from the group consisting of thymidine kinase of herpes simplex virus, thymidine kinase of varicella zoster virus, and bacterial cytosine deaminase. In specific embodiments, the suicide gene is thymidine kinase of herpes simplex virus. In certain embodiments, the nucleoside analogue is selected from the group consisting of ganciclovir, acyclovir, buciclovir, famciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2-deoxyuridine, 5-iodo-5-amino-2,5-dideoxyuridine, idoxuridine, AZT, AIU, dideoxycytidine, and AraC. In specific embodiments, the nucleoside analogue is ganciclovir.

Some embodiments relate to an isolated cell obtained using the method described above. In some embodiments, a composition comprising a population of the isolated cell. In some embodiments, a method of enhancing T-cell response in a subject and/or treating a tumor of the subject may include administering an effective amount of the composition.

In some embodiments relate to a method of generating a CAR T cell. The method may include proliferating a T cell by transferring one or more nucleic acid sequences to the T cell to obtain proliferable T cells; and introducing a nucleic acid sequence encoding a CAR into the proliferated T cells to obtain CAR T cells, wherein the CAR comprising an extracellular domain, a transmembrane domain, and an intracellular domain. For example, the one or more nucleic acid sequences comprise Tet-inducible HPV16-E6/E7 expression system.

In some embodiments, the T cell is a primary T cell extracted from a subject. In some embodiments, the T cell is a T cell having decreased immunogenicity as compared to a corresponding wild-type T cell in response to a T cell transfusion.

Some embodiments relate to a method of treating a disease or condition. The method may include administering to the human patient the pharmaceutical composition (e.g., a population of modified T cells) described herein. In certain embodiments, the disease or condition is AIDS, and an antigen binding domain of the CAR binds a molecule on the surface of HIV. In certain embodiments, the disease or condition is cancer, and an antigen binding domain of the CAR binds a molecule on a cancer cell, and the number of endogenous TCRs is reduced.

Some embodiments relate to a CAR T cell that includes a nucleic acid sequence encoding a CAR that comprises an extracellular domain, a transmembrane domain, and an intracellular domain comprising a CD3-zeta signaling domain and a signaling domain of a costimulatory molecule, wherein the TCR gene of the T cell is disrupted such that expression of the TCR is eliminated.

Some embodiments relate to a CAR T cell that includes a nucleic acid sequence encoding a CAR that comprises an extracellular domain, a transmembrane domain, and an intracellular domain comprising a CD3-zeta signaling domain and a signaling domain of a costimulatory molecule, wherein CD4 gene of the T cell is disrupted such that expression of the endogenous CD4 is reduced. For example, an antigen binding domain of the CAR binds a molecule on the surface of HIV and/or tumor cells.

Some embodiments relate to a method of producing conditionally proliferable T cells. The method may include transferring one or more nucleic acid sequences to the T cells to obtain proliferable T cells, wherein the one or more nucleic acid sequences encode a peptide such that expression of the peptide causes the T cells to become proliferable T cells, and the peptide is regulated by an inducible expression system, an inducible suicide system, or a combination thereof. In some embodiments, the peptide is hTERT, SV40LT, or a combination thereof. In certain embodiments, the inducible expression system is rtTA-TRE. In certain embodiments, the inducible suicide system is an HSV-TK system or an inducible caspase-9 system.

Some embodiments relate to a method of treating a disease or condition. The method may include preparing conditionally proliferable T cells using the method described herein; culturing the conditionally proliferable T cells in a medium containing tetracycline or doxycycline; culturing the conditionally proliferable T cell in a medium without any tetracycline or doxycycline to obtain T cells of which the expression of SV40LT gene or hTERT gene is reduced; and administering to a subject a pharmaceutical composition comprising the obtained T cells.

Some embodiments relate to a pharmaceutical composition obtained using a method described herein for use in the treatment of a disease or condition including preparing conditionally proliferable T cells using the method; culturing the conditionally proliferable T cells in a medium containing tetracycline or doxycycline; culturing the conditionally proliferable T cell in a medium without any tetracycline or doxycycline to obtain T cells of which the expression of SV40LT gene or hTERT gene is reduced; and administering to a subject a pharmaceutical composition comprising the obtained T cells. In certain embodiments, the method may further include administrating ganciclovir to the subject in response to a certain predetermined condition.

In some embodiments, an endogenous gene associated with a biosynthesis or transportation pathway of the TCR gene of the modified cell is disrupted such that expression of the endogenous TCR is reduced.

Some embodiments relate to a population of T cells comprising the modified cell described herein. In some embodiments, an endogenous gene associated with a biosynthesis or transportation pathway of PD-1 gene of the modified cell is disrupted such that expression of the endogenous TCR is reduced. In certain embodiments, the modified cell comprises a nucleic acid sequence that encodes truncated PD-1 that reduces an inhibitory effect of programmed death ligand 1 (PD-L1) on a human T cell.

In some embodiments relate to a method for preparation of modified cells. In some embodiments, the method may include obtaining cells comprising a chimeric antigen receptor (CAR); and culturing the cells in the presence of an agent that an extracellular domain of the CAR recognizes. In some embodiments, the method may be implemented for in vitro CAR cell preparation. The method may include providing cells; introducing a nucleic acid sequence encoding a CAR into the cells to obtain the CAR cells; and culturing the CAR cells in the presence of an agent that an extracellular domain of the CAR recognizes. In some embodiments, the method may be implemented to enrich cells expressing a CAR. The method may include providing cells; introducing a nucleic acid sequence encoding the CAR into the cells to obtain cells expressing the CAR (CAR cells) and cells not expressing the CAR; and culturing the CAR cells in the presence of an agent that binds an extracellular domain of the CAR to enrich the cells expressing the CAR. In some embodiments, the method may be implemented for in vitro CAR cell preparation. The method may include the following steps in the order named: (a) introducing a nucleic acid sequence encoding a CAR to the cells to obtain the CAR cells; (b) culturing the CAR cells using a first medium for a predetermined time; and (c) culturing the CAR cells using a second medium, wherein the first medium does not contain an agent; the second medium contains the agent, and the agent binds an extracellular domain of the CAR.

Some embodiments relate to isolated cells obtained by the methods above and a pharmaceutical composition containing the isolated cells. Some embodiments relate to a method for stimulating an anti-tumor immune response in a subject. The method comprising administering to the subject an effective amount of the pharmaceutical composition. Some embodiments relate to the pharmaceutical composition for use in the treatment of cancer comprising administering to the subject an effective amount of the pharmaceutical composition.

In some embodiments, the agent is a regulatory compound that binds an extracellular component of the CAR and mediates a response by the cells. In certain embodiments, the regulatory compound is a ligand for the extracellular domain of the CAR or an antigen that the extracellular domain of the CAR binds. In certain embodiments, the regulatory compound is an antibody that binds the extracellular domain of the CAR. In some instances, the antibody is a human IgG antibody and/or binds a Fab fragment of a human IgG. In certain embodiments, the regulatory compound may include an extracellular domain of at least one of CD19, FZD10, TSHR, PRLR, Muc 17, GUCY2C, CD207, CD3, CD5, or CD4. In certain embodiments, the regulatory compound comprises at least one of amino acid sequences: SEQ IDs: 41-47 and 61-63. In certain embodiments, the regulatory compound binds at least one of amino acid sequences: SEQ IDs: 55, 21, 48, 49, 40, 51-53, and 56-60. In certain embodiments, the regulatory compound comprises at least one of GCC, B7-H4, Prostate specific membrane antigen (PSMA), Carcinoembryonic Antigen (CEA), IL13Ralpha, her-2, CD19, CD20, CD22, CD123, NY-ES0-1, HIV-I Gag, Lewis Y antigen, Mart-I, gp100, tyrosinase, WT I, hTERT, MUC16, mesothelin, MIC-A, MIC-B, estrogen, progesterone, RON, or one or more members of the ULBP/RAETI family. In certain embodiments, the regulatory compound is a soluble antigen generated by a eukaryotic system or a bacterial expression system.

In some embodiments, a "soluble antigen" is a polypeptide that is not bound to a cell membrane. Soluble antigens are most commonly ligand-binding polypeptides (e.g., receptors) that lack transmembrane and cytoplasmic domains. Soluble antigens may include additional amino acid residues, such as affinity tags that provide for purification of the polypeptide or provide sites for attachment of the polypeptide to a substrate, or immunoglobulin constant region sequences. Soluble antigen polypeptides are said to be substantially free of transmembrane and intracellular polypeptide segments when they lack sufficient portions of these segments to provide membrane anchoring or signal transduction, respectively. For example, many cell-surface receptors have naturally occurring, while soluble counterparts that are produced by proteolysis.

In some embodiments, the agent is the extracellular domain of an antigen that the extracellular domain of the CAR binds. In certain embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

In some embodiments, the CAR comprises an extracellular domain, a transmembrane domain, and an intracellular domain comprising a CD3-zeta signaling domain and a signaling domain of a costimulatory molecule. In certain embodiments, the costimulatory molecule of CAR comprises at least one of CD27, CD28, 4-IBB, OX40, CD30, CD40, PD-L ICOS, lymphocyte function-associated antigen-I (LFA-1), CD2, CD7, LIGHT, NKG2C, or B7-H3.

In some embodiments, the cells are an NK cell, a T cell, or a combination thereof. For example, the cells are T cells derived from primary T cells obtained from a healthy donor or a subject.

In some embodiments, after culturing the CAR cells with an agent, a ratio of an amount of the agent and the number of CAR cells is 1:50 to 1:5 (μg/104 cell), 1:500 to 1:5 (μg/104 cell), or 1:5000 to 10:5 (μg/104 cell). In certain embodiments, a ratio of an amount of the agent and the number of CAR cells is 1:50 to 1:5 (μg/104 cell).

In some embodiments, the culture medium includes at least one of anti-CD3 beads, anti-CD28 beads, and IL2.

In some embodiments, the number of copies of CAR on the CAR cells is greater than the number when the CAR cells are cultured without the agent. In certain embodiments, a ratio of a number of the cells expressing the CAR and the cells not expressing the CAR is greater than the ratio when the cells are cultured without the agent.

In some embodiments, the CAR cells may be cultured in the presence of the agent for a predetermined period of time, or in the presence of the agent for at least 7, 8, 9, 10, 11, 12, 13, 14, 15, 16, 17, 18, 19, 20, 21, 22, 23, 24, 25, 26, 27, 28, 29, or 30 days. For example, the predetermined period of time is from 7-100 days. In other embodiments, the CAR cells may be cultured without the agent for at least 8, 9, 10, 11, 12, or 13 days after the introduction of a vector comprising a nucleic acid sequence encoding the CAR into the cells, and then cultured with the agent. In specific embodiments, the CAR cells may be cultured without the agent for about 10 days after the introduction of a vector comprising a nucleic acid sequence encoding the CAR into the cells, and then cultured with the agent. In certain embodiments, culturing the T cells in the presence of the agent comprises culturing the T cells with or without the agent for at least 8 days after introduction of a vector comprising a nucleic acid sequence encoding the CAR into the T cells, and then culturing the T cells with the agent after the at least 8 days. In certain embodiments, the culturing the T cells in the presence of the agent comprises culturing the T cells with or without the agent at least 10 days after introduction of a vector comprising a nucleic acid sequence encoding the CAR into the T cells, and then culturing the T cells with the agent after the at least 10 days.

In some embodiments, the number of the CAR cells producing a phenotype of memory T cells when cultured in the presence of an agent is greater than the number when the CAR cells are cultured without the agent.

In some embodiments, an amount of a cytokine produced by the CAR cells is greater than the amount of a cytokine produced by CAR cells when the CAR cells are cultured without the agent.

In some embodiments, the CAR cells are derived from a healthy donor and have a reduced expression of the endogenous TCR gene and/or HLA I. In certain embodiments, the CAR cells are derived from a healthy donor and elicit no graft-versus-host disease (GVHD) response or a reduced GVDH response in a human recipient as compared to the GVHD response elicited by a primary human T cell isolated from the same human donor and having no reduced expression of the endogenous TCR gene and/or HLA I, or that the expression of the endogenous TCR gene and/or HLA I is not disrupted and the endogenous TCR gene and/or HLA I are expressed as normal.

In some embodiments, the CAR T cells are T cells comprising a nucleic acid sequence encoding hTERT, a nucleic acid encoding SV40LT, or a combination thereof. In certain embodiments, the CAR T cells may include a nucleic acid sequence encoding hTERT and a nucleic acid encoding SV40LT. In certain embodiments, the expression of hTERT is regulated by an inducible expression system. In certain embodiments, the expression of SV40LT gene is regulated by an inducible expression system. In certain embodiments, the inducible expression system is rtTA-TRE, which increases or activates the expression of SV40LT gene, the hTERT gene, or a combination thereof.

In some embodiments, the CAR cell may include a nucleic acid sequence encoding a suicide gene. In certain embodiments, the suicide gene is an HSV-TK system.

Some embodiments relate to a method of in vivo cell expansion. In some embodiments, the method may include administering an effective amount of T cell comprising a CAR to the subject to provide a T cell response; and administering an effective amount of presenting cells expressing a soluble agent that an extracellular domain of the CAR recognizes. In some embodiments, the method may be implemented to enhance T cell response in a subject. The method may include administering an effective amount of T cell comprising a CAR to the subject to provide a T cell response, and administering an effective amount of presenting cells expressing a soluble agent that an extracellular domain of the CAR recognizes to enhance the T-cell response in the subject. In certain embodiments, the presenting cells are T cells, dendritic cells, and/or antigen presenting cells. In certain embodiments, the enhancing T cell response in the subject may include selectively enhancing proliferation of T cell comprising the CAR. In some embodiments, the method may be used to enhance treatment of a condition on a subject using CAR cells. The method may include administering a population of cells that express an agent or the agent that is formulated as a vaccine. In these instances, the CAR cells may include a nucleic acid sequence that encodes a CAR, and an extracellular domain of the CAR may recognize the agent. In some embodiments, the method may be implemented to enhance proliferation of CAR cells in a subject having a disease. The method may include preparing CAR cells comprising a CAR; administering an effective amount of the CAR cells to the subject; introducing, into cells, a nucleic acid sequence encoding an agent that an extracellular domain of the CAR recognizes, and administering an effective amount of the cells to the subject.

The T cell response in a subject refers to cell-mediated immunity associated with a helper, killer, regulatory, and other types of T cells. For example, T cell response may include activities such as assistance to other white blood cells in immunologic processes and identifying and destroying virus-infected cells and tumor cells. T cell response in the subject may be measured via various indicators such as a number of virus-infected cells and/or tumor cells that T cells kill, an amount of cytokines that T cells release in co-culturing with virus-infected cells and/or tumor cells, a level of proliferation of T cells in the subject, a phenotype change of T cells (e.g., changes to memory T cells), and a level longevity or lifetime of T cells in the subject.

In some embodiments, the in vitro killing assay may be performed by measuring the killing efficacy of CAR T cells by co-culturing CAR T cells with antigen-positive cells. CAR T cells may be considered to have a killing effect on the corresponding antigen-positive cells by showing a decrease in the number of corresponding antigen-positive cells co-cultured with CAR T cells and an increase in the release of IFNγ, TNFα, etc. as compared to control cells that do not express the corresponding antigen. Further, in vivo antitumor activity of the CAR t cells may be tested. For example, xenograft models may be established using the antigens described herein in immunodeficient mice. Heterotransplantation of human cancer cells or tumor biopsies into immunodeficient rodents (xenograft models) has, for the past two decades, constituted the major preclinical screen for the development of novel cancer therapeutics (Song et al., Cancer Res. PMC 2014 Aug. 21, and Morton et al., Nature Protocols, 2, -247-250 (2007)). To evaluate the anti-tumor activity of CAR T cells in vivo, immunodeficient mice bearing tumor xenografts can be used to evaluate CAR T's anti-tumor activity (e.g., a decrease in mouse tumors and mouse blood IFNγ, TNFα, and others. and/or retention time of CAR T in bone marrow/peripheral blood/spleen of the mice).

In some embodiments, the agent is a ligand for the extracellular domain of the CAR. In certain embodiments, the agent is an antigen that the extracellular domain of the CAR binds. In certain embodiments, the agent comprises an extracellular domain of at least one of Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, or CD4. In certain embodiments, the agent comprises at least one of amino acid sequences: SEQ IDs: 41-47 and 61-63. In certain embodiments, the agent binds at least one of amino acid sequences: SEQ IDs: 55, 21, 48, 49, 40, 51-53, and 56-60. In certain embodiments, the agent comprises at least one of GCC, B7-H4, Prostate specific membrane antigen (PSMA), Carcinoembryonic Antigen (CEA), IL13Ralpha, her-2, CD19, CD20, CD22, CD123, NY-ES0-1, HIV-I Gag, Lewis Y antigen, Mart-I, gp100, tyrosinase, WT-I, hTERT, MUC16, mesothelin, MIC-A, MIC-B, estrogen, progesterone, RON, or one or more members of the ULBP/RAETI family.

In some embodiments, the CAR comprises the extracellular domain, a transmembrane domain, and an intracellular domain comprising a CD3-zeta signaling domain and a signaling domain of a costimulatory molecule. In certain embodiments, the costimulatory molecule of CAR comprises at least one of CD27, CD28, 4-IBB, OX40, CD30, CD40, PD-L ICOS, lymphocyte function-associated antigen-I (LFA-1), CD2, CD7, LIGHT, NKG2C, or B7-H3.

In some embodiments, the cells or the isolated cells are NK cells, T cells, or a combination thereof. In certain embodiments, the cells are attenuated to be viable and replication incompetent. In certain embodiments, the cells are attenuated to be viable and replication incompetent by gamma irradiation or chemical inactivation. In certain embodiments, the cells or the isolated modified cell is obtained from the peripheral blood mononuclear cells (PBMC) of the subject. In certain embodiments, the cells are the T cells of the subject or a healthy donor. In certain embodiments, the cells are the T cells formulated as a vaccine. In certain embodiments, the cells are an attenuated tumor cell. In certain embodiments, the cells are modified cells that have reduced immunogenicity for an allogeneic CAR therapy, as compared to a wild-type cell.

In some embodiments, the agent is expressed by the cells, and the expression of the agent is regulated by an inducible expression system. In certain embodiments, the agent is expressed by the cells, and the expression of the agent is regulated by an inducible suicide gene expression system. In certain embodiments, the agent is a soluble antigen such that the antigen is released by the cells.

Some embodiments relate to an isolated nucleic acid sequence encoding a CAR having a spacer domain. In some embodiments, the isolated nucleic acid sequence may encode a CAR having an extracellular domain, a spacer domain, a transmembrane domain, and an intracellular domain, wherein the extracellular domain binds a tumor antigen, and the spacer domain comprises an amino acid sequence of SEQ ID NO.: 68 or 69. In some embodiments, the isolated nucleic acid sequence may encode a CAR having an extracellular domain, a spacer domain, a transmembrane domain, and an intracellular domain, wherein the extracellular domain binds a tumor antigen, the spacer domain comprises an amino acid sequence of SEQ ID NO.: 68, and the transmembrane domain comprises an amino acid sequence of SEQ ID NO.: 72 or 75.

Some embodiments relate to a vector comprising an isolated nucleic acid sequence and to a cell comprising the isolated nucleic acid sequence. For example, the cell may be an NK cell, a T cell, or a combination thereof. Some embodiments relate to a composition comprising a population of T cells having the isolated nucleic acid sequence.

Some embodiments relate to a method for preparing cells having the CAR and uses thereof. In some embodiments, the method may be implemented for stimulating an anti-tumor immune response or treating a condition in a subject. The method may include administering to the subject an effective amount of a pharmaceutical composition comprising a population of human T cell comprising the isolated nucleic acid sequence. In some embodiments, the method may include obtaining cells comprising the isolated nucleic acid sequence; and culturing the cells in the presence of an agent that an extracellular domain of the CAR recognizes. In some embodiments, the method may be implemented for in vitro CAR cell preparation. The method may include providing cells; introducing the isolated nucleic acid sequence into the cells to obtain the CAR cells; and culturing the CAR cells in the presence of an agent that an extracellular domain of the CAR recognizes. In some embodiments, the method may be implemented for enriching cells expressing a CAR. The method may include providing cells; introducing the isolated nucleic acid sequence of into the cells to obtain cells expressing the CAR (CAR cells) and cells not expressing a CAR; and culturing the CAR cells in the presence of an agent that binds an extracellular domain of the CAR to enrich the cells expressing the CAR.

In some embodiments, the antigen binding domain includes an antibody, a ligand, or an antigen-binding fragment thereof. In certain embodiments, the antigen-binding fragment includes a Fab or a scFv. In certain embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, or TEM8. In certain embodiments, the intracellular domain comprises a costimulatory signaling region that includes an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In certain embodiments, the intracellular domain comprises a CD3 zeta signaling domain.

In some embodiments, the agent is a ligand for the extracellular domain of the CAR. In certain, the agent is an antigen that extracellular domain of the CAR binds. In certain embodiments, the agent is the extracellular domain of the antigen. In certain embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, or CD4. In certain embodiments, the agent is an antibody that binds the extracellular domain of the CAR. In certain embodiments, the antibody is a human IgG antibody. For example, the antibody binds a Fab fragment of a human IgG. In certain embodiments, the agent comprises an extracellular domain of at least one of CD19, FZD10, TSHR, PRLR, Muc 17, GUCY2C, CD207, CD3, CD5, or CD4. In certain embodiments, the agent comprises at least one of amino acid SEQ IDs: 22 and 34. In certain embodiments, the agent binds at least one of amino acid SEQ IDs: 55, 21, 48, 49, 40, and 50-60. In certain embodiments, the agent activates the CAR and/or causes a co-stimulatory response of the cells.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from oncoretroviruses such as murine leukemia viruses in that they can transduce non-proliferating cells, such as hepatocytes. They also have the added advantage of low immunogenicity.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

Additional information related to expression synthetic nucleic acids encoding CARs and gene transfer into mammalian cells is provided in U.S. Pat. No. 8,906,682, incorporated by reference in its entirety.

The embodiments further relate to methods for treating a patient for illness including administering to the patient an effective amount of the engineered cells of the present disclosure. Various illnesses can be treated according to the present methods including cancer, such as ovarian carcinoma, breast carcinoma, colon carcinoma, glioblastoma multiforme, prostate carcinoma and leukemia. In some embodiments, the method includes administering to a human patient a pharmaceutical composition including an antitumor effective amount of a population of human T cells, wherein the human T cells of the population include human T cells that comprises the nucleic acid sequence as described in the present disclosure.

Some embodiments relate to compositions and methods for treating T cell leukemia. A modified cell may include a nucleic acid sequence encoding a chimeric antigen receptor (CAR) and a disruption of one or more exons of a gene associated with a cluster of differentiation molecule (CD). In these instances, an extracellular domain of the CAR recognizes the CD molecule. In certain embodiments, the CD molecule comprises CD2, CD3, CD4, CD5, CD7, CD8, or CD52. In other embodiments, the modified cell is a CAR NK cell or a CAR T cell.

T cell leukemia includes several different types of lymphoid leukemia which affect T cells: large granular lymphocytic leukemia, adult T cell leukemia/lymphoma, T cell prolymphocytic leukemia. For example, adult T-cell leukemia/lymphoma is often aggressive (fast-growing) T-cell lymphoma that can be found in the blood (leukemia), lymph nodes (lymphoma), skin, or multiple areas of the body. The chimeric antigen receptor T (CAR T) cell therapy is a newly developed adoptive antitumor treatment and has been proven to be effective for treating certain leukemia (e.g., B-cell lymphomas and B-cell chronic lymphocytic leukemia). However, conventional techniques of CAR T targeting would harm T cells including CAR T cells due to the issue of fratricide. Some embodiments use gene editing technology to modify certain genes of T/NK cells. For example, certain cluster of differentiation (CD) gene or related genes may be modified such that the modified cells may kill T cell tumor and avoid CAR T/NK cells from attacking each other.

In some embodiments, the CAR comprises the extracellular domain, a transmembrane domain, and an intracellular domain; the extracellular domain binds an antigen. In certain embodiments, the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

In some embodiments, the modified cell comprises a disruption of an endogenous gene associated with a biosynthesis or transportation pathway of CD2, CD3/TCR, CD4, CD5, CD7, CD8, or CD52 genes. In certain embodiments, the gene associated with the CD molecule is CD3/TCR gene, and the modified cell has a reduced amount of at least one of TCR subunits, or CD3 subunits, such as CD3γ, CD3δ, CD3ε, or CD3ζ subunit. Additional information of CD3 and disruption of CD3 subunit expression can be found in "A PCR-Based Method to Genotype Mice Knocked Out for All Four CD3 Subunits, the Standard Recipient Strain for Retrogenic TCR/CD3 Bone Marrow Reconstitution Technology," Alejandro Ferrer, Adam G. Schrum, and Diana Gil, BioResearch Open Access 2013 2:3, 222-226, which is incorporated by reference in its entirety. In certain embodiments, the gene associated with the CD molecule is CD3/TCR gene, the modified cell has a reduced amount of at least one of TRAC, CD3γ, CD3δ, or CD3ε subunits. In certain embodiments, the gene associated with the CD molecule is CD3/TCR gene, and the modified cell has a reduced expression of TRAC, CD3γ, CD3δ, and CD3ε subunits. In certain embodiments, the extracellular domain of the CAR binds CD3 or TCR, and the modified cell elicits a reduced amount or no T cell response caused by another modified cell in a subject as compared to the T cell response elicited by a cell that comprises the CAR of which the extracellular domain binds CD3 or TCR and does not have the disruption of endogenous CD3/TCR. In certain embodiments, the extracellular domain of the CAR comprises the amino acid sequence ID: 57. In certain embodiments, the extracellular domain of the CAR comprises the amino acid sequence ID: 88 and/or 89. In certain embodiments, the CD molecule is CD3, and the extracellular domain of the CAR comprises the amino acid sequence ID: 57, 88, or 89.

In some embodiments, the modified cell of any of embodiments 1-16, where the modified cell comprises an isolated zinc finger nuclease (ZFN) comprising: a first zinc finger protein (ZFP) binding to a first target site on a T cell receptor alpha constant (TRAC) gene (or nucleic acid sequence), the first ZFP comprising three or more zinc finger domains; a second ZFP binding to a second target site in the TRAC gene, the second ZFP comprising three or more zinc finger domains; and a cleavage domain. In some instances, the first ZFP comprising amino acid sequences SEQ ID NOS.: 278, 77, 80, 79, 78, and 87 ordered from a N-terminal of the first ZFP to a C-terminal of the first ZFP, and the second ZFP comprising amino acid sequences SEQ ID NOS.: 82, 83, 86, and 84 ordered from a N-terminal of the second ZFP to a C-terminal of the second ZFP. In other instances, the first ZFP comprising amino acid sequences SEQ ID NOS.: 26, 25, 26, 27, and 28 ordered from the N-terminal of the first ZFP to the C-terminal of the first ZFP, and the second ZFP comprising amino acid sequences SEQ ID NOS.: 30, 31, 26, 32 ordered from the N-terminal of the second ZFP to the C-terminal of the second ZFP. In some instances, the first target site comprises amino acid sequence SEQ ID NO: 81 and the second target site comprises amino acid sequence SEQ ID NO: 85. In other instances, the first target site comprises the amino acid sequence SEQ ID NO: 29, and the second target site comprises the amino acid sequence SEQ ID NO: 33.

In some embodiments, the CD molecule is CD4, and the extracellular domain of the CAR comprises amino acid sequence ID: 58, 90, or 91. In some embodiments, the CD molecule is CD4, and the extracellular domain of the CAR comprises amino acid sequence ID: 59, 92, or 93. In some embodiments, the CD molecule is CD5, and the extracellular domain of the CAR comprises the amino acid sequence ID: 94, 95, or 96.

In some embodiments, a modified cell may include a nucleic acid sequence encoding a CAR that binds one or more subunits of the CD3/TCR complex and disruption of one or more genes associated with the CD3/TCR complex. For example, the CD3/TCR complex includes multiple subunits or chains such as CD3γ, CD3δ, CD3ε, TCRα, and TCRβ. In certain embodiments, an extracellular domain of the CAR binds CD3 subunits (e.g., CD3γ, CD3δ, and CD3ε subunits), and the modified cell includes a reduced amount or no expression of TRAC. In some instances, the extracellular domain of the CAR includes amino acid sequence SEQ ID NO: 57, 58, 59, or 95. In some instances, the modified cell includes a zinc finger nuclease targeting TRAC and includes a reduced amount or no expression of TRAC.

In some embodiments, the method of preparing the modified cell described above may include introducing the nucleic acid sequence encoding the CAR to a cell to obtain the modified cell; and disrupting the one or more exons of the gene of the cell or the modified cell.

In some embodiments, the pharmaceutical composition comprises a population of the modified cells described above.

In some embodiments, the method of treating T cell leukemia may include administrating to a subject a therapeutically effective amount of the modified cell described above. In some embodiments, the T cell leukemia comprises at least one of large granular lymphocytic leukemia, adult T-cell leukemia/lymphoma, or T-cell prolymphocytic leukemia.

In some embodiments, the method of treating cancer expressing the CD molecule may include administering to a subject a therapeutically effective amount of the modified cell described above.

In some embodiments, a method of reducing a number of cells that express the CD molecule may include disrupting one or more exons of a gene associated with the CD molecule of cells comprising a CAR to obtain disrupted CAR cells; and contacting cells comprising the CD molecule with an effective amount of the disrupted CAR cells, wherein a level of proliferation and/or survival of the disrupted CAR cells is increased as compared to the CAR cells. In some embodiments, the disrupted CAR cells are the modified cells described above.

In some embodiments, a method of reducing the number of cells that express the CD molecule may include contacting the cells with an effective amount of the modified cell described above.

In some embodiments, a method of inhibiting proliferation or activity of cells that express the CD molecule may include contacting the cells with an effective amount of the modified cells described above.

Cancers that may be treated include tumors that are not vascularized, or not yet substantially vascularized, as well as vascularized tumors. The cancers may include non-solid tumors (such as hematological tumors, for example, leukemias and lymphomas) or may include solid tumors. Types of cancers to be treated with the CARs of the disclosure include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

For example, renal cell cancer is one of the common malignant neoplasms. The treatment of patients with early-stage renal cell carcinoma can achieve a five-year survival rate of 90% through surgical resection. However, the advanced patients with advanced stage of diffusion and metastasis have a five-year survival rate of only about 10%, ref (National Cancer Institute: SEER Stat Fact Sheets: Kidney and Renal Pelvis Cancer. Bethesda, Md.: National Cancer Institute. Available online. Last accessed Nov. 2, 2017). Pancreatic cancer is a malignant tumor of the digestive tract that is very malignant and difficult to diagnose and treat. Although medical technology has been greatly improved in the past two decades, there are still many problems in the diagnosis and treatment of pancreatic cancer. Due to the low initial diagnosis, pancreatic cancer often has metastases at the time of its discovery. Therefore, less than 20% of patients with surgical resection and an average of 5 years of survival of less than 10%. (American Cancer Society: Cancer Facts and FIGS. 2018. Atlanta, Ga.: American Cancer Society, 2018. Available online. Last accessed Jan. 5, 2018). Urothelial cancer is cancer that has evolved from urothelial cells in the urinary system and is a relatively rare malignancy. Although early diagnosis rate is high, and early treatment is effective, urothelial carcinoma is still a kind of malignant tumor with high recurrence, easy progress, and poor prognosis. Endometrial cancer refers to a group of epithelial malignancies originating in the endometrium. Endometrial cancer is one of the three major malignant tumors in the female reproductive tract. The 5-year survival rate of early patients is 62%-84%, but the efficacy of the patients in the late stage is poor. Breast cancer is a common malignant tumor, frequent in women, the incidence is high, due to the continuous improvement of medical means, breast cancer survival opportunities have been significantly improved, five-year survival can reach 90%. But for the triple negative breast cancer, treatment is still very tricky, strong invasion of tumor cells, the prognosis is poor. Prostate cancer is the most common cancer of the male reproductive system, mostly male elderly patients, is the second largest fatal cancer in the United States, according to statistics, 5-year survival of early prostate cancer can reach 90%, but advanced prostate cancer Patients 5-year survival rate of only 30%. Esophageal cancer is cancer arising from the esophagus, the incidence of esophageal cancer has risen in recent decades. The main reason for the poor prognosis is that most patients are often already locally advanced or have had distant metastases when diagnosed. Most ovarian cancer patients (60%) are diagnosed with the distant-stage disease, for which 5-year survival is 29%. The overall 5-year relative survival rate for ovarian cancer is low (47%). Colorectal cancer is a common malignant tumor. In addition to genetic factors, colorectal cancer is closely related to high fat, high protein, and low fiber dietary habits. The incidence of colorectal cancer in countries such as the United States is high, and the 5-year relative survival rate is about 60%. In summary of the current status of these cancers, it appears that the treatment of cancer is still a long way to go and there is still an urgent need to develop new methods for treating these cancers.

The cells activated and expanded as described herein may be utilized in the treatment and prevention of diseases that arise in individuals who are immunocompromised. In particular, the engineered cells of the present disclosure are used in the treatment of cancer. In certain embodiments, the cells of the present disclosure are used in the treatment of patients at risk for developing cancer. Thus, the present disclosure provides methods for the treatment or prevention of cancer comprising administering to a therapeutically effective amount of the modified T cells of the present disclosure.

The modified T cells of the present disclosure may be administered either alone or as a pharmaceutical composition in combination with diluents and/or with other components such as IL-2 or other cytokines or cell populations. Briefly, pharmaceutical compositions of the present disclosure may include a modified T cell population as described herein, in combination with one or more pharmaceutically or physiologically acceptable carriers, diluents or excipients. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can be stated that a pharmaceutical composition comprising the T cells described herein may be administered at a dosage of 104 to 109 cells/kg body weight, preferably 105 to 106 cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, may select out certain populations of T cells.

The administration of the pharmaceutical compositions described herein may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i. v.) injection, or intraperitoneally. In some embodiments, the T cell compositions of the present disclosure are administered to a patient by intradermal or subcutaneous injection. In another embodiment, the T cell compositions of the present disclosure are preferably administered by i.v. injection. The compositions of T cells may be injected directly into a tumor, lymph node, or site of infection.

In certain embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In someembodiments, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In other embodiments, the cell compositions of the present disclosure are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present disclosure. In other embodiments, expanded cells are administered before or following surgery.

The dosage of the above treatments to be administered to a patient will vary with the precise nature of the condition being treated and the recipient of the treatment. The scaling of dosages for human administration can be performed according to art-accepted practices by a physician depending on various factors.

Additional information on the methods of cancer treatment using engineered or modified T cells is provided in U.S. Pat. No. 8,906,682, incorporated by reference in its entirety.

Some embodiments relate to an in vitro method for preparing modified cells. The method may include obtaining a sample of cells from the subject. For example, the sample may include T cells or T cell progenitors. The method may further include transfecting the cells with a DNA encoding at least a CAR, culturing the population of CAR cells ex vivo in a medium that selectively enhances proliferation of CAR-expressing T cells. In some embodiments, the sample is a cryopreserved sample. In some embodiments, the sample of cells is from umbilical cord blood. In some embodiments, the sample of cells is a peripheral blood sample from the subject. In some embodiments, the sample of cells is obtained by apheresis. In some embodiments, the sample of cells is obtained by venipuncture. In some embodiments, the sample of cells is a subpopulation of T cells. In some embodiments, the genes of the CAR cells associated with an endogenous T cell receptor and/or endogenous HLA are disrupted such that immunogenicity of the CAR cells is reduced.

EXEMPLARY EMBODIMENTS

The following are exemplary embodiments:

1. A modified cell comprising a nucleic acid sequence encoding a chimeric antigen receptor (CAR) and a disruption of one or more exons of a gene associated with a cluster of differentiation molecule (CD), wherein an extracellular domain of the CAR recognizes the CD molecule.

2. The modified cell of embodiment 1, where the gene associated with the CD molecule comprises CD2, CD3/TCR, CD4, CD5, CD7, CD8, or CD52 genes.

3. The modified cell of embodiment 1 or 2, wherein the modified cell is a CAR NK cell or a CAR T cell.

4. The modified cell of any one of embodiments 1-3, wherein the CAR comprises the extracellular domain, a transmembrane domain, and an intracellular domain, wherein the extracellular domain binds an antigen.

5. The modified cell of any one of embodiments 1-4, wherein the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

6. The modified cell of any one of embodiments 1-5, wherein the modified cell has a disrupted endogenous gene associated with a biosynthesis or transportation pathway of CD2, CD3/TCR, CD4, CD5, CD7, CD8, or CD52 genes.

7. The modified cell of any one of embodiments 1-6, wherein the gene associated with the CD molecule is CD3/TCR gene, and the modified cell has a reduced amount of at least one of TCR subunits, or at least one of CD3γ, CD3δ, CD3ε, or CD3ζ subunits.

8. The modified cell of any one of embodiments 1-7, wherein the gene associated with the CD molecule is CD3/TCR gene, and the modified cell has a reduced amount of at least one of TRAC, CD3γ, CD3δ, or CD3ε subunits.

9. The modified cell of any one of embodiments 1-7, wherein the gene associated with the CD molecule is CD3/TCR gene, and the modified cell has a reduced expression of TRAC, CD3γ, CD3δ, and CD3ε subunits.

10. The modified cell of any one of embodiments 1-9, wherein the extracellular domain binds CD3 or TCR, and the modified cell elicits a reduced amount or no T cell response caused by another modified cell in a subject as compared to the T cell response elicited by a cell that comprises the CAR of which the extracellular domain binds CD3 or TCR and does not have a disruption of one or more exons of the gene associated with CD3/TCR.

11. The modified cell of any one of embodiments 1-10, wherein the extracellular domain of the CAR comprises amino acid sequence SEQ ID NO: 57.

12. The modified cell of any one of embodiments 1-11, wherein the extracellular domain of the CAR comprises amino acid sequence ID NO: 88 and/or 89.

13. The modified cell of any one of embodiments 1-12, wherein the gene associated with the CD molecule is CD3/TCR gene, and the extracellular domain of the CAR comprises amino acid sequence SEQ ID NO: 57, 88, or 89.

14. The modified cell of any one of embodiments 1-13, wherein the CD molecule is CD4, and the extracellular domain of the CAR comprises the amino acid sequence ID: 58, 90, or 91.

15. The modified cell of any one of embodiments 1-14, wherein the CD molecule is CD4, and the extracellular domain of the CAR comprises the amino acid sequence ID: 59, 92, or 93.

16. The modified cell of any one of embodiments 1-15, wherein the CD molecule is CD5, and the extracellular domain of the CAR comprises the amino acid sequence ID: 94, 95, or 96.

17. The modified cell of any one of embodiments 1-16, where the modified cell comprises an isolated zinc finger nuclease (ZFN) comprising: a first zinc finger protein (ZFP) binding to a first target site in a T-cell receptor alpha constant (TRAC) molecule, the first ZFP comprising three or more zinc finger domains; a second ZFP binding to a second target site in the TRAC gene, the second ZFP comprising three or more zinc finger domains; and a cleavage domain, wherein: the first ZFP comprising amino acid sequences SEQ ID NOS.: 278, 77, 80, 79, 78, and 87 ordered from a N-terminal of the first ZFP to a C-terminal of the first ZFP, and the second ZFP comprising amino acid sequences SEQ ID NOS.: 82, 83, 86, and 84 ordered from a N-terminal of the second ZFP to a C-terminal of the second ZFP, the first ZFP comprising amino acid sequences SEQ ID NOS.: 26, 25, 26, 27, and 28 ordered from the N-terminal of the first ZFP to the C-terminal of the first ZFP, and the second ZFP comprising amino acid sequences SEQ ID NOS.: 30, 31, 26, 32 ordered from the N-terminal of the second ZFP to the C-terminal of the second ZFP, the first target site comprising amino acid sequence SEQ ID NO: 81, and the second target site comprising amino acid sequence SEQ ID NO: 85, or the first target site comprising amino acid sequence SEQ ID NO: 29, and the second target site comprising amino acid sequence SEQ ID NO: 33.

18. A method of preparing the modified cell of any of embodiments 1-17, the method comprising: introducing the nucleic acid sequence encoding the CAR to a cell to obtain the modified cell; and disrupting the one or more exons of the gene of the cell or the modified cell.

19. A pharmaceutic composition comprising a population of the modified cells of any one of embodiments 1-17.

20. A method of treating T-cell leukemia, the method comprising:
administering to a subject a therapeutically effective amount of the modified cell of any one of embodiments 1-17, wherein the T-cell leukemia comprises at least one of large granular lymphocytic leukemia, adult T-cell leukemia/lymphoma, or T-cell prolymphocytic leukemia.

21. A method of treating cancer expressing a CD molecule, the method comprising: administering to a subject a therapeutically effective amount of the modified cell of any one of embodiments 1-17.

22. A method of reducing a number of cells that express a CD molecule, the method comprising: disrupting one or more exons of a gene associated with a CD molecule of cells comprising a CAR to obtain disrupted CAR cells; and contacting cells comprising the CD molecule with an effective amount of the disrupted CAR cells, wherein a level of proliferation and/or survival of the disrupted CAR cells is increased as compared to the CAR cells.

23. The method of embodiment 22, wherein the disrupted CAR cells are the modified cell of any of embodiments 2-17.

24. A method of reducing a number of cells that express a CD molecule, the method comprising: contacting the cells with an effective amount of the modified cell of any of embodiments 1-17.

25. A method of inhibiting proliferation or activity of cells that express a CD molecule, the method comprising: contacting the cells with an effective amount of the modified cell of any of embodiments 1-17.

EXAMPLES

The present disclosure is further described by reference to the following examples. These examples are provided for purposes of illustration only and are not intended to be limiting unless otherwise specified. Thus, the present disclosure should in no way be construed as being limited to the following examples, but rather, should be construed to encompass any and all variations which become evident as a result of the teaching provided herein.

Expression of CAR on HEK293T & K562 Cells

Lentiviral vectors that encode a CD19 CAR or a TSHR CAR were generated (see "Chimeric Receptors Containing CD137 Signal Transduction Domains Mediate Enhanced Survival of T Cells and Increased Antileukemic Efficacy," In Vivo Molecular Therapy vol. 17 no. 8, 1453-1464 August 2009, incorporated herein by reference).

Primary T cells were obtained from patients. The obtained primary T cells were transduced with lentiviral vectors to obtain modified T cells. Flow-cytometry was performed and analyzed to determine the expression of CARs in the primary T cells. Techniques related to cell cultures, construction of lentiviral vectors, and flow cytometry may be found in "Control of large, established tumor xenografts with genetically retargeted human T cells containing CD28 and CD137 domains," PNAS Mar. 3, 2009, vol. 106 no. 9, 3360-3365, which is incorporated herein by reference.

T cells were cultured using a media containing anti-CD3/CD28 beads but no CD19 ECD. Cell expansion rates of both non-transduced T cells and CD19 CAR T cells were observed and shown in FIG. 1.

Stimulation and Amplification of CAR T Cells in the Presence of CD19 Extracellular Domain (ECD)

The primary T cells were transduced with lentiviral vectors encoding a CD19 CAR to obtain modified T cells including CAR T cells expressing anti-CD19 (thereafter "CAR T19 cells") on day 1. The modified T cells were divided into two groups and cultured, respectively. CAR T19 cells in Group 1 were cultured with anti-CD3 & CD28 beads and IL2, while CAR T19 cells in Group 2 were cultured with soluble CD19 (e.g., extracellular domain (ECD) of CD19, SEQ ID: 41), anti-CD3 & CD28 beads and IL2. For Group 2, 500,000 CAR T19 cells were cultured with 2 micrograms of soluble CD19 at the starting point, and 4 micrograms of soluble CD19 were used after the CAR T19 cells were grown. The numbers of cells were measured, and ratios between CAR+cells and the modified T cell population were observed by flow cytometry. The number of CAR copies in the cell population was measured.

Figure 3:
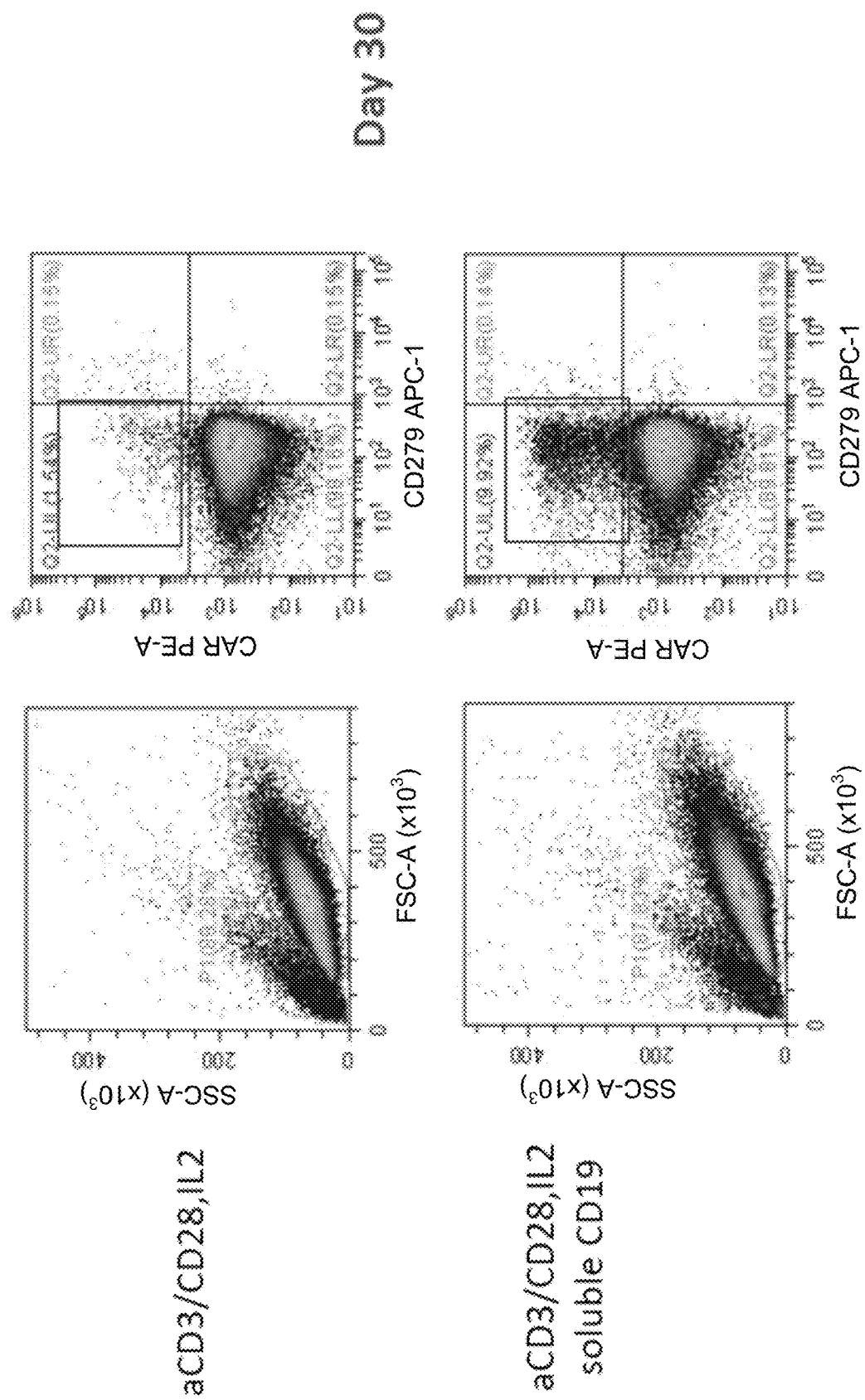
FIG. 3 shows the results of flow cytometry analysis indicating CD19 maintains CAR T 19 cells activities.

CAR T cells and T cells not expressing CAR were observed to have different degrees of growth, for example, on 22 days. As shown in column 5 of FIG. 2, copy numbers of CAR T19 cells in Group 2 was higher than those of Group 2 based on qPCR analysis. As shown in column 6 of FIG. 2, the ratio of CAR T19 cells and T cells in Group 2 was higher than that of Group 1 using flow cytometry analysis. As shown in FIG. 3, the vertical axis represents anti-scFv PE, and areas in the boxes indicate CAR T19 cells. Surprisingly, in response to adding of CD19 ECD in the media, both non-transduced T cells and CD19 CAR T cells exhibited no apparent increases in cell expansion as compared to culturing without CD19 ECD during the early stage, which is from about day 3 to day 10. After this stage, cell expansion rates of CD19 CAR T cells increased at a higher rate than those cultured without the CD19 ECD. These results demonstrated that CD19 stimulated or enhanced long-term maintenance of CAR T19 cells in vitro while showing no apparent enhancement for short-term maintenance (e.g., less than 10 days).

Stimulation and Amplification of CAR T Cell in Presence of TSHR ECD

Primary T cells were transduced with lentiviral vectors encoding a TSHR CAR to obtain modified T cells including CAR T cells expressing anti-TSHR (thereafter "CAR T-TSHR cells"). The modified T cells were frozen and stored for 30 days. Techniques related to freezing T cells and thawing frozen T cells may be found in Levine et al., Molecular Therapy—Methods & Clinical Development, Molecular Therapy, Vol 4, Mar. 17, 2017.

Figure 9:
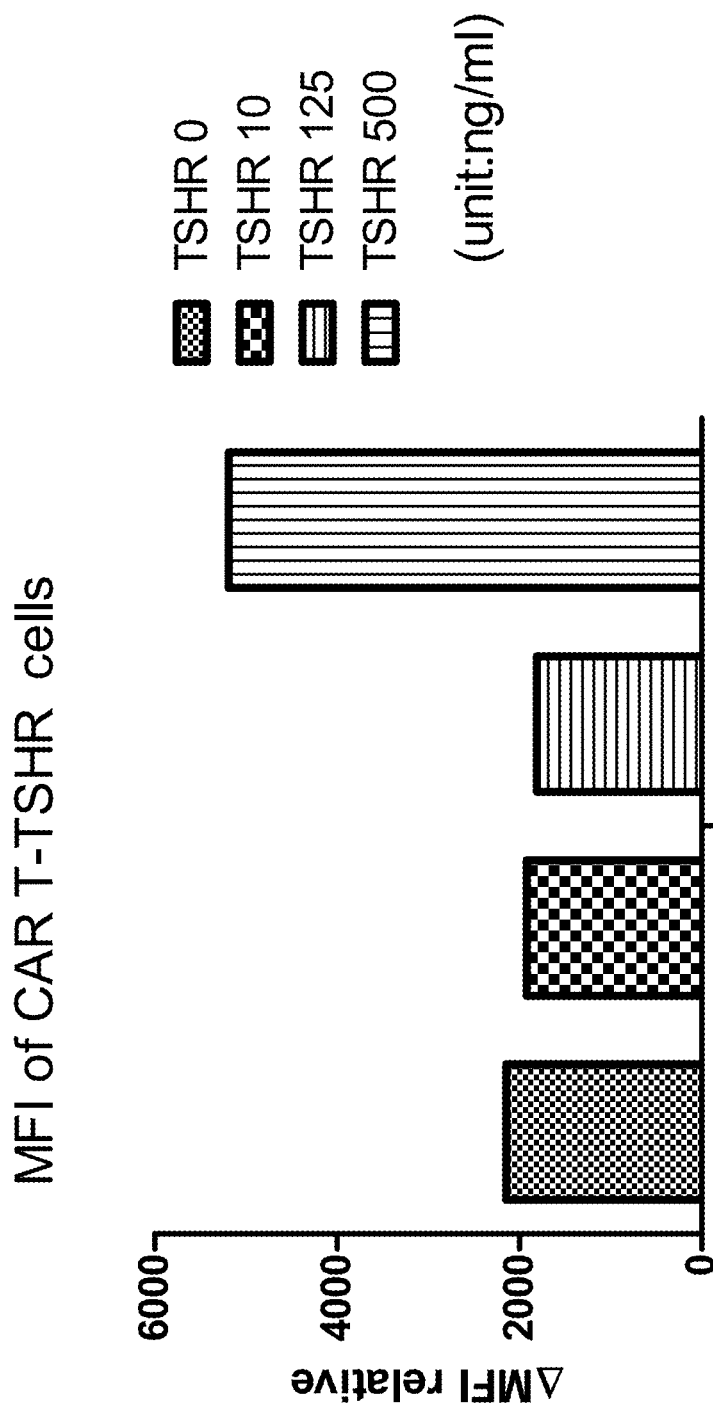
FIG. 9 shows ΔMFI (median fluorescence intensity) of CART-TSHR cells. MFI refers to the median fluorescence of the population of cells and is calculated as a numerical value.
Figure 10:
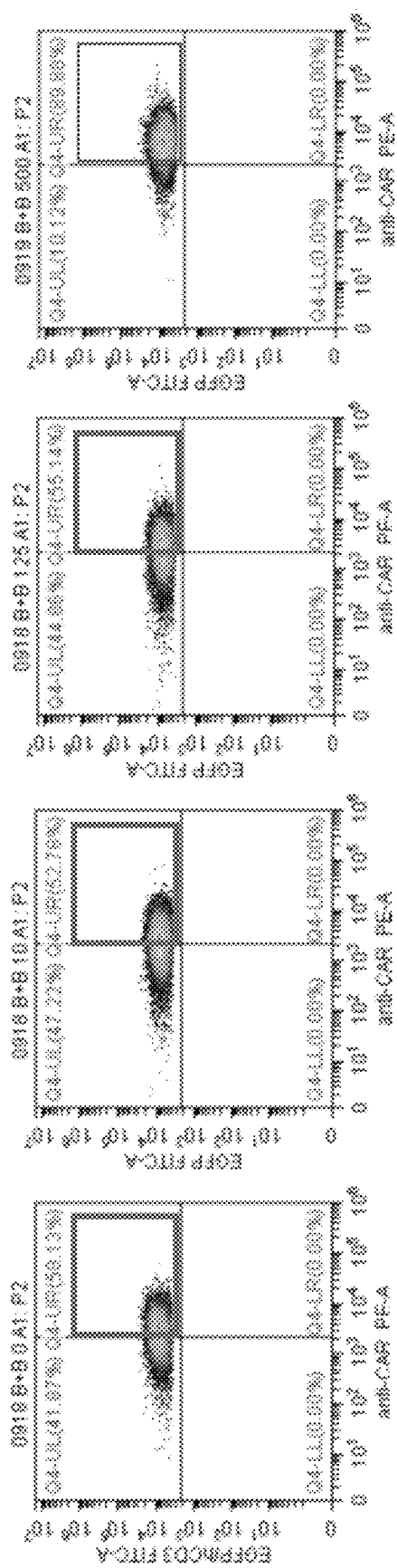
FIG. 10 shows additional results of flow cytometry analysis indicating TSHR maintains CAR T-TSHR cells activities
Figure 11:
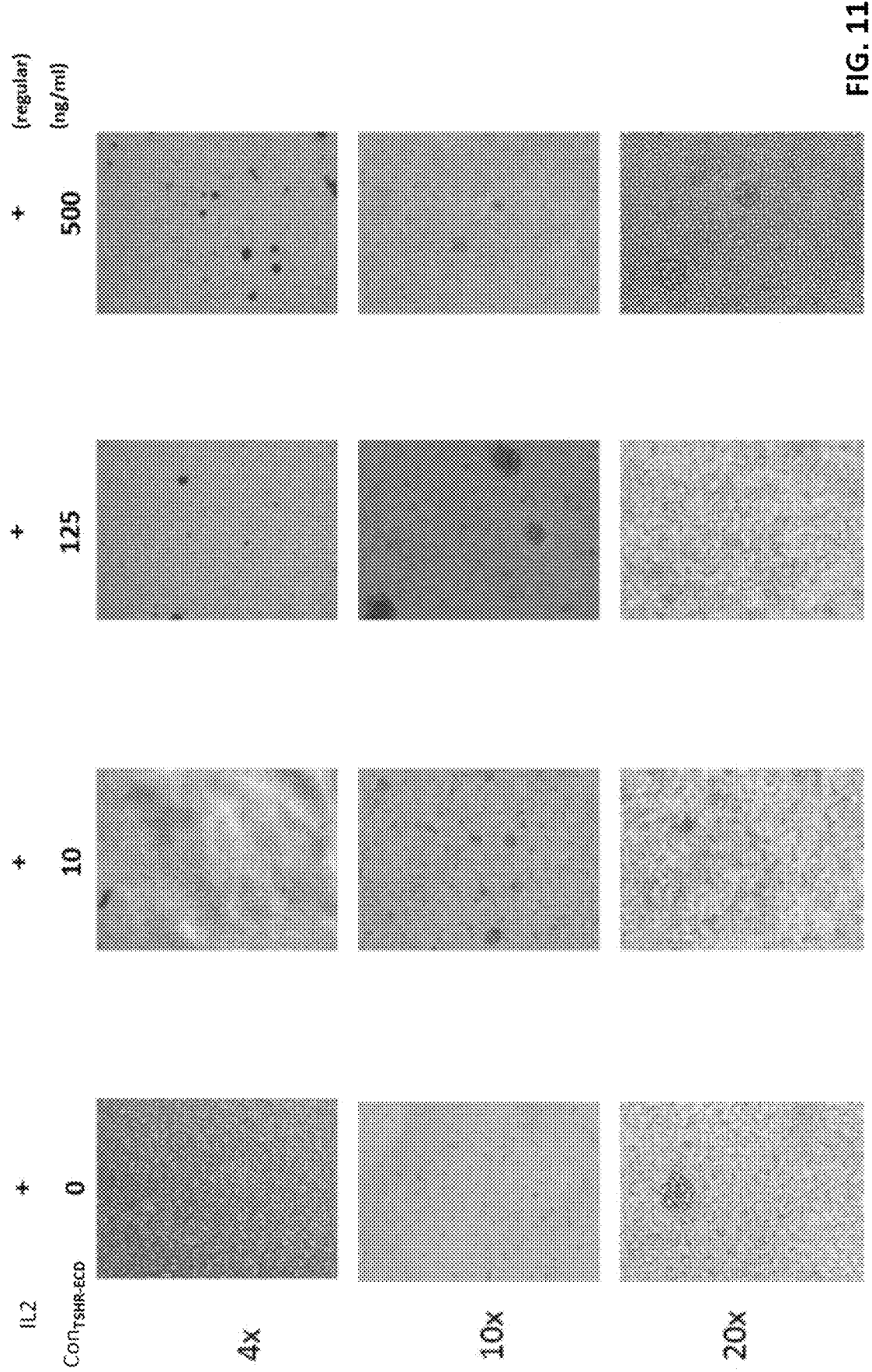
FIG. 11 shows cellular morphology of CAR T-TSHR cells cultured with and without TSHR.

The modified T cells were thawed and divided into two groups and cultured, respectively. CAR T-TSHR cells in Group 1 were cultured with anti-CD3 & CD28 beads and IL2 for 10 days, while CAR T-TSHR cells in Group 2 were cultured with various concentrations of soluble TSHR (e.g., extracellular domain of TSHR, SEQ ID: 34), anti-CD3 & CD28 beads and IL2. For Group 2, 500,000 CAR T-TSHR cells were cultured with 10, 125, 500 ng/ml of soluble TSHR ECD for 14 days. The T cell population was observed by flow cytometry (FIGS. 8 and 9), and cellular morphology of the T cell population was observed under microscopes (FIG. 10).

Figure 8:
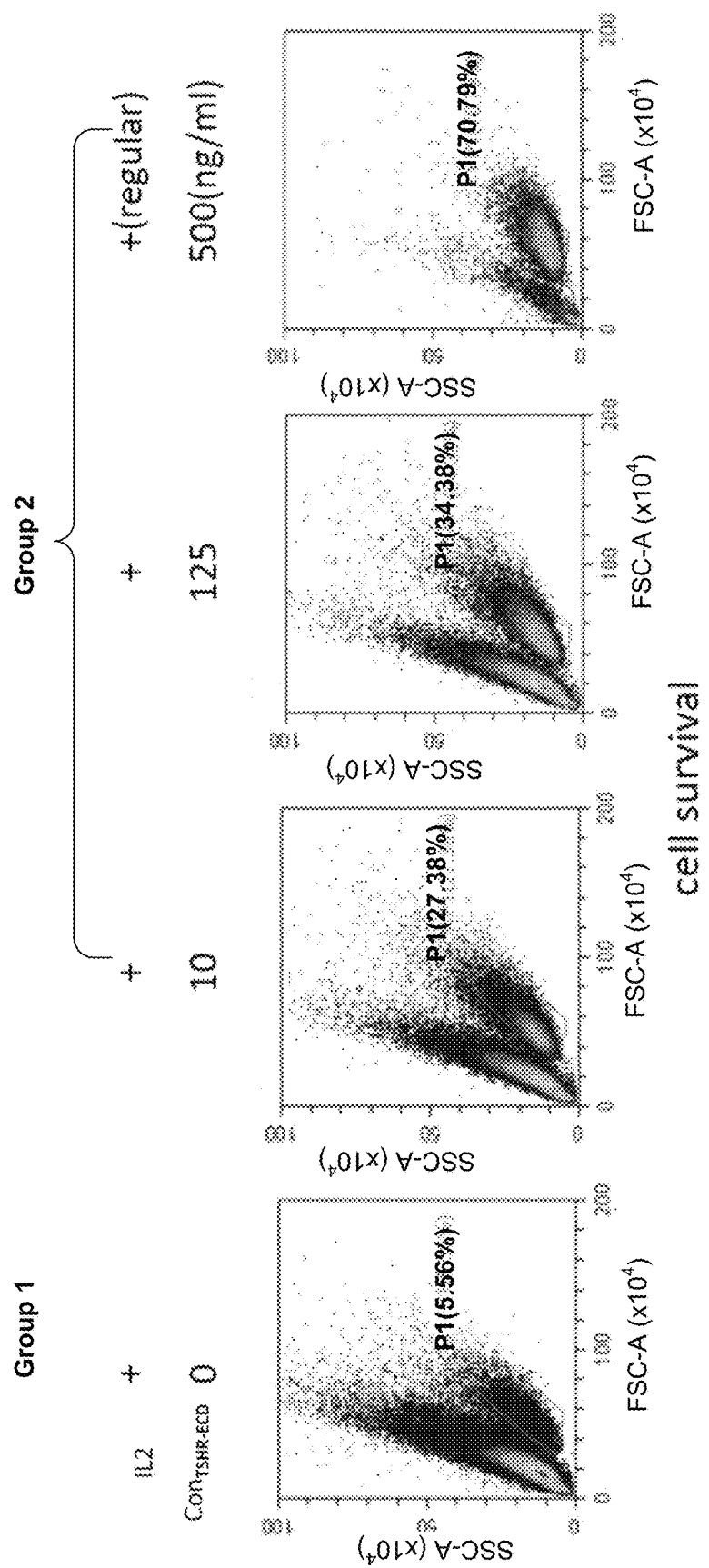
FIG. 8 shows the results of flow cytometry analysis indicating TSHR maintains CAR T-TSHR cells activities.

As shown in FIG. 8, SSC-A dispersible FSC low population decreased with increasing concentrations of TSHR ECD. As shown in FIG. 8, the ratio (P1) of CAR+ cells and the CAR T-TSHR cells significantly increased when 500 ng/ml of soluble TSHR ECD was added to the cells in Group 2. As shown in FIGS. 9 and 10, as the proportion of added antigen (TSHR-ECD) increased, cell debris decreased, which indicated that the cells were maintained in a better state than culturing without TSHR ECD. MFI (median fluorescence intensity) refers to the median fluorescent position of the population of cells and is calculated as a numerical value. As shown in FIG. 10, under 500 ng antigen stimulation, the CAR fluorescence (lower horizontal axis) moved to the right side of the population of cells. The proportion of CAR positive cells increased, the intensity increased, and the MFI value increased. These results demonstrated that TSHR stimulated or enhanced long-term maintenance of CAR T-TSHR cells in vitro.

Observation of T Cell Phenotype

Figure 4:
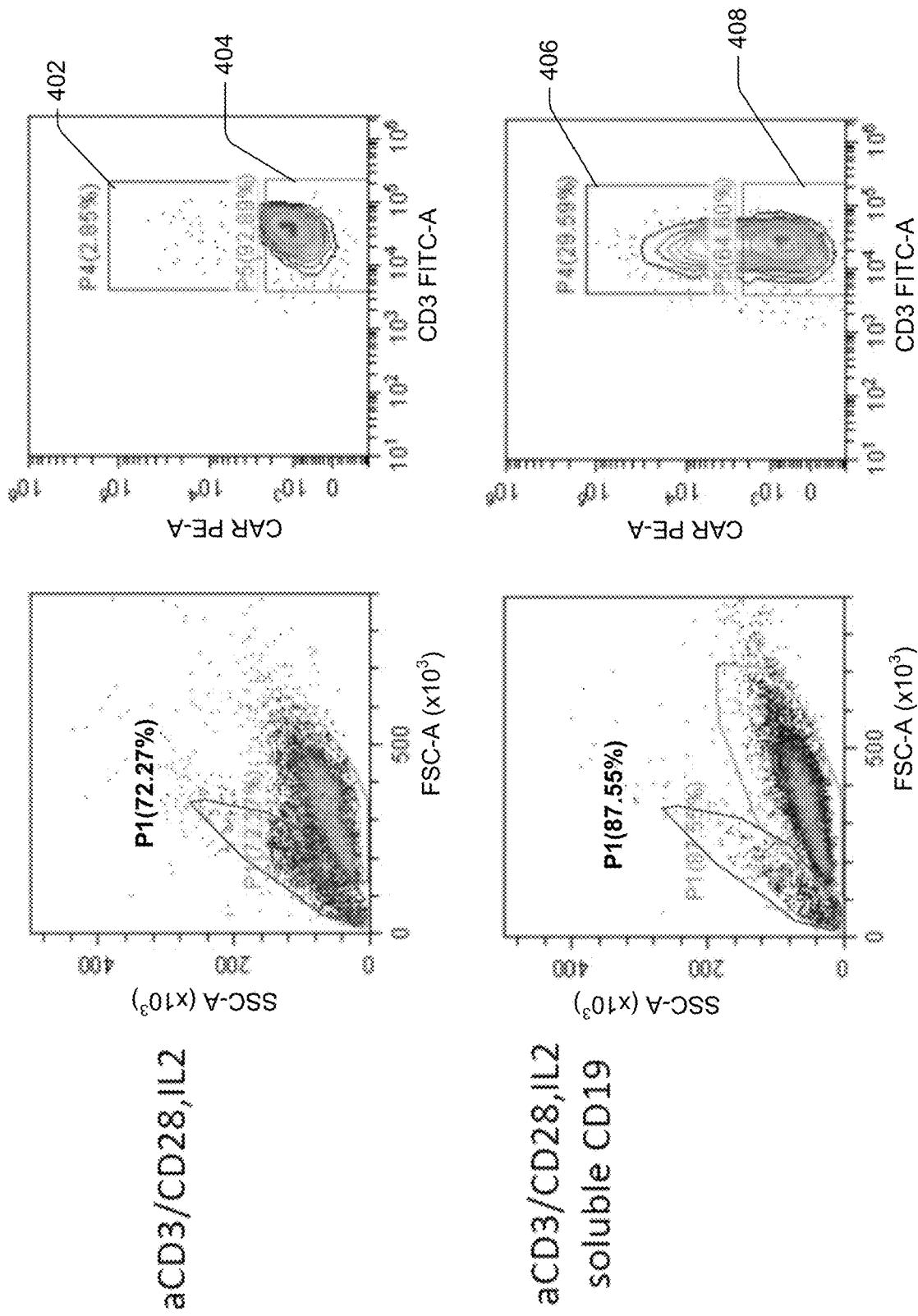
FIG. 4 shows the results of flow cytometry analysis indicating CD19 stimulates and/or induces CAR T cells to produce the phenotype of memory cells.

T cell phenotypes were further observed. On day 30 after the starting point, the ratio of CAR T19 cells and T cells in Group 2 continued to rise (See P4 boxes in FIG. 4). Memory cell marker CD62L on CAR+ and CAR-cells were analyzed to determine phenotypes of cultured T cell population. In CAR T19 cells of Group 2, the entire or majority cells of the T cell population showed the phenotype of memory cells (e.g., CD62L hi). The upper diagram of FIG. 5 showed CAR+cell analysis, and lower diagram showed CAR-cell analysis. These data indicated that CD19 induced CAR T cells to produce the phenotype of memory T cells.

Function Analysis of CAR T19 in Group 1 and Group 2

CAR T19 cells of Group 1 and Group 2 were cultured for about one to three weeks using the protocols described above, respectively. CAR T19 cells were then washed and placed into cultures without CD19. These CAR T19 cells were co-cultured with K562-CD19 (E:T 1:1 or 1:10). After 24 hours, 48 hours, and 72 hours, supernatant of the cultures were collected, and IFN-gamma released by the cells were measured to determine functions of CAR T19 cells.

Figure 6:
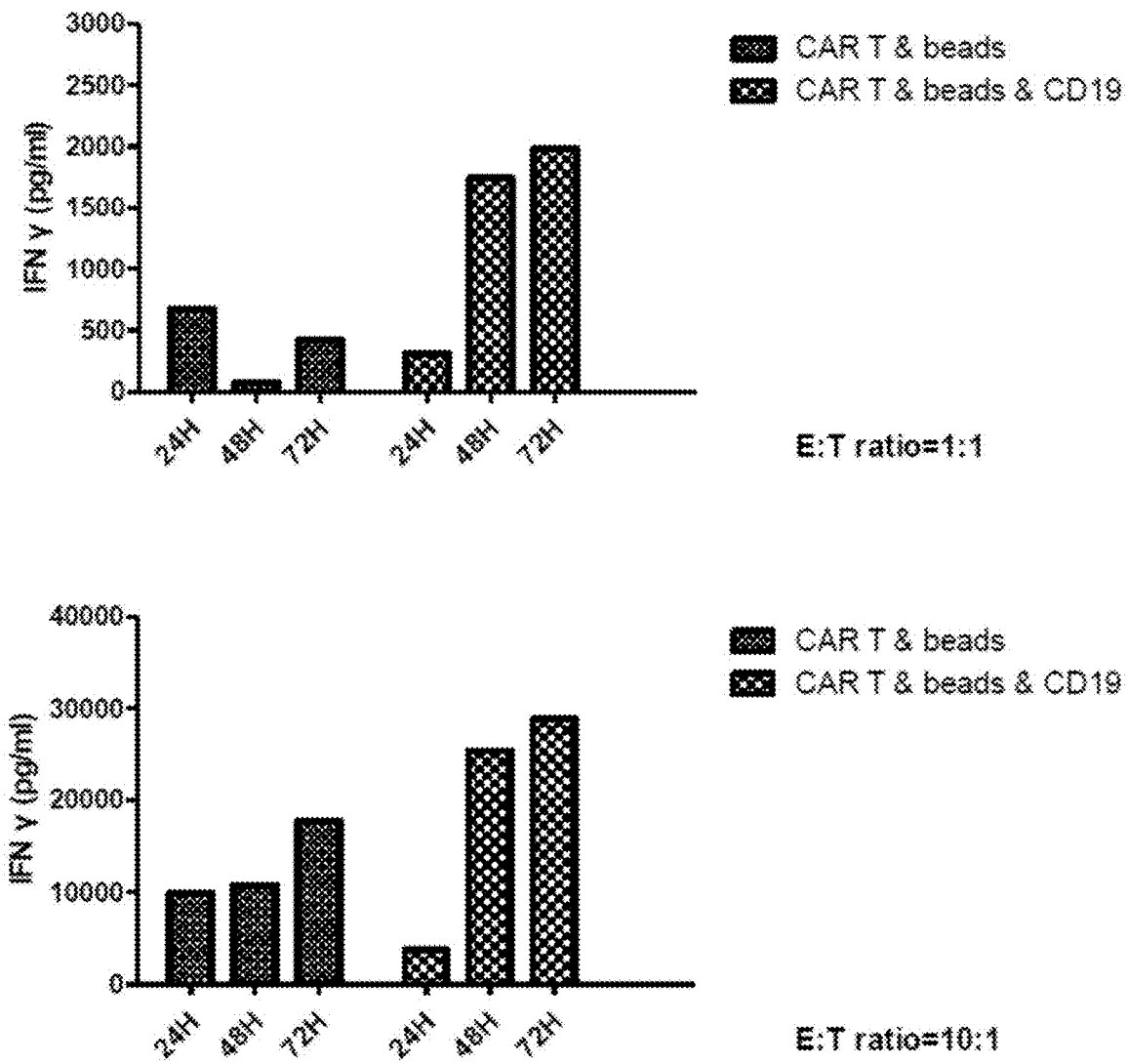
FIG. 6 shows histograms indicating CD19 enhances capability of releasing IFN gamma.

IFN-gamma was observed for both Group 1 and Group 2. As illustrated in FIG. 6, after 24 hours, IFN-gamma in Group 2 is significantly higher than those of Group 1. It seemed that CAR T cells in Group 1 were in a lower energy consumption state (e.g., memory T cell state), and it took a certain amount of time for the cells to become active (See FIG. 6). These data indicated that culturing CAR T cells with CD19 enhanced the CAR T cells' ability to release IFN-gamma.

Impact of CD19 Removal on CAR T19 Cells

Figure 7:
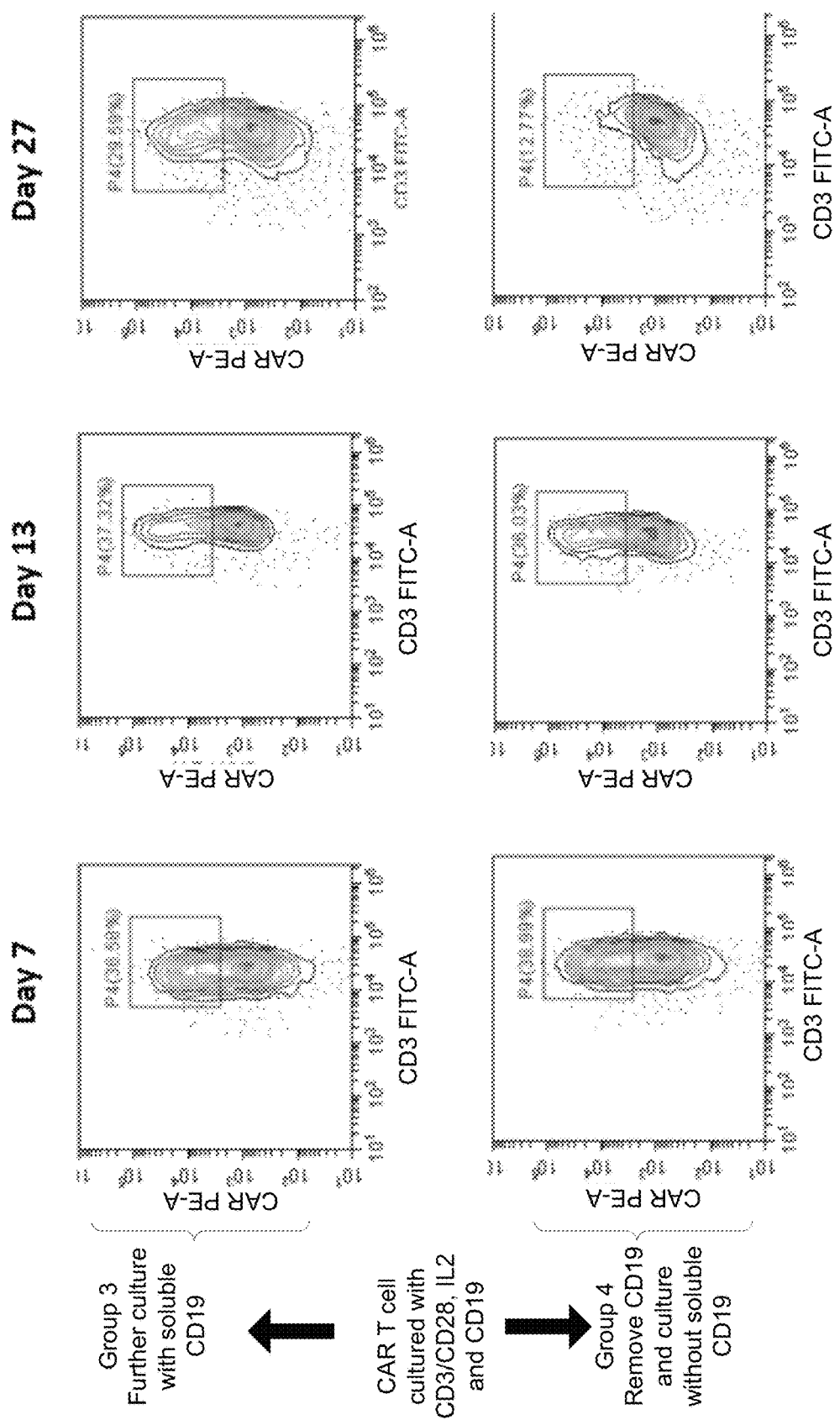
FIG. 7 shows the results of flow cytometry analysis indicating CD19 maintains the presence of CAR T cells.

CAR T19 cells were cultured with CD19 for over 15 days and then were divided into Group 3 and Group 4. CAR T19 cells in Group 3 were continuously cultured with soluble CD19, while CAR T19 cells in Group 4 were cultured without CD19. As shown in FIG. 7 (e.g., Day 27), numbers of CAR+ cells in Group 4 was relatively lower than those of Group 3. These data indicated that CD19 help to maintain the presence of CAR T19 cells.

Figure 12:
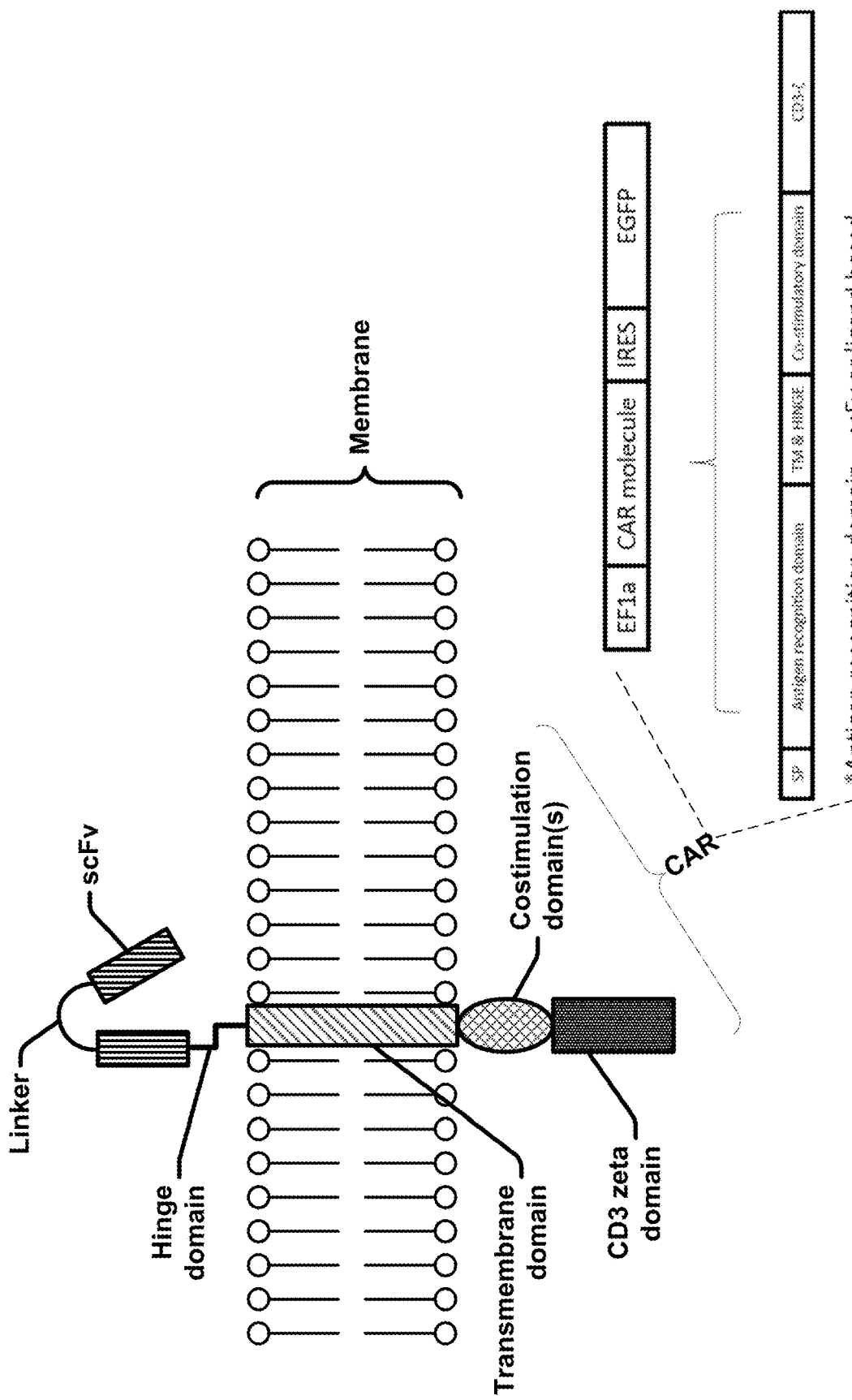
FIG. 12 shows a schematic diagram of the structures of an exemplary CAR molecule and a portion of the cell membrane.

Construction of CARs and Additional Amino Acids of Hinge Domain Promoting Expansion of CAR T Cells Various CARs (A, B, C, and D) were constructed by linking a signal peptide (SEQ ID NO: 38), antigen-specific single-chain variable fragment (scFv) (SEQ ID NO: 55 or 21), hinge domain (SEQ ID NOs: 68, 69, 70, or 71), a transmembrane domain (SEQ ID NO: 72, 73, 74, or 75), one or more co-stimulation domains (SEQ ID NO: 3), CD3-r (SEQ ID NO: 40), and EGFP, respectively (See FIGS. 12 and 13).

Primary T cells were obtained from the peripheral blood of volunteers. The magnetic beads negative selection was performed using Pan-T kit from Miltenyi Biotec, Inc. to collect T cells from the peripheral blood. On the second day after primary T cell isolation, the collected T cells were infected with lentivirus containing A, B, C, and D CARs, respectively (i.e., Lenti-CARs-IRES-EGFP) to prepare CAR T cells.

On the 14th day after infection, 15,000 CAR T cells of each group were collected, and cultured with 1000 ng/ml CD 19 antigen (i.e., recombinant human CD19 protein. After 15 days of stimulation, the concentration of CD19 was changed to 400 ng/ml. After 20 days of stimulation, the concentration of CD19 was changed to 200 ng/ml and maintained until about 130 days.

The expression of CARs and cell morphology were observed using flow cytometry on day-2, day 15 (FIGS. 14-17), day 17 (FIG. 20), day 65 and day 130 at the beginning of the stimulus. Combination of anti-F (ab2)'-biotin and PE-streptavidin antibodies were used to detect CAR expression. The FITC channel was used to detect the expression of EGFP, and parameters for detection of cell debris and cell survival rates were SSC/FSC.

At 130 days, K562-RFP-CD19, K562-RFP, and Nalm6 cells were used to examine the function of CAR T cells maintained by the protocol described above. Among them, K562-RFP-CD19 and Nalm6 were CD19 positive cells, while K562-RFP was CD19 negative cells. CAR T cell function was evaluated by measuring the killing effect (e.g., red fluorescence) and cytokine release (e.g., IFN-g). And the copy number of CAR molecules we examined.

Figure 14:
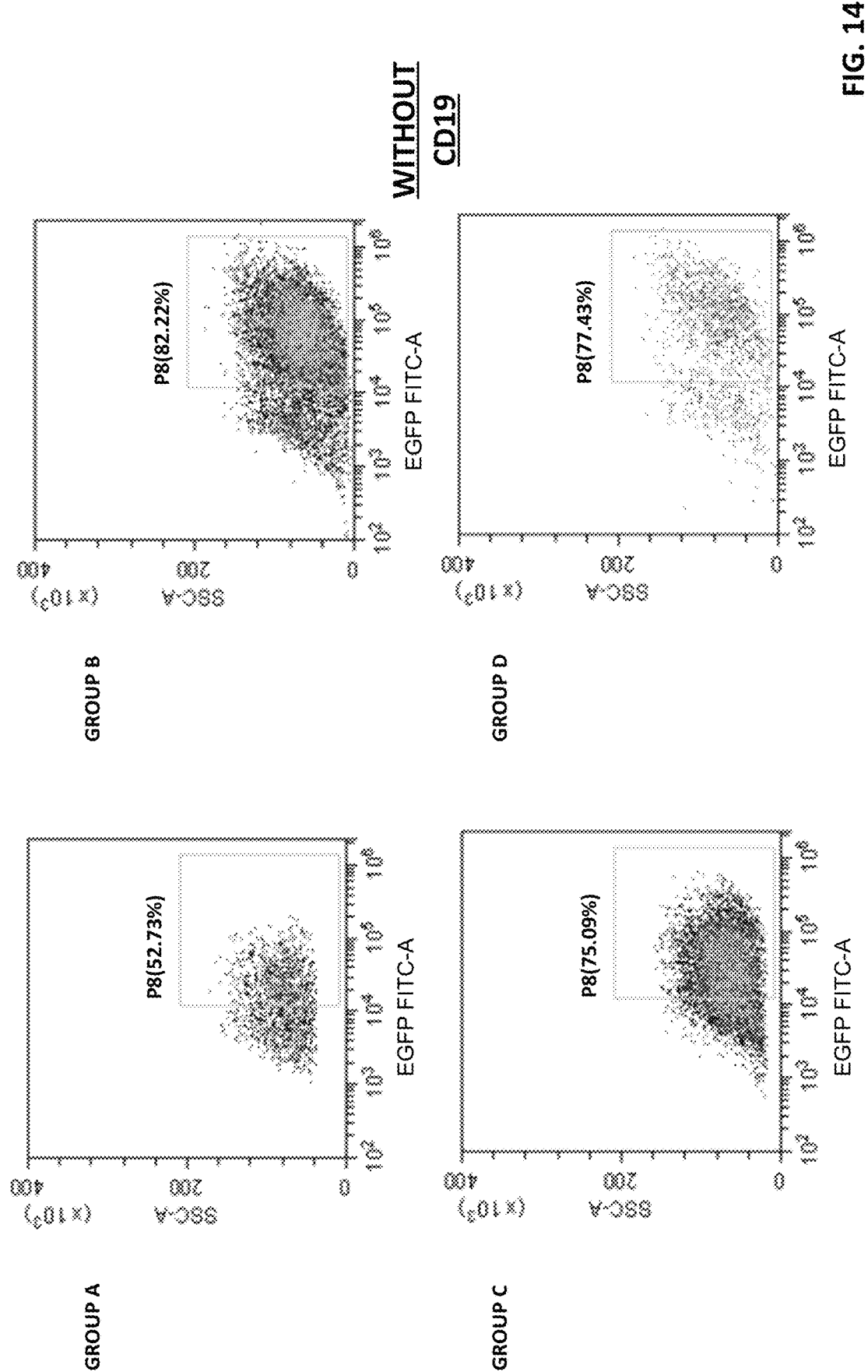
FIG. 14 shows flow cytometric analysis of CAR T cell expansion in the four groups, as indicated in FIG. 13. The CAR T cells were cultured without CD19 extracellular domain for 15 days.
Figure 15:
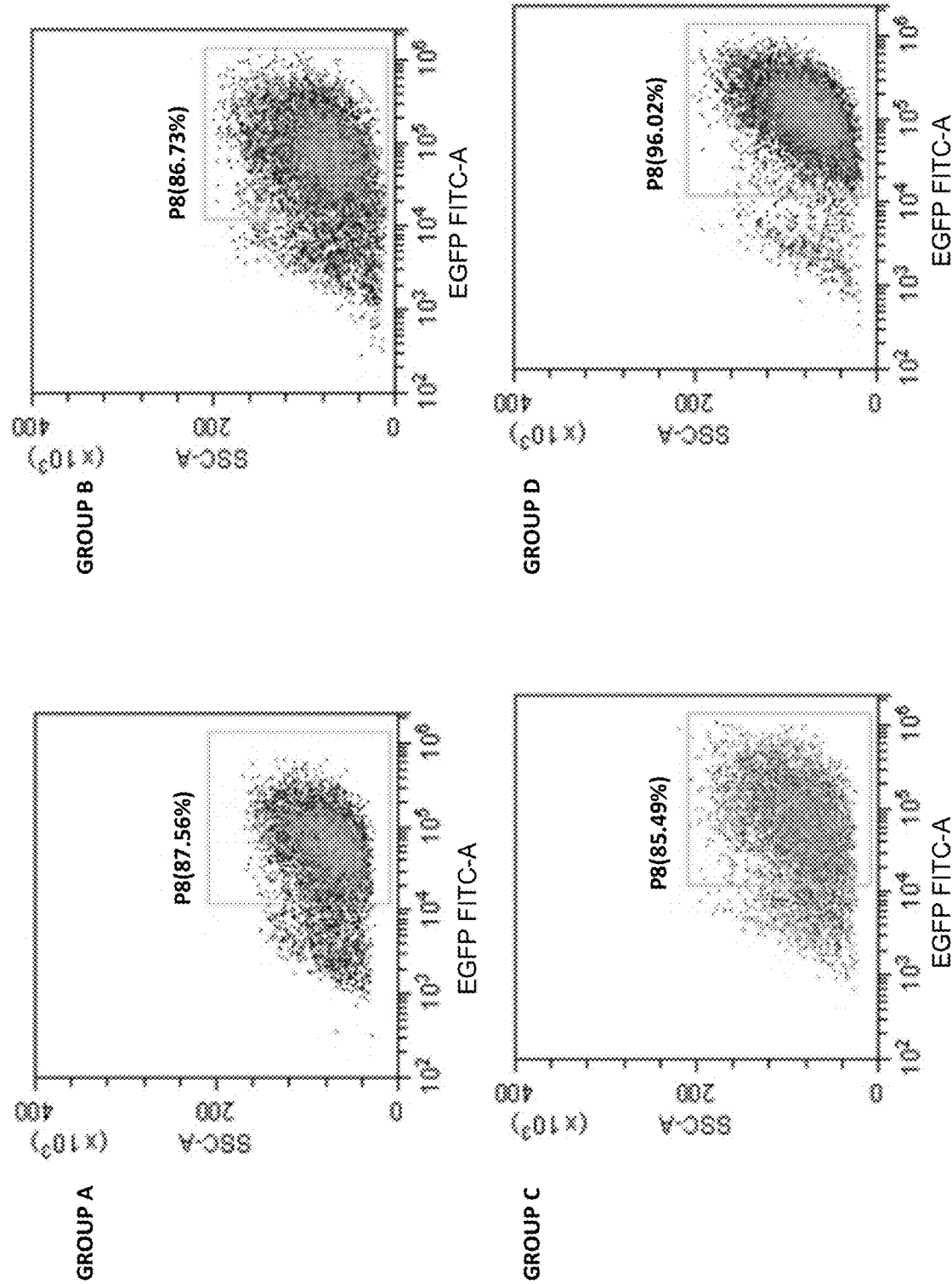
FIG. 15 shows flow cytometric analysis of CAR T cell expansion in the four groups, as indicated in FIG. 13. The CAR T cells were cultured with CD19 extracellular domain for 15 days.

FIGS. 14 and 15 show flow cytometric results of CAR T cells before or after and with or without CD19 co-culturing. Changes of EGFP expression in CAR T cells were observed. CAR molecules were EGF-bearing CAR-IRES-EGFP. Accordingly, after CARs were stimulated, green fluorescence was stronger as compared with unstimulated CARs. As shown in FIGS. 14 and 15, the intensity of EGFP expression in P8 boxes was found on the horizontal axis of EGFP-FITC. FIG. 14 shows the pre-stimulus (group B/D) and the group without parallel stimulation (group A/C), and FIG. 15 shows the after-stimulus (group B/D) and the group with parallel stimulation (group A/C).

Figure 16:
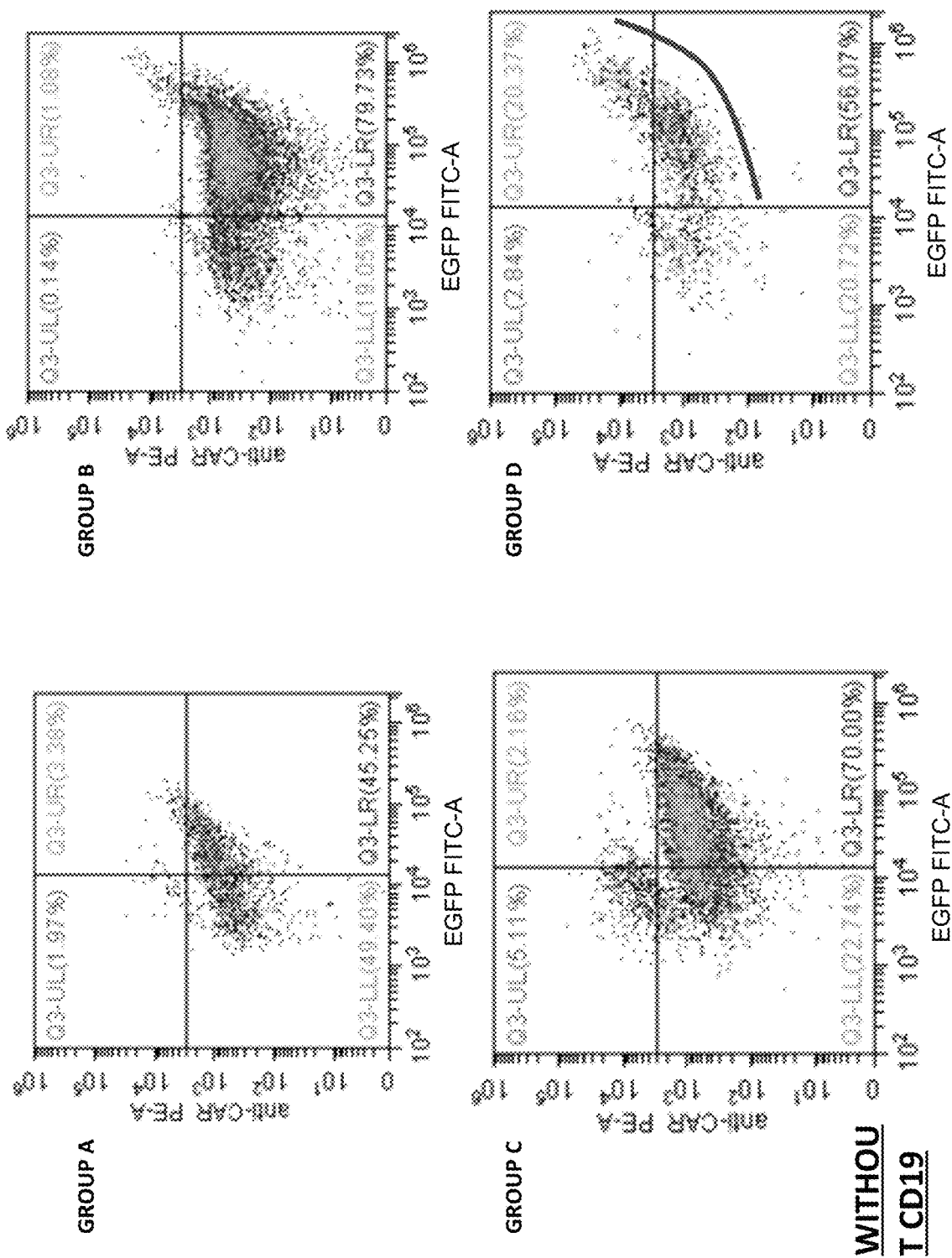
FIG. 16 shows flow cytometric analysis of CAR expression levels on CAR T cells in the four groups, as indicated in FIG. 13. The CAR T cells were cultured without CD19 extracellular domain for 15 days.
Figure 17:
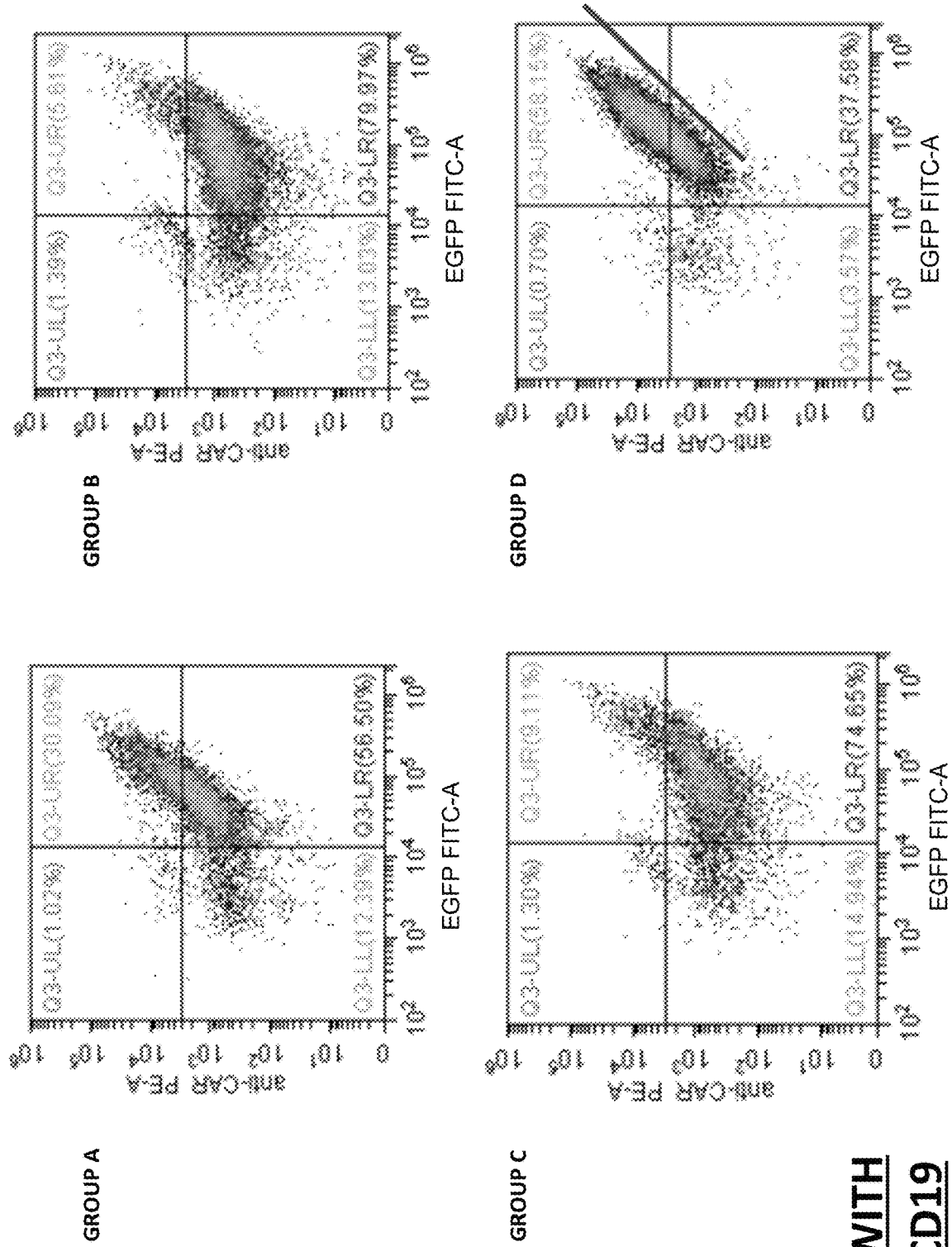
FIG. 17 shows flow cytometric analysis of CAR expression level on CAR T cells in the four groups, as indicated in FIG. 13. The CAR T cells were cultured with CD19 extracellular domain for 20 days.

FIGS. 16 and 17 show further flow cytometric results of CAR T cells before or after and with or without CD19 co-culturing. Changes of EGFP expression in CAR T cells were observed. CAR molecules were EGF-bearing CAR-IRES-EGFP. Accordingly, after CARs were stimulated, green fluorescence was stronger as compared with unstimulated CARs. As shown in FIGS. 16 and 17, the vertical axis is CAR-PE, and the horizontal axis is EGFP-FITC, and the CAR molecule was s EGFP-bearing (e.g., CAR-IRES-EGFP). Further, the intensity of CAR+EGFP+expression was shown in Q3-UR (upper left corner) boxes. FIG. 16 further shows the phenotype after receiving CD19 stimulation (B/D group) and in parallel culture without stimulation (A/C group). FIG. 20, similar to FIGS. 16 and 17, shows flow cytometric results of Groups A and D on Day 17. These results show that the proportion of CAR+EGFP+cells increase and these cells continue to grow.

These results demonstrate that CD19 stimulation can be used to maintain anti-CD19 CAR T cell growth (See FIGS. 12 and 13), CD19 stimulation can enrich or specifically stimulate T cells of CAR+(See FIGS. 14-16), and in Vitro CD19 protein can be used to activate T cells to continuously grow and enrich CAR-positive cells.

Figure 18:
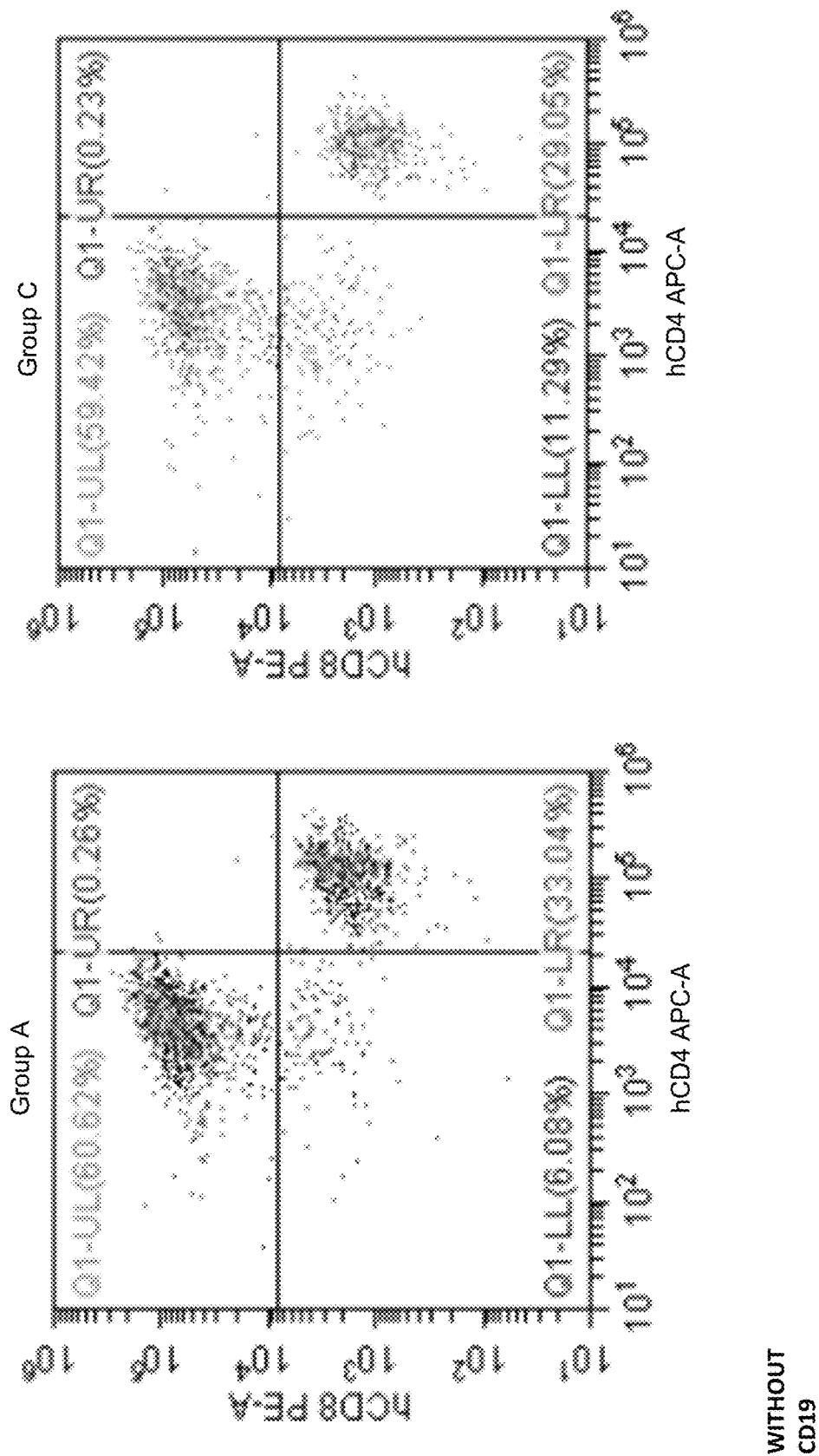
FIG. 18 shows flow cytometric analysis of CD4/CD8 phenotypic changes in CAR T cells.
Figure 19:
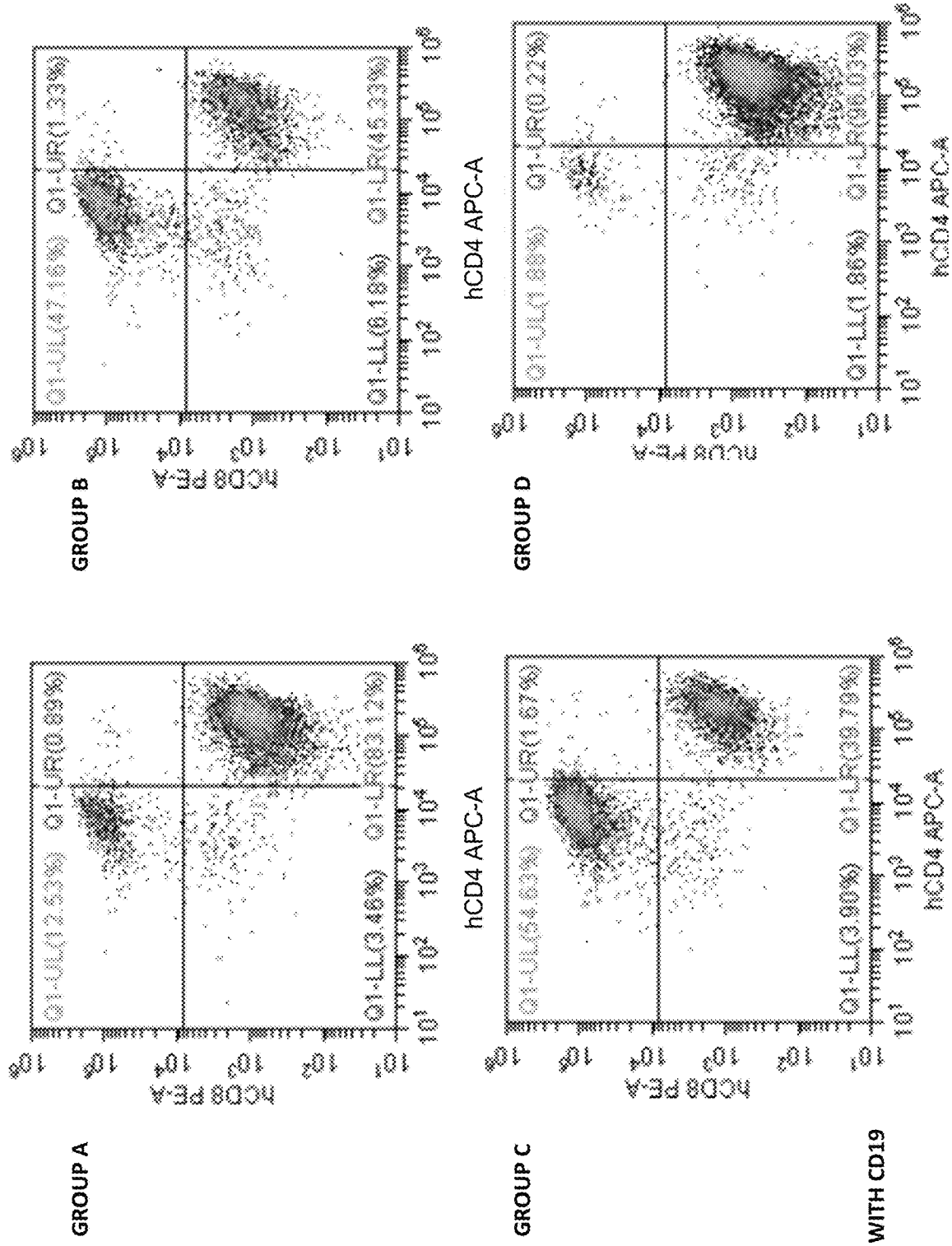
FIG. 19 shows flow cytometric analysis of CD4/CD8 phenotypic changes in CAR T cells.

FIGS. 18 and 19 show that CD4/CD8 phenotypic changes in CAR T cells. These two pictures show the same experiment, that is, the change of CD8 and CD4 ratio of CAR T cells with or without a different hinge before or after stimulation with CD19. It was previously observed that CAR T cells cultured in the presence of antigen-persistence gradually change to predominately CD4 cells. FIG. 18 shows flow cytometric results of the parallel untreated CAR T cell phenotype in A and C groups. The vertical axis is CD8, and the horizontal axis is CD4. The upper left area is CD8 +T cells, and the lower right area is CD4 +T cells. FIG. 19 is flow cytometric results of CD19-stimulated cells and shows an increased percentage of CD4 cells. These results indicate that anti-CD19 and other antigen stimulation can change the composition of T cells.

Figure 22:
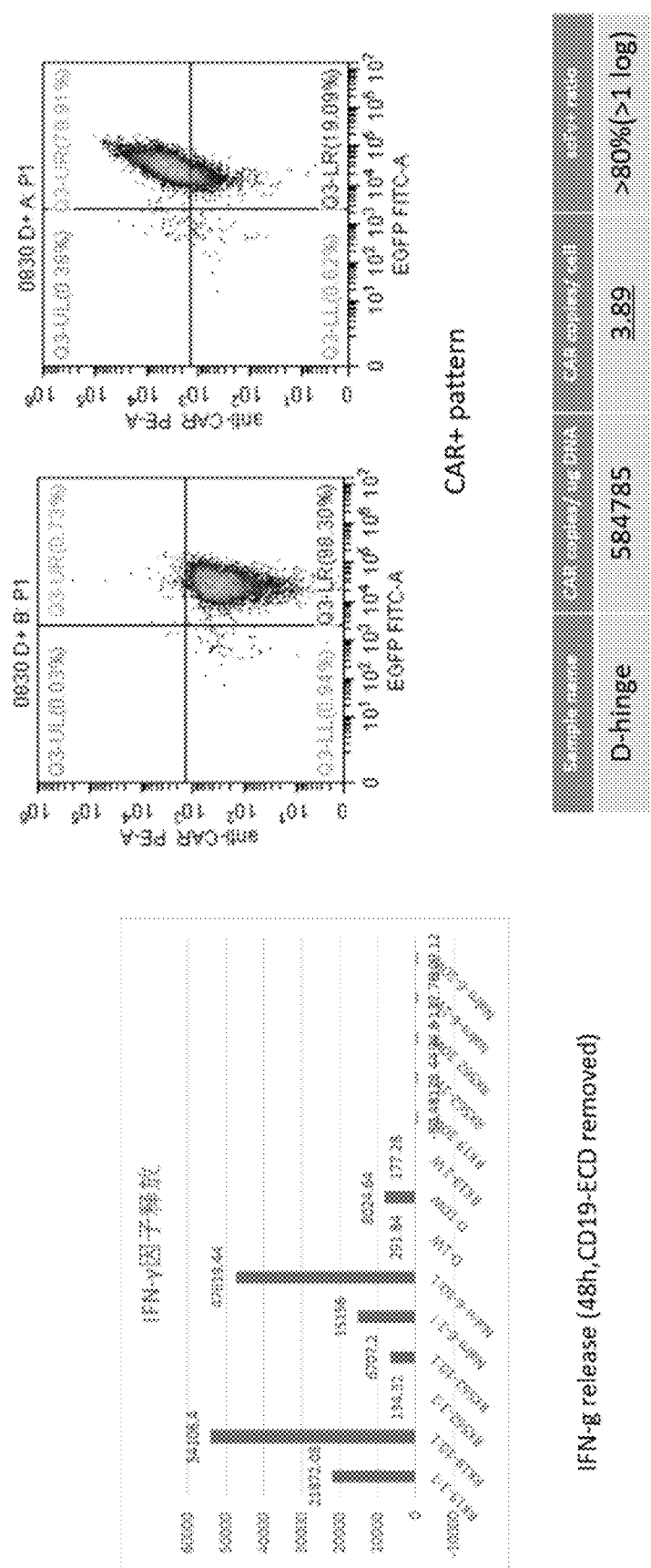
FIG. 22 shows flow cytometric analysis of IFN-g release of CAR T cells.

FIG. 21 shows a killing assay on CAR T cells of group D, which had been cultured using CD19 protein for 130 days. K562-RFP/K562 CD19-RFP cells were co-cultured with the CAR T cells, respectively, and their killing effects were examined on day 130. As shown in FIG. 21, the right three columns showed the significant killing of K562 CD19-RFP cells at 1:1 and 10:1, as shown in the box. Given the background stimulation of CD19 on CAR T cells, the CD19 protein was removed prior to the start of the experiment and replaced with CD19-free broth. These results of FIG. 21 demonstrate that the CAR T cells co-cultured with CD19 maintained the killing function. Further, Interferon gamma (IFN-g) release by these CAR T cells of group D was examined. FIG. 22 shows flow cytometry results of IFN-g release of CAR T cells of group D, and copy numbers were calculated. The CAR T cells of group D were co-cultured with the CD19 positive cell (K562-RFP-CD19, nalm-6) and cytokine release was measured. As shown in FIG. 22, CAR T cells co-cultured using CD19 for 130 days released IFN-g against CD19+cells (See the left panel of FIG. 22. On the top right panel, flow cytometric results indicated CAR expression of these CAR T cells. The horizontal axis is FITC for detection of EGFP, the vertical axis is PE for detection of CAR molecules, and Q3-UR shows CAR+EGFP+cell ratio. The bottom right panel shows the number of copies of the CAR T cells, which were measured using qPCR. These results demonstrate that CD19 stimulated CAR T cells released IFN-g against CD19+cells. Further, these CAR T cells maintained the CAR-positive cell phenotype on day 130. Also, CD19 continuously stimulated CAR T cells to grow at day 130. While CAR+closely reached full positive, the copy number was less than 4.

CAR-Jurkat T Cell Killing Assay

Jurkat T cells were introduced with a nucleic acid sequence encoding CD19-CAR. A killing assay was performed, and no or weak killing functions were observed. Further expression of T cell markers was analyzed. While expressing CD3, CAR-Jurkat T cells showed low expression of CD4 and no expression of CD8. These results demonstrated that proliferable T cells including the nucleic acid sequence encoding hTERT and/or SV40LT were better than CAR-Jurkat T cells with respect to inhibiting the growth of tumor cells.

Preparation of Modified Cells

Starting from the separation of the initial healthy human T cells (Day 0), on Day 1 human T cells were infected with hTERT alone, ("alone" means only this one), SV40LT alone, hTERT+SV40LT, hTERT+mouse CD19CAR, SV40LT+ mouse CD19CAR, hTERT+SV40LT+mouse CD19CAR (see FIG. 23). A total of 6 groups were tested.

The expression of CD3, CD4, CD8, CD279, mCAR was detected by FACS several times. And then the cells were cultured; on Day 92 the cells were analyzed to detect mCAR (mouse CAR). On Day 92, mCAR was transferred again. On day 95 co-culture (tumor and effector co-culture) was performed with ratios of E:T:1:1, 3:1, 10:1:30:1. (unit million cells)

4 h and 24 h killing effect were measured by collecting fluorescence signals. 24 h later, supernatant (co-culture) was collected, and the release of IFN-g was measured. m19CAR (yes) refers to the situation that m19CAR was infected at the beginning of the infection.

Figure 26:
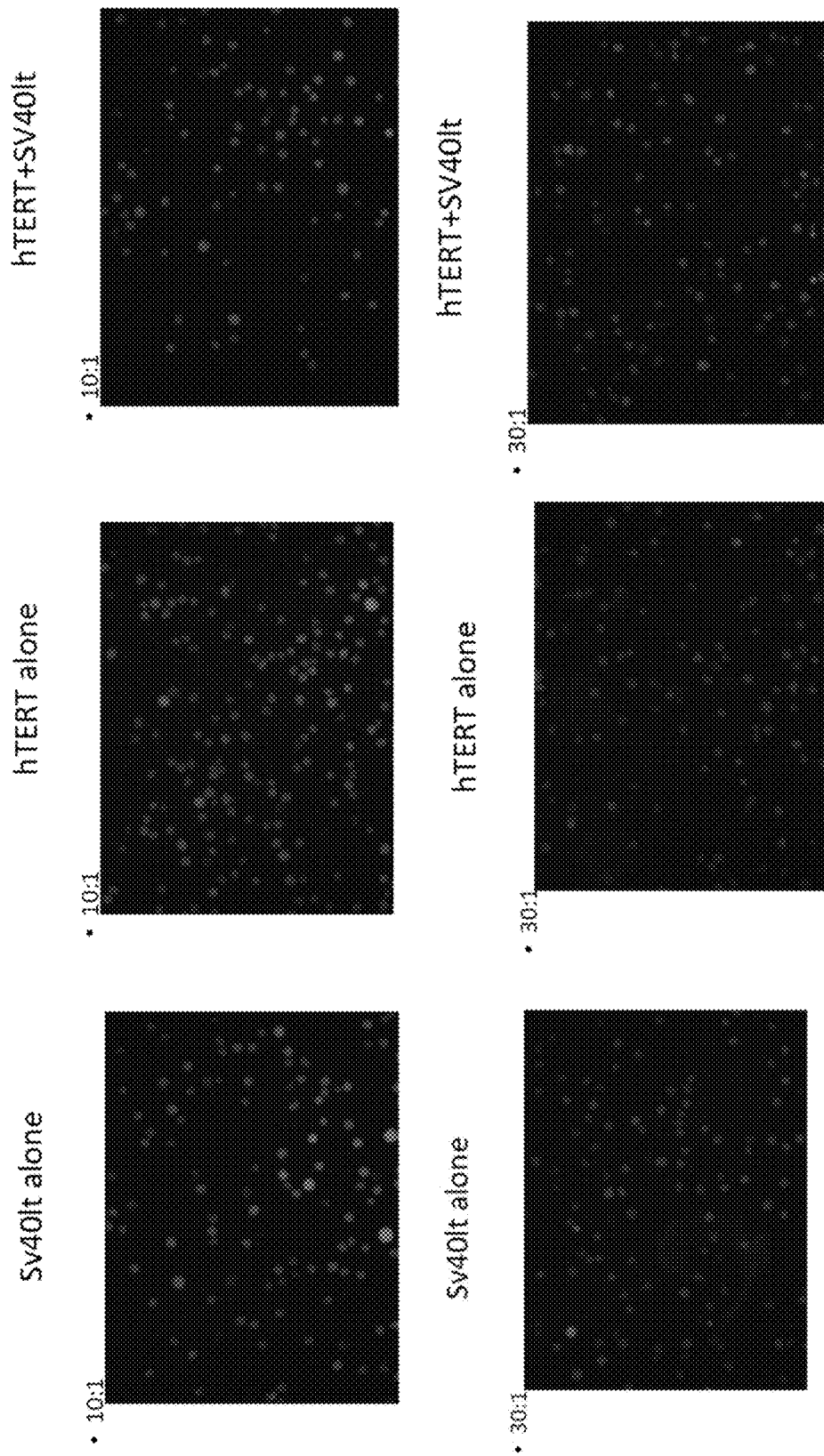
FIG. 26 shows fluorescence photographs of the killing effect of T cells.
Figure 27:
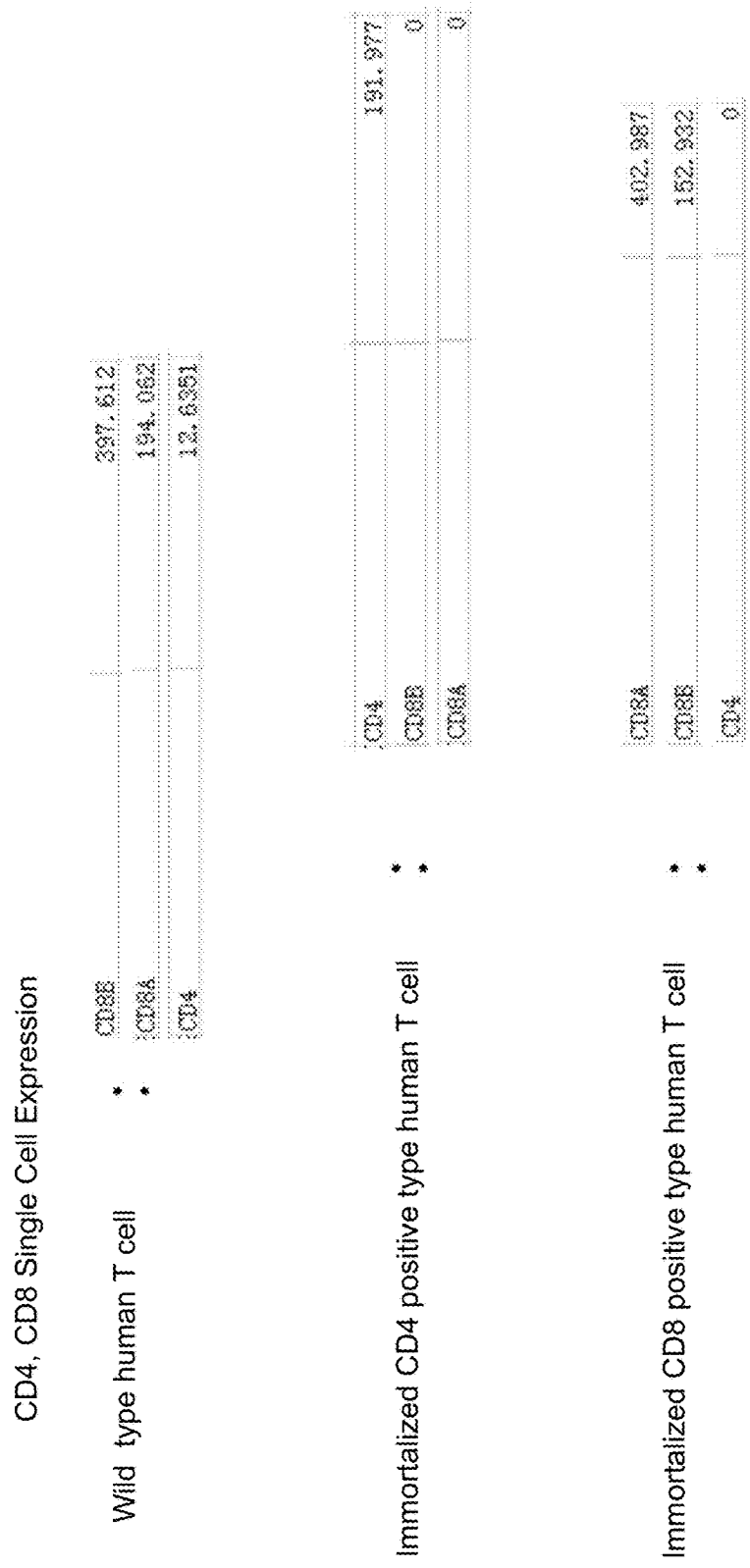
FIG. 27 shows a graph of multiple immortalized single-cell sequencing assays.
Figure 28:
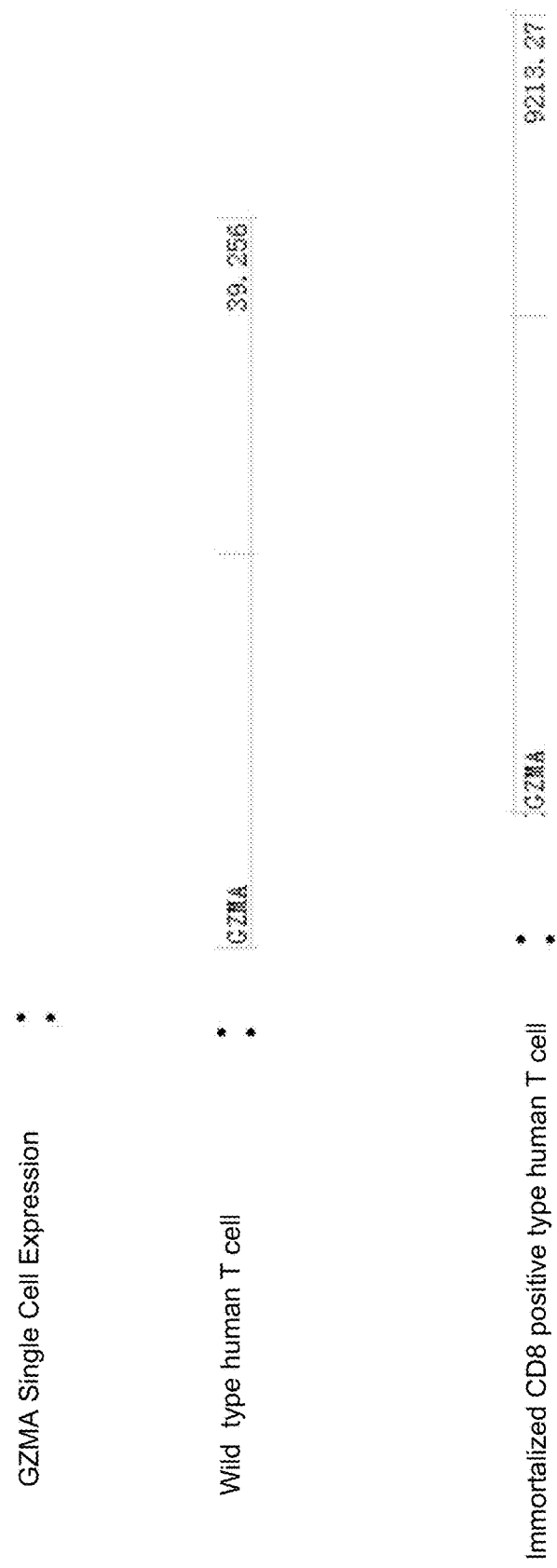
FIG. 28 shows a graph of multiple immortalized single-cell sequencing assays.
Figure 29:
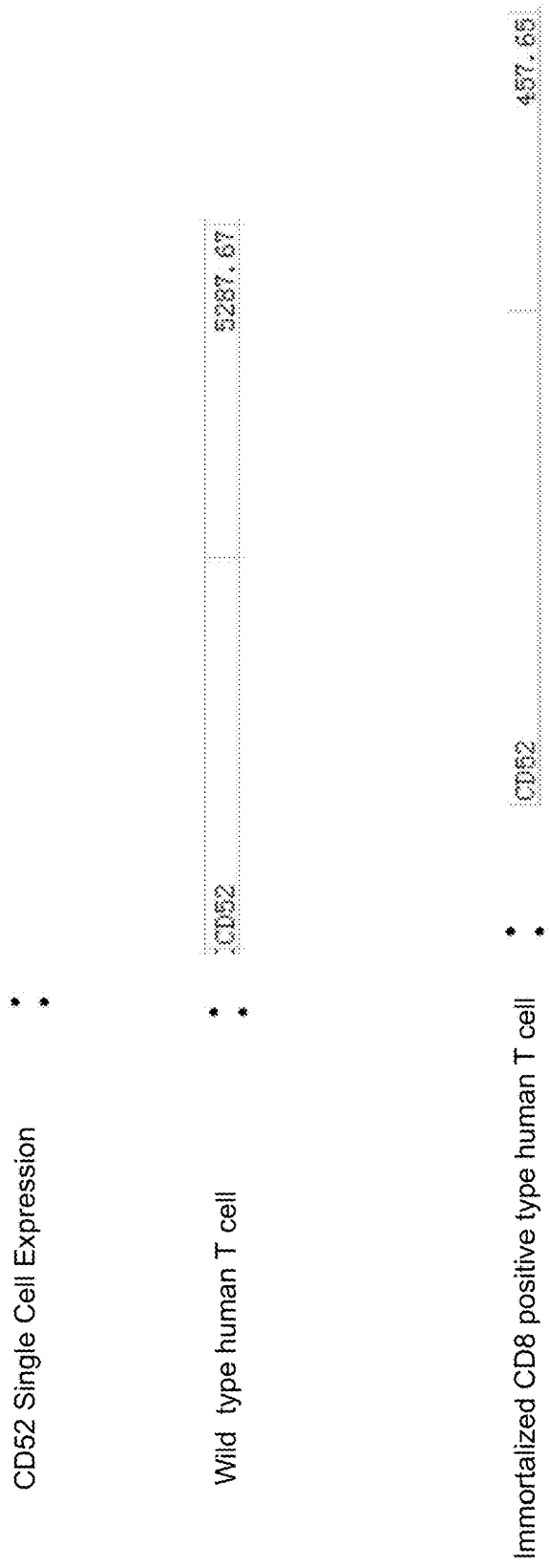
FIG. 29 shows a graph of multiple immortalized single-cell sequencing assays.
Figure 30:
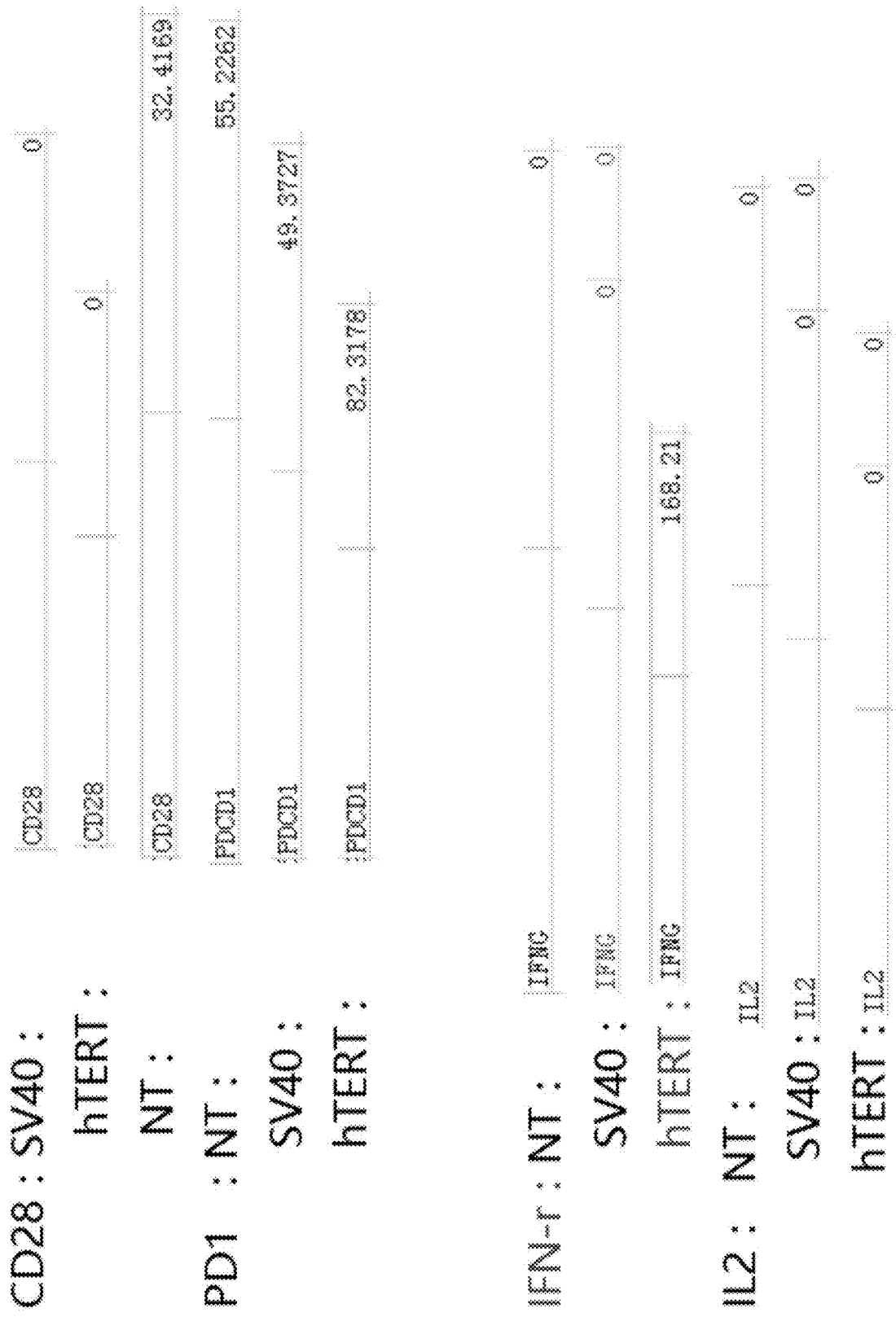
FIG. 30 shows a graph of multiple immortalized single-cell sequencing assays.

FIGS. 24, 25 and 26 are fluorescence photographs showing the killing effect of a plurality of T cells. K562-CD19 is a cell line constructed by overexpressing a CD19 protein on the surface of k562 cells (ratio of E:T:30:1 and 10:1). The results showed the killing effect for 24 hours. Immortalized T cells were infected with lentiviruses at 3 days in advance such that the immortalized T cells were transferred with the rat-derived CAR, allowing immortalized T cells to express CAR. These transferred cells were then co-cultured with tumor cells for killing and IFN-g release measurement.

In FIG. 24, K562-CD19 alone represents k562-CD19's own cell state (only the tumor itself without adding other cells). In the negative control 10:1, wild-type T cells and tumor cells (RK562-CD19) were co-cultured, showing no killing (ratio of E:T:10:1). In negative control 30:1, wild-type T cells and tumor cells (RK562-CD19) were co-cultured, showing no killing (ratio of E:T:30:1). In positive control m19CAR (1101): 30:1, CAR T cells (T cells infected with mCAR) and tumor cells (RK562-CD19) were co-cultured, showing a significant proportion of the killing (ratio of E:T:30:1).

FIG. 25 shows effectiveness validation regarding the immortalized cells. Regarding Sv40LT alone+m19CAR (Yes) 10:1, immortalized T cells were infected with murine mCAR virus (transferred with sv40LT) co-cultured with tumor cells (RK562-CD19), showing certain kill effect (ratio of E:T:10 Sv40lt alone+m19CAR T cell and a tumor cell. Regarding Sv40LT alone+m19CAR (Yes) 30:1, immortalized T cells were infected with the mCAR virus (transferred with sv40LT) and co-cultured with tumor cells (RK562-CD19), showing good killing effect (ratio of E:T:30:1:30 Sv40lt+m19CAR T cell to and a tumor cell). Regarding Sv40LT+hTERT+m19CAR (Yes) 10:1:immortalized T cells were infected with the mouse mCAR virus (transferred with the sv40LT and hTERT) and co-cultured with tumor cells (RK562-CD19), showing little killing effect (ratio of E:T: 10:1:10 Sv40LT+hTERT+m19CAR T cell and the tumor). Regarding Sv40lt+hTERT+ml 9CAR (Yes) 30:1:immortalized T cells were infected with mCAR virus (transferred with both sv40LT and hTERT) and co-cultured with tumor cells (RK562-CD19), showing killing effect (ratio of E:T:10 Sv40LT+hTERT+m19CAR T cell and a tumor cell).

FIG. 26 shows security validation regarding the immortalized cells. Regarding Sv40LT alone 10:1:immortalized T cells without infection of the CAR virus (transferred with sv40LT) were co-cultured with tumor cells (RK562-CD19), showing no killing effect (ratio of E:T:10 Sv40LT alone T cell and a tumor cell). Regarding Sv40LT alone 30:1: immortalized T cells without infection of the CAR virus (transferred with sv40LT) were co-cultured with tumor cells (RK562-CD19), showing no killing effect (ratio of E:T:30 Sv40lt alone T cell and a tumor cell). Regarding hTERT alone 10:1:immortalized T cells (transferred with hTERT)

were co-cultured with the tumor cells (RK562-CD19), showing no killing effect (ratio of E:T:10 hTERT alone T cell and a tumor cell). Regarding hTERT alone 30:1:immortalized T cells without infection of the CAR virus (transferred with hTERT) were co-cultured with tumor cells (RK562-CD19), showing no killing effect (ratio of E:T:30 hTERT alone T cell and a tumor cell). Regarding HTERT+SV40LT 10:1:immortalized T cells without infection of the CAR virus (transferred with hTERT and SV40LT) were co-cultured with tumor cells (RK562-CD19), showing no killing effect (ratio of E:T:10 hTERT+SV40LT T cell and a tumor cell). Regarding hTERT+SV40lt 30:1:immortalized T cells without infection of the CAR virus (transferred with hTERT and SV40LT) were co-cultured with tumor cells (RK562-CD19), showing no killing effect (ratio of E:T:30 hTERT+SV40LT T cell and a tumor cell).

FIGS. 27-31 are graphs showing multiple immortalized single cell sequencing assays. The analysis showed that certain gene expressions related to T cell killing functions increased, and thus the cytotoxicity of these T cells was improved. For example, the expression of GAMA was significantly increased in immortalized T cells compared to wild-type T cells.

Table 1 summarizes DNA and/or protein polypeptide sequences involved in the above experiments.

hTERT: SEQ ID NOs: 1, 2, 3, 4, 5, and 6 in the 5' to 3' order or ef1a-rtTA-TRE-hTERT: SEQ ID Nos: 1, 4, 5, and 6 in the 5' to 3' order) to obtain transduced T cells including immortalized T cells expressing anti-CD19 CAR (thereafter "anti-CD19 CAR proliferable T cells") on day one. The anti-CD19 CAR proliferable T cells were divided into various groups and cultured in different media: in the presence of various concentrations of doxycycline (Dox), CD19 extracellular domain (ECD), and/or Ganciclovir (GCV)). In some groups, CD19 ECD (SEQ ID NO: 22) was added to media (1 mg/250,000 CAR T cells), and percentages of cells expressing CD19 CAR increased.

Figure 32:
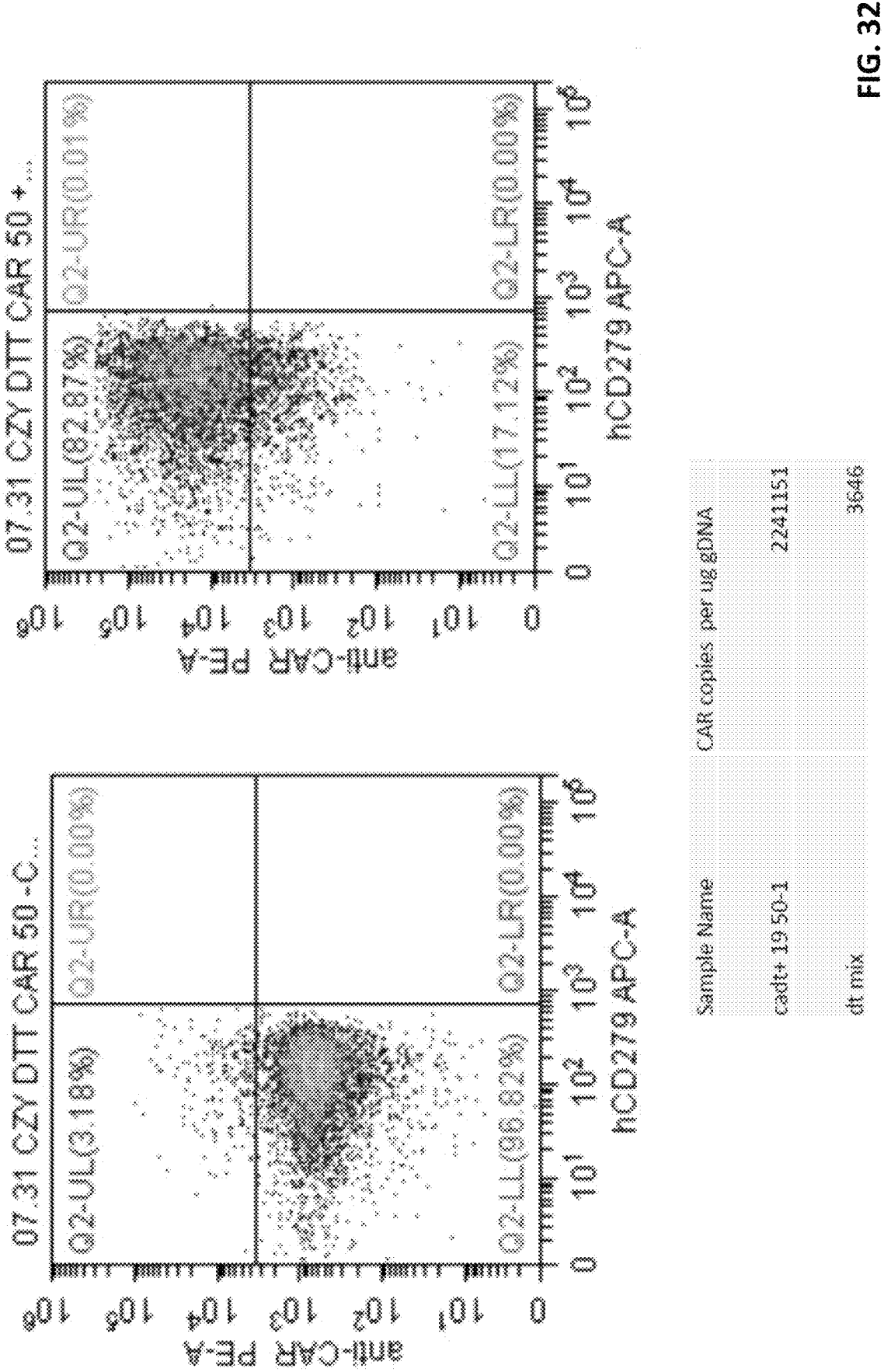
FIG. 32 shows flow cytometry results of CAR expression in immortalized T cells. The two ordinates in the above figures represent the expression of CAR. The abscissa is the expression of CD279 (PD1). The left is Isotype Control, and the right is the CAR antibody. A vector including DNA of ef1a-TK-IRES-rtTa-TRE-hTERT and a vector including DNA encoding hCD19 CAR were used to infect T cells. During the culturing, CD19 peptide was added to stimulate the growth of T cells. It can be seen that the expression of cell CAR 82.87%. Qualitative+quantitative results. The lower table shows the copy number experiment of CAR. It can be seen that there are 2241151 copies of CAR per 1 ug of gDNA in CAR T cells that induce expression of hCD19 in the expression system, which is a quantitative result. "dt mix" refers to a control group including cells that were merely transduced with ef1a-TK-IRES-rtTA-TRE-hTERT without DAN encoding anti-CD19 CAR.

In group one, transduced cells were cultured in a media containing Dox (2 µg/ml) from day 1. On day 42, CD19 ECD was added to the media ((500,000 CAR T cells/2 micrograms of soluble CD19). On day 90, flow cytometry analysis was performed on the transduced cells. FIG. 32 shows flow cytometry results CAR expression in immortalized T cells.

Figure 33:
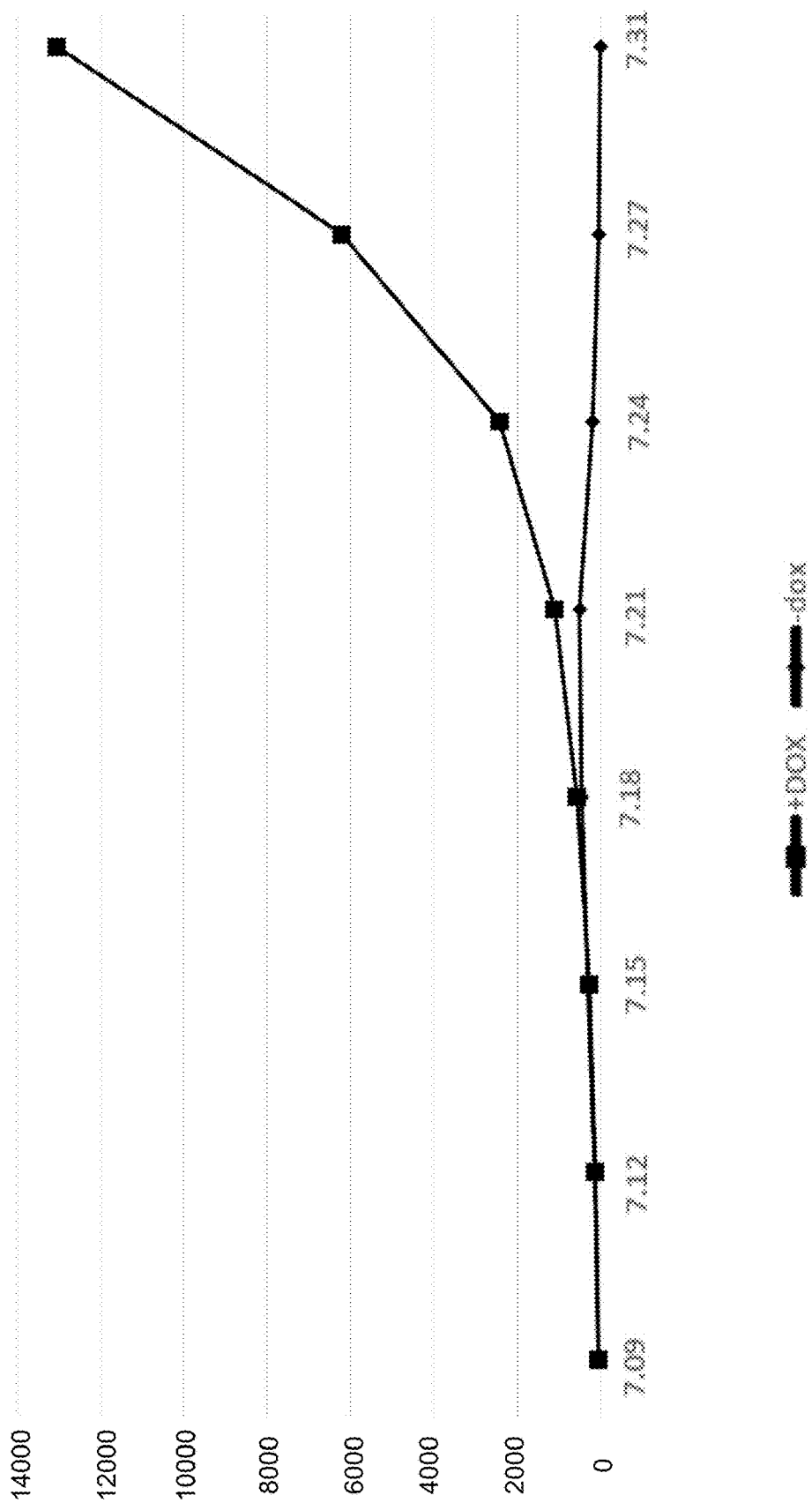
FIG. 33 shows a graph indicating that the cells are dual-switch T cell CD8+monoclonal cells (Dox concentration at 2 ug/ML). rTetR was used in the construction of anti-CD19 CAR proliferable T cells. Therefore, hTERT was expressed when doxycycline (Dox) was added to the culture. When Dox was not added, hTERT was not expressed, and the cells gradually began to die.

In group two, transduced cells were cultured using media containing Dox (2 µg/ml) for about 92 days and are divided into two subgroups. On day 92, Dox was removed from the subgroup 1 and Dox was maintained in the subgroup 2. Cell growth in these two subgroups was observed, and results were provided in FIG. 33.

| SEQ ID NO: | Identifier | SEQ ID NO: | Identifier | SEQ ID NO: | Identifier |
|---|---|---|---|---|---|
| 1 | Ef1α | 28 | ZFN | 54 | M Fokl |
| 2 | TK | 29 | Target DNA | 55 | scFv CD19 |
| 3 | IRES | 30 | ZFN | 56 | Prolactin (ligand) |
| 4 | rtTA | 31 | ZFN | 57 | scFv CD3 |
| 5 | TRE | 32 | ZFN | 58 | scFv CD4 |
| 6 | hTERT | 33 | Target DNA | 59 | scFv CD4-2 |
| 7 | SV40lt | 34 | TSHR ECD | 60 | CD3 antigen |
| 8 | humanized CD19 CAR | 35 | Hinge & TM domain | 61 | CD4 antigen |
| 9 | humanized CD19 CAR-Trancate | 36 | Hinge domain | 62 | CD5 antigen |
| 10 | humanized CD19 CAR-Mutation | 37 | TM domain | 63 | CAR CD19 nucleic acid |
| 11 | CD20 CAR | 38 | SP | 64 | Group B Hinge & TM domain |
| 12 | L2D8 whole sequence | 39 | Co-stimulatory region | 65 | Group A Hinge & TM domain |
| 13 | LV-ef1a-kozak-TK-IRES-rtTA-TRE-hTERT | 40 | CD3-zeta | 66 | Group D Hinge & TM domain |
| 14 | LV-ef1a-kozak-TK-IRES-rtTA-TRE-sv40LT | 41 | CD19 antigen | 67 | Group C Hinge & TM domain |
| 15 | Lv-ef1α-hTERT | 42 | FZD10 antigen | 68 | Group D Hinge domain |
| 16 | Lv-ef1α-L2D8-PD1-m | 43 | TSHR antigen | 69 | Group C Hinge domain |
| 17 | Lv-ef1α-L2D8-PD1-T | 44 | PRLR antigen | 70 | Group B Hinge domain |
| 18 | Lv-ef1α-sv40LT | 45 | Muc17 antigen | 71 | Group A Hinge domain |
| 19 | M971-CAR CD22 car | 46 | GUCY2C antigen | 72 | Group D TM domain |
| 20 | M972-CAR CD22 car | 47 | CD207 antigen | 73 | Group C TM domain |
| 21 | hCD19 scFV | 48 | scFv FZD10 | 74 | Group B TM domain |
| 22 | CD19 ECD | 49 | scFv TSHR | 75 | Group A TM domain |
| 23 | FoklW | 50 | scFv PRLR | 76 | GS linker |
| 24 | FoklM | 51 | scFv Muc17 | 77 | ZFLm1 (left) F2 |
| 25 | ZFN | 52 | scFv GUCY2C | 78 | ZFLm1 (left) F1 |
| 26 | ZFN | 53 | scFv CD207 | 79 | ZFLm1 (left) F4 |
| 27 | ZFN | 54 | M Fokl | 80 | ZFLm1 (left) F3 |
| 81 | ZFLm1 (left) Re SEQ | 82 | ZFRm1-4 (right) F1 | 83 | ZFRm1-4 (right) F2 |
| 84 | ZFRm1-4 (right) F4 | 85 | ZFRm1-4 (right) Re SEQ | 86 | ZFRm1-4 (right) F3 |
| 87 | ZFLm1 (left) F6 | 88 | VL CD3 | 89 | VH CD3 |
| 90 | VL CD4-1 | 91 | VH CD4-1 | 92 | VL CD4-2 |
| 93 | VH CD4-2 | 94 | scFv CD5 | 95 | VL CD5 |
| 96 | VH CD5 | | | | |

Figure 34:
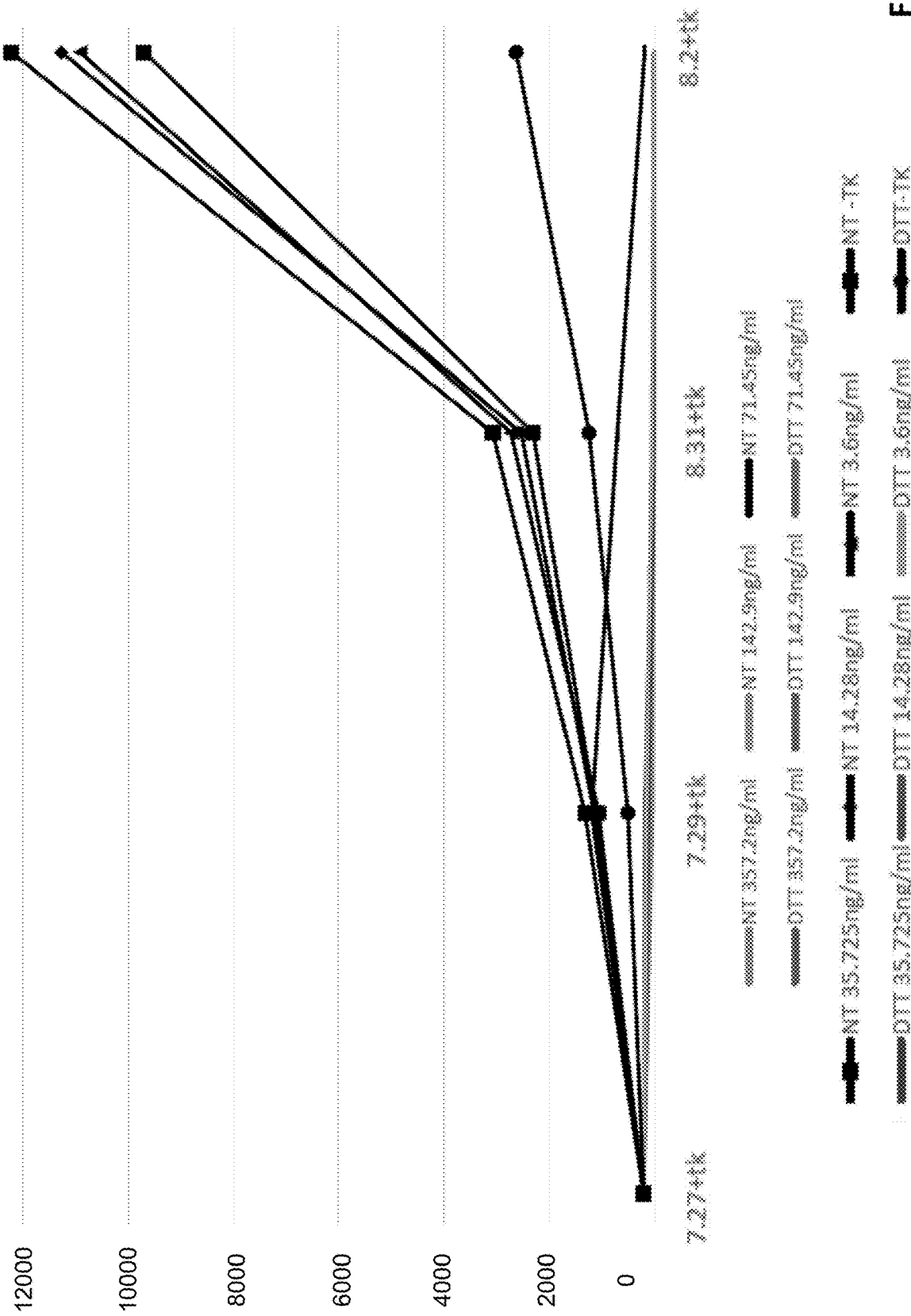
FIG. 34 shows a graph indicating dual-safety-T/CAR T cell 1+/−TK (ganciclovir).
Figure 35:
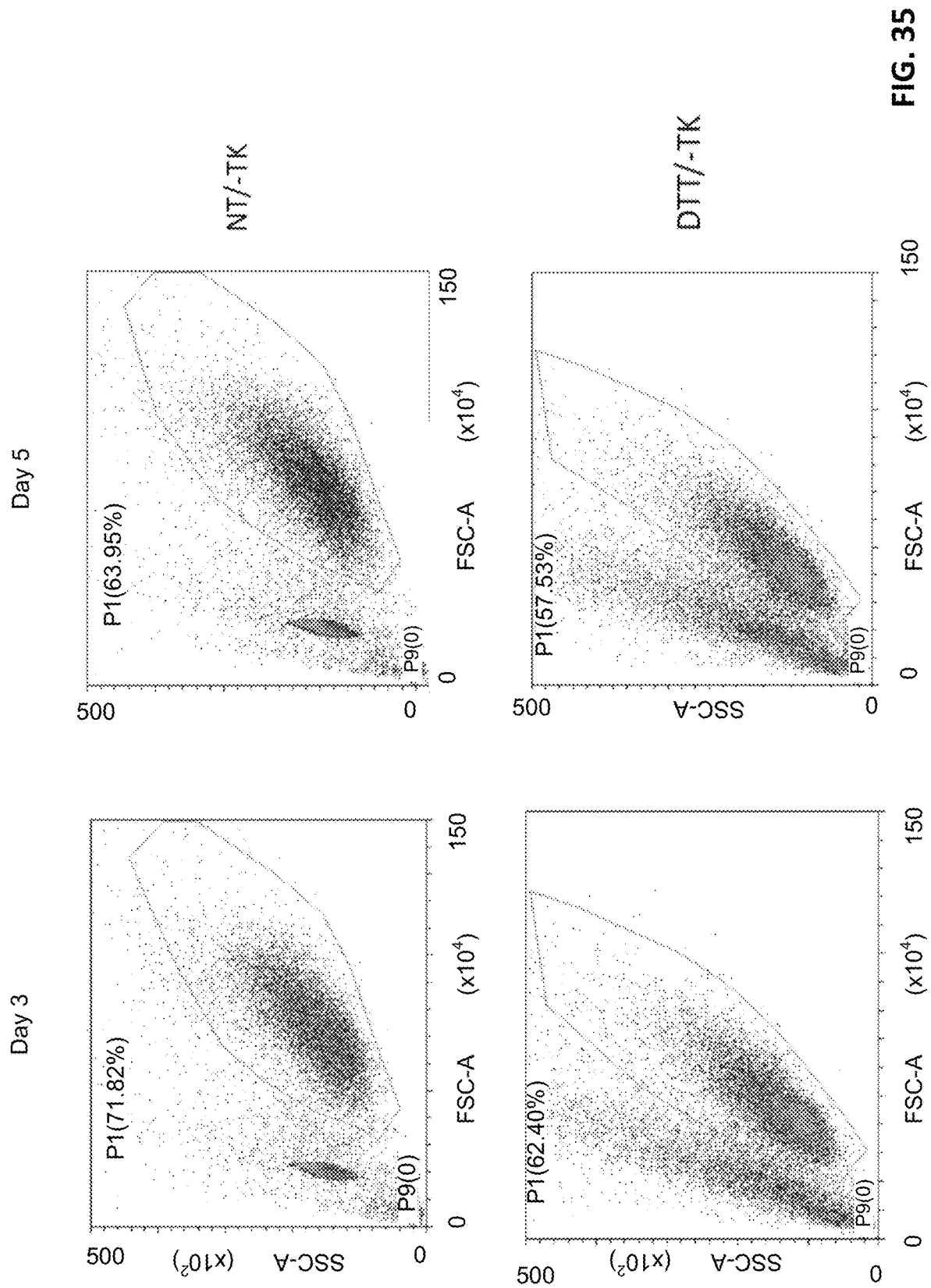
FIG. 35 shows results of flow cytometry analysis indicating dual-safety-T/CAR T cell 1+/−TK (ganciclovir).
Figure 36:
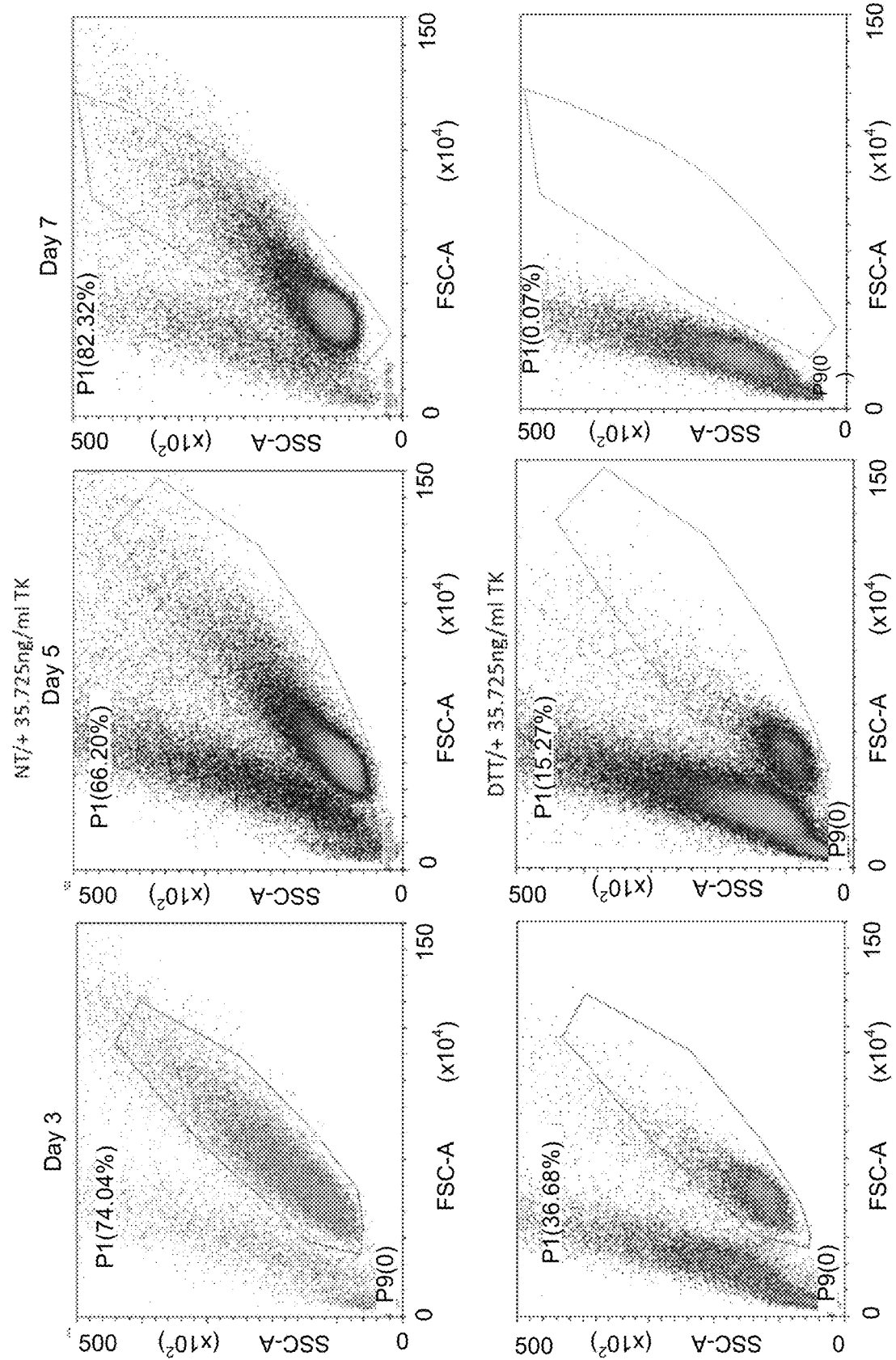
FIG. 36 shows results of flow cytometry analysis indicating dual-safety-T/CAR T cell 1+/−TK (ganciclovir). Experimental cells: CD8+CZY-1 SDS-T and NT cell; TK usage: Adult body concentration of 71.45 ng/ml/5000 ng/kg every 24 h injection. In vitro experimental concentration gradients: 357.2 ng/ml, 142.9 ng/ml, 71.45 ng/ml, 35.725 ng/ml, 14.28 ng/ml, 3.6 ng/ml. As an example.

The primary T cells obtained from a healthy donor were transduced with lentiviral vectors encoding a CD19 CAR (SEQ ID NO: 21) and lentiviral vectors including sequence 1 or 6 as illustrated in FIG. 1 (ef1a-TK-IRES-rtTA-TRE- In group three, transduced cells (ef1a-TK-IRES-rtTA-TRE-hTERT) were cultured using media containing Dox (2 µg/ml) and CD19 ECD (1 mg/250,000 CAR T cells). On day 90, various concentrations of GCV was added to the transduced cells. Cell growth in these two subgroups was observed, and results were provided in FIGS. 34-36. NT represents non-transduced T cells and continued to grow in the presence of GCV. DTT cells represent transduced T cells and grew poorly in the presence of GCV.

Figure 37:
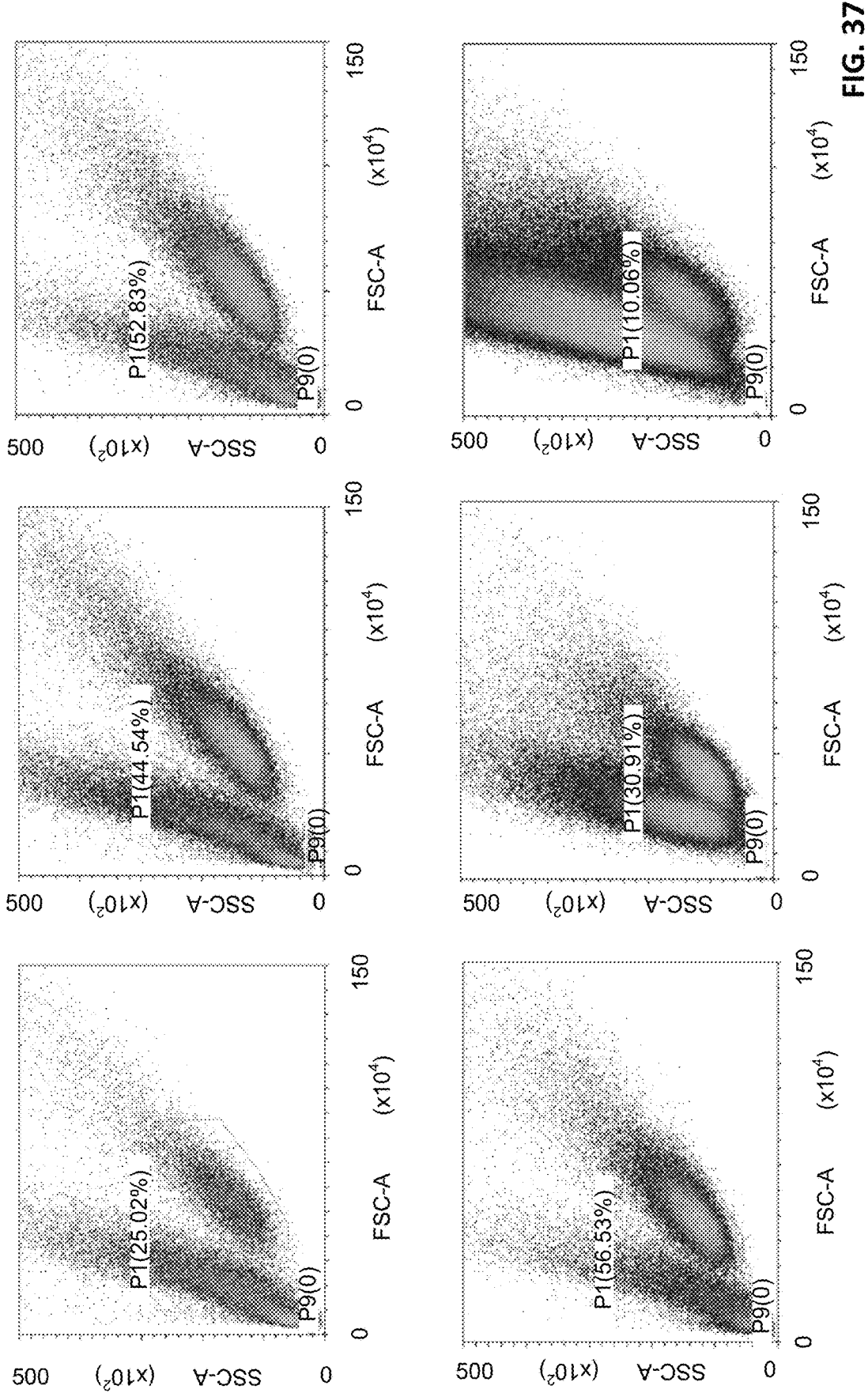
FIG. 37 shows concentration gradient culture function test showing CD8+dual-switch-CAR T cell.
Figure 38:
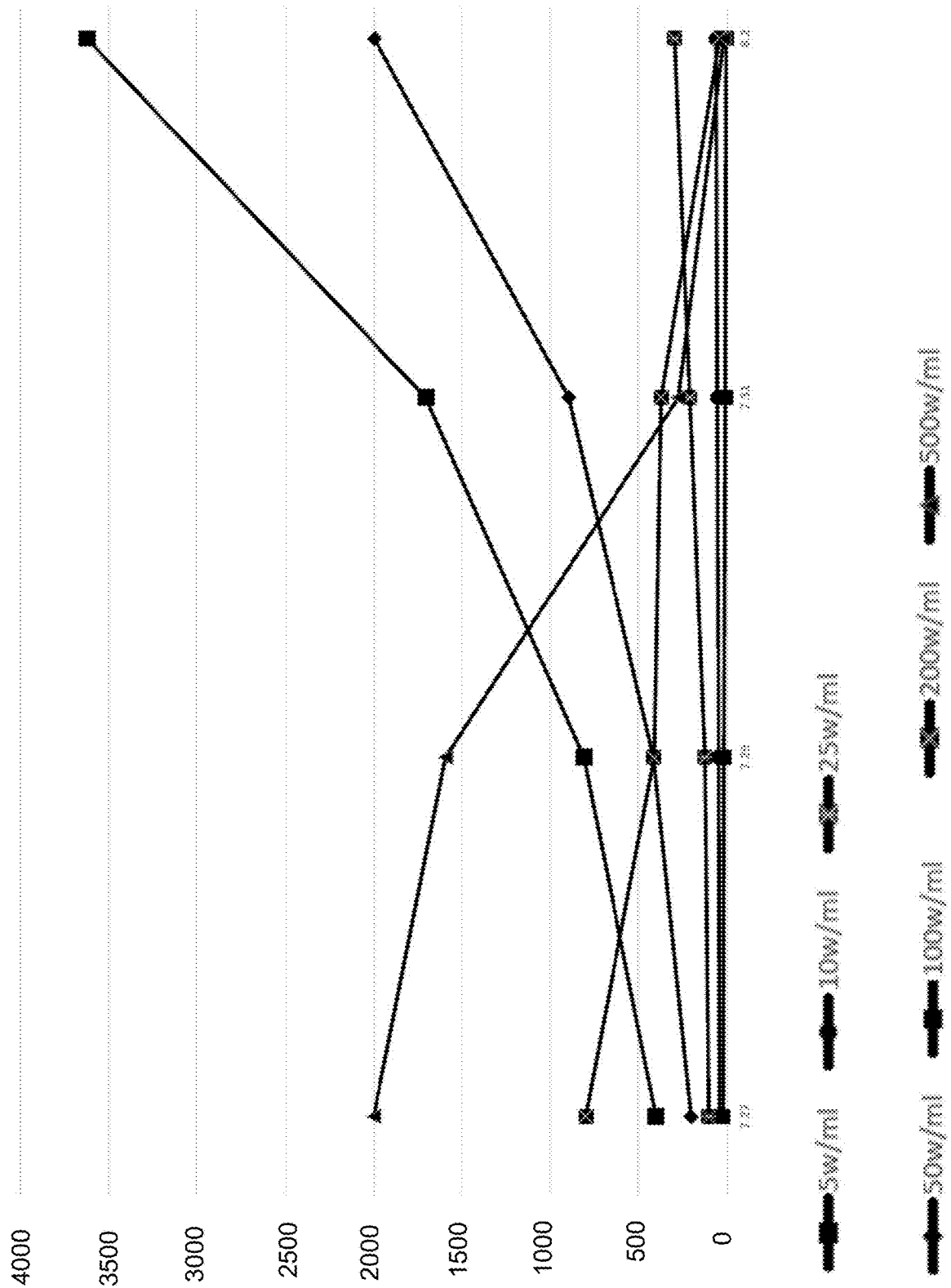
FIG. 38 shows optimum culture concentration: 50 w/ml to 100 w/ml, and Low or high concentrations can inhibit the growth of Dual-Switch T cells. W/ml refers to 10 thousand per ml.

In group four, transduced cells were cultured with different cell concentrations using media containing Dox (21 g/ml) and CD19 ECD (1 mg/250,000 CAR T cells). Cell growth was measured on day 90, and results were provided in FIGS. 37 and 38 as well as 44.

TABLE 2

| IDs of Zinc finger DNA binding protein | Target Sequence of TRAC gene (SEQ ID NO:) | F1 (SEQ ID NO:) | F2 (SEQ ID NO:) | F3 (SEQ ID NO:) | F4 (SEQ ID NO:) | F5 (SEQ ID NO:) | F6 (SEQ ID NO:) |
|---|---|---|---|---|---|---|---|
| ZFRm1 Right | 29 | 26 | 25 | 26 | 27 | 28 | |
| ZFLm1-4 Left | 33 | 30 | 31 | 26 | 32 | | |

TABLE 3

| ZFN | Recognition Sequence | F1 | F2 | F3 | F4 | F5 | F6 |
|---|---|---|---|---|---|---|---|
| ZFLm1 (left) | SEQ ID NO: 81 GTTGCTCCAGGCCACA GCA | SEQ ID NO: 78 QSGDLTR | SEQ ID NO: 77 QWGTRYR | SEQ ID NO: 80 ERGTLAR | SEQ ID NO: 79 RSDNLRE | SEQ ID NO: 78 QSGDLTR | SEQ ID NO: 87 TSGALTR |
| ZFRm1-4 (right) | 85 GACTTTGCATGT | SEQ ID NO: 82 WRSSLAS | SEQ ID NO: 83 QSGSLTR | SEQ ID NO: 86 HKWVLRQ | SEQ ID NO: 84 DRSNLTR | | |

In group five, transduced cells were cultured using media containing Dox (21 g/ml) and CD19 ECD (1 mg/250,000 CAR T cells). Killing assays on these cells were performed on day 90, and results were provided in FIG. 39.

Figure 41:
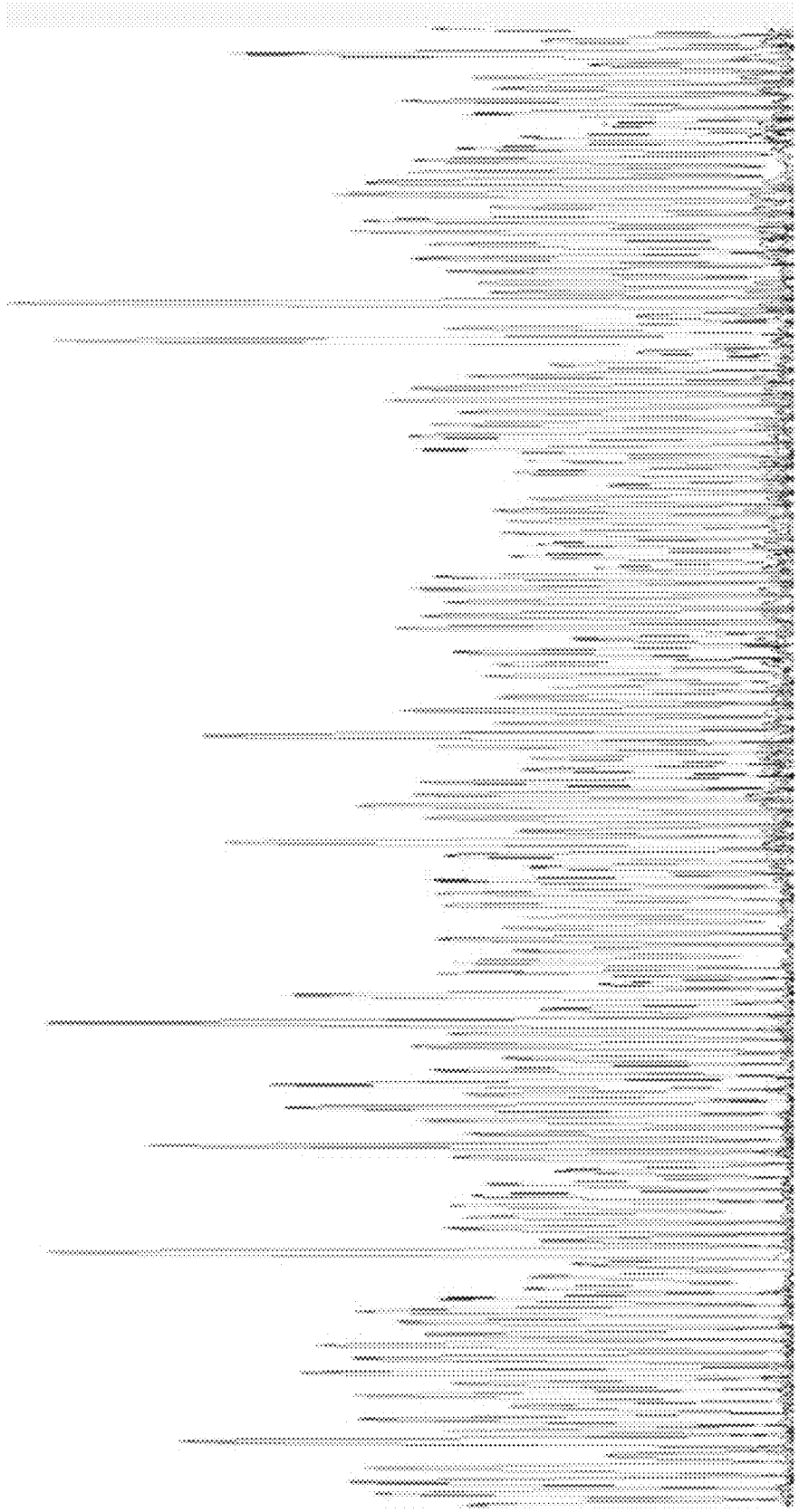
FIG. 41 shows the result of cells killing analysis.
Figure 42:
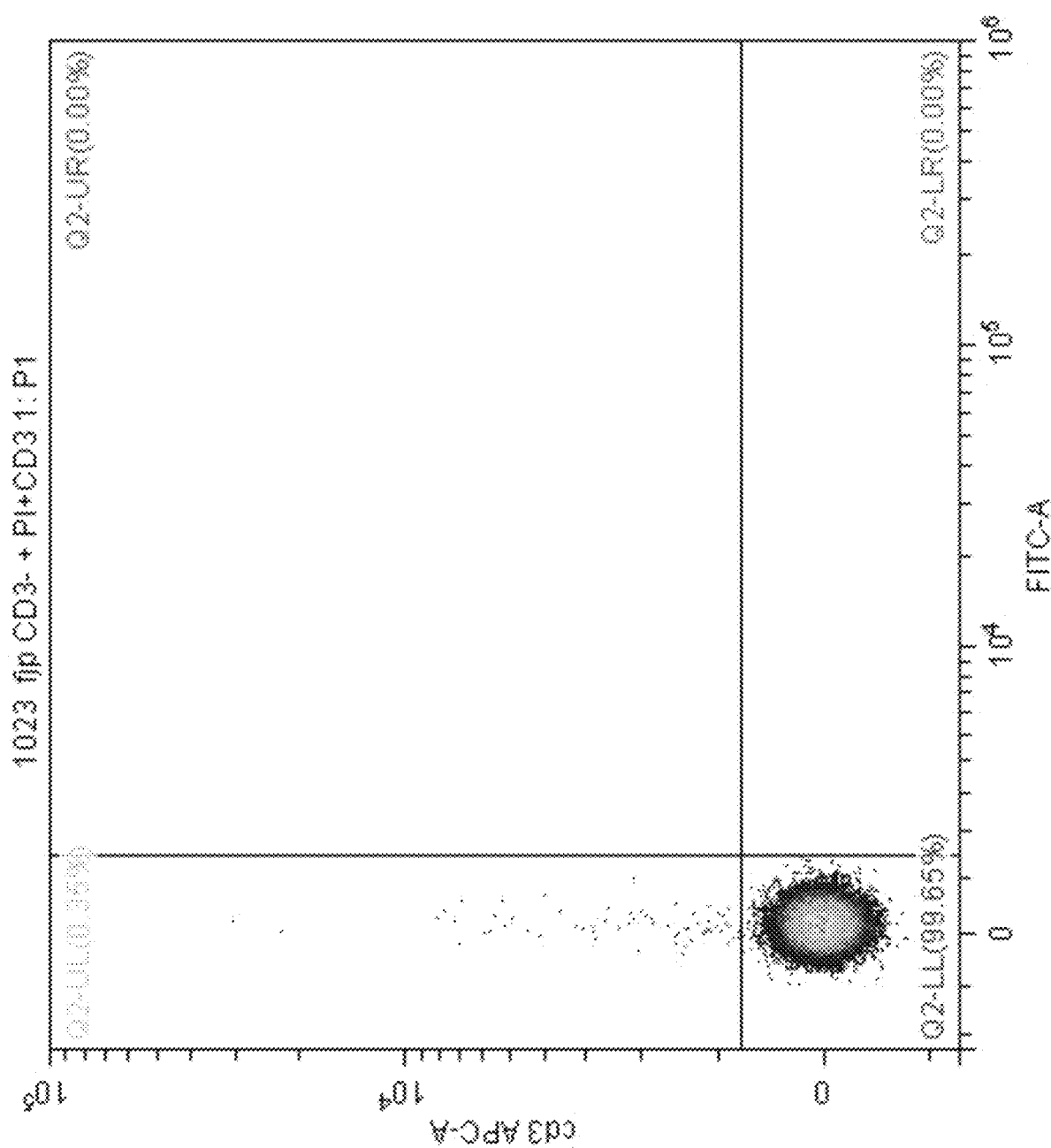
FIG. 42 shows CD3 negative cells obtained using ZFN and purified with CD3 microbeads. After purification, CD3 negative cells were seeded with APC-CD3 antibody, and the results of the flow cytometry showed that the knockout was successful and 99.7% of the cells are CD3−. Then, these CD3 negative cells were transfected with lentiviral copies of the dual-switch-hTERT and CAR into the genomes of these cells.

In group six, transduced cells were introduced with TRAC-specific ZFNs constructed to enable the site-specific introduction of mutations at TRAC gene. Various ZFNs were designed and incorporated into plasmids vectors essentially as described in Urnov et al. (2005) Nature 435(7042): 646-651, Lombardo et al. (2007) Nat Biotechnol. November; 25(11):1298-306, and U.S. Patent Publication 2008/0131962. The ZFNs includes various of combinations of Zinc finger binding domains (e.g., ZFN-left and ZFN-right binding domains), which were listed in Table 1 and Table 2 as well as Table 3. The cleavage domain of the ZFNs comprised an engineered FokI cleavage domain (SEQ ID NOS.: 23, or 24). mRNA encoding a pair of ZFNs (See Table 2) was introduced into the transduced cells to modify a target genomic locus associated with a chain of TCR. CD3 expression was measured, and results were provided in FIGS. 40-42.

Figure 44:
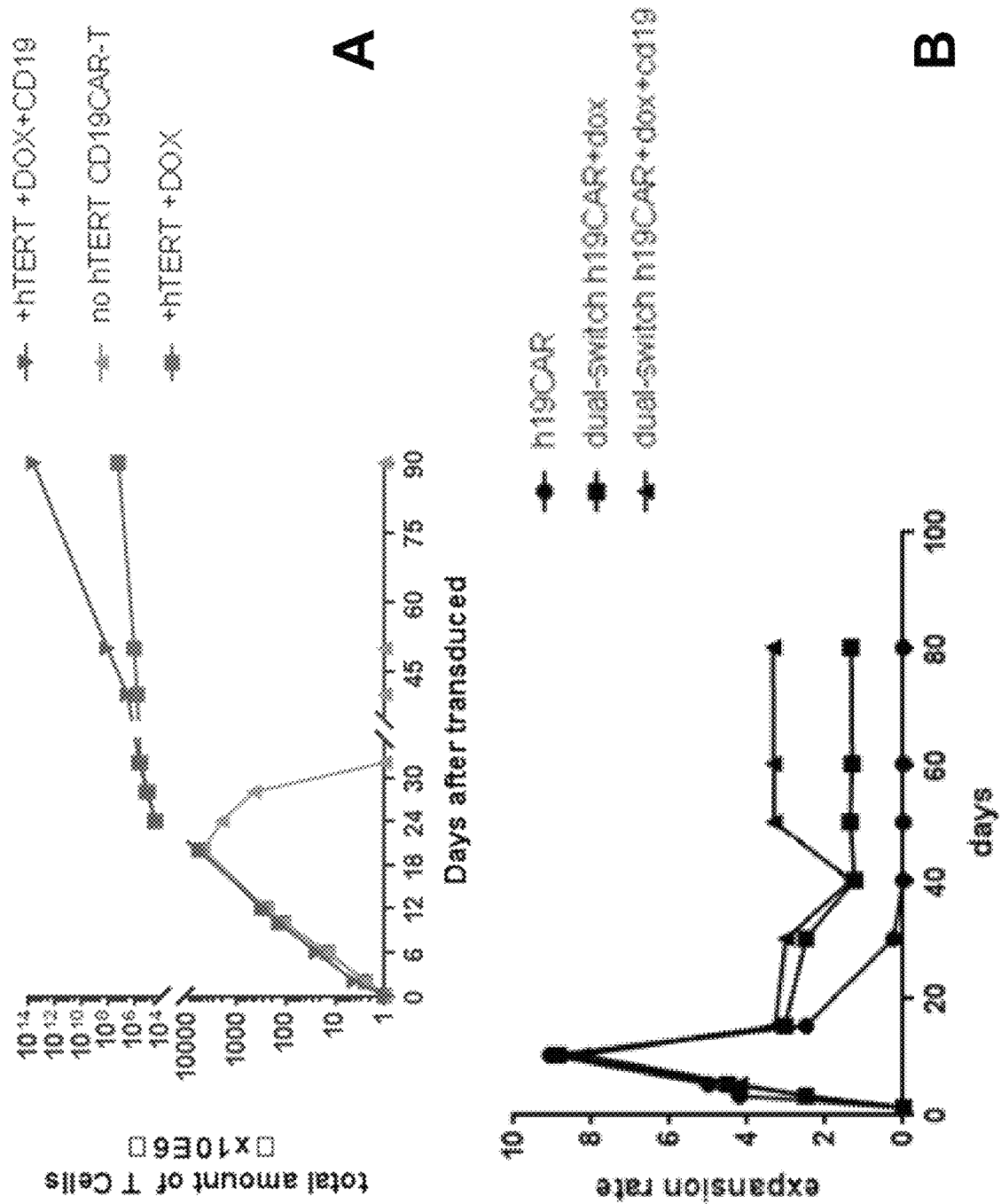
FIG. 44 shows cell growth of various groups of CAR T cells in different conditions. A: Group 1 (hTERT+DOX+CD19): proliferable CD19 CAR T cells (hTERT) were cultured in a media containing ECD CD19 and Dox. Group 2 (hTERT+DOX): proliferable CD19 CAR T cells (hTERT) were cultured in a media containing Dox without ECD CD19. Group 3 (no hTERT CD19CAR-T): CD19 CAR T cells were cultured in a media without Dox and ECD CD19. B: Group 1: CD19 CAR T cells (h19CAR) were cultured in a media without containing ECD CD19 and Dox. Group 2: proliferable CD19 CAR T cells with dual-switch (dual-switch h19CAR+dox) were cultured in a media containing Dox but no ECD CD19. Group 3: proliferable CD19 CAR T cells with dual-switch (dual-switch h19CAR+dox+cd19) were cultured in a media containing Dox and ECD CD19. These results demonstrate that the agent and/or the prolifeable modification contribute long term maintenance of CAR T cells in vitro.

Contributions of the agent (e.g., ECD CD19) and/or the proliferable modification (e.g., hTERT) were investigated. FIG. 44 shows cell growth of various groups CAR T cells in different conditions. A: Group 1: proliferable CD19 CAR T cells (hTERT) were cultured in a media containing ECD CD19 and Dox. Group 2: proliferable CD19 CAR T cells (hTERT) were cultured in a media containing Dox without ECD CD19. Group 3: CD19 CAR T cells were cultured in a media without containing Dox and ECD CD19. B: Group 1: CD19 CAR T cells (h19CAR) were cultured in a media without containing ECD CD19 and Dox. Group 2: proliferable CD19 CAR T cells with dual-switch (dual-switch h19CAR+dox) were cultured in a media containing Dox but no ECD CD19. Group 2: proliferable CD19 CAR T cells with dual-switch (dual-switch h19CAR+dox+cd19) were cultured in a media containing Dox and ECD CD19. These results demonstrated that the agent and/or the proliferable modification contributed to long term maintenance of CAR T cells in vitro.

Construction of Antigen-Expressed K562 Cell Lines

K562 cells were transduced with lentivirus including nucleic acid sequences encoding various antigens (FIG. 39) to establish target tumor cell lines (K562-CD19 tumor cells). The lentivirus included the IRES-mCherry (red) construct, which encodes red fluorescence for confirmation of antigen expression. Red fluorescent signals were observed from these cell lines, indicating that target solid tumor cell lines were successfully established (FIG. 39). Techniques of construction of cell lines may be found at "Chimeric Receptors Containing CD137 Signal Transduction Domains Mediate Enhanced Survival of T Cells and Increased Antileukemic Efficacy," In Vivo Molecular Therapy vol. 17 no. 8, 1453-1464 August 2009, which is incorporated herein by reference. K562 cells were obtained from American Type Culture Collection (ATCC).

Construction of CAR T Cells

Primary T cells were transduced with lentivirus including various CARs to establish different CAR T cell lines targeting different antigens listed in Table 1. In some experiments, the lentivirus may include a nucleic acid sequences 1-4, or 6 as illustrated in FIG. 23. These cells were obtained from healthy human donors. The lentivirus included a nucleic acid sequence encoding CAR molecules, respectively, and further included the IRES-mCherry (green) construct, which encodes green fluorescence for confirmation of CAR expression. Expression of CARs was measured to confirm that CAR T cell lines express specific anti-antigen molecules. Techniques related to cell cultures, construction of lentiviral vectors, and flow cytometry may be found in "Treatment of Advanced Leukemia in Mice with mRNA-Engineered T Cells," Human Gene Therapy, 22:1575-1586 (December 2011), which is incorporated herein by reference.

T Cell Killing Assay

CAR T cell killing assays were conducted to measure the effectiveness of CAR T cells. Primary T cells were obtained from blood samples of healthy human donors. These T cells were transduced with a nucleic acid sequence encoding a CAR and with a nucleic acid sequences 1-4, or 6 as illustrated in FIG. 23 (FIGS. 24-26 and 39), and CAR expression on T cells was measured using flow cytometry techniques.

K562 cells were transduced with nucleic acid sequences encoding corresponding human antigens, respectively, and antigen expression was measured using flow cytometry techniques. Further antigen-expression K562 cells were transduced with a nucleic acid sequence encoding fluorescent proteins (RFP) for killing assay analysis. Various CAR T cells were incubated with corresponding K562 cells for 24 hours in various E:T ratios (30:1, 10:1, 3:1, 1:1), and red fluorescence signals from cocultured cells were observed.

In Vivo Anti-Tumor Activity

Heterotransplantation of human cancer cells or tumor biopsies into immunodeficient rodents (xenograft models) has, for the past two decades, constituted the major preclinical screen for the development of novel cancer therapeutics (Song et al., Cancer Res. PMC 2014 Aug. 21, 2159-2169. and Morton et al., Nature Protocols, 2, 247-250 (2007)). To evaluate the anti-tumor activity of CAT T cells in vivo, immunodeficient mice bearing tumor xenografts were used to evaluate CAR T's anti-tumor activity.

K562-CD19-RFP cells were used to establish the immunodeficient mice bearing CD19 tumor xenografts. On day 120, K562-PRLR-RFP cells were injected into tail veins of the immunodeficient mice. On day 122 or 123, irradiation was performed on the immunodeficient mice in 2 Gy fractions. On day three, the formation of tumor cells in the immunodeficient mice was observed.

Figure 43:
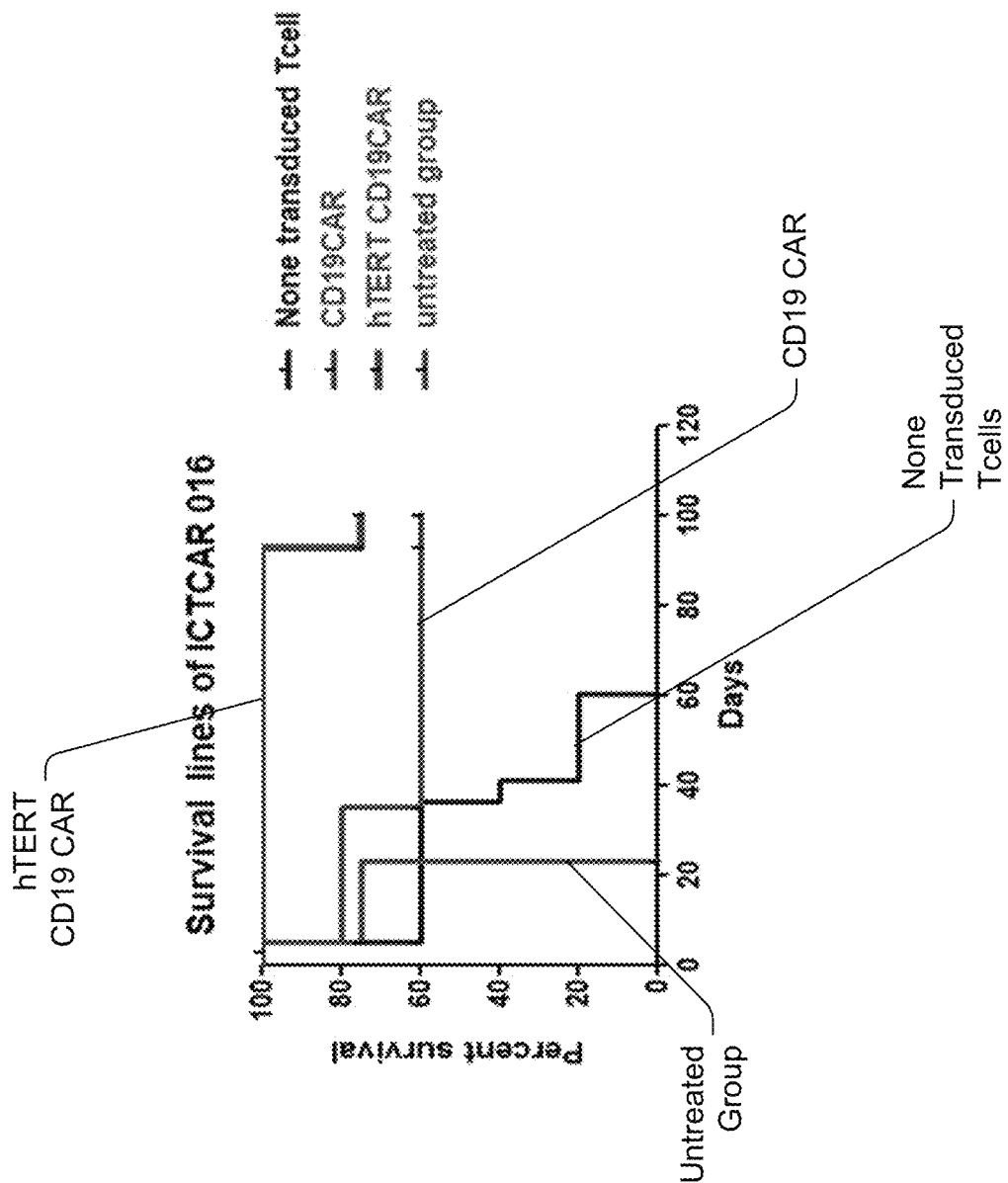
FIG. 43 shows survival and growth of various CAR T Cells. In Group 1 (hTert CD19 CAR), the primary T cells obtained from a healthy donor were transduced with a nucleic acid sequence encoding a CD19 CAR and a nucleic acid sequence encoding hTERT. In Group 2 (CD19 CAR), the primary T cells were transduced with the nucleic acid sequence encoding a CD19 CAR. CAR T cells comprising the nucleic acid sequence encoding hTERT show long-term survival. Among these CAR T cells, cells cultured using a cell medium containing CD19 ECD exhibit higher cell growth rates than those cultured using a cell medium containing no CD19 ECD. CAR T cells are not comprising the nucleic acid sequence encoding hTERT begun to die after about 20 days after cells were transduced with the nucleic acid sequence encoding CAR.

On day 123, anti-CD19 human CAR T cells (i.e., anti-CD19 CAR T) were transfused to the immunodeficient mice, and anti-tumor activities were observed in the immunodeficient mice. The anti-CD19 CAR T cells were made by the protocol described in this present disclosure. The presence of K562-CD19-RFP cells was evaluated using the peripheral blood of the immunodeficient mice by flow cytometry after three or four weeks after transfusion. In control, the buffer was transfused to the immunodeficient mice, and the immunodeficient mice died within four to six weeks. As for the immunodeficient mice transfused with anti-CD19 CAR T, the K562-CD19-RFP cells were not observed, and the immunodeficient mice behaved normally. Human CD3 cells were further observed in the immunodeficient mice (FIG. 43). It is concluded that CAR proliferable T cells have anti-tumor activity in mice. Additional information about the protocol was provided in Table 4 below.

TABLE 4

| Tumor cell | K562-CD19 RFP cells |
|---|---|
| Tumor cells transplanted | 5 * 10^5 cells/mouse |
| irradiation | 2Gy |
| CAR T cells infused | 1 * 10^7 cells/mouse |

Expression of CAR/Antigen on Primary T Cells

Figure 45:
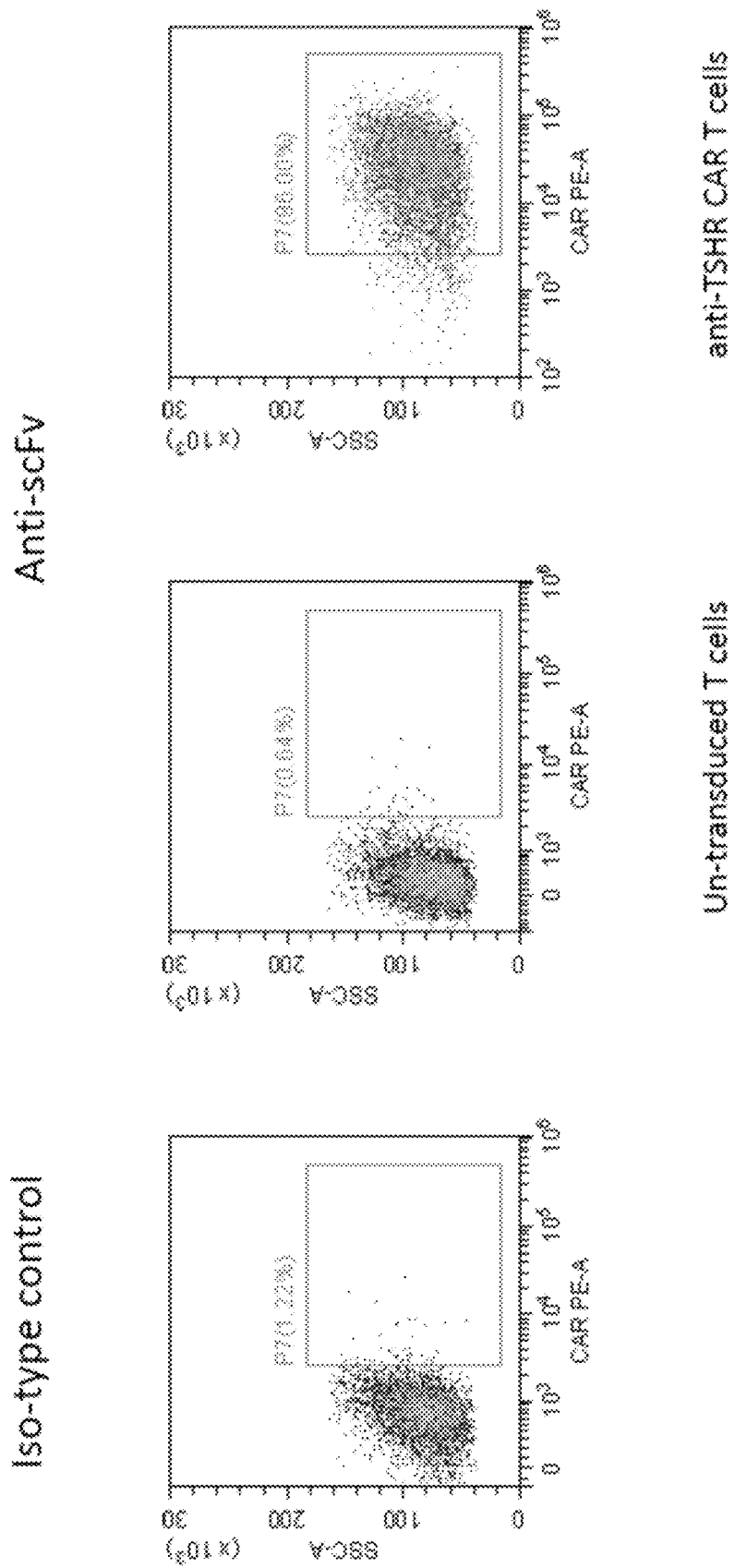
FIG. 45 shows flow cytometry analysis indicating expression of anti-TSHR CAR molecules on T cells (Gated by a single live cell). Anti-TSHR CAR T cells were constructed, and the expression of CAR molecules was detected by flow cytometry. Compared to non-transduced T cells, expression of CAR molecules was observed.
Figure 46:
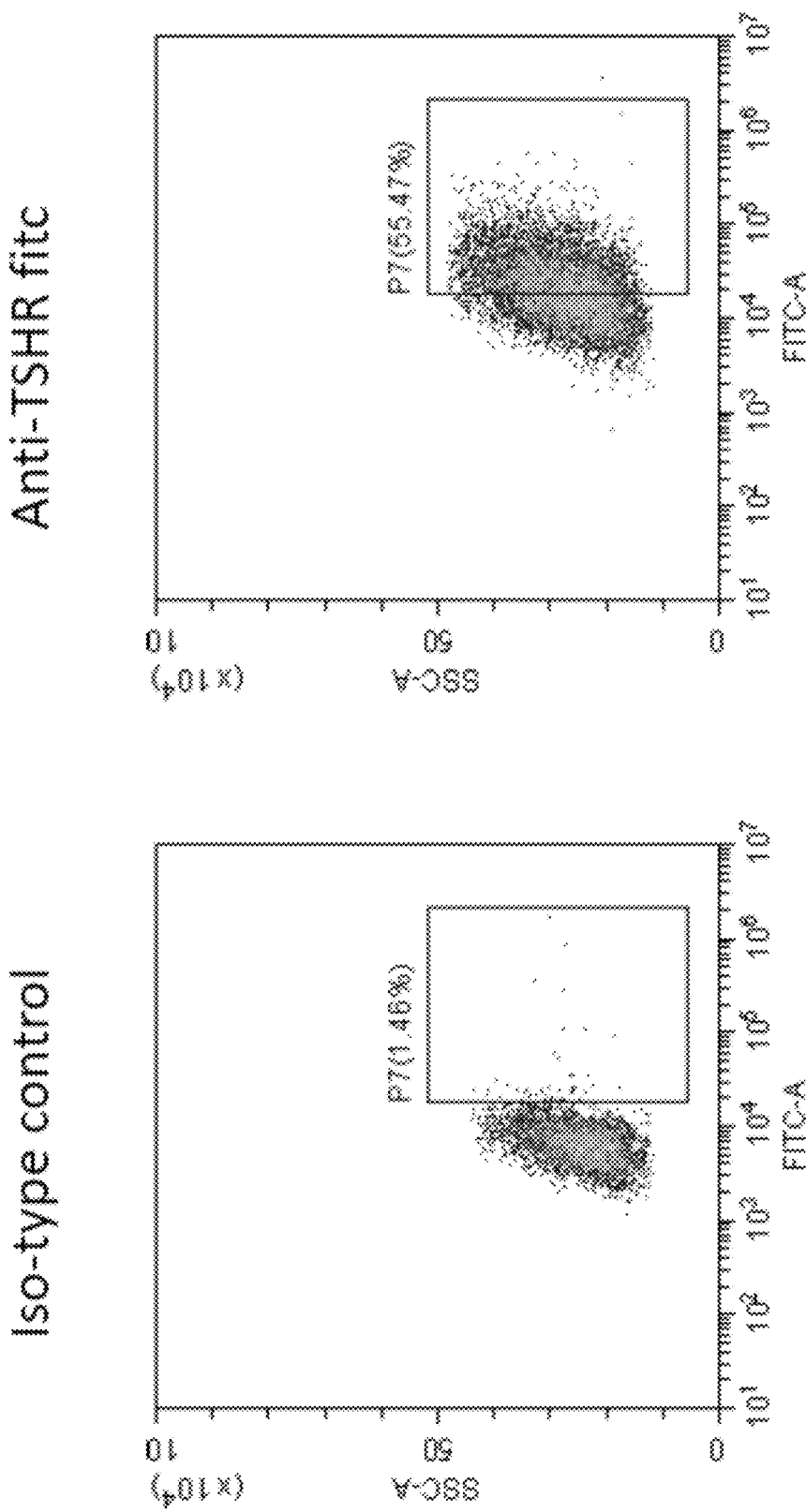
FIG. 46 shows flow cytometry analysis indicating overexpression of TSHR on T cells (Gated by a single live cell). Lentiviral vectors were used to construct antigen overexpressed T cells (TSHR). The expression of TSHR molecules on the surface of T cells was observed (IgG on the left and anti-TSHR FITC on the right).

Primary T cells were obtained from a patient. The obtained primary T cells were divided into two groups. Primary T cells in Group 1 were transduced with lentiviral vectors including a nucleic acid sequence encoding Anti-TSHR CAR (SEQ ID NO: 49). Primary T cells in Group 2 were transduced with lentiviral vectors including a nucleic acid sequence encoding TSHR (SEQ ID NO: 43). Flow-cytometry was performed and analyzed to determine the expression of CAR and TSHR in primary T cells, respectively (FIGS. 45 and 46). Techniques related to cell cultures, construction of lentiviral vectors, and flow cytometry may be found in "Control of large, established tumor xenografts with genetically retargeted human T cells containing CD28 and CD137 domains," 3360-3365 PNAS Mar. 3, 2009, vol. 106 no. 9, which is incorporated herein by reference.

In Vivo Cytokine Release Assay

Figure 47:
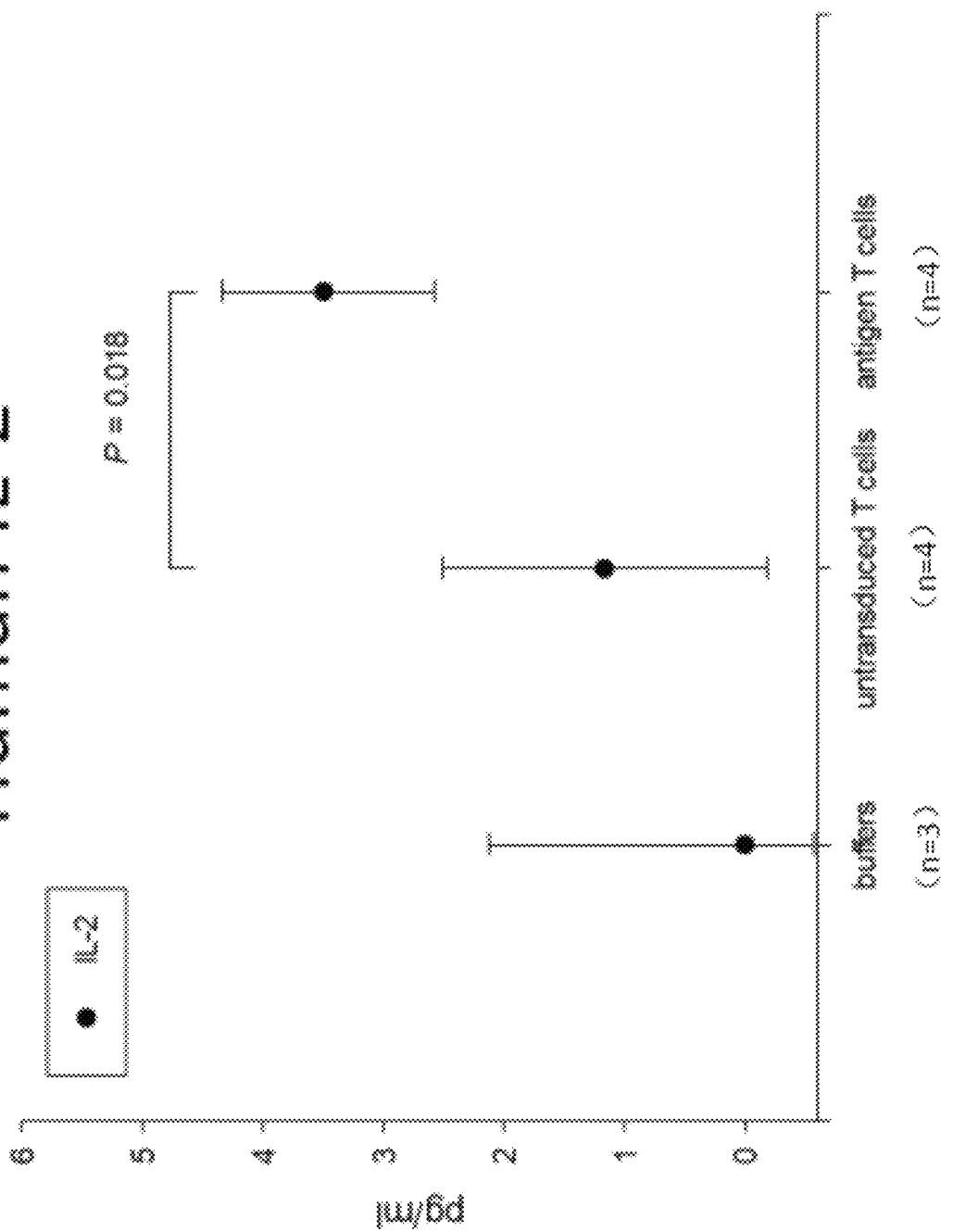
FIG. 47 shows cytokine release (IL-2) in mouse peripheral blood.
Figure 48:
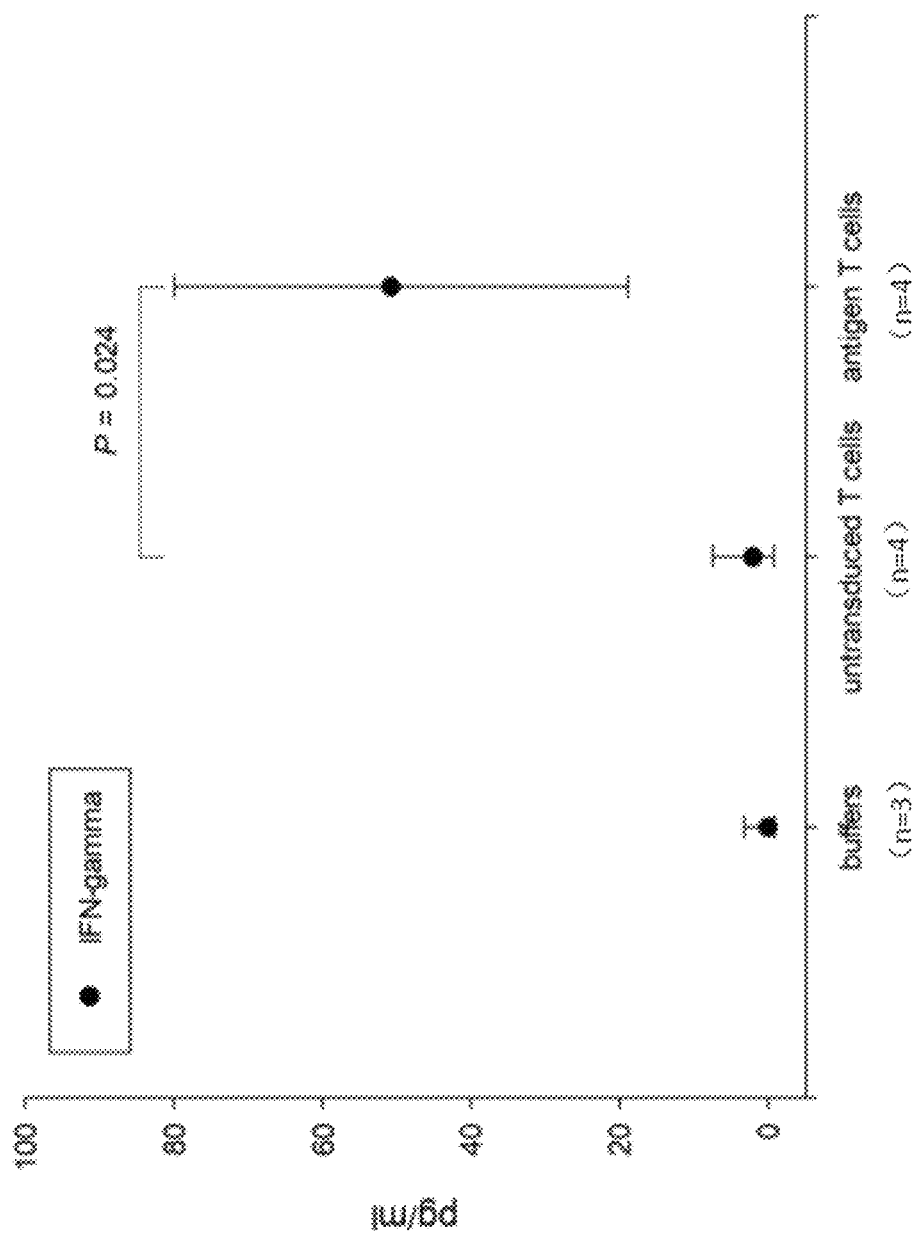
FIG. 48 shows cytokine release (IFN-gamma) in mouse peripheral blood.
Figure 49:
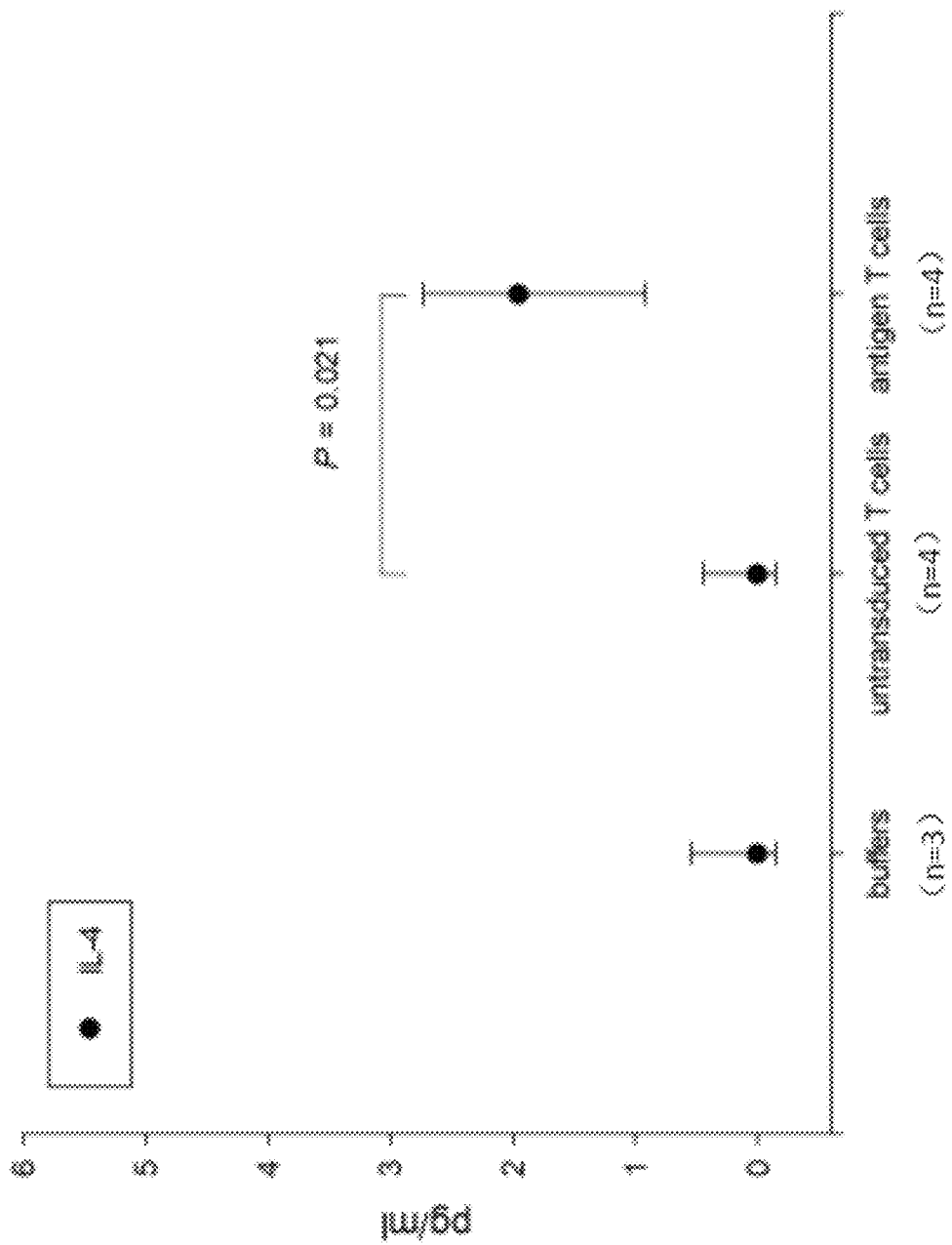
FIG. 49 shows cytokine release (IL-4) in mouse peripheral blood.

Primary T cells of Group 1 and Group 2 were infused into mice (Experimental Group). As control, Primary T cells of Group 1 alone or buffer were infused into mice (Control Group 1 and Control Group 2). Several parameters regarding cell infusion are provided in Table 5 below. NPG mice were irradiated, and a certain number of CAR T cells and corresponding control agents were infused into mice. For Control Group 2, three consecutive buffers were returned to the mice. For Control Group 1, T cells that do not express antigen were returned three times in succession. For Experimental Group, T cells expressing antigens were continuously transfused three times in succession. After the transfusion was completed, blood from the limbal vein was collected to analyze the T cells and factor release in the peripheral blood of the mice. The mice were then sacrificed and T ratios of each organ/CAR T Cell ratio/CAR T copy and other data were collected. Cytokine release assay was then performed. Various cytokines (e.g., IFN-g, IL4, IL2) in mice peripheral blood were measured for Experimental Group and Control Group. As shown in FIGS. 47-49, the amount of cytokine released in the Experimental Group was greater than those in Control Group. These results demonstrate that infusion of cells expressing an antigen enhances the corresponding CAR T cells' T cell response. The schedule for in vivo analysis is provided in Table 6 below.

TABLE 5

| Experimental Group | Control Group 1 | Control Group 2 |
|---|---|---|
| Anti-TSHR CAR T cells about 4 × 10^6/mouse | Anti-TSHR CAR T cells about 4 × 10^6/mouse | Anti-TSHR CAR T cells about 4 × 10^6/mouse |
| Antigen T (TSHR-overexpressed T cell) about 4 × 10^6/mouse per time | NT (non-transduced T cell) about 4 × 10^6/ mouse per time | NT (non-transduced T cell) about 4 × 10^6/ mouse per time |

TABLE 6

| Day 1 | Day 3 | Day 5 | Day 9 | Day 12 | Day 14 | Day 21 | Day 28 |
|---|---|---|---|---|---|---|---|
| irradiation at 1.5 Gy | anti-TSHR CAR T cells infusion | buffers/nt/ antigen T infusion | buffers/nt/ antigen T infusion | buffers/nt/ antigen T infusion | bleeding and analysis | bleeding and analysis | sacrifice and analysis |

As described above, the treatment methods described herein can easily be adapted for other species or subjects, such as humans.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

What is claimed is:

1. A method of producing chimeric antigen receptor (CAR) T cells, the method comprising:
providing T cells comprising a CAR and an exogenous nucleic acid encoding hTERT, an exogenous nucleic acid encoding SV40 large T antigen (SV40LT), or a combination thereof, wherein the exogenous nucleic acid encoding hTERT, SV40LT, or the combination thereof is integrated into the genome of the T cells and comprises (a) SEQ ID NO: 13, 14, 15, or 18; (b) SEQ ID NO: 13 and 14; or (c) SEQ ID NO: 15 and 18;
culturing the T cells in the presence of an agent that an extracellular domain of the CAR binds to obtain CAR T cells exhibiting enhanced functional activity as compared to corresponding T cells comprising a CAR and do not comprise the exogenous nucleic acid encoding hTERT, the exogenous nucleic acid encoding SV40LT, or the combination thereof, wherein the agent comprises protein or glycoprotein; and
allowing the T cells to expand, wherein expansion of the T cells is greater than T cells that do not comprise the exogenous nucleic acid encoding hTERT, the exogenous nucleic acid encoding SV40LT, or the combination thereof.

2. The method of claim 1, wherein the agent mediates a response by the T cells comprising the CAR.

3. The method of claim 1, wherein the agent is an extracellular domain of an antigen.

4. The method of claim 3, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

5. The method of claim 1, wherein a ratio of an amount of the agent to a number of the CAR T cells after culturing with the agent is from 1: 5000 to 1: 5 µg/$10^4$ cells.

6. The method of claim 1, wherein a concentration of the agent in a culture media is 2 to $10^4$ ng/ml.

7. The method of claim 1, wherein providing the T cells comprising the CAR comprises culturing the T cells without the agent for at least 8 days after introduction of a vector comprising a nucleic acid encoding the CAR and the exogenous nucleic acid encoding hTERT, the exogenous nucleic acid encoding SV40LT, or the combination thereof into the T cells, and culturing the T cells in the presence of the agent comprises culturing the T cells after the at least 8 days.

8. The method of claim 1, wherein a ratio of a number of the CAR T cells expressing the CAR to the T cells not expressing the CAR is greater than the ratio when the CAR T cells are cultured without the agent.

9. The method of claim 1, wherein the CAR comprises an extracellular domain, a spacer domain, a transmembrane domain, and an intracellular domain.

10. The method of claim 9, wherein the spacer domain of the CAR comprises SEQ ID NO: 68.

11. The method of claim 9, wherein the transmembrane domain of the CAR comprises SEQ ID NO: 72 and the spacer domain of the CAR comprises SEQ ID NO: 68.

12. The method of claim 1, wherein the agent comprises an extracellular domain of at least one of CD19, FZD10, TSHR, PRLR, Muc 17, GUCY2C, CD207, CD3, CD5, or CD4.

13. The method of claim 1, wherein the agent comprises SEQ ID NO: 22 or 41.

14. The method of claim 1, wherein the agent comprises at least one of GCC, B7-H4, Prostate specific membrane antigen (PSMA), Carcinoembryonic Antigen (CEA), IL13Ralpha, her-2, CD19, CD20, CD22, CD123, NY-ES0-1, HIV-I Gag, Lewis Y antigen, Mart-I, gp100, tyrosinase, WT-I, hTERT, MUC16, mesothelin, MIC-A, MIC B, RON, or one or more members of the ULBP/RAETI family.

15. The method of claim 1, wherein the CAR comprises an extracellular domain, a transmembrane domain, and an intracellular domain comprising a CD3-zeta signaling domain and a signaling domain of a costimulatory molecule.

16. The method of claim 1, wherein the T cells have reduced expression of an endogenous TCR gene and/or HLA I, and the T cells are derived from a healthy donor and elicit no graft-versus-host disease (GVHD) response or a reduced GVHD response in a human recipient as compared to the GVHD response elicited by a primary human T cell isolated from the same healthy donor and having no reduced expression of the endogenous TCR gene and/or HLA I.

17. The method of claim 1, wherein the agent is a soluble antigen generated by a eukaryotic system or a bacterial expression system.

18. The method of claim 1, wherein the functional activity comprises inhibiting the growth of tumor cells.

19. The method of claim 1, wherein the CAR T cells are produced for cell therapy.

20. A pharmaceutical composition comprising the CAR T cells obtained by the method of claim 1.

21. A method for treating cancer, the method comprising administering an effective amount of the pharmaceutical composition of claim 20 to a subject in need thereof, wherein the CAR comprises an antigen binding domain that binds a molecule on a cancer cell.

* * * * *

```
                        SEQUENCE LISTING

<160> NUMBER OF SEQ ID NOS: 96

<210> SEQ ID NO 1
<211> LENGTH: 231
<212> TYPE: DNA
<213> ORGANISM: Artificial Sequence
<220> FEATURE:
<223> OTHER INFORMATION: synthesis

<400> SEQUENCE: 1
cggctccggt gcccgtcagt gggcagagcg cacatcgccc acagtccccg agaagttggg      60
gggaggggtc ggcaattgaa ccggtgccta gagaaggtgc cgcggggtaa actgggaaag     120
tgatgtcgtg tactggctcc gccttttttcc cgagggtggg ggagaaccgt atataagtgc    180
agtagtcgcc gtgaacgttc ttttttcgcaa cgggtttgcc gccagaacac a             231

<210> SEQ ID NO 2
<211> LENGTH: 1131
<212> TYPE: DNA
<213> ORGANISM: Artificial Sequence
<220> FEATURE:
<223> OTHER INFORMATION: synthesis

<400> SEQUENCE: 2
atggcttcgt acccctgcca tcaacacgcg tctgcgttcg accaggctgc gcgttctcgc       60
ggccatagca accgacgtac ggcgttgcgc cctcgccggc agcaagaagc cacggaagtc      120
cgcccggagc agaaaatgcc cacgctactg cgggtttata tagacggtcc ccacgggatg      180
gggaaaacca ccaccacgca actgctggtg gccctgggtt cgcgcgacga tatcgtctac      240
gtacccgagc cgatgactta ctggcgggtg ctgggggctt ccgagacaat cgcgaacatc      300
tacaccacac aacaccgcct cgaccagggt gagatatcgg ccggggacgc ggcggtggta      360
atgacaagcg cccagataac aatgggcatg ccttatgccg tgaccgacgc cgttctggct      420
cctcatatcg ggggggaggc tgggagctca catgccccgc ccccggccct caccctcatc      480
ttcgaccgcc atcccatcgc cgccctcctg tgctacccgg ccgcgcgata ccttatgggc      540
agcatgaccc cccaggccgt gctggcgttc gtggccctca tcccgcgac cttgcccggc      600 acaaacatcg tgttgggggc ccttccggag gacagacaca tcgaccgcct ggccaaacgc      660
cagcgccccg gcgagcggct tgacctggct atgctggccg cgattcgccg cgtttacggg      720
ctgcttgcca atacggtgcg gtatctgcag ggcggcgggt cgtggcggga ggattgggga      780
cagctttcgg ggacggccgt gccgcccag ggtgccgagc cccagagcaa cgcgggccca       840
cgaccccata tcggggacac gttatttacc ctgtttcggg ccccgagtt gctggccccc       900 aacggcgacc tgtataacgt gtttgcctgg gccttggacg tcttggccaa acgctccgt      960 cccatgcacg tctttatcct ggattacgac caatcgcccg ccggctgccg ggacgccctg     1020
ctgcaactta cctccgggat ggtccagacc cacgtcacca ccccaggctc catccgacg      1080 atctgcgacc tggcgcgcac gtttgcccgg gagatggggg aggctaactg a              1131

<210> SEQ ID NO 3
<211> LENGTH: 585
```

```
<212> TYPE: DNA
<213> ORGANISM: Artificial Sequence
<220> FEATURE:
<223> OTHER INFORMATION: synthesis

<400> SEQUENCE: 3
cctctccctc cccccccct aacgttactg gccgaagccg cttggaataa ggccggtgtg      60
cgtttgtcta tatgttattt tccaccatat tgccgtcttt tggcaatgtg agggcccgga     120
aacctggccc tgtcttcttg acgagcattc ctagggtct ttcccctctc gccaaaggaa      180
tgcaaggtct gttgaatgtc gtgaaggaag cagttcctct ggaagcttct tgaagacaaa     240
caacgtctgt agcgaccctt tgcaggcagc ggaaccccc acctggcgac aggtgcctct      300
gcggccaaaa gccacgtgta taagatacac ctgcaaaggc ggcacaaccc cagtgccacg     360
ttgtgagttg gatagttgtg gaaagagtca aatggctctc ctcaagcgta ttcaacaagg     420
ggctgaagga tgcccagaag gtaccccatt gtatgggatc tgatctgggg cctcggtaca     480
catgctttac atgtgtttag tcgaggttaa aaaaacgtct aggccccccg aaccacgggg     540
acgtggtttt cctttgaaaa acacgatgat aatatggcca caacc                    585

<210> SEQ ID NO 4
<211> LENGTH: 1008
<212> TYPE: DNA
<213> ORGANISM: Artificial Sequence
<220> FEATURE:
<223> OTHER INFORMATION: synthesis

<400> SEQUENCE: 4
atgtctagat tagataaaag taaagtgatt aacagcgcat tagagctgct taatgaggtc      60
ggaatcgaag gtttaacaac ccgtaaactc gcccagaagc ttggtgtaga gcagcctaca     120
ctgtattggc atgtaaaaaa taagcgggct ttgctcgacg ccttagccat tgagatgtta     180
gataggcacc atactcactt tgcccttta aaaggggaaa gctggcaaga ttttttacgc      240
aataacgcta aagttttag atgtgcttta ctaagtcatc gcaatggagc aaaagtacat     300
tcagatacac ggcctacaga aaacagtat gaaactctcg aaaatcaatt agcctttta      360
tgccaacaag gtttttcact agagaacgcg ttatatgcac tcagcgctgt ggggcatttt    420
actttaggtt gcgtattgga agatcaagag catcaagtcg ctaaagaaga agggaaaca     480
cctactactg atagtatgcc gccattatta cgacaagcta tcgaattatt tgatcaccaa     540
ggtgcagagc cagccttctt attcggcctt gaattgatca tatgcggatt agaaaaacaa     600
cttaaatgtg aaagtgggtc gcgtacagc gcgcgcgta cgaaaaacaa ttacgggtct       660
accatcgagg gcctgctcga tctcccggac gacgacgccc ccgaagaggc ggggctggcg     720
gctccgcgcc tgtcctttct ccccgcggga cacacgcgca gactgtcgac ggccccccg      780
accgatgtca gcctggggga cgagctccac ttagacggcg aggacgtggc gatggcgcat     840
gccgacgcgc tagacgattt cgatctggac atgttggggg acgggattc cccgggtccg      900
ggatttaccc ccacgactc cgcccctac ggcgctctgg atatggccga cttcgagttt       960
gagcagatgt ttaccgatgc ccttggaatt gacgagtacg gtgggtag                 1008

<210> SEQ ID NO 5
<211> LENGTH: 438
<212> TYPE: DNA
<213> ORGANISM: Artificial Sequence
<220> FEATURE:
<223> OTHER INFORMATION: synthesis
```

<400> SEQUENCE: 5

```
ctcgagttta ccactcccta tcagtgatag agaaaagtga agtcgagtt taccactccc    60
tatcagtgat agagaaaagt gaaagtcgag tttaccactc cctatcagtg atagagaaaa   120
gtgaaagtcg agtttaccac tccctatcag tgatagagaa aagtgaaagt cgagtttacc   180
actccctatc agtgatagag aaagtgaaa gtcgagttta ccactcccta tcagtgatag    240
agaaaagtga agtcgagtt taccactccc tatcagtgat agagaaaagt gaaagtcgag    300
ctcggtaccc gggtcgagta ggcgtgtacg gtgggaggcc tatataagca gagctcgttt   360
agtgaaccgt cagatcgcct ggagacgcca tccacgctgt tttgacctcc atagaagaca   420
ccgggaccga tccagcct                                                438
```

<210> SEQ ID NO 6
<211> LENGTH: 3399
<212> TYPE: DNA
<213> ORGANISM: Artificial Sequence
<220> FEATURE:
<223> OTHER INFORMATION: synthesis

<400> SEQUENCE: 6

```
atgccgcgcg ctccccgctg ccgagccgtg cgctccctgc tgcgcagcca ctaccgcgag    60
gtgctgccgc tggccacgtt cgtgcggcgc ctggggcccc agggctggcg gctggtgcag   120
cgcggggacc cggcggcttt ccgcgcgctg gtgcccagt gcctggtgtg cgtgccctgg    180
gacgcacggc cgccccccgc cgccccctcc ttccgccagg tgtcctgcct gaaggagctg   240
gtggcccgag tgctgcagag gctgtgcgag cgcggcgcga agaacgtgct ggccttcggc   300
ttcgcgctgc tggacggggc ccgcggggcc ccccccgagg ccttcaccac cagcgtgcgc   360
agctacctgc ccaacacggt gaccgacgca ctgcggggga gcggggcgtg ggggctgctg   420
ctgcgccgcg tgggcgacga cgtgctggtt cacctgctgg cacgctgcgc gctctttgtg   480
ctggtggctc ccagctgcgc ctaccaggtg tgcgggccgc cgctgtacca gctcggcgct   540
gccactcagg cccggccccc gccacacgct agtggacccc gaaggcgtct gggatgcgaa   600
cgggcctgga accatagcgt cagggaggcc ggggtccccc tgggcctgcc agccccgggt   660
gcgaggaggc gcggggcag tgccagccga agtctgccgt tgcccaagag gcccaggcgt   720
ggcgctgccc ctgagccgga gcggacgccc gttgggcagg gtcctgggcc caccccgggc   780
aggacgcgtg gaccgagtga ccgtggtttc tgtgtggtgt cacctgccag acccgccgaa   840
gaagccacct ctttggaggg tgcgctctct ggcacgcgcc actccacccc atccgtgggc   900
cgccagcacc acgcgggccc cccatccaca tcgcggccac cacgtccctg ggacacgcct   960
tgtccccgg tgtacgccga gaccaagcac ttcctctact cctcaggcga caaggagcag  1020
ctgcggccct ccttcctact cagctctctg aggcccagcc tgactggcgc tcggaggctc  1080
gtggagacca tctttctggg ttccaggccc tggatgccag gactccccg caggttgccc  1140
cgcctgcccc agcgctactg gcaaatgcgg ccctgttc tggagctgct tgggaaccac  1200
gcgcagtgcc cctacggggt gctcctcaag acgcactgcc cgctgcgagc tgcggtcacc  1260
ccagcagccg tgtctgtgc ccgggagaag ccccagggct ctgtggcggc ccccgaggag  1320
gaggacacag accccgtcg cctggtgcag ctgctccgcc agcacagcag ccctggcag   1380
gtgtacggct tcgtgcgggc ctgcctgcgc cggctggtgc cccaggcct ctggggctcc  1440
aggcacaacg aacgccgctt cctcaggaac accaagaagt tcatctccct ggggaagcat  1500
gccaagctct cgctgcagga gctgacgtgg aagatgagcg tgcgggactg cgcttggctg  1560
```

```
cgcaggagcc cagggggttgg ctgtgttccg gccgcagagc accgtctgcg tgaggagatc    1620
ctggccaagt tcctgcactg gctgatgagt gtgtacgtcg tcgagctgct caggtctttc    1680
ttttatgtca cggagaccac gtttcaaaag aacaggctct ttttctaccg gaagagtgtc    1740
tggagcaagt tgcaaagcat tggaatcaga cagcacttga gagggtgca gctgcgggag     1800 ctgtcggaag cagaggtcag gcagcatcgg gaagccaggc ccgccctgct gacgtccaga    1860
ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgccccg gcctcctggg cgcctctgtg    2040
ctgggcctgg acgatatcca cagggcctgg cgcaccttcg tgctgcgtgt gcgggcccag    2100
gacccgccgc ctgagctgta ctttgtcaag gtggatgtga cgggcgcgta cgacaccatc    2160
ccccaggaca ggctcacgga ggtcatcgcc agcatcatca accccagaa cacgtactgc     2220 gtgcgtcggt atgccgtggt ccagaaggcc gcccatgggc acgtccgcaa ggccttcaag    2280
agccacgtct ctaccttgac agacctccag ccgtacatgc gacagttcgt ggctcacctg    2340
caggagacca gcccgctgag gatgccgtc gtcatcgagc agagctcctc cctgaatgag     2400
gccagcagtg gcctcttcga cgtcttccta cgcttcatgt gccaccacgc cgtgcgcatc    2460
aggggcaagt cctacgtcca gtgccagggg atcccgcagg gctccatcct ctccacgctg    2520
ctctgcagcc tgtgctacgg cgacatggag aacaagctgt ttgcggggat tcggcgggac    2580
gggctgctcc tgcgtttggt ggatgatttc ttgttggtga cacctcacct cacccacgcg    2640
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
cagatgccgg cccacggcct attcccctgg tgcggcctgc tgctggatac ccggaccctg    2820
gaggtgcaga gcgactactc cagctatgcc cggacctcca tcagagccag tctcaccttc    2880
aaccgcggct tcaaggctgg gaggaacatg cgtcgcaaac tctttggggt cttgcggctg    2940
aagtgtcaca gcctgtttct ggatttgcag gtgaacagcc tccagacggt gtgcaccaac    3000
atctacaaga tcctcctgct gcaggcgtac aggtttcacg catgtgtgct gcagctccca    3060
tttcatcagc aagtttggaa gaacccccaca tttttcctgc gcgtcatctc tgacacggcc    3120
tccctctgct actccatcct gaaagccaag aacgcaggga tgtcgctggg ggccaagggc    3180
gccgccggcc ctctgccctc cgaggccgtg cagtggctgt gccaccaagc attcctgctc    3240
aagctgactc gacaccgtgt cacctacgtg ccactcctgg ggtcactcag acagcccag     3300 acgcagctga gtcggaagct cccggggacg acgctgactg ccctggaggc cgcagccaac    3360
ccggcactgc cctcagactt caagaccatc ctggactga                           3399
```

<210> SEQ ID NO 7
<211> LENGTH: 2127
<212> TYPE: DNA
<213> ORGANISM: Artificial Sequence
<220> FEATURE:
<223> OTHER INFORMATION: synthesis

<400> SEQUENCE: 7

```
atggataaag ttttaaacag agaggaatct ttgcagctaa tggaccttct aggtcttgaa     60
aggagtgcct gggggaatat tcctctgatg agaaaggcat attttaaaaaa atgcaaggag   120 tttcatcctg ataaaggagg agatgaagaa aaaatgaaga aatgaatac tctgtacaag    180
```

| | |
|---|---|
| aaaatggaag atggagtaaa atatgctcat caacctgact ttggaggctt ctgggatgca | 240 |
| actgagattc caacctatgg aactgatgaa tgggagcagt ggtggaatgc ctttaatgag | 300 |
| gaaaacctgt tttgctcaga agaaatgcca tctagtgatg atgaggctac tgctgactct | 360 |
| caacattcta ctcctccaaa aaagaagaga aaggtagaag accccaagga ctttccttca | 420 |
| gaattgctaa gttttttgag tcatgctgtg tttagtaata gaactcttgc ttgctttgct | 480 |
| atttacacca caaaggaaaa agctgcactg ctatacaaga aaattatgga aaaatattct | 540 |
| gtaaccttta taagtaggca taacagttat aatcataaca tactgttttt tcttactcca | 600 |
| cacaggcata gagtgtctgc tattaataac tatgctcaaa aattgtgtac ctttagcttt | 660 |
| ttaatttgta aaggggttaa taaggaatat ttgatgtata gtgccttgac tagagatcca | 720 |
| tttttctgtta ttgaggaaag tttgccaggt gggttaaagg agcatgattt taatccagaa | 780 |
| gaagcagagg aaactaaaca agtgtcctgg aagcttgtaa cagagtatgc aatggaaaca | 840 |
| aaatgtgatg atgtgttgtt attgcttggg atgtacttgg aatttcagta cagttttgaa | 900 |
| atgtgtttaa aatgtattaa aaaagaacag cccagccact ataagtacca tgaaaagcat | 960 |
| tatgcaaatg ctgctatatt tgctgacagc aaaaaccaaa aaccatatg ccaacaggct | 1020 |
| gttgatactg ttttagctaa aaagcgggtt gatagcctac aattaactag agaacaaatg | 1080 |
| ttaacaaaca gatttaatga tcttttggat aggatggata taatgtttgg ttctacaggc | 1140 |
| tctgctgaca tagaagaatg gatggctgga gttgcttggc tacactgttt gttgcccaaa | 1200 |
| atggattcag tggtgtatga cttttttaaaa tgcatggtgt acaacattcc taaaaaaaga | 1260 |
| tactggctgt ttaaaggacc aattgatagt ggtaaaacta cattagcagc tgctttgctt | 1320 |
| gaattatgtg gggggaaagc tttaaatgtt aatttgccct tggacaggct gaactttgag | 1380 |
| ctaggagtag ctattgacca gttttagta gttttgagg atgtaaaggg cactggaggg | 1440 |
| gagtccagag atttgccttc aggtcaggga attaataacc tggacaattt aagggattat | 1500 |
| ttggatggca gtgttaaggt aaacttagaa aagaaacacc taaataaaag aactcaaata | 1560 |
| tttcccctg aatagtcac catgaatgag tacagtgtgc ctaaaacact gcaggccaga | 1620 |
| tttgtaaaac aaatagattt taggcccaaa gattatttaa agcattgcct ggaacgcagt | 1680 |
| gagttttgt tagaaaagag aataattcaa agtggcattg ctttgcttct tatgttaatt | 1740 |
| tggtacagac ctgtggctga gtttgctcaa agtattcaga gcagaattgt ggagtggaaa | 1800 |
| gagagattgg acaaagagtt tagtttgtca gtgtatcaaa aaatgaagtt taatgtggct | 1860 |
| atgggaattg gagtttttaga ttggctaaga aacagtgatg atgatgatga agacagccag | 1920 |
| gaaaatgctg ataaaaatga agatggtggg gagaagaaca tggaagactc agggcatgaa | 1980 |
| acaggcattg attcacagtc ccaaggctca tttcaggccc ctcagtcctc acagtctgtt | 2040 |
| catgatcata atcagccata ccacatttgt agaggtttta cttgctttaa aaaacctccc | 2100 |
| acacctcccc ctgaacctga aacataa | 2127 |

<210> SEQ ID NO 8
<211> LENGTH: 7902
<212> TYPE: DNA
<213> ORGANISM: Artificial Sequence
<220> FEATURE:
<223> OTHER INFORMATION: synthesis

<400> SEQUENCE: 8

| | |
|---|---|
| gtcgacacta gtaatcaacc tctgattac aaaatttgtg aaagattgac tggtattctt | 60 |
| aactatgttg ctccttttac gctatgtgga tacgctgctt taatgccttt gtatcatgct | 120 |

```
attgcttccc gtatggcttt cattttctcc tccttgtata aatcctggtt gctgtctctt      180
tatgaggagt tgtggcccgt tgtcaggcaa cgtggcgtgg tgtgcactgt gtttgctgac      240
gcaaccccca ctggttgggg cattgccacc acctgtcagc tcctttccgg gactttcgct      300
ttccccctcc ctattgccac ggcggaactc atcgccgcct gccttgcccg ctgctggaca      360
ggggctcggc tgttgggcac tgacaattcc gtggtgttgt cggggaagct gacgtccttt      420
ccatggctgc tcgcctgtgt tgccacctgg attctgcgcg ggacgtcctt ctgctacgtc      480
ccttcggccc tcaatccagc ggaccttcct cccgcggcc tgctgccggc tctgcggcct       540
cttccgcgtc ttcgccttcg ccctcagacg agtcggatct ccctttgggc cgcctccccg      600
cctgccgcgg aattcgagct cggtaccttt aagaccaatg acttacaagg cagctgtaga      660
tcttagccac ttttttaaaag aaaaggggggg actggaaggg ctaattcact cccaacgaag    720
acaagatctg cttttttgctt gtactgagtc tctctggtta gaccagatct gagcctggga    780
gctctctggc taactaggga acccactgct taagcctcaa taaagcttgc cttgagtgct      840
tcaagtagtg tgtgcccgtc tgttgtgtga ctctggtaac tagagatccc tcagaccctt      900
ttagtcagtg tggaaaatct ctagcagtag tagttcatgt catcttatta ttcagtattt      960
ataacttgca aagaaatgaa tatcagagag tgagaggaac ttgtttattg cagcttataa     1020
tggttacaaa taaagcaata gcatcacaaa tttcacaaat aaagcatttt ttcactgca      1080
ttctagttgt ggtttgtcca aactcatcaa tgtatcttat catgtctggc tctagctatc     1140
ccgcccctaa ctccgcccat cccgcccta actccgccca gttccgccca ttctccgccc     1200
catggctgac taatttttttt tatttatgca gaggccgagg ccgcctcggc ctctgagcta    1260
ttccagaagt agtgaggagg cttttttgga ggcctaggga cgtacccaat cgccctata    1320
gtgagtcgta ttacgcgcgc tcactggccg tcgttttaca acgtcgtgac tgggaaaacc    1380
ctggcgttac ccaacttaat cgccttgcag cacatccccc tttcgccagc tggcgtaata    1440
gcgaagaggc ccgcaccgat cgcccttccc aacagttgcg cagcctgaat ggcgaatggg    1500
acgcgcctg tagcggcgca ttaagcgcgg cgggtgtggt ggttacgcgc agcgtgaccg     1560
ctacacttgc cagcgcccta gcgcccgctc ctttcgcttt cttcccttcc tttctcgcca    1620
cgttcgccgg ctttccccgt caagctctaa atcgggggct ccctttaggg ttccgattta    1680
gtgctttacg gcacctcgac cccaaaaaac ttgattaggg tgatggttca cgtagtgggc    1740
catcgccctg atagacggtt tttcgccctt tgacgttgga gtccacgttc tttaatagtg    1800
gactcttgtt ccaaactgga acaacactca accctatctc ggtctattct tttgatttat    1860
aagggatttt gccgatttcg gcctattggt taaaaaatga gctgatttaa caaaaattta    1920
acgcgaattt taacaaaata ttaacgctta caatttaggt ggcactttc ggggaaatgt     1980
gcgcggaacc cctatttgtt tatttttcta aatacattca aatatgtatc cgctcatgag    2040
acaataaccc tgataaatgc ttcaataata ttgaaaagg aagagtatga gtattcaaca     2100
tttccgtgtc gcccttattc cctttttgc ggcattttgc cttcctgttt tgctcaccc      2160
agaaacgctg gtgaaagtaa agatgctga agatcagttg ggtgcacgag tgggttacat     2220
cgaactggat ctcaacagcg gtaagatcct tgagagtttt cgccccgaag aacgttttcc    2280
aatgatgagc acttttaaag ttctgctatg tggcgcggta ttatcccgta ttgacgccgg    2340
gcaagagcaa ctcggtcgcc gcatacacta ttctcagaat gacttggttg agtactcacc    2400
agtcacagaa aagcatctta cggatggcat gacagtaaga gaattatgca gtgctgccat    2460
```

```
aaccatgagt gataacactg cggccaactt acttctgaca acgatcggag gaccgaagga    2520
gctaaccgct tttttgcaca acatggggga tcatgtaact cgccttgatc gttgggaacc    2580
ggagctgaat gaagccatac caaacgacga gcgtgacacc acgatgcctg tagcaatggc    2640
aacaacgttg cgcaaactat taactggcga actacttact ctagcttccc ggcaacaatt    2700
aatagactgg atggaggcgg ataaagttgc aggaccactt ctgcgctcgg cccttccggc    2760
tggctggttt attgctgata atctggagc cggtgagcgt ggctctcgcg gtatcattgc     2820
agcactgggg ccagatggta agccctcccg tatcgtagtt atctacacga cggggagtca    2880
ggcaactatg gatgaacgaa atagacagat cgctgagata ggtgcctcac tgattaagca    2940
ttggtaactg tcagaccaag tttactcata tatactttag attgatttaa aacttcattt    3000
ttaatttaaa aggatctagg tgaagatcct tttgataat ctcatgacca aaatccctta     3060
acgtgagttt tcgttccact gagcgtcaga ccccgtagaa aagatcaaag gatcttcttg    3120
agatcctttt tttctgcgcg taatctgctg cttgcaaaca aaaaaaccac cgctaccagc    3180
ggtggtttgt ttgccggatc aagagctacc aactcttttt ccgaaggtaa ctggcttcag    3240
cagagcgcag ataccaaata ctgttcttct agtgtagccg tagttaggcc accacttcaa    3300
gaactctgta gcaccgccta catacctcgc tctgctaatc ctgttaccag tggctgctgc    3360
cagtggcgat aagtcgtgtc ttaccgggtt ggactcaaga cgatagttac cggataaggc    3420
gcagcggtcg ggctgaacgg ggggttcgtg cacacagccc agcttggagc gaacgaccta    3480
caccgaactg agatacctac agcgtgagct atgagaaagc gccacgcttc ccgaagggag    3540
aaaggcggac aggtatccgg taagcggcag ggtcggaaca ggagagcgca cgagggagct    3600
tccaggggga aacgcctggt atctttatag tcctgtcggg tttcgccacc tctgacttga    3660
gcgtcgattt tgtgatgct cgtcaggggg cggagccta tggaaaaacg ccagcaacgc      3720 ggcctttta cggttcctgg cctttgctg gccttttgct cacatgttct ttcctgcgtt      3780 atccctgat tctgtggata accgtattac cgcctttgag tgagctgata ccgctcgccg     3840
cagccgaacg accgagcgca gcgagtcagt gagcgaggaa gcggaagagc gcccaatacg    3900
caaaccgcct ctccccgcgc gttggccgat tcattaatgc agctggcacg acaggtttcc    3960
cgactggaaa gcgggcagtg agcgcaacgc aattaatgtg agttagctca ctcattaggc    4020
accccaggct ttacacttta tgcttccggc tcgtatgttg tgtggaattg tgagcggata    4080
acaatttcac acaggaaaca gctatgacca tgattacgcc aagcgcgcaa ttaaccctca    4140
ctaaagggaa caaagctgg agctgcaagc ttaatgtagt cttatgcaat actcttgtag     4200
tcttgcaaca tggtaacgat gagttagcaa catgccttac aaggagagaa aaagcaccgt    4260
gcatgccgat tggtggaagt aaggtggtac gatcgtgcct tattaggaag gcaacagacg    4320
ggtctgacat ggattggacg aaccactgaa ttgccgcatt gcagagatat tgtatttaag    4380
tgcctagctc gatacataaa cggctctctc tggttagacc agatctgagc ctgggagctc    4440
tctggctaac tagggaaccc actgcttaag cctcaataaa gcttgccttg agtgcttcaa    4500
gtagtgtgtg cccgtctgtt gtgtgactct ggtaactaga tccctcag accctttag       4560 tcagtgtgga aaatctctag cagtggcgcc cgaacaggga cttgaaagcg aaagggaaac    4620
cagaggagct ctctcgacgc aggactcggc ttgctgaagc gcgcacggca agaggcgagg    4680
ggcggcgact ggtgagtacg ccaaaaattt tgactagcgg aggctagaag gagagagatg    4740
ggtgcgagag cgtcagtatt aagcggggga gaattagatc gcgatgggaa aaaattcggt    4800
taaggccagg gggaaagaaa aaatataaat taaaacatat agtatgggca agcagggagc    4860
```

```
tagaacgatt cgcagttaat cctggcctgt tagaaacatc agaaggctgt agacaaatac    4920
tgggacagct acaaccatcc cttcagacag gatcagaaga acttagatca ttatataata    4980
cagtagcaac cctctattgt gtgcatcaaa ggatagagat aaaagacacc aaggaagctt    5040
tagacaagat agaggaagag caaaacaaaa gtaagaccac cgcacagcaa gcggccgctg    5100
atcttcagac ctggaggagg agatatgagg gacaattgga gaagtgaatt atataaatat    5160
aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tgggcgcagc gtcaatgacg ctgacggtac aggccagaca attattgtct    5340
ggtatagtgc agcagcagaa caatttgctg agggctattg aggcgcaaca gcatctgttg    5400
caactcacag tctggggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg gaatcacacg    5580
acctggatgg agtgggacag agaaattaac aattacacaa gcttaataca ctccttaatt    5640
gaagaatcgc aaaaccagca agaaaagaat gaacaagaat tattggaatt agataaatgg    5700
gcaagtttgt ggaattggtt taacataaca aattggctgt ggtatataaa attattcata    5760
atgatagtag gaggcttggt aggtttaaga atagttttg ctgtactttc tatagtgaat    5820
agagttaggc agggatattc accattatcg tttcagaccc acctcccaac cccgagggga    5880
cccgacaggc ccgaaggaat agaagaagaa ggtggagaga gagacagaga cagatccatt    5940
cgattagtga acggatctcg acggtatcga tcacgagact agcctcgaca caaatggcag    6000
tattcatcca caattttaaa agaaaagggg ggattggggg gtacagtgca ggggaaagaa    6060
tagtagacat aatagcaaca gacatacaaa ctaaagaatt acaaaaacaa attacaaaaa    6120
ttcaaaattt tcgggtttat tacagggaca gcagaaatcc actttggctc gagaagcttg    6180
atatcggctc cggtgcccgt cagtgggcag agcgcacatc gcccacagtc cccgagaagt    6240
tggggggagg ggtcggcaat tgaaccggtg cctagagaag gtggcgcggg gtaaactggg    6300
aaagtgatgt cgtgtactgg ctccgccttt ttcccgaggg tggggagaa ccgtatataa    6360 gtgcagtagt cgccgtgaac gttcttttc gcaacgggtt tgccgccaga acacaggatc    6420
cgccaccatg gccttaccag tgaccgcctt gctcctgccg ctggccttgc tgctccacgc    6480
cgccaggccg gatatccaga tgacccagag cccgagcagc ctgagcgcga gcgtgggtga    6540
tcgcgtgacc attcctgca gggcaagtca ggacattagt aaatatttaa attggtatca    6600
gcagaaaccg ggtaaagcgc cgaaactgtt aatttatcat acatcaagat tacactcagg    6660
cgtgccgtcg cgttttagcg gctcgggttc gggcaccgat tttaccctga ccatctcgag    6720
cttgcagccg gaggacttcg ccacctacta ttgccaacag ggtaatacgc ttccgtacac    6780
gttcggtcag ggcaccaaag tggagatcaa aggtggcggt ggctcgggcg gtggtgggtc    6840
gggtggcggc ggatctgagg tgcagctggt ggagtctggg ggaggcttgg tacagcctgg    6900
ggggtccctg agactctcct gtgcagcctc tggagtgtcc ctgcctgatt atggcgtgtc    6960
ctgggtccgc caggctccag ggaaggggct ggagtggtt tcagtgatct ggggcagcga    7020
gacaacctac tacaacagcg ccctgaagtc ccgattcacc atctccagag acaatgccaa    7080
gaactcactg tatctgcaaa tgaacagcct gagagccgag gacacggctg tgtattactg    7140
tgcgaagcac tactactacg gcggcagcta cgctatggac tactggggcc aaggaaccct    7200
```

| | |
|---|---|
| ggtcaccgtg tcctcaacca cgacgccagc gccgcgacca ccaacaccgg cgcccaccat | 7260 |
| cgcgtcgcag cccctgtccc tgcgcccaga ggcgtgccgg ccagcggcgg ggggcgcagt | 7320 |
| gcacacgagg gggctggact tcgcctgtga tatctacatc tgggcgccct tggccgggac | 7380 |
| ttgtggggtc cttctcctgt cactggttat caccctttac tgcaaacggg cagaaagaa | 7440 |
| actcctgtat atattcaaac aaccatttat gagaccagta caaactactc aagaggaaga | 7500 |
| tggctgtagc tgccgatttc cagaagaaga agaaggagga tgtgaactga gagtgaagtt | 7560 |
| cagcaggagc gcagacgccc ccgcgtacaa gcagggccag aaccagctct ataacgagct | 7620 |
| caatctagga cgaagagagg agtacgatgt tttggacaag aggcgtggcc gggaccctga | 7680 |
| gatgggggga aagccgagaa ggaagaaccc tcaggaaggc ctgtacaatg aactgcagaa | 7740 |
| agataagatg gcggaggcct acagtgagat tgggatgaaa ggcgagcgcc ggaggggcaa | 7800 |
| ggggcacgat ggccttacc agggtctcag tacagccacc aaggacacct cgacgccct | 7860 |
| tcacatgcag gccctgcccc ctcgctaatc tagaggcgcg cc | 7902 |

<210> SEQ ID NO 9
<211> LENGTH: 9162
<212> TYPE: DNA
<213> ORGANISM: Artificial Sequence
<220> FEATURE:
<223> OTHER INFORMATION: synthesis

<400> SEQUENCE: 9

| | |
|---|---|
| cctctccctc ccccccccct aacgttactg gccgaagccg cttggaataa ggccggtgtg | 60 |
| cgtttgtcta tatgttattt tccaccatat tgccgtcttt tggcaatgtg agggcccgga | 120 |
| aacctggccc tgtcttcttg acgagcattc ctaggggtct ttcccctctc gccaaggaa | 180 |
| tgcaaggtct gttgaatgtc gtgaaggaag cagttcctct ggaagcttct tgaagacaaa | 240 |
| caacgtctgt agcgaccctt tgcaggcagc ggaacccccc acctggcgac aggtgcctct | 300 |
| gcggccaaaa gccacgtgta taagatacac ctgcaaaggc ggcacaaccc cagtgccacg | 360 |
| ttgtgagttg gatagttgtg gaaagagtca atggctctc ctcaagcgta ttcaacaagg | 420 |
| ggctgaagga tgcccagaag gtaccccatt gtatgggatc tgatctgggg cctcggtaca | 480 |
| catgctttac atgtgtttag tcgaggttaa aaaaacgtct aggccccccg aaccacgggg | 540 |
| acgtggtttt cctttgaaaa acacgatgat aatatggcca caaccatgca gatcccacag | 600 |
| gcgccctggc cagtcgtctg ggcggtgcta caactgggct ggcggccagg atggttctta | 660 |
| gactccccag acaggccctg gaaccccccc accttctccc cagccctgct cgtggtgacc | 720 |
| gaagggacca acgccaccct cacctgcagc ttctccaaca catcggagag cttcgtgcta | 780 |
| aactggtacc gcatgagccc cagcaaccag acggacaagc tggccgcctt ccccgaggac | 840 |
| cgcagccagc ccggccagga ctgccgcttc cgtgtcacac aactgcccaa cgggcgtgac | 900 |
| ttccacatga gcgtggtcag ggccggcgc aatgacagcg gcacctacct ctgtggggcc | 960 |
| atctccctgg cccccaaggc gcagatcaaa gagagcctgc gggcagagct cagggtgaca | 1020 |
| gagagaaggg cagaagtgcc cacagcccac cccagcccct cacccaggcc agccggccag | 1080 |
| ttccaaaccc tggtggttgg tgtcgtgggc ggcctgctgg gcagcctggt gctgctagtc | 1140 |
| tgggtcctgg ccgtcatctg ctcccgggcc gcacgaggga caatagatta caaggatgac | 1200 |
| gacgataagg attacaagga tgacgacgat aaggattaca aggatgacga cgataagtaa | 1260 |
| gtcgacacta gtaatcaacc tctggattac aaaatttgtg aaagattgac tggtattctt | 1320 |
| aactatgttg ctccttttac gctatgtgga tacgctgctt taatgccttt gtatcatgct | 1380 |

```
attgcttccc gtatggcttt cattttctcc tccttgtata aatcctggtt gctgtctctt    1440
tatgaggagt tgtggcccgt tgtcaggcaa cgtggcgtgg tgtgcactgt gtttgctgac    1500
gcaaccccca ctggttgggg cattgccacc acctgtcagc tcctttccgg actttcgct    1560 ttcccctcc ctattgccac ggcggaactc atcgccgcct gccttgcccg ctgctggaca    1620
ggggctcggc tgttgggcac tgacaattcc gtggtgttgt cggggaagct gacgtccttt    1680
ccatggctgc tcgcctgtgt tgccacctgg attctgcgcg ggacgtcctt ctgctacgtc    1740
ccttcggccc tcaatccagc ggaccttcct tcccgcggcc tgctgccggc tctgcggcct    1800
cttccgcgtc ttcgccttcg ccctcagacg agtcggatct ccctttgggc cgcctccccg    1860
cctgccgcgg aattcgagct cggtaccttt aagaccaatg acttacaagg cagctgtaga    1920
tcttagccac tttttaaaag aaaaggggggg actggaaggg ctaattcact cccaacgaag    1980
acaagatctg cttttttgctt gtactgagtc tctctggtta gaccagatct gagcctggga    2040
gctctctggc taactaggga acccactgct taagcctcaa taaagcttgc cttgagtgct    2100
tcaagtagtg tgtgcccgtc tgttgtgtga ctctggtaac tagagatccc tcagaccctt    2160
ttagtcagtg tggaaaatct ctagcagtag tagttcatgt catcttatta ttcagtattt    2220
ataacttgca aagaaatgaa tatcagagag tgagaggaac ttgtttattg cagcttataa    2280
tggttacaaa taaagcaata gcatcacaaa tttcacaaat aaagcatttt ttcactgca    2340 ttctagttgt ggtttgtcca aactcatcaa tgtatcttat catgtctggc tctagctatc    2400
ccgcccctaa ctccgcccat cccgcccta actccgccca gttccgccca ttctccgccc    2460
catggctgac taatttttt tatttatgca gaggccgagg ccgcctcggc ctctgagcta    2520
ttccagaagt agtgaggagg ctttttggga ggcctaggga cgtacccaat cgccctata    2580 gtgagtcgta ttacgcgcgc tcactggccg tcgttttaca acgtcgtgac tgggaaaacc    2640
ctggcgttac ccaacttaat cgccttgcag cacatcccc tttcgccagc tggcgtaata    2700
gcgaagaggc ccgcaccgat cgcccttccc aacagttgcg cagcctgaat ggcgaatggg    2760 acgcgcctg tagcgcgca ttaagcgcgg cgggtgtggt ggttacgcgc agcgtgaccg    2820
ctacacttgc cagcgcccta gcgcccgctc ctttcgcttt cttcccttcc tttctcgcca    2880
cgttcgccgg cttccccgt caagctctaa atcgggggct cccttaaggg ttccgattta    2940
gtgctttacg gcacctcgac cccaaaaaac ttgattaggg tgatggttca cgtagtgggc    3000
catcgccctg atagacggtt tttcgccctt tgacgttgga gtccacgttc tttaatagtg    3060
gactcttgtt ccaaactgga acaacactca accctatctc ggtctattct tttgatttat    3120
aagggatttt gccgatttcg gcctattggt taaaaatga gctgatttaa caaaaattta    3180
acgcgaattt taacaaaata ttaacgctta caatttaggt ggcactttc ggggaaatgt    3240 gcgcggaacc cctatttgtt tatttttcta atacattca aatatgtatc cgctcatgag    3300
acaataaccc tgataaatgc ttcaataata ttgaaaagg aagagtatga gtattcaaca    3360
tttccgtgtc gcccttattc ccttttttgc ggcattttgc cttcctgttt ttgctcaccc    3420
agaaacgctg gtgaaagtaa aagatgctga agatcagttg ggtgcacgag tgggttacat    3480
cgaactggat ctcaacagcg gtaagatcct tgagagtttt cgccccgaag aacgttttcc    3540
aatgatgagc acttttaaag ttctgctatg tggcgcggta ttatcccgta ttgacgccgg    3600
gcaagagcaa ctcggtcgcc gcatacacta ttctcagaat gacttggttg agtactcacc    3660
agtcacagaa aagcatctta cggatggcat gacagtaaga gaattatgca gtgctgccat    3720
```

```
aaccatgagt gataacactg cggccaactt acttctgaca acgatcggag gaccgaagga    3780
gctaaccgct tttttgcaca acatgggggga tcatgtaact cgccttgatc gttgggaacc   3840
ggagctgaat gaagccatac caaacgacga gcgtgacacc acgatgcctg tagcaatggc    3900
aacaacgttg cgcaaactat taactggcga actacttact ctagcttccc ggcaacaatt    3960
aatagactgg atggaggcgg ataaagttgc aggaccactt ctgcgctcgg cccttccggc    4020
tggctggttt attgctgata aatctggagc cggtgagcgt ggctctcgcg gtatcattgc    4080
agcactgggg ccagatggta agccctcccg tatcgtagtt atctacacga cggggagtca    4140
ggcaactatg gatgaacgaa atagacagat cgctgagata ggtgcctcac tgattaagca    4200
ttggtaactg tcagaccaag tttactcata tatactttag attgatttaa aacttcattt    4260
ttaatttaaa aggatctagg tgaagatcct tttttgataat ctcatgacca aaatccctta   4320
acgtgagttt tcgttccact gagcgtcaga ccccgtagaa aagatcaaag gatcttcttg    4380
agatccttt tttctgcgcg taatctgctg cttgcaaaca aaaaaaccac cgctaccagc     4440
ggtggtttgt ttgccggatc aagagctacc aactcttttt ccgaaggtaa ctggcttcag    4500
cagagcgcag ataccaaata ctgttcttct agtgtagccg tagttaggcc accacttcaa    4560
gaactctgta gcaccgccta catacctcgc tctgctaatc ctgttaccag tggctgctgc    4620
cagtggcgat aagtcgtgtc ttaccgggtt ggactcaaga cgatagttac cggataaggc    4680
gcagcggtcg ggctgaacgg ggggttcgtg cacacagccc agcttggagc gaacgaccta    4740
caccgaactg agatacctac agcgtgagct atgagaaagc gccacgcttc ccgaagggag    4800
aaaggcggac aggtatccgg taagcggcag ggtcggaaca ggagagcgca cgagggagct    4860
tccaggggga aacgcctggt atctttatag tcctgtcggg tttcgccacc tctgacttga    4920
gcgtcgattt tgtgatgct cgtcaggggg gcggagccta tggaaaaacg ccagcaacgc     4980
ggccttttta cggttcctgg ccttttgctg ccttttgct cacatgttct ttcctgcgtt     5040
atcccctgat tctgtggata accgtattac cgcctttgag tgagctgata ccgctcgccg    5100
cagccgaacg accgagcgca gcgagtcagt gagcgaggaa gcggaagagc gcccaatacg    5160
caaaccgcct ctccccgcgc gttggccgat tcattaatgc agctggcacg acaggtttcc    5220
cgactggaaa gcgggcagtg agcgcaacgc aattaatgtg agttagctca ctcattaggc    5280
accccaggct ttacactttta tgcttccggc tcgtatgttg tgtggaattg tgagcggata   5340
acaatttcac acaggaaaca gctatgacca tgattacgcc aagcgcgcaa ttaaccctca    5400
ctaaagggaa caaagctgg agctgcaagc ttaatgtagt cttatgcaat actcttgtag     5460
tcttgcaaca tggtaacgat gagttagcaa catgccttac aaggagagaa aaagcaccgt    5520
gcatgccgat tggtggaagt aaggtggtac gatcgtgcct tattaggaag caacagacg     5580
ggtctgacat ggattggacg aaccactgaa ttgccgcatt gcagagatat tgtatttaag    5640
tgcctagctc gatacataaa cggctctctc tggttagacc agatctgagc ctgggagctc    5700
tctggctaac tagggaaccc actgcttaag cctcaataaa gcttgccttg agtgcttcaa    5760
gtagtgtgtg cccgtctgtt gtgtgactct ggtaactaga gatccctcag accccttttag   5820
tcagtgtgga aaatctctag cagtggcgcc cgaacaggga cttgaaagcg aaagggaaac    5880
cagaggagct ctctcgacgc aggactcggc ttgctgaagc gcgcacggca agaggcgagg    5940
ggcggcgact ggtgagtacg ccaaaaaattt tgactagcgg aggctagaag gagagagatg   6000
ggtgcgagag cgtcagtatt aagcggggga gaattagatc gcgatgggaa aaaattcggt    6060
taaggccagg gggaaagaaa aaatataaat taaaacatat agtatgggca agcagggagc    6120
```

```
tagaacgatt cgcagttaat cctggcctgt tagaaacatc agaaggctgt agacaaatac    6180
tgggacagct acaaccatcc cttcagacag gatcagaaga acttagatca ttatataata    6240
cagtagcaac cctctattgt gtgcatcaaa ggatagagat aaaagacacc aaggaagctt    6300
tagacaagat agaggaagag caaaacaaaa gtaagaccac cgcacagcaa gcggccgctg    6360
atcttcagac ctggaggagg agatatgagg gacaattgga gaagtgaatt atataaatat    6420
aaagtagtaa aaattgaacc attaggagta gcacccacca aggcaaagag aagagtggtg    6480
cagagagaaa aaagagcagt gggaatagga gctttgttcc ttgggttctt gggagcagca    6540
ggaagcacta tgggcgcagc gtcaatgacg ctgacggtac aggccagaca attattgtct    6600
ggtatagtgc agcagcagaa caatttgctg agggctattg aggcgcaaca gcatctgttg    6660
caactcacag tctggggcat caagcagctc caggcaagaa tcctggctgt ggaaagatac    6720
ctaaaggatc aacagctcct ggggatttgg ggttgctctg gaaaactcat ttgcaccact    6780
gctgtgcctt ggaatgctag ttggagtaat aaatctctgg aacagatttg gaatcacacg    6840
acctggatgg agtgggacag agaaattaac aattacacaa gcttaataca ctccttaatt    6900
gaagaatcgc aaaaccagca agaaaagaat gaacaagaat tattggaatt agataaatgg    6960
gcaagtttgt ggaattggtt taacataaca aattggctgt ggtatataaa attattcata    7020
atgatagtag gaggcttggt aggtttaaga atagttttg ctgtactttc tatagtgaat    7080
agagttaggc agggatattc accattatcg tttcagaccc acctcccaac cccgagggga    7140
cccgacaggc ccgaaggaat agaagaagaa ggtggagaga gagacagaga cagatccatt    7200
cgattagtga acggatctcg acggtatcga tcacgagact agcctcgaca caatggcag    7260 tattcatcca caattttaaa agaaaagggg ggattggggg gtacagtgca ggggaaagaa    7320
tagtagacat aatagcaaca gacatacaaa ctaaagaatt acaaaaacaa attacaaaaa    7380
ttcaaaattt tcgggtttat tacagggaca gcagaaatcc actttggctc gagaagcttg    7440
atatcggctc cggtgcccgt cagtgggcag agcgcacatc gcccacagtc cccgagaagt    7500
tggggggagg ggtcggcaat tgaaccggtg cctagagaag gtggcgcggg gtaaactggg    7560
aaagtgatgt cgtgtactgg ctccgccttt ttcccgaggg tggggagaa ccgtatataa    7620 gtgcagtagt cgccgtgaac gttcttttc gcaacgggtt tgccgccaga acacaggatc    7680
cgccaccatg gccttaccag tgaccgcctt gctcctgccg ctggccttgc tgctccacgc    7740
cgccaggccg gatatccaga tgacccagag cccgagcagc ctgagcgcga gcgtgggtga    7800
tcgcgtgacc attcctgca gggcaagtca ggacattagt aaatatttaa attggtatca    7860
gcagaaaccg ggtaaagcgc cgaaactgtt aatttatcat acatcaagat tacactcagg    7920
cgtgccgtcg cgttttagcg gctcgggttc gggcaccgat tttaccctga ccatctcgag    7980
cttgcagccg gaggacttcg ccacctacta ttgccaacag ggtaatacgc ttccgtacac    8040
gttcggtcag ggcaccaaag tggagatcaa aggtggcggt ggctcgggcg gtggtgggtc    8100
gggtggcggc ggatctgagg tgcagctggt ggagtctggg ggaggcttgg tacagcctgg    8160
ggggtccctg agactctcct gtgcagcctc tggagtgtcc ctgcctgatt atggcgtgtc    8220
ctgggtccgc caggctccag ggaaggggct ggagtgggtt tcagtgatct ggggcagcga    8280
gacaacctac tacaacagcg ccctgaagtc ccgattcacc atctccagag acaatgccaa    8340
gaactcactg tatctgcaaa tgaacagcct gagagccgag gacacggctg tgtattactg    8400
tgcgaagcac tactactacg gcggcagcta cgctatggac tactggggcc aaggaaccct    8460
```

```
ggtcaccgtg tcctcaacca cgacgccagc gccgcgacca ccaacaccgg cgcccaccat   8520
cgcgtcgcag cccctgtccc tgcgcccaga ggcgtgccgg ccagcggcgg ggggcgcagt   8580
gcacacgagg gggctggact tcgcctgtga tatctacatc tgggcgccct tggccgggac   8640 ttgtgggggtc cttctcctgt cactggttat cacccttac tgcaaacggg gcagaaagaa   8700
actcctgtat atattcaaac aaccatttat gagaccagta caaactactc aagaggaaga   8760
tggctgtagc tgccgatttc cagaagaaga agaaggagga tgtgaactga gagtgaagtt   8820
cagcaggagc gcagacgccc ccgcgtacaa gcagggccag aaccagctct ataacgagct   8880
caatctagga cgaagagagg agtacgatgt tttggacaag aggcgtggcc gggaccctga   8940
gatgggggga aagccgagaa ggaagaaccc tcaggaaggc ctgtacaatg aactgcagaa   9000
agataagatg gcggaggcct acagtgagat tgggatgaaa ggcgagcgcc ggaggggcaa   9060
ggggcacgat ggcctttacc agggtctcag tacagccacc aaggacacct acgacgccct   9120
tcacatgcag gccctgcccc ctcgctaatc tagaggcgcg cc                      9162
```

<210> SEQ ID NO 10
<211> LENGTH: 9354
<212> TYPE: DNA
<213> ORGANISM: Artificial Sequence
<220> FEATURE:
<223> OTHER INFORMATION: synthesis

<400> SEQUENCE: 10

```
cctctccctc cccccccct aacgttactg gccgaagccg cttggaataa ggccggtgtg   60
cgtttgtcta tatgttattt tccaccatat tgccgtcttt ggcaatgtg agggcccgga   120 aacctggccc tgtcttcttg acgagcattc ctaggggtct ttcccctctc gccaaggaa   180 tgcaaggtct gttgaatgtc gtgaaggaag cagttcctct ggaagcttct tgaagacaaa   240
caacgtctgt agcgaccctt tgcaggcagc ggaaccccc acctggcgac aggtgcctct   300
gcggccaaaa gccacgtgta taagatacac ctgcaaaggc ggcacaaccc cagtgccacg   360
ttgtgagttg atagttgtg gaaagagtca atggctctc ctcaagcgta ttcaacaagg   420
ggctgaagga tgcccagaag gtaccccatt gtatgggatc tgatctgggg cctcggtaca   480
catgctttac atgtgtttag tcgaggttaa aaaaacgtct aggccccccg aaccacgggg   540
acgtggtttt cctttgaaaa acacgatgat aatatggcca caaccatgca gatcccacag   600
gcgccctggc cagtcgtctg gcggtgcta caactgggct ggcggccagg atggttctta   660
gactccccag acaggccctg gaaccccccc accttctccc cagccctgct cgtggtgacc   720 gaagggggaca acgccacctt cacctgcagc ttctccaaca catcggagag cttcgtgcta   780
aactggtacc gcatgagccc cagcaaccag acggacaagc tggccgcctt ccccgaggac   840
cgcagccagc ccggccagga ctgccgcttc cgtgtcacac aactgcccaa cgggcgtgac   900
ttccacatga gcgtggtcag ggccggggc aatgacagcg gcacctacct ctgtggggcc   960
atctccctgg cccccaaggc gcagatcaaa gagagcctgc gggcagagct cagggtgaca   1020
gagagaaggg cagaagtgcc cacagcccac cccagcccct cacccaggcc agccggccag   1080
ttccaaaccc tggtggttgg tgtcgtgggc ggcctgctgg gcagcctggt gctgctagtc   1140
tgggtcctgg ccgtcatctg ctcccgggcc gcacgaggga cataggagc caggcgcacc   1200 ggccagcccc tgaaggagga cccctcagcc gtgcctgtgt tctctgtgga cgccggggag   1260
ctggatttcc agtggcgaga gaagaccccg gagcccccg tgcctgtgt ccctgagcag   1320 acggaggccg ccaccattgt ctttcctagc ggaatgggca cctcatcccc cgcccgcagg   1380
```

```
ggctcagctg acggccctcg gagtgcccag ccactgaggc ctgaggatgg acactgctct    1440
tggcccctct gagtcgacac tagtaatcaa cctctggatt acaaaatttg tgaaagattg    1500
actggtattc ttaactatgt tgctcctttt acgctatgtg gatacgctgc tttaatgcct    1560
ttgtatcatg ctattgcttc ccgtatggct ttcattttct cctccttgta taaatcctgg    1620
ttgctgtctc tttatgagga gttgtggccc gttgtcaggc aacgtggcgt ggtgtgcact    1680
gtgtttgctg acgcaacccc cactggttgg ggcattgcca ccacctgtca gctccttttcc   1740 gggactttcg ctttcccccct ccctattgcc acggcggaac tcatcgccgc ctgccttgcc   1800
cgctgctgga caggggctcg gctgttgggc actgacaatt ccgtggtgtt gtcggggaag    1860
ctgacgtcct ttccatggct gctcgcctgt gttgccacct ggattctgcg cgggacgtcc    1920
ttctgctacg tcccttcggc cctcaatcca gcggaccttc cttcccgcgg cctgctgccg    1980
gctctgcggc ctcttccgcg tcttcgcctt cgccctcaga cgagtcggat ctcccttttgg   2040 gccgcctccc cgcctgccgc ggaattcgag ctcggtacct taagaccaa tgacttacaa    2100 ggcagctgta gatcttagcc actttttaaa agaaaagggg ggactggaag gctaattca    2160 ctcccaacga agacaagatc tgcttttttgc ttgtactgag tctctctggt tagaccagat   2220
ctgagcctgg gagctctctg gctaactagg gaacccactg cttaagcctc aataaagctt    2280
gccttgagtg cttcaagtag tgtgtgcccg tctgttgtgt gactctggta actagagatc    2340
cctcagaccc ttttagtcag tgtggaaaat ctctagcagt agtagttcat gtcatcttat    2400
tattcagtat ttataacttg caaagaaatg aatatcagag agtgagagga acttgtttat    2460
tgcagcttat aatggttaca aataaagcaa tagcatcaca aatttcacaa ataaagcatt    2520
tttttcactg cattctagtt gtggtttgtc caaactcatc aatgtatctt atcatgtctg    2580
gctctagcta tcccgcccct aactccgccc atcccgcccc taactccgcc cagttccgcc    2640
cattctccgc cccatggctg actaattttt tttatttatg cagaggccga ggccgcctcg    2700
gcctctgagc tattccagaa gtagtgagga ggcttttttg gaggcctagg gacgtaccca    2760
attcgcccta tagtgagtcg tattacgcgc gctcactggc cgtcgtttta caacgtcgtg    2820
actgggaaaa ccctggcgtt acccaactta atcgccttgc agcacatccc cctttcgcca    2880
gctggcgtaa tagcgaagag gcccgcaccg atcgcccttc ccaacagttg cgcagcctga    2940
atggcgaatg ggacgcgccc tgtagcggcg cattaagcgc ggcgggtgtg gtggttacgc    3000
gcagcgtgac cgctacactt gccagcgccc tagcgcccgc tcctttcgct ttcttccctt    3060
cctttctcgc cacgttcgcc ggctttcccc gtcaagctct aaatcggggg ctccctttag    3120
ggttccgatt tagtgcttta cggcacctcg accccaaaaa acttgattag ggtgatggtt    3180
cacgtagtgg gccatcgccc tgatagacgg ttttcgccc tttgacgttg gagtccacgt    3240
tctttaatag tggactcttg ttccaaactg gaacaacact caaccctatc tcggtctatt    3300
cttttgattt ataagggatt tgccgattt cggcctattg gttaaaaaat gagctgattt    3360
aacaaaaatt taacgcgaat tttaacaaaa tattaacgct acaatttag gtggcacttt    3420 tcggggaaat gtgcgcggaa cccctatttg tttatttttc taaatacatt caaatatgta    3480
tccgctcatg agacaataac cctgataaat gcttcaataa tattgaaaaa ggaagagtat    3540
gagtattcaa catttccgtg tcgcccttat tccctttttt gcggcatttt gccttcctgt    3600
ttttgctcac ccagaaacgc tggtgaaagt aaaagatgct gaagatcagt tgggtgcacg    3660
agtgggttac atcgaactgg atctcaacag cggtaagatc cttgagagtt ttcgccccga    3720
```

```
agaacgtttt ccaatgatga gcacttttaa agttctgcta tgtggcgcgg tattatcccg    3780
tattgacgcc gggcaagagc aactcggtcg ccgcatacac tattctcaga atgacttggt    3840
tgagtactca ccagtcacag aaaagcatct tacggatggc atgacagtaa gagaattatg    3900
cagtgctgcc ataaccatga gtgataacac tgcggccaac ttacttctga caacgatcgg    3960
aggaccgaag gagctaaccg cttttttgca caacatgggg gatcatgtaa ctcgccttga    4020
tcgttgggaa ccgagctga atgaagccat accaaacgac gagcgtgaca ccacgatgcc    4080
tgtagcaatg gcaacaacgt tgcgcaaact attaactggc gaactactta ctctagcttc    4140
ccggcaacaa ttaatagact ggatggaggc ggataaagtt gcaggaccac ttctgcgctc    4200
ggcccttccg gctggctggt ttattgctga taaatctgga gccggtgagc gtggctctcg    4260
cggtatcatt gcagcactgg ggccagatgg taagccctcc cgtatcgtag ttatctacac    4320
gacggggagt caggcaacta tggatgaacg aaatagacag atcgctgaga taggtgcctc    4380
actgattaag cattggtaac tgtcagacca agtttactca tatatacttt agattgattt    4440
aaaacttcat ttttaattta aaaggatcta ggtgaagatc ctttttgata atctcatgac    4500
caaaatccct taacgtgagt tttcgttcca ctgagcgtca ccccgtag aaaagatcaa    4560
aggatcttct tgagatcctt ttttctgcg cgtaatctgc tgcttgcaaa caaaaaaacc    4620
accgctacca gcggtggttt gtttgccgga tcaagagcta ccaactcttt ttccgaaggt    4680
aactggcttc agcagagcgc agataccaaa tactgttctt ctagtgtagc cgtagttagg    4740
ccaccacttc aagaactctg tagcaccgcc tacatacctc gctctgctaa tcctgttacc    4800
agtggctgct gccagtggcg ataagtcgtg tcttaccggg ttggactcaa gacgatagtt    4860
accggataag gcgcagcggt cgggctgaac ggggggttcg tgcacacagc ccagcttgga    4920
gcgaacgacc tacaccgaac tgagatacct acagcgtgag ctatgagaaa gcgccacgct    4980
tcccgaaggg agaaaggcgg acaggtatcc ggtaagcggc agggtcggaa caggagagcg    5040
cacgagggag cttccagggg gaaacgcctg gtatctttat agtcctgtcg ggtttcgcca    5100
cctctgactt gagcgtcgat ttttgtgatg ctcgtcaggg gggcggagcc tatggaaaaa    5160
cgccagcaac gcggcctttt tacgttcct ggccttttgc tggccttttg ctcacatgtt    5220
ctttcctgcg ttatcccctg attctgtgga taaccgtatt accgcctttg agtgagctga    5280
taccgctcgc cgcagccgaa cgaccgagcg cagcgagtca gtgagcgagg aagcggaaga    5340
gcgcccaata cgcaaaccgc ctctccccgc gcgttggccg attcattaat gcagctggca    5400
cgacaggttt cccgactgga aagcgggcag tgagcgcaac gcaattaatg tgagttagct    5460
cactcattag gcaccccagg ctttacactt tatgcttccg gctcgtatgt tgtgtggaat    5520
tgtgagcgga taacaatttc acacaggaaa cagctatgac catgattacg ccaagcgcgc    5580
aattaaccct cactaaaggg aacaaaagct ggagctgcaa gcttaatgta gtcttatgca    5640
atactcttgt agtcttgcaa catggtaacg atgagttagc aacatgcctt acaaggagag    5700
aaaaagcacc gtgcatgccg attggtgaa gtaaggtggt acgatcgtgc cttattagga    5760
aggcaacaga cgggtctgac atggattgga cgaaccactg aattgccgca ttgcagagat    5820
attgtattta agtgcctagc tcgatacata aacggctctc tctggttaga ccagatctga    5880
gcctgggagc tctctggcta actagggaac ccactgctta agcctcaata aagcttgcct    5940
tgagtgcttc aagtagtgtg tgcccgtctg ttgtgtgact ctggtaacta gagatccctc    6000
agacccttttt agtcagtgtg gaaaatctct agcagtggcg cccgaacagg gacttgaaag    6060
cgaaagggaa accagaggag ctctctcgac gcaggactcg gcttgctgaa gcgcgcacgg    6120
```

```
caagaggcga ggggcggcga ctggtgagta cgccaaaaat tttgactagc ggaggctaga    6180
aggagagaga tgggtgcgag agcgtcagta ttaagcgggg gagaattaga tcgcgatggg    6240
aaaaaattcg gttaaggcca gggggaaaga aaaaatataa attaaaacat atagtatggg    6300
caagcaggga gctagaacga ttcgcagtta atcctggcct gttagaaaca tcagaaggct    6360
gtagacaaat actgggacag ctacaaccat cccttcagac aggatcagaa gaacttagat    6420
cattatataa tacagtagca accctctatt gtgtgcatca aaggatagag ataaaagaca    6480
ccaaggaagc tttagacaag atagaggaag agcaaaacaa aagtaagacc accgcacagc    6540
aagcggccgc tgatcttcag acctggagga ggagatatga gggacaattg agaagtgaa    6600 ttatataaat ataaagtagt aaaaattgaa ccattaggag tagcacccac caaggcaaag    6660
agaagagtgg tgcagagaga aaaaagagca gtgggaatag gagctttgtt ccttgggttc    6720
ttgggagcag caggaagcac tatgggcgca gcgtcaatga cgctgacggt acaggccaga    6780
caattattgt ctggtatagt gcagcagcag aacaatttgc tgagggctat tgaggcgcaa    6840
cagcatctgt tgcaactcac agtctggggc atcaagcagc tccaggcaag aatcctggct    6900
gtggaaagat acctaaagga tcaacagctc ctggggattt ggggttgctc tggaaaactc    6960
atttgcacca ctgctgtgcc ttggaatgct agttggagta ataaatctct ggaacagatt    7020
tggaatcaca cgacctggat ggagtgggac agagaaatta acaattacac aagcttaata    7080
cactccttaa ttgaagaatc gcaaaaccag caagaaaaga atgaacaaga attattggaa    7140
ttagataaat gggcaagttt gtggaattgg tttaacataa caattggct gtggtatata    7200 aaattattca taatgatagt aggaggcttg gtaggtttaa gaatagtttt tgctgtactt    7260
tctatagtga atagagttag gcagggatat tcaccattat cgtttcagac ccacctccca    7320 acccgagg gacccgacag gcccgaagga atagaagaag aaggtggaga gagagacaga    7380
gacagatcca ttcgattagt gaacggatct cgacggtatc gatcacgaga ctagcctcga    7440
cacaaatggc agtattcatc cacaatttta aagaaaagg ggggattggg gggtacagtg    7500
caggggaaag aatagtagac ataatagcaa cagacataca aactaaagaa ttacaaaaac    7560
aaattacaaa aattcaaaat tttcgggttt attacaggga cagcagaaat ccactttggc    7620
tcgagaagct tgatatcggc tccggtgccc gtcagtgggc agagcgcaca tcgcccacag    7680
tccccgagaa gttgggggga ggggtcggca attgaaccgg tgcctagaga aggtggcgcg    7740
gggtaaactg ggaaagtgat gtcgtgtact ggctccgcct ttttcccgag ggtgggggag    7800
aaccgtatat aagtgcagta gtcgccgtga acgttctttt tcgcaacggg tttgccgcca    7860
gaacacagga tccgccacca tggccttacc agtgaccgcc ttgctcctgc cgctggcctt    7920
gctgctccac gccgccaggc cggatatcca gatgacccag agcccagca gcctgagcgc    7980 gagcgtgggt gatcgcgtga ccattacctg cagggcaagt caggacatta gtaaatattt    8040
aaattggtat cagcagaaac cgggtaaagc gccgaaactg ttaatttatc atacatcaag    8100
attacactca ggcgtgccgt cgcgttttag cggctcgggt tcgggcaccg attttaccct    8160
gaccatctcg agcttgcagc cggaggactt cgccacctac tattgccaac agggtaatac    8220
gcttccgtac acgttcggtc agggcaccaa agtgagatc aaaggtggcg gtggctcggg    8280
cggtggtggg tcgggtggcg gcggatctga ggtgcagctg gtggagtctg ggggaggctt    8340
ggtacagcct gggggtccc tgagactctc ctgtgcagcc tctggagtgt ccctgcctga    8400
ttatggcgtg tcctgggtcc gccaggctcc agggaagggg ctggagtggg tttcagtgat    8460
```

| | |
|---|---|
| ctggggcagc gagacaacct actacaacag cgccctgaag tcccgattca ccatctccag | 8520 |
| agacaatgcc aagaactcac tgtatctgca aatgaacagc ctgagagccg aggacacggc | 8580 |
| tgtgtattac tgtgcgaagc actactacta cggcggcagc tacgctatgg actactgggg | 8640 |
| ccaaggaacc ctggtcaccg tgtcctcaac cacgacgcca gcgccgcgac caccaacacc | 8700 |
| ggcgcccacc atcgcgtcgc agcccctgtc cctgcgccca gaggcgtgcc ggccagcggc | 8760 |
| gggggcgca gtgcacacga gggggctgga cttcgcctgt gatatctaca tctgggcgcc | 8820 |
| cttggccggg acttgtgggg tccttctcct gtcactggtt atcaccctt actgcaaacg | 8880 |
| gggcagaaag aaactcctgt atatattcaa acaaccattt atgagaccag tacaaactac | 8940 |
| tcaagaggaa gatggctgta gctgccgatt ccagaagaa gaagaaggag gatgtgaact | 9000 |
| gagagtgaag ttcagcagga gcgcagacgc ccccgcgtac aagcagggcc agaaccagct | 9060 |
| ctataacgag ctcaatctag gacgaagaga ggagtacgat gttttggaca agaggcgtgg | 9120 |
| ccgggaccct gagatggggg gaaagccgag aaggaagaac cctcaggaag gcctgtacaa | 9180 |
| tgaactgcag aaagataaga tggcggaggc ctacagtgag attgggatga aaggcgagcg | 9240 |
| ccggaggggc aaggggcacg atggccttta ccagggtctc agtacagcca ccaaggacac | 9300 |
| ctacgacgcc cttcacatgc aggccctgcc ccctcgctaa tctagaggcg cgcc | 9354 |

<210> SEQ ID NO 11
<211> LENGTH: 7893
<212> TYPE: DNA
<213> ORGANISM: Artificial Sequence
<220> FEATURE:
<223> OTHER INFORMATION: synthesis

<400> SEQUENCE: 11

| | |
|---|---|
| gtcgacacta gtaatcaacc tctggattac aaaatttgtg aaagattgac tggtattctt | 60 |
| aactatgttg ctccttttac gctatgtgga tacgctgctt taatgccttt gtatcatgct | 120 |
| attgcttccc gtatggcttt cattttctcc tccttgtata atcctggtt gctgtctctt | 180 |
| tatgaggagt tgtggcccgt tgtcaggcaa cgtggcgtgg tgtgcactgt gtttgctgac | 240 |
| gcaaccccca ctggttgggg cattgccacc acctgtcagc tcctttccgg gactttcgct | 300 |
| ttccccctcc ctattgccac ggcggaactc atcgccgcct gccttgcccg ctgctggaca | 360 |
| ggggctcggc tgttgggcac tgacaattcc gtggtgttgt cggggaagct gacgtccttt | 420 |
| ccatggctgc tcgcctgtgt tgccacctgg attctgcgcg gacgtcctt ctgctacgtc | 480 |
| ccttcggccc tcaatccagc ggaccttcct tcccgcggcc tgctgccggc tctgcggcct | 540 |
| cttccgcgtc ttcgccttcg ccctcagacg agtcggatct ccctttgggc cgcctccccg | 600 |
| cctgccgcgg aattcgagct cggtaccttt aagaccaatg acttacaagg cagctgtaga | 660 |
| tcttagccac tttttaaaag aaaaggggg actggaaggg ctaattcact cccaacgaag | 720 |
| acaagatctg ctttttgctt gtactgagtc tctctggtta gaccagatct gagcctggga | 780 |
| gctctctggc taactaggga acccactgct taagcctcaa taaagcttgc cttgagtgct | 840 |
| tcaagtagtg tgtgcccgtc tgttgtgtga ctctggtaac tagagatccc tcagaccctt | 900 |
| ttagtcagtg tggaaaatct ctagcagtag tagttcatgt catcttatta ttcagtattt | 960 |
| ataacttgca aagaaatgaa tatcagagag tgagaggaac ttgtttattg cagcttataa | 1020 |
| tggttacaaa taaagcaata gcatcacaaa tttcacaaat aaagcatttt ttcactgca | 1080 |
| ttctagttgt ggtttgtcca aactcatcaa tgtatcttat catgtctggc tctagctatc | 1140 |
| ccgcccctaa ctccgcccat cccgccccta actccgccca gttccgccca ttctccgccc | 1200 |

```
catggctgac taatttttt  tatttatgca gaggccgagg ccgcctcggc ctctgagcta   1260
ttccagaagt agtgaggagg cttttttgga ggcctaggga cgtacccaat tcgccctata   1320
gtgagtcgta ttacgcgcgc tcactggccg tcgttttaca acgtcgtgac tgggaaaacc   1380
ctggcgttac ccaacttaat cgccttgcag cacatccccc tttcgccagc tggcgtaata   1440
gcgaagaggc ccgcaccgat cgcccttccc aacagttgcg cagcctgaat ggcgaatggg   1500
acgcgccctg tagcggcgca ttaagcgcgg cgggtgtggt ggttacgcgc agcgtgaccg   1560
ctacacttgc cagcgcccta gcgcccgctc ctttcgcttt cttcccttcc tttctcgcca   1620
cgttcgccgg ctttccccgt caagctctaa atcgggggct ccctttaggg ttccgattta   1680
gtgctttacg gcacctcgac cccaaaaaac ttgattaggg tgatggttca cgtagtgggc   1740
catcgccctg atagacggtt tttcgccctt tgacgttgga gtccacgttc tttaatagtg   1800
gactcttgtt ccaaactgga acaacactca accctatctc ggtctattct tttgatttat   1860
aagggatttt gccgatttcg gcctattggt taaaaaatga gctgatttaa caaaaattta   1920
acgcgaattt taacaaaata ttaacgctta caatttaggt ggcacttttc ggggaaatgt   1980
gcgcggaacc cctatttgtt tatttttcta aatacattca aatatgtatc cgctcatgag   2040
acaataaccc tgataaatgc ttcaataata ttgaaaaagg aagagtatga gtattcaaca   2100
tttccgtgtc gcccttattc cctttttttgc ggcattttgc cttcctgttt ttgctcaccc   2160
agaaacgctg gtgaaagtaa aagatgctga agatcagttg ggtgcacgag tgggttacat   2220
cgaactggat ctcaacagcg gtaagatcct tgagagtttt cgccccgaag aacgttttcc   2280
aatgatgagc acttttaaag ttctgctatg tggcgcggta ttatcccgta ttgacgccgg   2340
gcaagagcaa ctcggtcgcc gcatacacta ttctcagaat gacttggttg agtactcacc   2400
agtcacagaa aagcatctta cggatggcat gacagtaaga gaattatgca gtgctgccat   2460
aaccatgagt gataacactg cggccaactt acttctgaca acgatcggag gaccgaagga   2520
gctaaccgct ttttttgcaca acatggggga tcatgtaact cgccttgatc gttgggaacc   2580
ggagctgaat gaagccatac caaacgacga gcgtgacacc acgatgcctg tagcaatggc   2640
aacaacgttg cgcaaactat taactggcga actacttact ctagcttccc ggcaacaatt   2700
aatagactgg atggaggcgg ataaagttgc aggaccactt ctgcgctcgg cccttccggc   2760
tggctggttt attgctgata atctggagcc ggtgagcgt ggctctcgcg gtatcattgc   2820
agcactgggg ccagatggta agccctcccg tatcgtagtt atctacacga cggggagtca   2880
ggcaactatg gatgaacgaa atagacagat cgctgagata ggtgcctcac tgattaagca   2940
ttggtaactg tcagaccaag tttactcata tatactttag attgatttaa aacttcattt   3000
ttaatttaaa aggatctagg tgaagatcct ttttgataat ctcatgacca aaatccctta   3060
acgtgagttt tcgttccact gagcgtcaga ccccgtagaa aagatcaaag gatcttcttg   3120
agatcctttt tttctgcgcg taatctgctg cttgcaaaca aaaaaaccac cgctaccagc   3180
ggtggtttgt ttgccggatc aagagctacc aactcttttt ccgaaggtaa ctggcttcag   3240
cagagcgcag ataccaaata ctgttcttct agtgtagccg tagttaggcc accacttcaa   3300
gaactctgta gcaccgccta catacctcgc tctgctaatc ctgttaccag tggctgctgc   3360
cagtggcgat aagtcgtgtc ttaccgggtt ggactcaaga cgatagttac cggataaggc   3420
gcagcggtcg ggctgaacgg ggggttcgtg cacacagccc agcttggagc gaacgaccta   3480
caccgaactg agatacctac agcgtgagct atgagaaagc gccacgcttc ccgaagggag   3540
```

```
aaaggcggac aggtatccgg taagcggcag ggtcggaaca ggagagcgca cgagggagct    3600
tccaggggga aacgcctggt atctttatag tcctgtcggg tttcgccacc tctgacttga    3660
gcgtcgattt ttgtgatgct cgtcaggggg gcggagccta tggaaaaacg ccagcaacgc    3720 ggcttttta cggttcctgg cctttgctg gccttttgct cacatgttct ttcctgcgtt    3780
atcccctgat tctgtggata accgtattac cgcctttgag tgagctgata ccgctcgccg    3840
cagccgaacg accgagcgca gcgagtcagt gagcgaggaa gcggaagagc gcccaatacg    3900
caaaccgcct ctccccgcgc gttggccgat tcattaatgc agctggcacg acaggtttcc    3960
cgactggaaa gcgggcagtg agcgcaacgc aattaatgtg agttagctca ctcattaggc    4020
accccaggct ttacactta tgcttccggc tcgtatgttg tgtggaattg tgagcggata    4080
acaatttcac acaggaaaca gctatgacca tgattacgcc aagcgcgcaa ttaaccctca    4140
ctaaagggaa caaaagctgg agctgcaagc ttaatgtagt cttatgcaat actcttgtag    4200
tcttgcaaca tggtaacgat gagttagcaa catgccttac aaggagagaa aaagcaccgt    4260
gcatgccgat tggtggaagt aaggtggtac gatcgtgcct tattaggaag gaacagacg    4320 ggtctgacat ggattggacg aaccactgaa ttgccgcatt gcagagatat tgtatttaag    4380
tgcctagctc gatacataaa cggctctctc tggttagacc agatctgagc ctgggagctc    4440
tctggctaac tagggaaccc actgcttaag cctcaataaa gcttgccttg agtgcttcaa    4500
gtagtgtgtg cccgtctgtt gtgtgactct ggtaactaga gatccctcag accccttttag   4560 tcagtgtgga aaatctctag cagtggcgcc cgaacaggga cttgaaagcg aaagggaaac    4620
cagaggagct ctctcgacgc aggactcggc ttgctgaagc gcgcacggca agaggcgagg    4680
ggcggcgact ggtgagtacg ccaaaaattt tgactagcgg aggctagaag gagagagatg    4740
ggtgcgagag cgtcagtatt aagcggggga gaattagatc gcgatgggaa aaaattcggt    4800
taaggccagg gggaaagaaa aaatataaat taaaacatat agtatgggca agcagggagc    4860
tagaacgatt cgcagttaat cctggcctgt tagaaacatc agaaggctgt agacaaatac    4920
tgggacagct acaaccatcc cttcagacag gatcagaaga acttagatca ttatataata    4980
cagtagcaac cctctattgt gtgcatcaaa ggatagagat aaaagacacc aaggaagctt    5040
tagacaagat agaggaagag caaaacaaaa gtaagaccac cgcacagcaa gcggccgctg    5100
atcttcagac ctgaggagg agatatgagg gacaattgga gaagtgaatt atataaatat    5160
aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tgggcgcagc gtcaatgacg ctgacggtac aggccagaca attattgtct    5340
ggtatagtgc agcagcagaa caatttgctg agggctattg aggcgcaaca gcatctgttg    5400
caactcacag tctgggggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg gaatcacacg    5580
acctggatgg agtgggacag agaaattaac aattacacaa gcttaataca ctccttaatt    5640
gaagaatcgc aaaaccagca agaaaagaat gaacaagaat tattggaatt agataaatgg    5700
gcaagtttgt ggaattggtt taacataaca aattggctgt ggtatataaa attattcata    5760
atgatagtag gaggcttggt aggtttaaga atagttttg ctgtactttc tatagtgaat    5820
agagttaggc agggatattc accattatcg tttcagaccc acctcccaac cccgagggga    5880
cccgacaggc ccgaaggaat agaagaagaa ggtggagaga gagacagaga cagatccatt    5940
```

```
cgattagtga acggatctcg acggtatcga tcacgagact agcctcgaca caaatggcag    6000
tattcatcca caatttaaa agaaaagggg ggattggggg gtacagtgca ggggaaagaa    6060
tagtagacat aatagcaaca gacatacaaa ctaaagaatt acaaaaacaa attacaaaaa    6120
ttcaaaattt tcgggtttat tacagggaca gcagaaatcc actttggctc gagaagcttg    6180
atatcggctc cggtgcccgt cagtgggcag agcgcacatc gcccacagtc cccgagaagt    6240
tggggggagg ggtcggcaat tgaaccggtg cctagaaag gtggcgcggg gtaaactggg    6300
aaagtgatgt cgtgtactgg ctccgccttt tccccgaggg tgggggagaa ccgtatataa    6360
gtgcagtagt cgccgtgaac gttctttttc gcaacgggtt tgccgccaga acacaggatc    6420
cgccaccatg gccttaccag tgaccgcctt gctcctgccg ctggccttgc tgctccacgc    6480
cgccaggccg cagatcgtgc tgagccagag ccccgccatt ctgagcgcta gccccggcga    6540
gaaggtgacc atgacctgca gggccagcag cagcgtgagc tacatccact ggttccagca    6600
gaaacccggc agcagcccca agccctggat ctacgccacc agcaacctgg ccagcggagt    6660 gccccgtgaga tttagcggct ccggcagcgg cacctcctat tccctgacca tctccagggt    6720
ggaagccgaa gacgccgcca cctactactg ccagcagtgg accagcaacc cccctacctt    6780
tggcggcggc accaagctgg agattaaggg cggaggaagc ggaggaggaa gcggaggagg    6840
aagccaggtg cagctgcagc agcccggagc cgaactggtg aagcccggag ccagcgtgaa    6900
gatgtcctgt aaggcctccg gctacacctt cacctcctac aacatgcact gggtgaagca    6960
aacccctggc agaggcctgg agtggattgg cgccatctac cccggcaacg gcgacaccag    7020
ctacaaccag aagttcaagg gcaaggccac cctgaccgcc gacaaaagca gcagcaccgc    7080
ctatatgcag ctgagctccc tgacaagcga ggatagcgcc gtgtactact gcgccagaag    7140
cacctactac ggcggcgact ggtacttcaa cgtgtggggc gccggcacca cagtgacagt    7200
ggcctccacc acgacgccag cgccgcgacc accaacaccg gcgcccacca tcgcgtcgca    7260
gcccctgtcc ctgcgcccag aggcgtgccg gccagcggcg gggggcgcag tgcacacgag    7320
ggggctggac ttcgcctgtg atatctacat ctgggcgccc ttggccggga cttgtgggt    7380 ccttctcctg tcactggtta tcacccttta ctgcaaacgg ggcagaaaga aactcctgta    7440
tatattcaaa caaccattta tgagaccagt acaaactact caagaggaag atggctgtag    7500
ctgccgattt ccagaagaag aagaaggagg atgtgaactg agagtgaagt tcagcaggag    7560
cgcagacgcc cccgcgtaca gcagggccca gaaccagctc tataacgagc tcaatctagg    7620
acgaagagag gagtacgatg ttttggacaa gaggcgtggc cggaccctg agatgggggg    7680 aaagccgaga aggaagaacc ctcaggaagg cctgtacaat gaactgcaga agataagat    7740 ggcggaggcc tacagtgaga ttgggatgaa aggcagcgc cggaggggca aggggcacga    7800
tggcctttac cagggtctca gtacagccac caaggacacc tacgacgccc ttcacatgca    7860 ggcccctgccc cctcgctaat ctagaggcgc gcc                               7893
```

<210> SEQ ID NO 12
<211> LENGTH: 7902
<212> TYPE: DNA
<213> ORGANISM: Artificial Sequence
<220> FEATURE:
<223> OTHER INFORMATION: synthesis

<400> SEQUENCE: 12

```
gtcgacacta gtaatcaacc tctggattac aaaatttgtg aaagattgac tggtattctt    60
```

```
aactatgttg ctccttttac gctatgtgga tacgctgctt taatgccttt gtatcatgct    120
attgcttccc gtatggcttt cattttctcc tccttgtata aatcctggtt gctgtctctt    180
tatgaggagt tgtggcccgt tgtcaggcaa cgtggcgtgg tgtgcactgt gtttgctgac    240
gcaaccccca ctggttgggg cattgccacc acctgtcagc tcctttccgg gactttcgct    300 ttcccccctcc ctattgccac ggcggaactc atcgccgcct gccttgcccg ctgctggaca    360
ggggctcggc tgttgggcac tgacaattcc gtggtgttgt cggggaagct gacgtccttt    420
ccatggctgc tcgcctgtgt tgccacctgg attctgcgcg ggacgtcctt ctgctacgtc    480
ccttcggccc tcaatccagc ggaccttcct tcccgcggcc tgctgccggc tctgcggcct    540
cttccgcgtc ttcgccttcg ccctcagacg agtcggatct cccctttgggc cgcctccccg    600 cctgccgcgg aattcgagct cggtaccttt aagaccaatg acttacaagg cagctgtaga    660
tcttagccac ttttaaaag aaaggggggg actggaaggg ctaattcact cccaacgaag    720
acaagatctg cttttgctt gtactgagtc tctctggtta gaccagatct gagcctggga    780
gctctctggc taactaggga acccactgct taagcctcaa taaagcttgc cttgagtgct    840
tcaagtagtg tgtgcccgtc tgttgtgtga ctctggtaac tagagatccc tcagaccctt    900
ttagtcagtg tggaaaatct ctagcagtag tagttcatgt catcttatta ttcagtattt    960
ataacttgca agaaatgaa tatcagagag tgagaggaac ttgttttattg cagcttataa   1020 tggttacaaa taaagcaata gcatcacaaa tttcacaaat aaagcatttt tttcactgca   1080
ttctagttgt ggtttgtcca aactcatcaa tgtatcttat catgtctggc tctagctatc   1140
ccgcccctaa ctccgcccat cccgcccta actccgccca gttccgccca ttctccgccc   1200
catggctgac taattttttt tatttatgca gaggccgagg ccgcctcggc ctctgagcta   1260
ttccagaagt agtgaggagg ctttttttgga ggcctaggga cgtacccaat tcgccctata   1320
gtgagtcgta ttacgcgcgc tcactggccg tcgttttaca acgtcgtgac tgggaaaacc   1380
ctggcgttac ccaacttaat cgccttgcag cacatccccc tttcgccagc tggcgtaata   1440
gcgaagaggc ccgcaccgat cgcccttccc aacagttgcg cagcctgaat ggcgaatggg   1500
acgcgccctg tagcggcgca ttaagcgcgg cgggtgtggt ggttacgcgc agcgtgaccg   1560
ctacacttgc cagcgcccta gcgcccgctc ctttcgcttt cttcccttcc tttctcgcca   1620
cgttcgccgg ctttccccgt caagctctaa atcgggggct ccctttaggg ttccgattta   1680
gtgctttacg gcacctcgac cccaaaaaac ttgattaggg tgatggttca cgtagtgggc   1740
catcgccctg atagacggtt tttcgccctt tgacgttgga gtccacgttc tttaatagtg   1800
gactcttgtt ccaaactgga acaacactca accctatctc ggtctattct tttgatttat   1860
aagggatttt gccgatttcg gcctattggt taaaaatga gctgatttaa caaaaattta   1920
acgcgaattt taacaaaata ttaacgctta caatttaggt ggcacttttc ggggaaatgt   1980
gcgcggaacc cctatttgtt tatttttcta aatacattca aatatgtatc cgctcatgag   2040
acaataaccc tgataaatgc ttcaataata ttgaaaaagg aagagtatga gtattcaaca   2100
tttccgtgtc gcccttattc ccttttttgc ggcattttgc cttcctgttt tgctcaccc   2160 agaaacgctg tgaaagtaa agatgctga agatcagttg ggtgcacgag tgggttacat   2220
cgaactggat ctcaacagcg gtaagatcct tgagagtttt cgccccgaag aacgttttcc   2280
aatgatgagc acttttaaag ttctgctatg tggcgcggta ttatcccgta ttgacgccgg   2340
gcaagagcaa ctcggtcgcc gcatacacta ttctcagaat gacttggttg agtactcacc   2400
agtcacagaa aagcatctta cggatggcat gacagtaaga gaattatgca gtgctgccat   2460
```

```
aaccatgagt gataacactg cggccaactt acttctgaca acgatcggag gaccgaagga    2520
gctaaccgct tttttgcaca acatggggga tcatgtaact cgccttgatc gttgggaacc    2580
ggagctgaat gaagccatac caaacgacga gcgtgacacc acgatgcctg tagcaatggc    2640
aacaacgttg cgcaaactat taactggcga actacttact ctagcttccc ggcaacaatt    2700
aatagactgg atggaggcgg ataaagttgc aggaccactt ctgcgctcgg cccttccggc    2760
tggctggttt attgctgata atctggagc cggtgagcgt ggctctcgcg gtatcattgc    2820
agcactgggg ccagatggta agccctcccg tatcgtagtt atctacacga cggggagtca    2880
ggcaactatg gatgaacgaa atagacagat cgctgagata ggtgcctcac tgattaagca    2940
ttggtaactg tcagaccaag tttactcata tatactttag attgatttaa aacttcattt    3000
ttaatttaaa aggatctagg tgaagatcct ttttgataat ctcatgacca aaatccctta    3060
acgtgagttt tcgttccact gagcgtcaga ccccgtagaa aagatcaaag gatcttcttg    3120
agatcctttt tttctgcgcg taatctgctg cttgcaaaca aaaaaaccac cgctaccagc    3180
ggtggtttgt ttgccggatc aagagctacc aactcttttt ccgaaggtaa ctggcttcag    3240
cagagcgcag ataccaaata ctgttcttct agtgtagccg tagttaggcc accacttcaa    3300
gaactctgta gcaccgccta catacctcgc tctgctaatc ctgttaccag tggctgctgc    3360
cagtggcgat aagtcgtgtc ttaccgggtt ggactcaaga cgatagttac cggataaggc    3420
gcagcggtcg ggctgaacgg ggggttcgtg cacacagccc agcttggagc gaacgaccta    3480
caccgaactg agatacctac agcgtgagct atgagaaagc gccacgcttc ccgaagggag    3540
aaaggcggac aggtatccgg taagcggcag ggtcggaaca ggagagcgca cgagggagct    3600
tccaggggga aacgcctggt atctttatag tcctgtcggg tttcgccacc tctgacttga    3660
gcgtcgattt ttgtgatgct cgtcaggggg gcggagccta tggaaaaacg ccagcaacgc    3720
ggccttttta cggttcctgg ccttttgctg gccttttgct cacatgttct ttcctgcgtt    3780
atcccctgat tctgtggata accgtattac cgcctttgag tgagctgata ccgctcgccg    3840
cagccgaacg accgagcgca gcgagtcagt gagcgaggaa gcggaagagc gcccaatacg    3900
caaaccgcct ctccccgcgc gttggccgat tcattaatgc agctggcacg acaggtttcc    3960
cgactggaaa gcgggcagtg agcgcaacgc aattaatgtg agttagctca ctcattaggc    4020
accccaggct ttacacttta tgcttccggc tcgtatgttg tgtggaattg tgagcggata    4080
acaatttcac acaggaaaca gctatgacca tgattacgcc aagcgcgcaa ttaaccctca    4140
ctaaagggaa caaaagctgg agctgcaagc ttaatgtagt cttatgcaat actcttgtag    4200
tcttgcaaca tggtaacgat gagttagcaa catgccttac aaggagagaa aaagcaccgt    4260
gcatgccgat tggtggaagt aaggtggtac gatcgtgcct tattaggaag caacagacg    4320
ggtctgacat ggattggacg aaccactgaa ttgccgcatt gcagagatat tgtatttaag    4380
tgcctagctc gatacataaa cggctctctc tggttagacc agatctgagc ctgggagctc    4440
tctggctaac tagggaaccc actgcttaag cctcaataaa gcttgccttg agtgcttcaa    4500
gtagtgtgtg cccgtctgtt gtgtgactct ggtaactaga gatccctcag acccttttag    4560
tcagtgtgga aaatctctag cagtggcgcc cgaacaggga cttgaaagcg aaagggaaac    4620
cagaggagct ctctcgacgc aggactcggc ttgctgaagc gcgcacggca agaggcgagg    4680
ggcggcgact ggtgagtacg ccaaaaattt tgactagcgg aggctagaag gagagagatg    4740
ggtgcgagag cgtcagtatt aagcggggga gaattagatc gcgatgggaa aaaattcggt    4800
```

```
taaggccagg gggaaagaaa aaatataaat taaaacatat agtatgggca agcagggagc    4860
tagaacgatt cgcagttaat cctggcctgt tagaaacatc agaaggctgt agacaaatac    4920
tgggacagct acaaccatcc cttcagacag gatcagaaga acttagatca ttatataata    4980
cagtagcaac cctctattgt gtgcatcaaa ggatagagat aaaagacacc aaggaagctt    5040
tagacaagat agaggaagag caaaacaaaa gtaagaccac cgcacagcaa gcggccgctg    5100
atcttcagac ctggaggagg agatatgagg gacaattgga gaagtgaatt atataaaatat    5160 aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tgggcgcagc gtcaatgacg ctgacggtac aggccagaca attattgtct    5340
ggtatagtgc agcagcagaa caatttgctg agggctattg aggcgcaaca gcatctgttg    5400
caactcacag tctggggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg gaatcacacg    5580
acctggatgg agtgggacag agaaattaac aattacacaa gcttaataca ctccttaatt    5640
gaagaatcgc aaaaccagca agaaaagaat gaacaagaat tattggaatt agataaatgg    5700
gcaagtttgt ggaattggtt taacataaca aattggctgt ggtatataaa attattcata    5760
atgatagtag gaggcttggt aggtttaaga atagttttg ctgtactttc tatagtgaat    5820
agagttaggc agggatattc accattatcg tttcagaccc acctcccaac cccgagggga    5880
cccgacaggc ccgaaggaat agaagaagaa ggtggagaga gagacagaga cagatccatt    5940
cgattagtga acggatctcg acggtatcga tcacgagact agcctcgaca caaatggcag    6000
tattcatcca caatttttaaa agaaaagggg ggattggggg gtacagtgca ggggaaagaa    6060
tagtagacat aatagcaaca gacatacaaa ctaaagaatt acaaaaacaa attacaaaaa    6120
ttcaaaattt tcgggtttat tacagggaca gcagaaatcc actttggctc gagaagcttg    6180
atatcggctc cggtgcccgt cagtgggcag agcgcacatc gcccacagtc cccgagaagt    6240
tggggggagg ggtcggcaat tgaaccggtg cctagaaag gtggcgcggg gtaaactggg    6300
aaagtgatgt cgtgtactgg ctccgccttt ttcccgaggg tgggggagaa ccgtatataa    6360
gtgcagtagt cgccgtgaac gttcttttc gcaacgggtt tgccgccaga acacaggatc    6420
cgccaccatg gccttaccag tgaccgcctt gctcctgccg ctggccttgc tgctccacgc    6480
cgccaggccg gatatccaga tgacccgag cccgagcagc ctgagcgcga gcgtgggtga    6540
tcgcgtgacc attacctgca gggcaagtca ggacattagt aaatatttaa attggtatca    6600
gcagaaaccg ggtaaagcgc cgaaactgtt aatttatcat acatcaagat tacactcagg    6660
cgtgccgtcg cgttttagcg gctcgggttc gggcaccgat tttaccctga ccatctcgag    6720
cttgcagccg gaggacttcg ccacctacta ttgccaacag ggtaatacgc ttccgtacac    6780
gttcggtcag ggcaccaaag tggagatcaa aggtggcggt ggctcgggcg gtggtgggtc    6840
gggtggcggc ggatctgagg tgcagctggt ggagtctggg ggaggcttgg tacagcctgg    6900
ggggtccctg agactctcct gtgcagcctc tggagtgtcc ctgcctgatt atggcgtgtc    6960
ctgggtccgc caggctccag ggaaggggct ggagtgggtt tcagtgatct ggggcagcga    7020
gacaacctac tacaacagcg ccctgaagtc ccgattcacc atctccagag acaatgccaa    7080
gaactcactg tatctgcaaa tgaacagcct gagagccgag gacacggctg tgtattactg    7140 tgccgaagcac tactactacg gcggcagcta cgctatggac tactggggcc aaggaacccct    7200
```

```
ggtcaccgtg tcctcaacca cgacgccagc gccgcgacca ccaacaccgg cgcccaccat   7260
cgcgtcgcag cccctgtccc tgcgcccaga ggcgtgccgg ccagcggcgg ggggcgcagt   7320
gcacacgagg gggctggact tcgcctgtga tatctacatc tgggcgccct tggccgggac   7380
ttgtggggtc cttctcctgt cactggttat caccctttac tgcaaacggg cagaaagaa    7440 actcctgtat atattcaaac aaccatttat gagaccagta caaactactc aagaggaaga   7500
tggctgtagc tgccgatttc agaagaaga agaaggagga tgtgaactga gagtgaagtt   7560
cagcaggagc gcagacgccc ccgcgtacaa gcagggccag aaccagctct ataacgagct   7620
caatctagga cgaagagagg agtacgatgt tttggacaag aggcgtggcc gggaccctga   7680 gatggggga aagccgagaa ggaagaaccc tcaggaaggc ctgtacaatg aactgcagaa    7740
agataagatg gcggaggcct acagtgagat tgggatgaaa ggcgagcgcc ggaggggcaa   7800
ggggcacgat ggcctttacc agggtctcag tacagccacc aaggacacct acgacgccct   7860
tcacatgcag gccctgcccc ctcgctaatc tagaggcgcg cc                     7902

<210> SEQ ID NO 13
<211> LENGTH: 11052
<212> TYPE: DNA
<213> ORGANISM: Artificial Sequence
<220> FEATURE:
<223> OTHER INFORMATION: synthesis

<400> SEQUENCE: 13
caggtggcac ttttcgggga aatgtgcgcg gaacccctat ttgtttattt ttctaaatac     60
attcaaatat gtatccgctc atgagacaat aaccctgata aatgcttcaa taatattgaa    120
aaaggaagag tatgagtatt caacatttcc gtgtcgccct tattccctt ttttgcggcat    180 tttgccttcc tgtttttgct cacccagaaa cgctggtgaa agtaaaagat gctgaagatc    240
agttgggtgc acgagtgggt tacatcgaac tggatctcaa cagcggtaag atccttgaga    300
gttttcgccc cgaagaacgt tttccaatga tgagcacttt taaagttctg ctatgtggcg    360
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgcttttt gcacaacatg ggggatcatg     600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt cattttaat ttaaaaggat ctaggtgaag atccttttg     1080 ataatctcat gaccaaaatc ccttaacgtg agttttcgtt ccactgagcg tcagaccccg   1140
tagaaaagat caaaggatct tcttgagatc ctttttttct gcgcgtaatc tgctgcttgc   1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
```

```
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gattttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttaat   2220
gtagtcttat gcaatactct tgtagtcttg caacatggta acgatgagtt agcaacatgc   2280
cttacaagga gagaaaaagc accgtgcatg ccgattggtg gaagtaaggt ggtacgatcg   2340
tgccttatta ggaaggcaac agacgggtct gacatggatt ggacgaacca ctgaattgga   2400
ggcgtggcct gggcgggact ggggagtggc gagccctcag atcctgcata taagcagctg   2460 cttttgcct gtactgggtc tctctggtta gaccagatct gagcctggga gctctctggc   2520
taactaggga acccactgct taagcctcaa taaagcttgc cttgagtgct tcaagtagtg   2580
tgtgcccgtc tgttgtgtga ctctggtaac tagagatccc tcagaccctt ttagtcagtg   2640
tggaaaatct ctagcagtgg cgcccgaaca gggacctgaa agcgaaaggg aaaccagagc   2700
tctctcgacg caggactcgg cttgctgaag cgcgcacggc aagaggcgag gggcggcgac   2760
tggtgagtac gccaaaaatt ttgactagcg gaggctagaa ggagagagat gggtgcgaga   2820
gcgtcagtat taagcggggg agaattagat cgcgatggga aaaaattcgg ttaaggccag   2880
ggggaaagaa aaaatataaa ttaaaacata tagtatgggc aagcagggag ctagaacgat   2940
tcgcagttaa tcctggcctg ttagaaacat cagaaggctg tagacaaata ctgggacagc   3000
tacaaccatc ccttcagaca ggatcagaag aacttagatc attatataat acagtagcaa   3060
ccctctattg tgtgcatcaa aggatagaga taaaagacac caaggaagct ttagacaaga   3120
tagaggaaga gcaaaacaaa agtaagacca ccgcacagca agcggccgct gatcttcaga   3180
cctggaggag gagatatgag ggacaattgg agaagtgaat tatataaata taagtagta   3240 aaaattgaac cattaggagt agcacccacc aaggcaaaga gaagagtggt gcagagagaa   3300
aaaagagcag tgggaatagg agctttgttc cttgggttct gggagcagca ggaagcact   3360 atgggcgcag cctcaatgac gctgacggta caggccagac aattattgtc tggtatagtg   3420
cagcagcaga acaatttgct gagggctatt gaggcgcaac agcatctgtt gcaactcaca   3480
gtctggggca tcaagcagct ccaggcaaga atcctggctg tggaaagata cctaaaggat   3540
caacagctcc tggggatttg gggttgctct ggaaaactca tttgcaccac tgctgtgcct   3600
tggaatgcta gttggagtaa taatctctg aacagattg gaatcacacg acctggatgg   3660
agtgggacag agaaattaac aattacacaa gcttaataca ctccttaatt gaagaatcgc   3720
```

```
aaaaccagca agaaaagaat gaacaagaat tattggaatt agataaatgg gcaagtttgt    3780
ggaattggtt taacataaca aattggctgt ggtatataaa attattcata atgatagtag    3840
gaggcttggt aggtttaaga atagtttttg ctgtactttc tatagtgaat agagttaggc    3900
agggatattc accattatcg tttcagaccc acctcccaac cccgagggga cccgacaggc    3960
ccgaaggaat agaagaagaa ggtggagaga gagacagaga cagatccatt cgattagtga    4020
acggatctcg acggtatcga tcacgagact agcctcgaca caaatggcag tattcatcca    4080
caattttaaa agaaaagggg ggattggggg gtacagtgca ggggaaagaa tagtagacat    4140
aatagcaaca gacatacaaa ctaaagaatt acaaaaacaa attacaaaaa ttcaaaattt    4200
tcgggtttat tacagggaca gcagaaatcc actttggctc gagaagcttg atatcggctc    4260
cggtgcccgt cagtgggcag agcgcacatc gcccacagtc cccgagaagt tggggggagg    4320
ggtcggcaat tgaaccggtg cctagagaag gtggcgcggg gtaaactggg aaagtgatgt    4380
cgtgtactgg ctccgccttt ttcccgaggg tgggggagaa ccgtatataa gtgcagtagt    4440
cgccgtgaac gttcttttc gcaacggggtt tgccgccaga acacagccac catggcttcg    4500 taccctgcc atcaacacgc gtctgcgttc gaccaggctg cgcgttctcg cggccatagc    4560
aaccgacgta cggcgttgcg ccctcgccgg cagcaagaag ccacggaagt ccgcccggag    4620
cagaaaatgc ccacgctact gcgggtttat atagacggtc cccacgggat ggggaaaacc    4680
accaccacgc aactgctggt ggccctgggt tcgcgcgacg atatcgtcta cgtacccgag    4740
ccgatgactt actggcgggt gctgggggct tccgagacaa tcgcgaacat ctacaccaca    4800
caacaccgcc tcgaccaggg tgagatatcg gccggggacg cggcggtggt aatgacaagc    4860
gcccagataa caatgggcat gccttatgcc gtgaccgacg ccgttctggc tcctcatatc    4920 ggggggggagg ctgggagctc acatgccccg ccccccggccc tcaccctcat cttcgaccgc    4980
catcccatcg ccgccctcct gtgctacccg gccgcgcgat acctttatggg cagcatgacc    5040 ccccaggccg tgctggcgtt cgtggccctc atcccgccga ccttgcccgg cacaaacatc    5100 gtgttgggggg cccttccgga ggacagacac atcgaccgcc tggccaaacg ccagcgcccc    5160
ggcgagcggc ttgacctggc tatgctggcc gcgattcgcc gcgtttacgg gctgcttgcc    5220
aatacggtgc ggtatctgca gggcggcggg tcgtggcggg aggattgggg acagctttcg    5280
gggacggccg tgccgcccca gggtgccgag ccccagagca acgcgggccc acgacccccat    5340 atcggggaca cgttatttac cctgtttcgg gccccccgagt tgctggcccc caacggcgac    5400
ctgtataacg tgtttgcctg ggccttggac gtcttggcca aacgcctccg tcccatgcac    5460
gtctttatcc tggattacga ccaatcgccc gccggctgcc gggacgccct gctgcaactt    5520
acctccggga tggtccagac ccacgtcacc accccaggct ccataccgac gatctgcgac    5580
ctggcgcgca cgtttgcccg ggagatgggg gaggctaact gacctctccc tccccccccc    5640
ctaacgttac tggccgaagc cgcttggaat aaggccggtg tgcgtttgtc tatatgttat    5700
tttccaccat attgccgtct tttggcaatg tgagggcccg gaaacctggc cctgtcttct    5760
tgacgagcat tcctagggggt ctttcccctc tcgccaaagg aatgcaaggt ctgttgaatg    5820
tcgtgaagga agcagttcct ctggaagctt cttgaagaca acaacgtct gtagcgaccc    5880 tttgcaggca gcggaacccc ccacctggcg acaggtgcct ctgcggccaa aagccacgtg    5940
tataagatac acctgcaaag gcggcacaac cccagtgcca cgttgtgagt tggatagttg    6000
tggaaagagt caaatggctc tcctcaagcg tattcaacaa ggggctgaag gatgcccaga    6060
```

```
aggtacccca ttgtatggga tctgatctgg ggcctcggta cacatgcttt acatgtgttt    6120
agtcgaggtt aaaaaaacgt ctaggccccc cgaaccacgg ggacgtggtt ttcctttgaa    6180
aaacacgatg ataatatggc cacaaccatg tctagattag ataaaagtaa agtgattaac    6240
agcgcattag agctgcttaa tgaggtcgga atcgaaggtt taacaacccg taaactcgcc    6300
cagaagcttg gtgtagagca gcctacactg tattggcatg taaaaaataa gcgggctttg    6360
ctcgacgcct tagccattga gatgttagat aggcaccata ctcacttttg ccctttaaaa    6420
ggggaaagct ggcaagattt tttacgcaat aacgctaaaa gttttagatg tgctttacta    6480
agtcatcgca atggagcaaa agtacattca gatacacggc ctacagaaaa acagtatgaa    6540
actctcgaaa atcaattagc cttttatgc caacaaggtt tttcactaga gaacgcgtta    6600
tatgcactca gcgctgtggg gcattttact ttaggttgcg tattggaaga tcaagagcat    6660
caagtcgcta aagaagaaag ggaaacacct actactgata gtatgccgcc attattacga    6720
caagctatcg aattatttga tcaccaaggt gcagagccag ccttcttatt cggccttgaa    6780
ttgatcatat gcggattaga aaaacaactt aaatgtgaaa gtgggtccgc gtacagccgc    6840
gcgcgtacga aaaacaatta cgggtctacc atcgagggcc tgctcgatct cccggacgac    6900
gacgcccccg aagaggcggg gctggcggct ccgcgcctgt cctttctccc cgcgggacac    6960
acgcgcagac tgtcgacggc ccccccgacc gatgtcagcc tggggacga gctccactta    7020 gacggcgagg acgtggcgat ggcgcatgcc gacgcgctag acgatttcga tctggacatg    7080 ttggggacg gggattcccc gggtccggga tttacccccc acgactccgc cccctacggc    7140
gctctggata tggccgactt cgagtttgag cagatgttta ccgatgccct tggaattgac    7200
gagtacggtg ggtagctcga gtttaccact ccctatcagt gatagagaaa agtgaaagtc    7260
gagtttacca ctcccatca gtgatagaga aagtgaaag tcgagtttac cactccctat    7320
cagtgataga gaaagtgaa agtcgagttt accactccct atcagtgata gagaaaagtg    7380
aaagtcgagt ttaccactcc ctatcagtga tagagaaaag tgaaagtcga gtttaccact    7440
ccctatcagt gatagagaaa agtgaaagtc gagtttacca ctccctatca gtgatagaga    7500
aaagtgaaag tcgagctcgg tacccgggtc gagtaggcgt gtacggtggg aggcctatat    7560
aagcagagct cgtttagtga accgtcagat cgcctggaga cgccatccac gctgttttga    7620
cctccataga agacaccggg accgatccag cctatgccgc gcgctccccg ctgccgagcc    7680
gtgcgctccc tgctgcgcag ccactaccgc gaggtgctgc cgctggccac gttcgtgcgg    7740
cgcctggggc cccagggctg gcggctggtg cagcgcgggg accggcggc tttccgcgcg    7800 ctggtggccc agtgcctggt gtgcgtgccc tgggacgcac ggccgccccc cgccgccccc    7860
tccttccgcc aggtgtcctg cctgaaggag ctggtggccc gagtgctgca gaggctgtgc    7920
gagcgcggcg cgaagaacgt gctggccttc ggcttcgcgc tgctggacgg ggcccgcggg    7980 ggccccccg aggccttcac caccagcgtg cgcagctacc tgcccaacac ggtgaccgac    8040
gcactgcggg ggagcggggc gtggggctg ctgctgcgcc gcgtgggcga cgacgtgctg    8100
gttcacctgc tggcacgctg cgcgctcttt gtgctggtgg ctcccagctg cgcctaccag    8160
gtgtgcgggc cgccgctgta ccagctcggc gctgccactc aggcccggcc ccgccacac    8220 gctagtggac cccgaaggcg tctgggatgc gaacgggcct ggaaccatag cgtcagggag    8280
gccggggtcc ccctgggcct gccagccccg ggtgcgagga ggcgcgggg cagtgccagc    8340 cgaagtctgc cgttgcccaa gaggcccagg cgtggcgctg cccctgagcc ggagcggacg    8400
cccgttgggc aggggtcctg ggcccacccg ggcaggacgc gtggaccgag tgaccgtggt    8460
```

```
ttctgtgtgg tgtcacctgc cagacccgcc gaagaagcca cctctttgga gggtgcgctc    8520
tctggcacgc gccactccca cccatccgtg ggccgccagc accacgcggg ccccccatcc    8580
acatcgcggc caccacgtcc ctgggacacg ccttgtcccc cggtgtacgc cgagaccaag    8640
cacttcctct actcctcagg cgacaaggag cagctgcggc cctccttcct actcagctct    8700
ctgaggccca gcctgactgg cgctcggagg ctcgtggaga ccatctttct gggttccagg    8760
ccctggatgc cagggactcc ccgcaggttg ccccgcctgc cccagcgcta ctggcaaatg    8820
cggcccctgt ttctggagct gcttgggaac cacgcgcagt gccctacgg ggtgctcctc     8880 aagacgcact gcccgctgcg agctgcggtc accccagcag ccgtgtctg tgcccgggag     8940 aagccccagg gctctgtggc ggccccgag gaggaggaca cagaccccg tcgcctggtg      9000 cagctgctcc gccagcacag cagccctggg caggtgtacg gcttcgtgcg ggcctgcctg    9060
cgccggctgg tgcccccagg cctctggggc tccaggcaca acgaacgccg cttcctcagg    9120
aacaccaaga agttcatctc cctggggaag catgccaagc tcgctgca ggagctgacg      9180 tggaagatga gcgtgcggga ctgcgcttgg ctgcgcagga gcccaggggt tggctgtgtt    9240
ccggccgcag agcaccgtct gcgtgaggag atcctggcca agttcctgca ctggctgatg    9300
agtgtgtacg tcgtcgagct gctcaggtct ttcttttatg tcacggagac cacgtttcaa    9360
aagaacaggc tcttttttcta ccggaagagt gtctggagca agttgcaaag cattggaatc    9420
agacagcact tgaagagggt gcagctgcgg gagctgtcgg aagcagaggt caggcagcat    9480
cgggaagcca ggcccgccct gctgacgtcc agactccgct tcatccccaa gcctgacggg    9540
ctgcggccga ttgtgaacat ggactacgtc gtgggagcca gaacgttccg cagagaaaag    9600
agggccgagc gtctcacctc gagggtgaag gcactgttca gcgtgctcaa ctacgagcgg    9660
gcgcggcgcc ccggcctcct gggcgcctct gtgctgggcc tggacgatat ccacagggcc    9720
tggcgcacct tcgtgctgcg tgtgcgggcc caggacccgc cgcctgagct gtactttgtc    9780
aaggtggatg tgacgggcgc gtacgacacc atcccccagg acaggctcac ggaggtcatc    9840
gccagcatca tcaaaccca gaacacgtac tgcgtgcgtc ggtatgccgt ggtccagaag    9900
gccgcccatg ggcacgtccg caaggccttc aagagccacg tctctacctt gacagacctc    9960
cagccgtaca tgcgacagtt cgtggctcac ctgcaggaga ccagcccgct gagggatgcc    10020
gtcgtcatcg agcagagctc ctccctgaat gaggccagca gtggcctctt cgacgtcttc    10080
ctacgcttca tgtgccacca cgccgtgcgc atcagggca agtcctacgt ccagtgccag    10140 gggatccgc agggctccat cctctccacg ctgctctgca gcctgtgcta cggcgacatg    10200
gagaacaagc tgtttgcggg gattcggcgg acgggctgc tcctgcgttt ggtggatgat    10260
ttcttgttgg tgacacctca cctcacccac gcgaaaacct tcctcaggac cctggtccga    10320
ggtgtccctg agtatggctg cgtggtgaac ttgcggaaga cagtggtgaa cttccctgta    10380
gaagacgagg ccctggtgg cacggctttt gttcagatgc cggcccacgg cctattcccc    10440
tggtgcggcc tgctgctgga taccccggacc ctggaggtgc agagcgacta ctccagctat    10500
gcccggacct ccatcagagc cagtctcacc ttcaaccgcg gcttcaaggc tgggaggaac    10560
atgcgtcgca aactctttgg ggtcttgcgg ctgagtgtc acagcctgtt tctggatttg    10620
caggtgaaca gcctccagac ggtgtgcacc aacatctaca agatcctcct gctgcaggcg    10680
tacaggtttc acgcatgtgt gctgcagctc ccatttcatc agcaagtttg gaagaacccc    10740
acatttttcc tgcgcgtcat ctctgacacg gcctccctct gctactccat cctgaaagcc    10800
```

| | |
|---|---|
| aagaacgcag ggatgtcgct gggggccaag ggcgccgccg gccctctgcc ctccgaggcc | 10860 |
| gtgcagtggc tgtgccacca agcattcctg ctcaagctga ctcgacaccg tgtcacctac | 10920 |
| gtgccactcc tggggtcact caggacagcc cagacgcagc tgagtcggaa gctcccgggg | 10980 |
| acgacgctga ctgccctgga ggccgcagcc aacccggcac tgccctcaga cttcaagacc | 11040 |
| atcctggact ga | 11052 |

<210> SEQ ID NO 14
<211> LENGTH: 9780
<212> TYPE: DNA
<213> ORGANISM: Artificial Sequence
<220> FEATURE:
<223> OTHER INFORMATION: synthesis

<400> SEQUENCE: 14

| | |
|---|---|
| caggtggcac ttttcgggga aatgtgcgcg gaacccctat ttgtttattt ttctaaatac | 60 |
| attcaaatat gtatccgctc atgagacaat aaccctgata aatgcttcaa taatattgaa | 120 |
| aaaggaagag tatgagtatt caacatttcc gtgtcgccct tattcccttt tttgcggcat | 180 |
| tttgccttcc tgttttgct cacccagaaa cgctggtgaa agtaaaagat gctgaagatc | 240 |
| agttgggtgc acgagtgggt tacatcgaac tggatctcaa cagcggtaag atccttgaga | 300 |
| gttttcgccc cgaagaacgt tttccaatga tgagcacttt taaagttctg ctatgtggcg | 360 |
| cggtattatc ccgtattgac gccgggcaag agcaactcgg tcgccgcata cactattctc | 420 |
| agaatgactt ggttgagtac tcaccagtca cagaaaagca tcttacggat ggcatgacag | 480 |
| taagagaatt atgcagtgct gccataacca tgagtgataa cactgcggcc aacttacttc | 540 |
| tgacaacgat cggaggaccg aaggagctaa ccgcttttt gcacaacatg ggggatcatg | 600 |
| taactcgcct tgatcgttgg gaaccggagc tgaatgaagc cataccaaac gacgagcgtg | 660 |
| acaccacgat gcctgtagca atggcaacaa cgttgcgcaa actattaact ggcgaactac | 720 |
| ttactctagc ttcccggcaa caattaatag actggatgga ggcggataaa gttgcaggac | 780 |
| cacttctgcg ctcggccctt ccggctggct ggtttattgc tgataaatct ggagccggtg | 840 |
| agcgtgggtc tcgcggtatc attgcagcac tggggccaga tggtaagccc tcccgtatcg | 900 |
| tagttatcta cacgacgggg agtcaggcaa ctatggatga acgaaataga cagatcgctg | 960 |
| agataggtgc ctcactgatt aagcattggt aactgtcaga ccaagtttac tcatatatac | 1020 |
| tttagattga tttaaaactt catttttaat ttaaaaggat ctaggtgaag atccttttg | 1080 |
| ataatctcat gaccaaaatc ccttaacgtg agttttcgtt ccactgagcg tcagaccccg | 1140 |
| tagaaaagat caaaggatct tcttgagatc cttttttct gcgcgtaatc tgctgcttgc | 1200 |
| aaacaaaaaa accaccgcta ccagcggtgg tttgtttgcc ggatcaagag ctaccaactc | 1260 |
| tttttccgaa ggtaactggc ttcagcagag cgcagatacc aaatactgtc cttctagtgt | 1320 |
| agccgtagtt aggccaccac ttcaagaact ctgtagcacc gcctacatac ctcgctctgc | 1380 |
| taatcctgtt accagtggct gctgccagtg gcgataagtc gtgtcttacc gggttggact | 1440 |
| caagacgata gttaccggat aaggcgcagc ggtcgggctg aacggggggt tcgtgcacac | 1500 |
| agcccagctt ggagcgaacg acctacaccg aactgagata cctacagcgt gagctatgag | 1560 |
| aaagcgccac gcttcccgaa gggagaaagg cggacaggta tccggtaagc ggcagggtcg | 1620 |
| gaacaggaga gcgcacgagg gagcttccag gggaaacgc ctggtatctt tatagtcctg | 1680 |
| tcgggtttcg ccacctctga cttgagcgtc gatttttgtg atgctcgtca ggggggcgga | 1740 |
| gcctatggaa aaacgccagc aacgcggcct ttttacggtt cctggccttt tgctggcctt | 1800 |

```
ttgctcacat gttctttcct gcgttatccc ctgattctgt ggataaccgt attaccgcct    1860
ttgagtgagc tgataccgct cgccgcagcc gaacgaccga gcgcagcgag tcagtgagcg    1920
aggaagcgga agagcgccca atacgcaaac cgcctctccc cgcgcgttgg ccgattcatt    1980
aatgcagctg gcacgacagg tttcccgact ggaaagcggg cagtgagcgc aacgcaatta    2040
atgtgagtta gctcactcat taggcacccc aggctttaca ctttatgctt ccggctcgta    2100
tgttgtgtgg aattgtgagc ggataacaat ttcacacagg aaacagctat gaccatgatt    2160
acgccaagcg cgcaattaac cctcactaaa gggaacaaaa gctggagctg caagcttaat    2220
gtagtcttat gcaatactct tgtagtcttg caacatggta acgatgagtt agcaacatgc    2280
cttacaagga gagaaaaagc accgtgcatg ccgattggtg gaagtaaggt ggtacgatcg    2340
tgccttatta ggaaggcaac agacgggtct gacatggatt ggacgaacca ctgaattgga    2400
ggcgtggcct gggcgggact ggggagtggc gagccctcag atcctgcata taagcagctg    2460 cttttttgcct gtactgggtc tctctggtta gaccagatct gagcctggga gctctctggc    2520
taactaggga acccactgct taagcctcaa taaagcttgc cttgagtgct tcaagtagtg    2580
tgtgcccgtc tgttgtgtga ctctggtaac tagagatccc tcagacccct ttagtcagtg    2640
tggaaaatct ctagcagtgg cgcccgaaca gggacctgaa agcgaaaggg aaaccagagc    2700
tctctcgacg caggactcgg cttgctgaag cgcgcacggc aagaggcgag gggcggcgac    2760
tggtgagtac gccaaaaatt ttgactagcg gaggctagaa ggagagagat gggtgcgaga    2820
gcgtcagtat taagcggggg agaattagat cgcgatggga aaaaattcgg ttaaggccag    2880
ggggaaagaa aaatataaa ttaaaacata tagtatgggc aagcagggag ctagaacgat    2940
tcgcagttaa tcctggcctg ttagaaacat cagaaggctg tagacaaata ctgggacagc    3000
tacaaccatc ccttcagaca ggatcagaag aacttagatc attatataat acagtagcaa    3060
ccctctattg tgtgcatcaa aggatagaga taaaagacac caaggaagct ttagacaaga    3120
tagaggaaga gcaaaacaaa agtaagacca ccgcacagca agcggccgct gatcttcaga    3180
cctggaggag gagatatgag ggacaattgg agaagtgaat tatataaata taagtagta    3240 aaaattgaac cattaggagt agcacccacc aaggcaaaga gaagagtggt gcagagagaa    3300
aaaagagcag tgggaatagg agctttgttc cttgggttct tgggagcagc aggaagcact    3360
atgggcgcag cctcaatgac gctgacggta caggccagac aattattgtc tggtatagtg    3420
cagcagcaga caatttgct gagggctatt gaggcgcaac agcatctgtt gcaactcaca    3480
gtctggggca tcaagcagct ccaggcaaga atcctggctg tggaaagata cctaaaggat    3540
caacagctcc tggggatttg gggttgctct ggaaaactca tttgcaccac tgctgtgcct    3600
tggaatgcta gttggagtaa taatctctg gaacagattg gaatcacacg acctggatgg    3660
agtgggacag agaaattaac aattacacaa gcttaataca ctccttaatt gaagaatcgc    3720
aaaaccagca agaaaagaat gaacaagaat tattggaatt agataaatgg gcaagtttgt    3780
ggaattggtt taacataaca aattggctgt ggtatataaa attattcata atgatagtag    3840
gaggcttggt aggtttaaga atagtttttg ctgtactttc tatagtgaat agagttaggc    3900
agggatattc accattatcg tttcagaccc acctcccaac cccgagggga cccgacaggc    3960
ccgaaggaat agaagaagaa ggtggagaga gagacagaga cagatccatt cgattagtga    4020
acggatctcg acggtatcga tcacgagact agcctgaca caaatggcag tattcatcca    4080 caatttaaa agaaaggggg ggattggggg gtacagtgca ggggaaagaa tagtagacat    4140
```

-continued

```
aatagcaaca gacatacaaa ctaaagaatt acaaaaacaa attacaaaaa ttcaaaattt      4200
tcgggtttat tacagggaca gcagaaatcc actttggctc gagaagcttg atatcggctc      4260
cggtgcccgt cagtgggcag agcgcacatc gcccacagtc cccgagaagt tgggggggagg    4320 ggtcggcaat tgaaccggtg cctagagaag gtggcgcggg gtaaactggg aaagtgatgt     4380
cgtgtactgg ctccgccttt ttcccgaggg tgggggagaa ccgtatataa gtgcagtagt     4440
cgccgtgaac gttcttttc gcaacggggtt tgccgccaga acacagccac catggcttcg     4500 taccccctgcc atcaacacgc gtctgcgttc gaccaggctg cgcgttctcg cggccatagc    4560
aaccgacgta cggcgttgcg ccctcgccgg cagcaagaag ccacggaagt ccgcccggag     4620
cagaaaatgc ccacgctact gcgggtttat atagacggtc cccacgggat ggggaaaacc     4680
accaccacgc aactgctggt ggccctgggt tcgcgcgacg atatcgtcta cgtacccgag     4740
ccgatgactt actggcgggt gctggggggct tccgagacaa tcgcgaacat ctacaccaca    4800
caacaccgcc tcgaccaggg tgagatatcg gccggggacg cggcggtggt aatgacaagc     4860
gcccagataa caatgggcat gccttatgcc gtgaccgacg ccgttctggc tcctcatatc     4920
gggggggagg ctgggagctc acatgccccg cccccggccc tcaccctcat cttcgaccgc     4980
catcccatcg ccgccctcct gtgctacccg gccgcgcgat accttatggg cagcatgacc     5040
ccccaggccg tgctggcgtt cgtggcccctc atcccgccga ccttgcccgg cacaaacatc    5100
gtgttggggg cccttccgga ggacagacac atcgaccgcc tggccaaacg ccagcgcccc    5160
ggcgagcggc ttgacctggc tatgctggcc gcgattcgcc gcgtttacgg gctgcttgcc     5220
aatacggtgc ggtatctgca gggcggcggg tcgtggcggg aggattgggg acagcttttcg    5280 gggacggccg tgccgccccca gggtgccgag ccccagagca acgcgggccc acgacccccat   5340 atcggggaca cgttatttac cctgtttcgg gccccccgagt tgctggcccc caacggcgac    5400
ctgtataacg tgtttgcctg ggccttggac gtcttggcca aacgcctccg tcccatgcac    5460
gtctttatcc tggattacga ccaatcgccc gccggctgcc gggacgccct gctgcaactt     5520
acctccggga tggtccagac ccacgtcacc accccaggct ccataccgac gatctgcgac    5580
ctggcgcgca cgtttgcccg ggagatgggg gaggctaact gacctctccc tcccccccc     5640 ctaacgttac tggccgaagc cgcttggaat aaggccggtg tgcgtttgtc tatatgttat     5700
tttccaccat attgccgtct tttggcaatg tgagggcccg gaaacctggc cctgtcttct     5760
tgacgagcat tcctaggggt cttttccctc tcgccaaagg aatgcaaggt ctgttgaatg     5820
tcgtgaagga agcagttcct ctggaagctt cttgaagaca aacaacgtct gtagcgaccc     5880
tttgcaggca gcggaacccc ccacctggcg acaggtgcct ctgcggccaa aagccacgtg    5940
tataagatac acctgcaaag gcggcacaac cccagtgcca cgttgtgagt tggatagttg    6000
tggaaagagt caaatggctc tcctcaagcg tattcaacaa ggggctgaag gatgcccaga    6060
aggtacccca ttgtatggga tctgatctgg ggcctcggta cacatgcttt acatgtgttt    6120
agtcgaggtt aaaaaaacgt ctaggcccccc cgaaccacgg ggacgtggtt ttcctttgaa   6180
aaacacgatg ataatatggc cacaaccatg tctagattag ataaaagtaa agtgattaac    6240
agcgcattag agctgcttaa tgaggtcgga atcgaaggtt taacaacccg taaactcgcc    6300
cagaagcttg gtgtagagca gcctacactg tattggcatg taaaaaataa gcgggctttg   6360
ctcgacgcct tagccattga gatgttagat aggcaccata tcacttttg ccctttaaaa     6420 ggggaaagct ggcaagattt tttacgcaat aacgctaaaa gttttagatg tgctttacta   6480
agtcatcgca atggagcaaa agtacattca gatacacggc ctacagaaaa acagtatgaa    6540
```

```
actctcgaaa atcaattagc cttttatgc caacaaggtt tttcactaga gaacgcgtta    6600
tatgcactca gcgctgtggg gcattttact ttaggttgcg tattggaaga tcaagagcat    6660
caagtcgcta aagaagaaag ggaaacacct actactgata gtatgccgcc attattacga    6720
caagctatcg aattatttga tcaccaaggt gcagagccag ccttcttatt cggccttgaa    6780
ttgatcatat gcggattaga aaaacaactt aaatgtgaaa gtgggtccgc gtacagccgc    6840
gcgcgtacga aaaacaatta cgggtctacc atcgagggcc tgctcgatct cccgacgac     6900 gacgccccg aagaggcggg gctggcggct ccgcgcctgt cctttctccc cgcgggacac     6960
acgcgcagac tgtcgacggc cccccgacc gatgtcagcc tggggacga gctccactta      7020 gacggcgagg acgtggcgat ggcgcatgcc gacgcgctag acgatttcga tctggacatg    7080 ttggggacg gggattcccc gggtccggga tttaccccc acgactccgc ccctacggc       7140 gctctggata tggccgactt cgagtttgag cagatgttta ccgatgccct tggaattgac    7200
gagtacggtg gtagctcga gtttaccact ccctatcagt gatagagaaa agtgaaagtc     7260
gagtttacca ctccctatca gtgatagaga aagtgaaag tcgagtttac cactccctat     7320
cagtgataga gaaagtgaa agtcgagttt accactccct atcagtgata gagaaaagtg    7380
aaagtcgagt ttaccactcc ctatcagtga tagagaaaag tgaaagtcga gtttaccact    7440
ccctatcagt gatagagaaa agtgaaagtc gagtttacca ctccctatca gtgatagaga    7500
aaagtgaaag tcgagctcgg taccggggtc gagtaggcgt gtacggtggg aggcctatat    7560
aagcagagct cgtttagtga accgtcagat cgcctggaga cgccatccac gctgttttga    7620
cctccataga agacaccggg accgatccag cctatggata aagtttaaaa cagagaggaa    7680
tctttgcagc taatggacct tctaggtctt gaaaggagtg cctgggggaa tattcctctg    7740
atgagaaagg catatttaaa aaaatgcaag gagtttcatc ctgataaagg aggagatgaa    7800
gaaaaaatga agaaaatgaa tactctgtac aagaaaatgg aagatggagt aaaatatgct    7860
catcaacctg actttggagg cttctgggat gcaactgaga ttccaaccta tggaactgat    7920
gaatgggagc agtggtggaa tgcctttaat gaggaaaacc tgttttgctc agaagaaatg    7980
ccatctagtg atgatgaggc tactgctgac tctcaacatt ctactcctcc aaaaaagaag    8040
agaaaggtag aagaccccaa ggactttcct tcagaattgc taagtttttt gagtcatgct    8100
gtgtttagta atagaactct tgcttgcttt gctatttaca ccacaaagga aaagctgca      8160 ctgctataca agaaaattat ggaaaaatat tctgtaacct ttataagtag gcataacagt    8220
tataatcata acatactgtt ttttcttact ccacacaggc atagagtgtc tgctattaat    8280
aactatgctc aaaaattgtg tacctttagc ttttaatttt gtaaggggt taataaggaa     8340 tatttgatgt atagtgcctt gactagagat ccattttctg ttattgagga agtttgcca    8400 ggtgggttaa aggagcatga ttttaatcca gaagaagcag aggaaactaa acaagtgtcc    8460
tggaagcttg taacagagta tgcaatggaa acaaaatgtg atgatgtgtt gttattgctt    8520
gggatgtact tggaatttca gtacagtttt gaaatgtgtt taaaatgtat taaaaaagaa    8580
cagcccagcc actataagta ccatgaaaag cattatgcaa atgctgctat atttgctgac    8640
agcaaaaacc aaaaaaccat atgccaacag gctgttgata ctgttttagc taaaaagcgg    8700
gttgatagcc tacaattaac tagagaacaa atgttaacaa acagatttaa tgatcttttg    8760
gataggatgg atataatgtt tggttctaca ggctctgctg acatagaaga atggatggct    8820
ggagttgctt ggctacactg tttgttgccc aaaatggatt cagtggtgta tgacttttta    8880
```

```
aaatgcatgg tgtacaacat tcctaaaaaa agatactggc tgtttaaagg accaattgat   8940
agtggtaaaa ctacattagc agctgctttg cttgaattat gtgggggaa agctttaaat    9000
gttaatttgc ccttggacag gctgaacttt gagctaggag tagctattga ccagttttta   9060
gtagttttg aggatgtaaa gggcactgga ggggagtcca gagatttgcc ttcaggtcag    9120
ggaattaata acctggacaa tttaagggat tatttggatg gcagtgttaa ggtaaactta   9180
gaaaagaaac acctaaataa aagaactcaa atatttcccc ctggaatagt caccatgaat   9240
gagtacagtg tgcctaaaac actgcaggcc agatttgtaa aacaaataga ttttaggccc   9300
aaagattatt taaagcattg cctgaacgc agtgagtttt tgttagaaaa gagaataatt     9360
caaagtggca ttgctttgct tcttatgtta atttggtaca gacctgtggc tgagtttgct   9420
caaagtattc agagcagaat tgtggagtgg aaagagagat tggacaaaga gtttagtttg   9480
tcagtgtatc aaaaaatgaa gtttaatgtg gctatgggaa ttggagtttt agattggcta   9540
agaaacagtg atgatgatga tgaagacagc caggaaaatg ctgataaaaa tgaagatggt   9600
ggggagaaga acatggaaga ctcagggcat gaaacaggca ttgattcaca gtcccaaggc   9660
tcatttcagg cccctcagtc ctcacagtct gttcatgatc ataatcagcc ataccacatt   9720
tgtagaggtt ttacttgctt taaaaaacct cccacacctc cccctgaacc tgaaacataa   9780
```

<210> SEQ ID NO 15
<211> LENGTH: 9840
<212> TYPE: DNA
<213> ORGANISM: Artificial Sequence
<220> FEATURE:
<223> OTHER INFORMATION: synthesis

<400> SEQUENCE: 15

```
gtcgacacta gtaatcaacc tctggattac aaaatttgtg aaagattgac tggtattctt     60
aactatgttg ctccttttac gctatgtgga tacgctgctt taatgccttt gtatcatgct   120
attgcttccc gtatggcttt cattttctcc tccttgtata aatcctggtt gctgtctctt   180
tatgaggagt tgtggcccgt tgtcaggcaa cgtggcgtgg tgtgcactgt gtttgctgac   240
gcaaccccca ctggttgggg cattgccacc acctgtcagc tcctttccgg acttttcgct   300
ttccccctcc ctattgccac ggcggaactc atcgccgcct gccttgcccg ctgctggaca   360
ggggctcggc tgttgggcac tgacaattcc gtggtgttgt cggggaagct gacgtccttt   420
ccatggctgc tcgcctgtgt tgccacctgg attctgcgcg gacgtccttt ctgctacgtc   480
ccttcggccc tcaatccagc ggaccttcct tcccgcggcc tgctgccggc tctgcggcct   540
cttccgcgtc ttcgccttcg ccctcagacg agtcggatct ccctttgggc cgcctccccg   600
cctgccgcgg aattcgagct cggtaccttt aagaccaatg acttacaagg cagctgtaga   660
tcttagccac tttttaaaag aaaaggggg actggaaggg ctaattcact cccaacgaag   720
acaagatctg cttttgcttg tactgagtc tctctggtta gaccagatct gagcctggga   780
gctctctggc taactaggga acccactgct taagcctcaa taaagcttgc cttgagtgct   840
tcaagtagtg tgtgcccgtc tgttgtgtga ctctggtaac tagagatccc tcagaccctt   900
ttagtcagtg tggaaaatct ctagcagtag tagttcatgt catcttatta ttcagtattt   960
ataacttgca aagaaatgaa tatcagagag tgagaggaac ttgtttattg cagcttataa  1020
tggttacaaa taaagcaata gcatcacaaa tttcacaaat aaagcatttt ttcactgca   1080
ttctagttgt ggtttgtcca aactcatcaa tgtatcttat catgtctggc tctagctatc   1140
ccgcccctaa ctccgcccat cccgccccta actccgccca gttccgccca ttctccgccc   1200
```

```
catggctgac taatttttt tatttatgca gaggccgagg ccgcctcggc ctctgagcta    1260
ttccagaagt agtgaggagg cttttttgga ggcctaggga cgtacccaat tcgccctata    1320
gtgagtcgta ttacgcgcgc tcactggccg tcgttttaca acgtcgtgac tgggaaaacc    1380
ctggcgttac ccaacttaat cgccttgcag cacatccccc tttcgccagc tggcgtaata    1440
gcgaagaggc ccgcaccgat cgcccttccc aacagttgcg cagcctgaat ggcgaatggg    1500
acgcgccctg tagcggcgca ttaagcgcgg cgggtgtggt ggttacgcgc agcgtgaccg    1560
ctacacttgc cagcgcccta gcgcccgctc ctttcgcttt cttcccttcc tttctcgcca    1620
cgttcgccgg ctttccccgt caagctctaa atcgggggct ccctttaggg ttccgattta    1680
gtgctttacg gcacctcgac cccaaaaaac ttgattaggg tgatggttca cgtagtgggc    1740
catcgccctg atagacggtt tttcgccctt tgacgttgga gtccacgttc tttaatagtg    1800
gactcttgtt ccaaactgga acaacactca accctatctc ggtctattct tttgatttat    1860
aagggatttt gccgatttcg gcctattggt taaaaaatga gctgatttaa caaaaattta    1920
acgcgaattt taacaaaata ttaacgctta caatttaggt ggcacttttc ggggaaatgt    1980
gcgcggaacc cctatttgtt tatttttcta aatacattca aatatgtatc cgctcatgag    2040
acaataaccc tgataaatgc ttcaataata ttgaaaaagg aagagtatga gtattcaaca    2100
tttccgtgtc gcccttattc ccttttttgc ggcattttgc cttcctgttt ttgctcaccc    2160
agaaacgctg gtgaaagtaa aagatgctga agatcagttg ggtgcacgag tgggttacat    2220
cgaactggat ctcaacagcg gtaagatcct tgagagtttt cgccccgaag aacgttttcc    2280
aatgatgagc acttttaaag ttctgctatg tggcgcggta ttatcccgta ttgacgccgg    2340
gcaagagcaa ctcggtcgcc gcatacacta ttctcagaat gacttggttg agtactcacc    2400
agtcacagaa aagcatctta cggatggcat gacagtaaga gaattatgca gtgctgccat    2460
aaccatgagt gataacactg cggccaactt acttctgaca acgatcggag gaccgaagga    2520
gctaaccgct tttttgcaca acatggggga tcatgtaact cgccttgatc gttgggaacc    2580
ggagctgaat gaagccatac caaacgacga gcgtgacacc acgatgcctg tagcaatggc    2640
aacaacgttg cgcaaactat taactggcga actacttact ctagcttccc ggcaacaatt    2700
aatagactgg atggaggcgg ataaagttgc aggaccactt ctgcgctcgg cccttccggc    2760
tggctggttt attgctgata aatctggagc cggtgagcgt ggctctcgcg gtatcattgc    2820
agcactgggg ccagatggta agccctcccg tatcgtagtt atctacacga cggggagtca    2880
ggcaactatg gatgaacgaa atagacagat cgctgagata ggtgcctcac tgattaagca    2940
ttggtaactg tcagaccaag tttactcata tatactttag attgatttaa aacttcattt    3000
ttaatttaaa aggatctagg tgaagatcct ttttgataat ctcatgacca aaatccctta    3060
acgtgagttt tcgttccact gagcgtcaga ccccgtagaa aagatcaaag gatcttcttg    3120
agatcctttt tttctgcgcg taatctgctg cttgcaaaca aaaaaaccac cgctaccagc    3180
ggtggtttgt ttgccggatc aagagctacc aactctttt ccgaaggtaa ctggcttcag    3240
cagagcgcag ataccaaata ctgttcttct agtgtagccg tagttaggcc accacttcaa    3300
gaactctgta gcaccgccta catacctcgc tctgctaatc ctgttaccag tggctgctgc    3360
cagtggcgat aagtcgtgtc ttaccgggtt ggactcaaga cgatagttac cggataaggc    3420
gcagcggtcg ggctgaacgg ggggttcgtg cacacagccc agcttggagc gaacgaccta    3480
caccgaactg agatacctac agcgtgagct atgagaaagc gccacgcttc ccgaagggag    3540
```

```
aaaggcggac aggtatccgg taagcggcag ggtcggaaca ggagagcgca cgagggagct    3600
tccaggggga aacgcctggt atctttatag tcctgtcggg tttcgccacc tctgacttga    3660
gcgtcgattt ttgtgatgct cgtcaggggg gcggagccta tggaaaaacg ccagcaacgc    3720 ggcctttta cggttcctgg cctttgctg gcctttgct cacatgttct ttcctgcgtt       3780
atcccctgat tctgtggata accgtattac cgcctttgag tgagctgata ccgctcgccg    3840
cagccgaacg accgagcgca gcgagtcagt gagcgaggaa gcggaagagc gcccaatacg    3900
caaaccgcct ctccccgcgc gttggccgat tcattaatgc agctggcacg acaggtttcc    3960
cgactggaaa gcgggcagtg agcgcaacgc aattaatgtg agttagctca ctcattaggc    4020
accccaggct ttacacttta tgcttccggc tcgtatgttg tgtggaattg tgagcggata    4080
acaatttcac acaggaaaca gctatgacca tgattacgcc aagcgcgcaa ttaaccctca    4140
ctaaagggaa caaaagctgg agctgcaagc ttaatgtagt cttatgcaat actcttgtag    4200
tcttgcaaca tggtaacgat gagttagcaa catgccttac aaggagagaa aaagcaccgt    4260
gcatgccgat tggtggaagt aaggtggtac gatcgtgcct tattaggaag gcaacagacg    4320
ggtctgacat ggattggacg aaccactgaa ttgccgcatt gcagagatat tgtatttaag    4380
tgcctagctc gatacataaa cggctctctc tggttagacc agatctgagc ctgggagctc    4440
tctggctaac tagggaaccc actgcttaag cctcaataaa gcttgccttg agtgcttcaa    4500
gtagtgtgtg cccgtctgtt gtgtgactct ggtaactaga gatccctcag accctttag    4560 tcagtgtgga aaatctctag cagtggcgcc cgaacaggga cttgaaagcg aaagggaaac    4620
cagaggagct ctctcgacgc aggactcggc ttgctgaagc gcgcacggca agaggcgagg    4680
ggcggcgact ggtgagtacg ccaaaaattt tgactagcgg aggctagaag gagagagatg    4740
ggtgcgagag cgtcagtatt aagcggggga gaattagatc gcgatgggaa aaaattcggt    4800
taaggccagg gggaaagaaa aaatataaat taaaacatat agtatgggca agcagggagc    4860
tagaacgatt cgcagttaat cctggcctgt tagaaacatc agaaggctgt agacaaatac    4920
tgggacagct acaaccatcc cttcagacag gatcagaaga acttagatca ttatataata    4980
cagtagcaac cctctattgt gtgcatcaaa ggatagagat aaaagacacc aaggaagctt    5040
tagacaagat agaggaagag caaaacaaaa gtaagaccac cgcacagcaa gcggccgctg    5100
atcttcagac ctggaggagg agatatgagg gacaattgga gaagtgaatt atataaatat    5160
aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tgggcgcagc gtcaatgacg ctgacggtac aggccagaca attattgtct    5340
ggtatagtgc agcagcagaa caatttgctg agggctattg aggcgcaaca gcatctgttg    5400
caactcacag tctgggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg gaatcacacg    5580
acctggatgg agtgggacag agaaattaac aattacacaa gcttaataca ctccttaatt    5640
gaagaatcgc aaaaccagca agaaaagaat gaacaagaat tattggaatt agataaatgg    5700
gcaagtttgt ggaattggtt taacataaca aattggctgt ggtatataaa attattcata    5760
atgatagtag gaggcttggt aggtttaaga atagtttttg ctgtactttc tatagtgaat    5820
agagttaggc agggatattc accattatcg tttcagaccc acctcccaac cccgagggga    5880
cccgacaggc ccgaaggaat agaagaagaa ggtggagaga gagacagaga cagatccatt    5940
```

```
cgattagtga acggatctcg acggtatcga tcacgagact agcctcgaca caaatggcag      6000
tattcatcca caattttaaa agaaaagggg ggattggggg gtacagtgca ggggaaagaa      6060
tagtagacat aatagcaaca gacatacaaa ctaaagaatt acaaaaacaa attacaaaaa      6120
ttcaaaattt tcgggtttat tacagggaca gcagaaatcc actttggctc gagaagcttg      6180
atatcggctc cggtgcccgt cagtgggcag agcgcacatc gcccacagtc cccgagaagt      6240 tgggggagg ggtcggcaat tgaaccggtg cctagaaag gtggcgcggg gtaaactggg        6300
aaagtgatgt cgtgtactgg ctccgccttt tcccgaggg tgggggagaa ccgtatataa       6360
gtgcagtagt cgccgtgaac gttcttttc gcaacgggtt tgccgccaga acacaggatc      6420
cgccaccatg ccgcgcgctc cccgctgccg agccgtgcgc tccctgctgc gcagccacta      6480
ccgcgaggtg ctgccgctgg ccacgttcgt gcggcgcctg gggccccagg gctggcggct      6540
ggtgcagcgc ggggacccgg cggctttccg cgcgctggtg gcccagtgcc tggtgtgcgt      6600
gccctgggac gcacggccgc cccccgccgc cccctccttc cgccaggtgt cctgcctgaa      6660
ggagctggtg gcccgagtgc tgcagaggct gtgcgagcgc ggcgcgaaga acgtgctggc      6720
cttcggcttc gcgctgctgg acggggcccg cggggccccc cccgaggcct tcaccaccag      6780
cgtgcgcagc tacctgccca acacggtgac cgacgcactg cggggagcg gggcgtgggg       6840 gctgctgctg cgccgcgtgg gcgacgacgt gctggttcac ctgctggcac gctgcgcgct      6900
ctttgtgctg gtggctccca gctgcgccta ccaggtgtgc gggccgccgc tgtaccagct      6960
cggcgctgcc actcaggccc ggcccccgcc acacgctagt ggaccccgaa ggcgtctggg      7020
atgcgaacgg gcctggaacc atagcgtcag ggaggccggg gtcccctgg gcctgccagc       7080 cccgggtgcg aggaggcgcg ggggcagtgc cagccgaagt ctgccgttgc ccaagaggcc      7140
caggcgtggc gctgccctg agccggagcg gacgcccgtt gggcaggggt cctgggccca       7200
cccgggcagg acgcgtggac cgagtgaccg tggtttctgt gtggtgtcac ctgccagacc      7260
cgccgaagaa gccacctctt tggagggtgc gctctctggc acgcgccact cccacccatc      7320
cgtgggccgc cagcaccacg cgggcccccc atccacatcg cggccaccac gtccctggga      7380
cacgccttgt ccccggtgt acgccgagac caagcacttc ctctactcct caggcgacaa       7440
ggagcagctg cggccctcct tcctactcag ctctctgagg cccagcctga ctggcgctcg      7500
gaggctcgtg gagaccatct ttctgggttc caggccctgg atgccaggga ctccccgcag      7560
gttgccccgc ctgccccagc gctactggca aatgcggccc ctgtttctgg agctgcttgg      7620
gaaccacgcg cagtgcccct acggggtgct cctcaagacg cactgccgc tgcgagctgc       7680 ggtcacccca gcagccggtg tctgtgcccg ggagaagccc cagggctctg tggcggcccc      7740
cgaggaggag gacacagacc ccgtcgcct ggtgcagctg ctccgccagc acagcagccc       7800
ctggcaggtg tacggcttcg tgcgggcctg cctgcgccgg ctggtgcccc caggcctctg      7860
gggctccagg cacaacgaac gccgcttcct caggaacacc aagaagttca tctccctggg      7920
gaagcatgcc aagctctcgc tgcaggagct gacgtggaag atgagcgtgc gggactgcgc      7980
ttggctgcgc aggagcccag gggttggctg tgttccggcc gcagagcacc gtctgcgtga      8040
ggagatcctg gccaagttcc tgcactggct gatgagtgtg tacgtcgtcg agctgctcag      8100
gtctttcttt tatgtcacgg agaccacgtt tcaaaagaac aggctctttt tctaccggaa      8160
gagtgtctgg agcaagttgc aaagcattgg aatcagacag cacttgaaga gggtgcagct      8220
gcgggagctg tcggaagcag aggtcaggca gcatcgggaa gccaggcccg ccctgctgac      8280
```

| | |
|---|---|
| gtccagactc cgcttcatcc ccaagcctga cgggctgcgg ccgattgtga acatggacta | 8340 |
| cgtcgtggga gccagaacgt tccgcagaga aaagagggcc gagcgtctca cctcgagggt | 8400 |
| gaaggcactg ttcagcgtgc tcaactacga gcgggcgcgg cgccccggcc tcctgggcgc | 8460 |
| ctctgtgctg ggcctggacg atatccacag ggcctggcgc accttcgtgc tgcgtgtgcg | 8520 |
| ggcccaggac ccgccgcctg agctgtactt tgtcaaggtg gatgtgacgg gcgcgtacga | 8580 |
| caccatcccc caggacaggc tcacggaggt catcgccagc atcatcaaac ccagaacac | 8640 |
| gtactgcgtg cgtcggtatg ccgtggtcca gaaggccgcc catgggcacg tccgcaaggc | 8700 |
| cttcaagagc cacgtctcta ccttgacaga cctccagccg tacatgcgac agttcgtggc | 8760 |
| tcacctgcag gagaccagcc cgctgaggga tgccgtcgtc atcgagcaga gctcctccct | 8820 |
| gaatgaggcc agcagtggcc tcttcgacgt cttcctacgc ttcatgtgcc accacgccgt | 8880 |
| gcgcatcagg ggcaagtcct acgtccagtg ccaggggatc ccgcagggct ccatcctctc | 8940 |
| cacgctgctc tgcagcctgt gctacggcga catggagaac aagctgtttg cggggattcg | 9000 |
| gcgggacggg ctgctcctgc gtttggtgga tgatttcttg ttggtgacac ctcacctcac | 9060 |
| ccacgcgaaa accttcctca ggaccctggt ccgaggtgtc cctgagtatg gctgcgtggt | 9120 |
| gaacttgcgg aagacagtgg tgaacttccc tgtagaagac gaggccctgg gtggcacggc | 9180 |
| ttttgttcag atgccggccc acggcctatt ccctggtgc ggcctgctgc tggatacccg | 9240 |
| gaccctggag gtgcagagcg actactccag ctatgcccgg acctccatca gagccagtct | 9300 |
| caccttcaac cgcggcttca aggctgggag gaacatgcgt cgcaaactct ttggggtctt | 9360 |
| gcggctgaag tgtcacagcc tgtttctgga tttgcaggtg aacagcctcc agacggtgtg | 9420 |
| caccaacatc tacaagatcc tcctgctgca ggcgtacagg tttcacgcat gtgtgctgca | 9480 |
| gctcccattt catcagcaag tttgaagaa ccccacattt ttcctgcgcg tcatctctga | 9540 |
| cacggcctcc ctctgctact ccatcctgaa agccaagaac gcaggatgt cgctgggggc | 9600 |
| caagggcgcc gccggccctc tgccctccga ggccgtgcag tggctgtgcc accaagcatt | 9660 |
| cctgctcaag ctgactcgac accgtgtcac ctacgtgcca ctcctggggt cactcaggac | 9720 |
| agcccagacg cagctgagtc ggaagctccc ggggacgacg ctgactgccc tggaggccgc | 9780 |
| agccaacccg gcactgcccct cagacttcaa gaccatcctg gactgatcta gaggcgcgcc | 9840 |

<210> SEQ ID NO 16
<211> LENGTH: 9354
<212> TYPE: DNA
<213> ORGANISM: Artificial Sequence
<220> FEATURE:
<223> OTHER INFORMATION: synthesis

<400> SEQUENCE: 16

| | |
|---|---|
| cctctccctc cccccccct aacgttactg gccgaagccg cttggaataa ggccggtgtg | 60 |
| cgtttgtcta tatgttattt tccaccatat tgccgtcttt tggcaatgtg agggcccgga | 120 |
| aacctggccc tgtcttcttg acgagcattc ctaggggtct ttcccctctc gccaaaggaa | 180 |
| tgcaaggtct gttgaatgtc gtgaaggaag cagttcctct ggaagcttct tgaagacaaa | 240 |
| caacgtctgt agcgacccctt tgcaggcagc ggaaccccc acctggcgac aggtgcctct | 300 |
| gcggccaaaa gccacgtgta taagatacac ctgcaaaggc ggcacaaccc cagtgccacg | 360 |
| ttgtgagttg gatagttgtg gaaagagtca aatggctctc ctcaagcgta ttcaacaagg | 420 |
| ggctgaagga tgcccagaag gtaccccatt gtatgggatc tgatctgggg cctcggtaca | 480 |
| catgctttac atgtgtttag tcgaggttaa aaaaacgtct aggccccccg aaccacgggg | 540 |

```
acgtggtttt cctttgaaaa acacgatgat aatatggcca caaccatgca gatcccacag    600
gcgccctggc cagtcgtctg ggcggtgcta caactgggct ggcggccagg atggttctta    660
gactccccag acaggccctg gaaccccccc accttctccc cagccctgct cgtggtgacc    720 gaagggggaca cgccaccttc acctgcagc ttctccaaca catcggagag cttcgtgcta    780
aactggtacc gcatgagccc cagcaaccag acggacaagc tggccgcctt ccccgaggac    840
cgcagccagc ccggccagga ctgccgcttc cgtgtcacac aactgcccaa cgggcgtgac    900
ttccacatga gcgtggtcag ggcccggcgc aatgacagcg gcacctacct ctgtggggcc    960
atctccctgg cccccaaggc gcagatcaaa gagagcctgc gggcagagct cagggtgaca   1020
gagagaaggg cagaagtgcc cacagcccac cccagcccct cacccaggcc agccggccag   1080
ttccaaaccc tggtggttgg tgtcgtgggc ggcctgctgg gcagcctggt gctgctagtc   1140
tgggtcctgg ccgtcatctg ctcccgggcc gcacgaggga caataggagc caggcgcacc   1200
ggccagcccc tgaaggagga cccctcagcc gtgcctgtgt tctctgtgga cgccggggag   1260
ctggatttcc agtggcgaga aagaccccg gagcccccg tgcctgtgt ccctgagcag   1320 acggaggccg ccaccattgt ctttcctagc ggaatgggca cctcatcccc cgcccgcagg   1380
ggctcagctg acggccctcg gagtgcccag ccactgaggc ctgaggatgg acactgctct   1440
tggcccctct gagtcgacac tagtaatcaa cctctggatt acaaaatttg tgaaagattg   1500
actggtattc ttaactatgt tgctcctttt acgctatgtg gatacgctgc tttaatgcct   1560
ttgtatcatg ctattgcttc ccgtatggct ttcattttct cctccttgta taaatcctgg   1620
ttgctgtctc tttatgagga gttgtggccc gttgtcaggc aacgtggcgt ggtgtgcact   1680
gtgtttgctg acgcaacccc cactggttgg ggcattgcca ccacctgtca gctcctttcc   1740
gggactttcg ctttccccct ccctattgcc acggcggaac tcatcgccgc ctgccttgcc   1800
cgctgctgga caggggctcg gctgttgggc actgacaatt ccgtggtgtt gtcggggaag   1860
ctgacgtcct ttccatggct gctcgcctgt gttgccacct ggattctgcg cgggacgtcc   1920
ttctgctacg tcccttcggc cctcaatcca gcggaccttc cttcccgcgg cctgctgccg   1980
gctctgcggc ctcttccgcg tcttcgcctt cgccctcaga cgagtcggat ctccctttgg   2040
gccgcctccc cgcctgccgc ggaattcgag ctcggtacct ttaagaccaa tgacttacaa   2100
ggcagctgta gatcttagcc acttttttaaa agaaaagggg ggactggaag gctaattca   2160 ctcccaacga agacaagatc tgcttttttgc ttgtactgag tctctctggt tagaccagat   2220
ctgagcctgg gagctctctg gctaactagg gaacccactg cttaagcctc aataaagctt   2280
gccttgagtg cttcaagtag tgtgtgcccg tctgttgtgt gactctggta actagagatc   2340
cctcagaccc ttttagtcag tgtggaaaat ctctagcagt agtagttcat gtcatcttat   2400
tattcagtat ttataacttg caaagaaatg aatatcagag agtgagagga acttgtttat   2460
tgcagcttat aatggttaca aataaagcaa tagcatcaca aatttcacaa ataaagcatt   2520
tttttcactg cattctagtt gtggtttgtc caaactcatc aatgtatctt atcatgtctg   2580
gctctagcta tcccgcccct aactccgccc atcccgcccc taactccgcc cagttccgcc   2640
cattctccgc cccatggctg actaatttt tttatttatg cagaggccga ggccgcctcg   2700
gcctctgagc tattccagaa gtagtgagga ggcttttttg gaggcctagg acgtacccca   2760
attcgcccta tagtgagtcg tattacgcgc gctcactggc cgtcgtttta caacgtcgtg   2820
actgggaaaa ccctggcgtt acccaactta atcgccttgc agcacatccc cctttcgcca   2880
```

```
gctggcgtaa tagcgaagag gcccgcaccg atcgcccttc ccaacagttg cgcagcctga    2940
atggcgaatg ggacgcgccc tgtagcggcg cattaagcgc ggcgggtgtg gtggttacgc    3000
gcagcgtgac cgctacactt gccagcgccc tagcgcccgc tcctttcgct ttcttccctt    3060
cctttctcgc cacgttcgcc ggctttcccc gtcaagctct aaatcggggg ctcccttag    3120 ggttccgatt tagtgcttta cggcacctcg accccaaaaa acttgattag ggtgatggtt    3180
cacgtagtgg gccatcgccc tgatagacgt tttttcgccc tttgacgttg gagtccacgt    3240
tctttaatag tggactcttg ttccaaactg gaacaacact caaccctatc tcggtctatt    3300
cttttgattt ataagggatt ttgccgattt cggcctattg gttaaaaaat gagctgattt    3360
aacaaaaatt taacgcgaat tttaacaaaa tattaacgct tacaatttag gtggcactt    3420 tcggggaaat gtgcgcggaa cccctatttg tttatttttc taaatacatt caaatatgta    3480
tccgctcatg agacaataac cctgataaat gcttcaataa tattgaaaaa ggaagagtat    3540
gagtattcaa catttccgtg tcgcccttat tcccttttt gcggcatttt gccttcctgt    3600
ttttgctcac ccagaaacgc tggtgaaagt aaaagatgct gaagatcagt tgggtgcacg    3660
agtgggttac atcgaactgg atctcaacag cggtaagatc cttgagagtt ttcgccccga    3720
agaacgtttt ccaatgatga gcacttttaa agttctgcta tgtggcgcgg tattatcccg    3780
tattgacgcc gggcaagagc aactcggtcg ccgcatacac tattctcaga atgacttggt    3840
tgagtactca ccagtcacag aaaagcatct tacgatggc atgacagtaa gagaattatg    3900
cagtgctgcc ataaccatga gtgataacac tgcggccaac ttacttctga caacgatcgg    3960
aggaccgaag gagctaaccg cttttttgca caacatgggg gatcatgtaa ctcgccttga    4020
tcgttgggaa ccggagctga atgaagccat accaaacgac gagcgtgaca ccacgatgcc    4080
tgtagcaatg gcaacaacgt tgcgcaaact attaactggc gaactactta ctctagcttc    4140
ccggcaacaa ttaatagact ggatggaggc ggataaagtt gcaggaccac ttctgcgctc    4200
ggcccttccg gctggctggt ttattgctga taaatctgga gccggtgagc gtggctctcg    4260
cggtatcatt gcagcactgg ggccagatgg taagccctcc cgtatcgtag ttatctacac    4320
gacggggagt caggcaacta tggatgaacg aaatagacag atcgctgaga taggtgcctc    4380
actgattaag cattggtaac tgtcagacca agtttactca tatatacttt agattgattt    4440
aaaacttcat ttttaattta aaaggatcta ggtgaagatc ctttttgata atctcatgac    4500
caaaatccct taacgtgagt tttcgttcca ctgagcgtca gaccccgtag aaaagatcaa    4560
aggatcttct tgagatcctt ttttctgcg cgtaatctgc tgcttgcaaa caaaaaaacc    4620
accgctacca gcggtggttt gtttgccgga tcaagagcta ccaactcttt ttccgaaggt    4680
aactggcttc agcagagcgc agataccaaa tactgttctt ctagtgtagc cgtagttagg    4740
ccaccacttc aagaactctg tagcaccgcc tacatacctc gctctgctaa tcctgttacc    4800
agtggctgct gccagtggcg ataagtcgtg tcttaccggg ttggactcaa gacgatagtt    4860
accggataag gcgcagcggt cgggctgaac ggggggttcg tgcacacagc ccagcttgga    4920
gcgaacgacc tacaccgaac tgagatacct acagcgtgag ctatgagaaa gcgccacgct    4980
tcccgaaggg agaaaggcgg acaggtatcc ggtaagcggc agggtcggaa caggagagcg    5040
cacgagggag cttccagggg gaaacgcctg gtatctttat agtcctgtcg gtttcgcca    5100 cctctgactt gagcgtcgat ttttgtgatg ctcgtcaggg gggcggagcc tatgaaaaa    5160 cgccagcaac gcggcctttt tacgttcct ggccttttgc tggccttttg ctcacatgtt    5220
ctttcctgcg ttatccctg attctgtgga taaccgtatt accgcctttg agtgagctga    5280
```

```
taccgctcgc cgcagccgaa cgaccgagcg cagcgagtca gtgagcgagg aagcggaaga    5340
gcgcccaata cgcaaaccgc ctctccccgc gcgttggccg attcattaat gcagctggca    5400
cgacaggttt cccgactgga aagcgggcag tgagcgcaac gcaattaatg tgagttagct    5460
cactcattag gcaccccagg ctttacactt tatgcttccg gctcgtatgt tgtgtggaat    5520
tgtgagcgga taacaatttc acacaggaaa cagctatgac catgattacg ccaagcgcgc    5580
aattaaccct cactaaaggg aacaaaagct ggagctgcaa gcttaatgta gtcttatgca    5640
atactcttgt agtcttgcaa catggtaacg atgagttagc aacatgcctt acaaggagag    5700
aaaaagcacc gtgcatgccg attggtgaa gtaaggtggt acgatcgtgc cttattagga    5760
aggcaacaga cgggtctgac atggattgga cgaaccactg aattgccgca ttgcagagat    5820
attgtattta gtgcctagc tcgatacata aacggctctc tctggttaga ccagatctga    5880
gcctgggagc tctctggcta actagggaac ccactgctta agcctcaata agcttgcct    5940
tgagtgcttc aagtagtgtg tgcccgtctg ttgtgtgact ctggtaacta gagatccctc    6000
agacccttt agtcagtgtg gaaaatctct agcagtggcg cccgaacagg gacttgaaag    6060
cgaaagggaa accagaggag ctctctcgac gcaggactcg gcttgctgaa gcgcgcacgg    6120
caagaggcga ggggcggcga ctggtgagta cgccaaaaat tttgactagc ggaggctaga    6180
aggagagaga tgggtgcgag agcgtcagta ttaagcgggg gagaattaga tcgcgatggg    6240
aaaaaattcg gttaaggcca ggggggaaga aaaaatataa attaaaacat atagtatggg    6300
caagcaggga gctagaacga ttcgcagtta atcctggcct gttagaaaca tcagaaggct    6360
gtagacaaat actgggacag ctacaaccat cccttcagac aggatcagaa gaacttagat    6420
cattatataa tacagtagca accctctatt gtgtgcatca aaggatagag ataaaagaca    6480
ccaaggaagc tttagacaag atagaggaag agcaaaacaa aagtaagacc accgcacagc    6540
aagcggccgc tgatcttcag acctggagga ggagatatga gggacaattg gagaagtgaa    6600
ttatataaat ataaagtagt aaaaattgaa ccattaggag tagcacccac caaggcaaag    6660
agaagagtgg tgcagagaga aaaaagagca gtgggaatag gagctttgtt ccttgggttc    6720
ttgggagcag caggaagcac tatgggcgca gcgtcaatga cgctgacggt acaggccaga    6780
caattattgt ctggtatagt gcagcagcag aacaatttgc tgagggctat tgaggcgcaa    6840
cagcatctgt tgcaactcac agtctggggc atcaagcagc tccaggcaag aatcctggct    6900
gtggaaagat acctaaagga tcaacagctc ctggggattt ggggttgctc tggaaaactc    6960
atttgcacca ctgctgtgcc ttggaatgct agttggagta taaatctct ggaacagatt    7020
tggaatcaca cgacctggat ggagtgggac agagaaatta acaattacac aagcttaata    7080
cactccttaa ttgaagaatc gcaaaaccag caagaaaaga atgaacaaga attattggaa    7140
ttagataaat gggcaagttt gtggaattgg tttaacataa caattggct gtggtatata    7200
aaattattca taatgatagt aggaggcttg gtaggtttaa gaatagtttt tgctgtactt    7260
tctatagtga atagagttag gcagggatat tcaccattat cgtttcagac ccacctccca    7320
accccgaggg gacccgacag gcccgaagga atagaagaag aaggtggaga gagacaga    7380
gacagatcca ttcgattagt gaacggatct cgacggtatc gatcacgaga ctagcctcga    7440
cacaaatggc agtattcatc cacaatttta aagaaaagg ggggattggg gggtacagtg    7500
caggggaaag aatagtagac ataatagcaa cagacataca aactaaagaa ttacaaaaac    7560
aaattacaaa aattcaaaat tttcgggttt attacaggga cagcagaaat ccactttggc    7620
```

| | |
|---|---:|
| tcgagaagct tgatatcggc tccggtgccc gtcagtgggc agagcgcaca tcgcccacag | 7680 |
| tccccgagaa gttgggggga ggggtcggca attgaaccgg tgcctagaga aggtggcgcg | 7740 |
| gggtaaactg ggaaagtgat gtcgtgtact ggctccgcct ttttcccgag ggtgggggag | 7800 |
| aaccgtatat aagtgcagta gtcgccgtga acgttctttt tcgcaacggg tttgccgcca | 7860 |
| gaacacagga tccgccacca tggccttacc agtgaccgcc ttgctcctgc cgctggcctt | 7920 |
| gctgctccac gccgccaggc cggatatcca gatgacccag agcccgagca gcctgagcgc | 7980 |
| gagcgtgggt gatcgcgtga ccattacctg cagggcaagt caggacatta gtaaatattt | 8040 |
| aaattggtat cagcagaaac cgggtaaagc gccgaaactg ttaatttatc atacatcaag | 8100 |
| attacactca ggcgtgccgt cgcgttttag cggctcgggt tcgggcaccg attttaccct | 8160 |
| gaccatctcg agcttgcagc cggaggactt cgccacctac tattgccaac agggtaatac | 8220 |
| gcttccgtac acgttcggtc agggcaccaa agtggagatc aaaggtggcg gtggctcggg | 8280 |
| cggtggtggg tcgggtggcg gcggatctga ggtgcagctg gtggagtctg ggggaggctt | 8340 |
| ggtacagcct ggggggtccc tgagactctc ctgtgcagcc tctggagtgt ccctgcctga | 8400 |
| ttatggcgtg tcctgggtcc gccaggctcc agggaagggg ctggagtggg tttcagtgat | 8460 |
| ctggggcagc gagacaacct actacaacag cgccctgaag tcccgattca ccatctccag | 8520 |
| agacaatgcc aagaactcac tgtatctgca aatgaacagc ctgagagccg aggacacggc | 8580 |
| tgtgtattac tgtgcgaagc actactacta cggcggcagc tacgctatgg actactgggg | 8640 |
| ccaaggaacc ctggtcaccg tgtcctcaac cacgacgcca gcgccgcgac caccaacacc | 8700 |
| ggcgcccacc atcgcgtcgc agcccctgtc cctgcgccca gaggcgtgcc ggccagcggc | 8760 |
| ggggggcgca gtgcacacga ggggctgga cttcgcctgt gatatctaca tctgggcgcc | 8820 |
| cttggccggg acttgtgggg tccttctcct gtcactggtt atcacccttt actgcaaacg | 8880 |
| gggcagaaag aaactcctgt atatattcaa acaaccattt atgagaccag tacaaactac | 8940 |
| tcaagaggaa gatggctgta gctgccgatt tccagaagaa gaagaaggag gatgtgaact | 9000 |
| gagagtgaag ttcagcagga gcgcagacgc ccccgcgtac aagcagggcc agaaccagct | 9060 |
| ctataacagc ctcaatctag gacgaagaga ggagtacgat gttttggaca gaggcgtgg | 9120 |
| ccgggaccct gagatggggg gaaagccgag aaggaagaac cctcaggaag gcctgtacaa | 9180 |
| tgaactgcag aaagataaga tggcggaggc ctacagtgag attgggatga aggcgagcg | 9240 |
| ccggaggggc aaggggcacg atggccttta ccagggtctc agtacagcca ccaaggacac | 9300 |
| ctacgcgcc cttcacatgc aggccctgcc ccctcgctaa tctagaggcg cgcc | 9354 |

<210> SEQ ID NO 17
<211> LENGTH: 9162
<212> TYPE: DNA
<213> ORGANISM: Artificial Sequence
<220> FEATURE:
<223> OTHER INFORMATION: synthesis

<400> SEQUENCE: 17

| | |
|---|---:|
| cctctccctc cccccccct aacgttactg gccgaagccg cttggaataa ggccggtgtg | 60 |
| cgtttgtcta tatgttattt tccaccatat tgccgtcttt tggcaatgtg agggcccgga | 120 |
| aacctggccc tgtcttcttg acgagcattc ctaggggtct ttcccctctc gccaaggaa | 180 |
| tgcaaggtct gttgaatgtc gtgaaggaag cagttcctct ggaagcttct tgaagacaaa | 240 |
| caacgtctgt agcgaccctt tgcaggcagc ggaaccccc acctggcgac aggtgcctct | 300 |
| gcggccaaaa gccacgtgta agatacac ctgcaaaggc ggcacaaccc cagtgccacg | 360 |

```
ttgtgagttg atagttgtg gaaagagtca aatggctctc ctcaagcgta ttcaacaagg    420
ggctgaagga tgcccagaag gtaccccatt gtatgggatc tgatctgggg cctcggtaca    480
catgctttac atgtgtttag tcgaggttaa aaaaacgtct aggcccccg aaccacgggg     540 acgtggtttt cctttgaaaa acacgatgat aatatggcca caaccatgca gatcccacag    600
gcgccctggc cagtcgtctg gcggtgcta caactgggct ggcggccagg atggttctta     660
gactccccag acaggccctg gaacccccc accttctccc cagccctgct cgtggtgacc     720 gaagggggaca acgccacctt cacctgcagc ttctccaaca catcggagag cttcgtgcta   780
aactggtacc gcatgagccc cagcaaccag acggacaagc tggccgcctt ccccgaggac    840
cgcagccagc ccggccagga ctgccgcttc cgtgtcacac aactgcccaa cgggcgtgac    900
ttccacatga gcgtggtcag ggcccggcgc aatgacagcg gcacctacct ctgtggggcc    960
atctccctgg cccccaaggc gcagatcaaa gagagcctgc gggcagagct cagggtgaca    1020
gagagaaggg cagaagtgcc cacagcccac cccagcccct cacccaggcc agccggccag    1080
ttccaaaccc tggtggttgg tgtcgtgggc ggcctgctgg gcagcctggt gctgctagtc    1140
tgggtcctgg ccgtcatctg ctcccgggcc gcacgaggga caatagatta caaggatgac    1200
gacgataagg attacaagga tgacgacgat aaggattaca aggatgacga cgataagtaa    1260
gtcgacacta gtaatcaacc tctggattac aaaatttgtg aaagattgac tggtattctt    1320
aactatgttg ctccttttac gctatgtgga tacgctgctt taatgccttt gtatcatgct    1380
attgcttccc gtatggcttt cattttctcc tccttgtata aatcctggtt gctgtctctt    1440
tatgaggagt tgtggcccgt tgtcaggcaa cgtggcgtgg tgtgcactgt gtttgctgac    1500
gcaaccccca ctggttgggg cattgccacc acctgtcagc tcctttccgg gactttcgct    1560 ttcccctcc ctattgccac ggcggaactc atcgccgcct gccttgcccg ctgctggaca    1620
ggggctcggc tgttgggcac tgacaattcc gtggtgttgt cggggaagct gacgtccttt    1680
ccatggctgc tcgcctgtgt tgccacctgg attctgcgcg ggacgtcctt ctgctacgtc    1740
ccttcggccc tcaatccagc ggaccttcct tcccgcggcc tgctgccggc tctgcggcct    1800
cttccgcgtc ttcgccttcg ccctcagacg agtcggatct ccctttgggc cgcctccccg    1860
cctgccgcgg aattcgagct cggtacctt aagaccaatg acttacaagg cagctgtaga    1920
tcttagccac tttttaaaag aaaaggggg actggaaggg ctaattcact cccaacgaag    1980
acaagatctg cttttttgctt gtactgagtc tctctggtta gaccagatct gagcctggga   2040
gctctctggc taactaggga acccactgct taagcctcaa taaagcttgc cttgagtgct    2100
tcaagtagtg tgtgcccgtc tgttgtgtga ctctggtaac tagagatccc tcagaccctt    2160
ttagtcagtg tggaaaatct ctagcagtag tagttcatgt catcttatta ttcagtattt    2220
ataacttgca aagaaatgaa tatcagagag tgagaggaac ttgtttattg cagcttataa    2280
tggttacaaa taaagcaata gcatcacaaa tttcacaaat aaagcatttt ttcactgca    2340 ttctagttgt ggtttgtcca aactcatcaa tgtatcttat catgtctggc tctagctatc    2400
ccgcccctaa ctccgcccat cccgcccta actccgccca gttccgccca ttctccgccc    2460
catggctgac taatttttt tatttatgca gaggccgagg ccgcctcggc ctctgagcta    2520
ttccagaagt agtgaggagg cttttttgga ggcctaggga cgtacccaat tcgccctata    2580
gtgagtcgta ttacgcgcgc tcactggccg tcgttttaca acgtcgtgac tgggaaaacc    2640
ctggcgttac ccaacttaat cgccttgcag cacatcccc tttcgccagc tggcgtaata    2700
```

```
gcgaagaggc ccgcaccgat cgcccttccc aacagttgcg cagcctgaat ggcgaatggg    2760
acgcgccctg tagcggcgca ttaagcgcgg cgggtgtggt ggttacgcgc agcgtgaccg    2820
ctacacttgc cagcgcccta cgcccgctc  ctttcgcttt cttcccttcc tttctcgcca    2880
cgttcgccgg ctttccccgt caagctctaa atcgggggct cccttttaggg ttccgattta   2940
gtgctttacg gcacctcgac cccaaaaaac ttgattaggg tgatggttca cgtagtgggc    3000
catcgccctg atagacggtt tttcgcccctt tgacgttgga gtccacgttc tttaatagtg   3060
gactcttgtt ccaaactgga acaacactca accctatctc ggtctattct tttgatttat    3120
aagggatttt gccgatttcg gcctattggt taaaaatga gctgatttaa caaaaattta     3180
acgcgaattt taacaaaata ttaacgctta caatttaggt ggcacttttc ggggaaatgt    3240
gcgcggaacc cctatttgtt tattttcta  aatacattca aatatgtatc cgctcatgag    3300
acaataaccc tgataaatgc ttcaataata ttgaaaaagg aagagtatga gtattcaaca    3360
tttccgtgtc gcccttattc ccttttttgc ggcattttgc cttcctgttt ttgctcaccc    3420
agaaacgctg gtgaaagtaa aagatgctga agatcagttg ggtgcacgag tgggttacat    3480
cgaactggat ctcaacagcg gtaagatcct tgagagtttt cgccccgaag aacgttttcc    3540
aatgatgagc acttttaaag ttctgctatg tggcgcggta ttatcccgta ttgacgccgg    3600
gcaagagcaa ctcggtcgcc gcatacacta ttctcagaat gacttggttg agtactcacc    3660
agtcacagaa aagcatctta cggatggcat gacagtaaga gaattatgca gtgctgccat    3720
aaccatgagt gataacactg cggccaactt acttctgaca acgatcggag gaccgaagga    3780
gctaaccgct ttttttgcaca acatggggga tcatgtaact cgccttgatc gttgggaacc    3840
ggagctgaat gaagccatac caaacgacga gcgtgacacc acgatgcctg tagcaatggc    3900
aacaacgttg cgcaaactat taactggcga actacttact ctagcttccc ggcaacaatt    3960
aatagactgg atggaggcgg ataaagttgc aggaccactt ctgcgctcgg cccttccggc    4020
tggctggttt attgctgata atctggagc cggtgagcgt ggctctcgcg gtatcattgc     4080
agcactgggg ccagatggta agccctcccg tatcgtagtt atctacacga cggggagtca    4140
ggcaactatg gatgaacgaa atagacagat cgctgagata ggtgcctcac tgattaagca    4200
ttggtaactg tcagaccaag tttactcata tatactttag attgatttaa aacttcattt    4260
ttaatttaaa aggatctagg tgaagatcct ttttgataat ctcatgacca aaatccctta    4320
acgtgagttt tcgttccact gagcgtcaga ccccgtagaa aagatcaaag gatcttcttg    4380
agatcctttt tttctgcgcg taatctgctg cttgcaaaca aaaaaaccac cgctaccagc    4440
ggtggtttgt ttgccggatc aagagctacc aactcttttt ccgaaggtaa ctggcttcag    4500
cagagcgcag ataccaaata ctgttcttct agtgtagccg tagttaggcc accacttcaa    4560
gaactctgta gcaccgccta catacctcgc tctgctaatc ctgttaccag tggctgctgc    4620
cagtggcgat aagtcgtgtc ttaccgggtt ggactcaaga cgatagttac cggataaggc    4680
gcagcggtcg ggctgaacgg ggggttcgtg cacacagccc agcttggagc gaacgaccta    4740
caccgaactg agatacctac agcgtgagct atgagaaagc gccacgcttc ccgaagggag    4800
aaaggcggac aggtatccgg taagcggcag ggtcggaaca ggagagcgca cgagggagct    4860
tccaggggga aacgcctggt atctttatag tcctgtcggg tttcgccacc tctgacttga    4920
gcgtcgattt ttgtgatgct cgtcaggggg gcggagccta tggaaaaacg ccagcaacgc    4980
ggcctttta  cggttcctgg cctttgctg  gccttttgct cacatgttct ttcctgcgtt    5040
atcccctgat tctgtggata accgtattac cgcctttgag tgagctgata ccgctcgccg    5100
```

```
cagccgaacg accgagcgca gcgagtcagt gagcgaggaa gcggaagagc gcccaatacg   5160
caaaccgcct ctccccgcgc gttggccgat tcattaatgc agctggcacg acaggtttcc   5220
cgactggaaa gcgggcagtg agcgcaacgc aattaatgtg agttagctca ctcattaggc   5280
accccaggct ttacacttta tgcttccggc tcgtatgttg tgtggaattg tgagcggata   5340
acaatttcac acaggaaaca gctatgacca tgattacgcc aagcgcgcaa ttaaccctca   5400
ctaaagggaa caaaagctgg agctgcaagc ttaatgtagt cttatgcaat actcttgtag   5460
tcttgcaaca tggtaacgat gagttagcaa catgccttac aaggagagaa aaagcaccgt   5520
gcatgccgat tggtggaagt aaggtggtac gatcgtgcct tattaggaag caacagacg   5580 ggtctgacat ggattggacg aaccactgaa ttgccgcatt gcagagatat tgtatttaag   5640
tgcctagctc gatacataaa cggctctctc tggttagacc agatctgagc ctgggagctc   5700
tctggctaac tagggaaccc actgcttaag cctcaataaa gcttgccttg agtgcttcaa   5760
gtagtgtgtg cccgtctgtt gtgtgactct ggtaactaga gatccctcag acccttttag   5820
tcagtgtgga aaatctctag cagtggcgcc cgaacaggga cttgaaagcg aaagggaaac   5880
cagaggagct ctctcgacgc aggactcggc ttgctgaagc gcgcacggca agaggcgagg   5940
ggcggcgact ggtgagtacg ccaaaaattt tgactagcgg aggctagaag gagagagatg   6000
ggtgcgagag cgtcagtatt aagcggggga gaattagatc gcgatgggaa aaattcggt   6060 taaggccagg gggaagaaa aaatataaat taaaacatat agtatgggca agcagggagc   6120
tagaacgatt cgcagttaat cctggcctgt tagaaacatc agaaggctgt agacaaatac   6180
tgggacagct acaaccatcc cttcagacag gatcagaaga acttagatca ttatataata   6240
cagtagcaac cctctattgt gtgcatcaaa ggatagagat aaaagacacc aaggaagctt   6300
tagacaagat agaggaagag caaaacaaaa gtaagaccac cgcacagcaa gcggccgctg   6360
atcttcagac ctggaggagg agatatgagg gacaattgga gaagtgaatt atataaatat   6420
aaagtagtaa aaattgaacc attaggagta gcacccacca aggcaaagag aagagtggtg   6480
cagagagaaa aaagagcagt gggaatagga gctttgttcc ttgggttctt gggagcagca   6540
ggaagcacta tgggcgcagc gtcaatgacg ctgacggtac aggccagaca attattgtct   6600
ggtatagtgc agcagcagaa caatttgctg agggctattg aggcgcaaca gcatctgttg   6660
caactcacag tctggggcat caagcagctc caggcaagaa tcctggctgt ggaaagatac   6720
ctaaaggatc aacagctcct ggggatttgg ggttgctctg gaaaactcat ttgcaccact   6780
gctgtgcctt ggaatgctag ttggagtaat aaatctctgg aacagatttg gaatcacacg   6840
acctggatgg agtgggacag agaaattaac aattacacaa gcttaataca ctccttaatt   6900
gaagaatcgc aaaaccagca agaaaagaat gaacaagaat tattggaatt agataaatgg   6960
gcaagtttgt ggaattggtt taacataaca aattggctgt ggtatataaa attattcata   7020
atgatagtag gaggcttggt aggtttaaga atagtttttg ctgtactttc tatagtgaat   7080
agagttaggc agggatattc accattatcg tttcagaccc acctcccaac cccgagggga   7140
cccgacaggc ccgaaggaat agaagaagaa ggtggagaga gagacagaga cagatccatt   7200
cgattagtga acggatctcg acggtatcga tcacgagact agcctcgaca caaatggcag   7260
tattcatcca caattttaaa agaaaagggg ggattggggg gtacagtgca ggggaaagaa   7320
tagtagacat aatagcaaca gacatacaaa ctaaagaatt acaaaaacaa attacaaaaa   7380
ttcaaaattt tcgggtttat tacagggaca gcagaaatcc actttggctc gagaagcttg   7440
```

| | |
|---|---|
| atatcggctc cggtgcccgt cagtgggcag agcgcacatc gcccacagtc cccgagaagt | 7500 |
| tgggggagg ggtcggcaat tgaaccggtg cctagagaag gtggcgcggg gtaaactggg | 7560 |
| aaagtgatgt cgtgtactgg ctccgccttt ttcccgaggg tgggggagaa ccgtatataa | 7620 |
| gtgcagtagt cgccgtgaac gttcttttc gcaacgggtt tgccgccaga acacaggatc | 7680 |
| cgccaccatg gccttaccag tgaccgcctt gctcctgccg ctggccttgc tgctccacgc | 7740 |
| cgccaggccg gatatccaga tgacccgag cccgagcagc ctgagcgcga gcgtgggtga | 7800 |
| tcgcgtgacc attacctgca gggcaagtca ggacattagt aaatatttaa attggtatca | 7860 |
| gcagaaaccg ggtaaagcgc cgaaactgtt aatttatcat acatcaagat tacactcagg | 7920 |
| cgtgccgtcg cgttttagcg gctcgggttc gggcaccgat tttaccctga ccatctcgag | 7980 |
| cttgcagccg gaggacttcg ccacctacta ttgccaacag ggtaatacgc ttccgtacac | 8040 |
| gttcggtcag ggcaccaaag tggagatcaa aggtggcggt ggctcgggcg gtggtgggtc | 8100 |
| gggtggcggc ggatctgagg tgcagctggt ggagtctggg ggaggcttgg tacagcctgg | 8160 |
| ggggtccctg agactctcct gtgcagcctc tggagtgtcc ctgcctgatt atggcgtgtc | 8220 |
| ctgggtccgc caggctccag ggaaggggct ggagtgggtt tcagtgatct ggggcagcga | 8280 |
| gacaacctac tacaacagcg ccctgaagtc ccgattcacc atctccagag acaatgccaa | 8340 |
| gaactcactg tatctgcaaa tgaacagcct gagagccgag gacacggctg tgtattactg | 8400 |
| tgcgaagcac tactactacg gcggcagcta cgctatggac tactgggcc aaggaaccct | 8460 |
| ggtcaccgtg tcctcaacca cgacgccagc gccgcgacca ccaacaccgg cgcccaccat | 8520 |
| cgcgtcgcag cccctgtccc tgcgcccaga ggcgtgccgg ccagcggcgg ggggcgcagt | 8580 |
| gcacacgagg gggctggact tcgcctgtga tatctacatc tgggcgcct tggccgggac | 8640 |
| ttgtggggtc cttctcctgt cactggttat caccctttac tgcaaacggg gcagaaagaa | 8700 |
| actcctgtat atattcaaac aaccatttat gagaccagta caaactactc aagaggaaga | 8760 |
| tggctgtagc tgccgatttc cagaagaaga agaaggagga tgtgaactga gagtgaagtt | 8820 |
| cagcaggagc gcagacgccc ccgcgtacaa gcagggccag aaccagctct ataacgagct | 8880 |
| caatctagga cgaagagagg agtacgatgt tttggacaag aggcgtggcc gggaccctga | 8940 |
| gatgggggga aagccagaa ggaagaaccc tcaggaaggc ctgtacaatg aactgcagaa | 9000 |
| agataagatg gcggaggcct acagtgagat tgggatgaaa ggcgagcgcc ggaggggcaa | 9060 |
| ggggcacgat ggcctttacc agggtctcag tacagccacc aaggacacct acgacgccct | 9120 |
| tcacatgcag gccctgcccc ctcgctaatc tagaggcgcg cc | 9162 |

<210> SEQ ID NO 18
<211> LENGTH: 8568
<212> TYPE: DNA
<213> ORGANISM: Artificial Sequence
<220> FEATURE:
<223> OTHER INFORMATION: synthesis

<400> SEQUENCE: 18

| | |
|---|---|
| gtcgacacta gtaatcaacc tctggattac aaaatttgtg aaagattgac tggtattctt | 60 |
| aactatgttg ctccttttac gctatgtgga tacgctgctt taatgccttt gtatcatgct | 120 |
| attgcttccc gtatggcttt cattttctcc tccttgtata atcctggtt gctgtctctt | 180 |
| tatgaggagt tgtggcccgt tgtcaggcaa cgtggcgtgg tgtgcactgt gtttgctgac | 240 |
| gcaaccccca ctggttgggg cattgccacc acctgtcagc tcctttccgg gactttcgct | 300 |
| ttccccctcc ctattgccac ggcggaactc atcgccgcct gccttgcccg ctgctggaca | 360 |

```
ggggctcggc tgttgggcac tgacaattcc gtggtgttgt cggggaagct gacgtccttt    420
ccatggctgc tcgcctgtgt tgccacctgg attctgcgcg ggacgtcctt ctgctacgtc    480
ccttcggccc tcaatccagc ggaccttcct tcccgcggcc tgctgccggc tctgcggcct    540
cttccgcgtc ttcgccttcg ccctcagacg agtcggatct ccctttgggc cgcctccccg    600
cctgccgcgg aattcgagct cggtaccttt aagaccaatg acttacaagg cagctgtaga    660
tcttagccac tttttaaaag aaaggggggg actggaaggg ctaattcact cccaacgaag    720
acaagatctg cttttttgctt gtactgagtc tctctggtta daccagatct gagcctggga    780
gctctctggc taactaggga acccactgct taagcctcaa taaagcttgc cttgagtgct    840
tcaagtagtg tgtgcccgtc tgttgtgtga ctctggtaac tagagatccc tcagaccctt    900
ttagtcagtg tggaaaatct ctagcagtag tagttcatgt catcttatta ttcagtattt    960
ataacttgca aagaaatgaa tatcagagag tgagaggaac ttgtttattg cagcttataa   1020
tggttacaaa taaagcaata gcatcacaaa tttcacaaat aaagcatttt tttcactgca   1080
ttctagttgt ggtttgtcca aactcatcaa tgtatcttat catgtctggc tctagctatc   1140
ccgcccctaa ctccgcccat cccgcccta actccgccca gttccgccca ttctccgccc   1200
catggctgac taatttttttt tatttatgca gaggccgagg ccgcctcggc ctctgagcta   1260
ttccagaagt agtgaggagg ctttttttgga ggcctaggga cgtacccaat tcgccctata   1320
gtgagtcgta ttacgcgcgc tcactggccg tcgttttaca acgtcgtgac tgggaaaacc   1380
ctggcgttac ccaacttaat cgccttgcag cacatccccc tttcgccagc tggcgtaata   1440
gcgaagaggc ccgcaccgat cgcccttccc aacagttgcg cagcctgaat ggcgaatggg   1500
acgcgccctg tagcggcgca ttaagcgcgg cgggtgtggt ggttacgcgc agcgtgaccg   1560
ctacacttgc cagcgcccta gcgcccgctc ctttcgcttt cttcccttcc tttctcgcca   1620
cgttcgccgg ctttccccgt caagctctaa atcgggggct ccctttaggg ttccgattta   1680
gtgctttacg gcacctcgac cccaaaaaac ttgattaggg tgatggttca cgtagtgggc   1740
catcgccctg atagacggtt tttcgccctt tgacgttgga gtccacgttc tttaatagtg   1800
gactcttgtt ccaaactgga acaacactca accctatctc ggtctattct tttgatttat   1860
aagggatttt gccgatttcg gcctattggt taaaaaatga gctgatttaa caaaaattta   1920
acgcgaattt taacaaaata ttaacgctta catttaggt ggcacttttc ggggaaatgt   1980
gcgcggaacc cctatttgtt tatttttcta aatacattca aatatgtatc cgctcatgag   2040
acaataaccc tgataaatgc ttcaataata ttgaaaagg aagagtatga gtattcaaca   2100
tttccgtgtc gcccttattc cctttttgc ggcattttgc cttcctgttt tgctcaccc   2160 agaaacgctg gtgaaagtaa aagatgctga agatcagttg ggtgcacgag tgggttacat   2220
cgaactggat ctcaacagcg gtaagatcct tgagagtttt cgccccgaag aacgttttcc   2280
aatgatgagc acttttaaag ttctgctatg tggcgcggta ttatcccgta ttgacgccgg   2340
gcaagagcaa ctcggtcgcc gcatacacta ttctcagaat gacttggttg agtactcacc   2400
agtcacagaa aagcatctta cggatggcat gacagtaaga gaattatgca gtgctgccat   2460
aaccatgagt gataacactg cggccaactt acttctgaca acgatcggag gaccgaagga   2520
gctaaccgct ttttttgcaca acatggggga tcatgtaact cgccttgatc gttgggaacc   2580
ggagctgaat gaagccatac caaacgacga gcgtgacacc acgatgcctg tagcaatggc   2640
aacaacgttg cgcaaactat taactggcga actacttact ctagcttccc ggcaacaatt   2700
```

```
aatagactgg atggaggcgg ataaagttgc aggaccactt ctgcgctcgg cccttccggc    2760
tggctggttt attgctgata aatctggagc cggtgagcgt ggctctcgcg gtatcattgc    2820
agcactgggg ccagatggta agccctcccg tatcgtagtt atctacacga cggggagtca    2880
ggcaactatg gatgaacgaa atagacagat cgctgagata ggtgcctcac tgattaagca    2940
ttggtaactg tcagaccaag tttactcata tatactttag attgatttaa aacttcattt    3000
ttaatttaaa aggatctagg tgaagatcct ttttgataat ctcatgacca aaatccctta    3060
acgtgagttt tcgttccact gagcgtcaga ccccgtagaa aagatcaaag gatcttcttg    3120 agatccttt tttctgcgcg taatctgctg cttgcaaaca aaaaaaccac cgctaccagc    3180
ggtggtttgt ttgccggatc aagagctacc aactcttttt ccgaaggtaa ctggcttcag    3240
cagagcgcag ataccaaata ctgttcttct agtgtagccg tagttaggcc accacttcaa    3300
gaactctgta gcaccgccta catacctcgc tctgctaatc ctgttaccag tggctgctgc    3360
cagtggcgat aagtcgtgtc ttaccgggtt ggactcaaga cgatagttac cggataaggc    3420
gcagcggtcg ggctgaacgg ggggttcgtg cacacagccc agcttggagc gaacgaccta    3480
caccgaactg agatacctac agcgtgagct atgagaaagc gccacgcttc ccgaagggag    3540
aaaggcggac aggtatccgg taagcggcag ggtcggaaca ggagagcgca cgagggagct    3600
tccaggggga aacgcctggt atctttatag tcctgtcggg tttcgccacc tctgacttga    3660
gcgtcgattt ttgtgatgct cgtcaggggg gcggagccta tggaaaaacg ccagcaacgc    3720
ggccttttta cggttcctgg ccttttgctg gccttttgct cacatgttct ttcctgcgtt    3780
atcccctgat tctgtggata accgtattac cgcctttgag tgagctgata ccgctcgccg    3840
cagccgaacg accgagcgca gcgagtcagt gagcgaggaa gcggaagagc gcccaatacg    3900
caaaccgcct ctccccgcgc gttggccgat tcattaatgc agctggcacg acaggtttcc    3960
cgactggaaa gcgggcagtg agcgcaacgc aattaatgtg agttagctca ctcattaggc    4020
accccaggct ttacacttta tgcttccggc tcgtatgttg tgtggaattg tgagcggata    4080
acaatttcac acaggaaaca gctatgacca tgattacgcc aagcgcgcaa ttaaccctca    4140
ctaaagggaa caaaagctgg agctgcaagc ttaatgtagt cttatgcaat actcttgtag    4200
tcttgcaaca tggtaacgat gagttagcaa catgccttac aaggagagaa aaagcaccgt    4260
gcatgccgat tggtggaagt aaggtggtac gatcgtgcct tattaggaag caacagacg    4320 ggtctgacat ggattggacg aaccactgaa ttgccgcatt gcagagatat tgtatttaag    4380
tgcctagctc gatacataaa cggctctctc tggttagacc agatctgagc ctgggagctc    4440
tctggctaac tagggaaccc actgcttaag cctcaataaa gcttgccttg agtgcttcaa    4500
gtagtgtgtg cccgtctgtt gtgtgactct ggtaactaga gatccctcag acccttttag    4560
tcagtgtgga aaatctctag cagtggcgcc cgaacaggga cttgaaagcg aaagggaaac    4620
cagaggagct ctctcgacgc aggactcggc ttgctgaagc gcgcacggca agaggcgagg    4680
ggcggcgact ggtgagtacg ccaaaaattt tgactagcgg aggctagaag gagagagatg    4740
ggtgcgagag cgtcagtatt aagcggggga gaattagatc gcgatgggaa aaaattcggt    4800
taaggccagg gggaaagaaa aaatataaat taaaacatat agtatgggca agcagggagc    4860
tagaacgatt cgcagttaat cctggcctgt tagaaacatc agaaggctgt agacaaatac    4920
tgggacagct acaaccatcc cttcagacag gatcagaaga acttagatca ttatataata    4980
cagtagcaac cctctattgt gtgcatcaaa ggatagagat aaaagacacc aaggaagctt    5040
tagacaagat agaggaagag caaaacaaaa gtaagaccac cgcacagcaa gcggccgctg    5100
```

```
atcttcagac ctggaggagg agatatgagg acaattgga gaagtgaatt atataaatat    5160
aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tgggcgcagc gtcaatgacg ctgacggtac aggccagaca attattgtct    5340
ggtatagtgc agcagcagaa caatttgctg agggctattg aggcgcaaca gcatctgttg    5400
caactcacag tctggggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg gaatcacacg    5580
acctggatgg agtgggacag agaaattaac aattacacaa gcttaataca ctccttaatt    5640
gaagaatcgc aaaaccagca agaaaagaat gaacaagaat tattggaatt agataaatgg    5700
gcaagtttgt ggaattggtt taacataaca aattggctgt ggtatataaa attattcata    5760
atgatagtag gaggcttggt aggtttaaga atagttttg ctgtactttc tatagtgaat    5820
agagttaggc agggatattc accattatcg tttcagaccc acctcccaac cccgagggga    5880
cccgacaggc ccgaaggaat agaagaagaa ggtggagaga gagacagaga cagatccatt    5940
cgattagtga acggatctcg acggtatcga tcacgagact agcctcgaca caaatggcag    6000
tattcatcca caattttaaa agaaaagggg ggattggggg gtacagtgca ggggaaagaa    6060
tagtagacat aatagcaaca gacatacaaa ctaaagaatt acaaaaacaa attacaaaaa    6120
ttcaaaattt tcgggtttat tacagggaca gcagaaatcc actttggctc gagaagcttg    6180
atatcggctc cggtgcccgt cagtgggcag agcgcacatc gcccacagtc cccgagaagt    6240
tggggggagg ggtcggcaat tgaaccggtg cctagagaag gtggcgcggg gtaaactggg    6300
aaagtgatgt cgtgtactgg ctccgccttt ttcccgaggg tgggggagaa ccgtatataa    6360
gtgcagtagt cgccgtgaac gttcttttc gcaacgggtt tgccgccaga cacaggatc     6420 cgccaccatg gataaagttt taaacagaga ggaatctttg cagctaatgg accttctagg    6480
tcttgaaagg agtgcctggg ggaatattcc tctgatgaga aaggcatatt taaaaaaatg    6540
caaggagttt catcctgata aaggaggaga tgaagaaaaa atgaagaaaa tgaatactct    6600
gtacaagaaa atggaagatg gagtaaaata tgctcatcaa cctgactttg gaggcttctg    6660
ggatgcaact gagattccaa cctatggaac tgatgaatgg gagcagtggt ggaatgcctt    6720
taatgaggaa aacctgtttt gctcagaaga aatgccatct agtgatgatg aggctactgc    6780
tgactctcaa cattctactc ctccaaaaaa gaagagaaag gtagaagacc ccaaggactt    6840
tccttcagaa ttgctaagtt ttttgagtca tgctgtgttt agtaatagaa ctcttgcttg    6900
ctttgctatt tacaccacaa aggaaaaagc tgcactgcta tacaagaaaa ttatggaaaa    6960
atattctgta acctttataa gtaggcataa cagttataat cataacatac tgttttttct    7020
tactccacac aggcatagag tgtctgctat taataactat gctcaaaaat tgtgtacctt    7080
tagcttttta atttgtaaag gggttaataa ggaatatttg atgtatagtg ccttgactag    7140
agatccattt tctgttattg aggaaagttt gccaggtggg ttaaaggagc atgattttaa    7200
tccagaagaa gcagaggaaa ctaaacaagt gtcctggaag cttgtaacag agtatgcaat    7260
ggaaacaaaa tgtgatgatg tgttgttatt gcttgggatg tacttggaat tcagtacag     7320 ttttgaaatg tgtttaaaat gtattaaaaa agaaacagcc cagccactata agtaccatga    7380 aaagcattat gcaaatgctg ctatatttgc tgacagcaaa aaccaaaaaa ccatatgcca    7440
```

| | |
|---|---:|
| acaggctgtt gatactgttt tagctaaaaa gcgggttgat agcctacaat taactagaga | 7500 |
| acaaatgtta acaaacagat ttaatgatct tttggatagg atggatataa tgtttggttc | 7560 |
| tacaggctct gctgacatag aagaatggat ggctggagtt gcttggctac actgtttgtt | 7620 |
| gcccaaaatg gattcagtgg tgtatgactt tttaaaatgc atggtgtaca acattcctaa | 7680 |
| aaaaagatac tggctgttta aaggaccaat tgatagtggt aaaactacat tagcagctgc | 7740 |
| tttgcttgaa ttatgtgggg ggaaagcttt aaatgttaat ttgcccttgg acaggctgaa | 7800 |
| cttttgagcta ggagtagcta ttgaccagtt tttagtagtt tttgaggatg taaagggcac | 7860 |
| tggaggggag tccagagatt tgccttcagg tcagggaatt aataacctgg acaatttaag | 7920 |
| ggattatttg gatggcagtg ttaaggtaaa cttagaaaag aaacacctaa ataaaagaac | 7980 |
| tcaaatattt cccctggaa tagtcaccat gaatgagtac agtgtgccta aaacactgca | 8040 |
| ggccagattt gtaaaacaaa tagattttag gcccaaagat tatttaaagc attgcctgga | 8100 |
| acgcagtgag ttttgttag aaaagagaat aattcaaagt ggcattgctt tgcttcttat | 8160 |
| gttaatttgg tacagacctg tggctgagtt tgctcaaagt attcagagca gaattgtgga | 8220 |
| gtggaaagag agattggaca aagagtttag tttgtcagtg tatcaaaaaa tgaagtttaa | 8280 |
| tgtggctatg ggaattggag ttttagattg gctaagaaac agtgatgatg atgatgaaga | 8340 |
| cagccaggaa aatgctgata aaatgaaga tggtggggag aagaacatgg aagactcagg | 8400 |
| gcatgaaaca ggcattgatt cacagtccca aggctcattt caggcccctc agtcctcaca | 8460 |
| gtctgttcat gatcataatc agccatacca catttgtaga ggttttactt gctttaaaaa | 8520 |
| acctcccaca cctccccctg aacctgaaac ataatctaga ggcgcgcc | 8568 |

<210> SEQ ID NO 19
<211> LENGTH: 7914
<212> TYPE: DNA
<213> ORGANISM: Artificial Sequence
<220> FEATURE:
<223> OTHER INFORMATION: synthesis

<400> SEQUENCE: 19

| | |
|---|---:|
| gtcgacacta gtaatcaacc tctggattac aaaatttgtg aaagattgac tggtattctt | 60 |
| aactatgttg ctccttttac gctatgtgga tacgctgctt taatgccttt gtatcatgct | 120 |
| attgcttccc gtatggcttt cattttctcc tccttgtata aatcctggtt gctgtctctt | 180 |
| tatgaggagt tgtggcccgt tgtcaggcaa cgtggcgtgg tgtgcactgt gtttgctgac | 240 |
| gcaaccccca ctggttgggg cattgccacc acctgtcagc tcctttccgg gactttcgct | 300 |
| ttccccctcc ctattgccac ggcggaactc atcgccgcct gccttgcccg ctgctggaca | 360 |
| ggggctcggc tgttgggcac tgacaattcc gtggtgttgt cggggaagct gacgtccttt | 420 |
| ccatggctgc tcgcctgtgt tgccacctgg attctgcgcg gacgtccttt ctgctacgtc | 480 |
| ccttcggccc tcaatccagc ggaccttcct cccgcggcc tgctgccggc tctgcggcct | 540 |
| cttccgcgtc ttcgccttcg ccctcagacg agtcggatct ccctttgggc cgcctccccg | 600 |
| cctgccgcgg aattcgagct cggtaccttt aagaccaatg acttacaagg cagctgtaga | 660 |
| tcttagccac ttttttaaaag aaaaggggggg actggaaggg ctaattcact cccaacgaag | 720 |
| acaagatctg cttttgctt gtactgagtc tctctggtta gaccagatct gagcctggga | 780 |
| gctctctggc taactaggga acccactgct taagcctcaa taaagcttgc cttgagtgct | 840 |
| tcaagtagtg tgtgcccgtc tgttgtgtga ctctggtaac tagagatccc tcagaccctt | 900 |
| ttagtcagtg tggaaaatct ctagcagtag tagttcatgt catcttatta ttcagtattt | 960 |

```
ataacttgca aagaaatgaa tatcagagag tgagaggaac ttgtttattg cagcttataa    1020
tggttacaaa taaagcaata gcatcacaaa tttcacaaat aaagcatttt tttcactgca    1080
ttctagttgt ggtttgtcca aactcatcaa tgtatcttat catgtctggc tctagctatc    1140
ccgcccctaa ctccgcccat cccgcccta actccgccca gttccgccca ttctccgccc    1200
catggctgac taattttttt tatttatgca gaggccgagg ccgcctcggc ctctgagcta    1260
ttccagaagt agtgaggagg cttttttgga ggcctaggga cgtacccaat tcgccctata    1320
gtgagtcgta ttacgcgcgc tcactggccg tcgttttaca acgtcgtgac tgggaaaacc    1380
ctggcgttac ccaacttaat cgccttgcag cacatccccc tttcgccagc tggcgtaata    1440
gcgaagaggc ccgcaccgat cgcccttccc aacagttgcg cagcctgaat ggcgaatggg    1500
acgcgccctg tagcggcgca ttaagcgcgg cgggtgtggt ggttacgcgc agcgtgaccg    1560
ctacacttgc cagcgcccta gcgcccgctc ctttcgcttt cttcccttcc tttctcgcca    1620
cgttcgccgg ctttccccgt caagctctaa atcgggggct ccctttaggg ttccgattta    1680
gtgctttacg gcacctcgac cccaaaaaac ttgattaggg tgatggttca cgtagtgggc    1740
catcgccctg atagacggtt tttcgccctt gacgttgga gtccacgttc tttaatagtg    1800
gactcttgtt ccaaactgga acaacactca accctatctc ggtctattct tttgatttat    1860
aagggatttt gccgatttcg gcctattggt taaaaaatga ctgatttaa caaaaattta    1920 acgcgaattt taacaaaata ttaacgctta caatttaggt ggcacttttc ggggaaatgt    1980
gcgcggaacc cctatttgtt tatttttcta aatacattca aatatgtatc cgctcatgag    2040
acaataaccc tgataaatgc ttcaataata ttgaaaaagg aagagtatga gtattcaaca    2100
tttccgtgtc gcccttattc ccttttttgc ggcattttgc cttcctgttt ttgctcaccc    2160
agaaacgctg gtgaaagtaa aagatgctga agatcagttg ggtgcacgag tgggttacat    2220
cgaactggat ctcaacagcg gtaagatcct tgagagtttt cgccccgaag aacgttttcc    2280
aatgatgagc acttttaaag ttctgctatg tggcgcggta ttatcccgta ttgacgccgg    2340
gcaagagcaa ctcggtcgcc gcatacacta ttctcagaat gacttggttg agtactcacc    2400
agtcacagaa aagcatctta cggatggcat gacagtaaga gaattatgca gtgctgccat    2460
aaccatgagt gataacactg cggccaactt acttctgaca acgatcggag gaccgaagga    2520
gctaaccgct tttttgcaca acatggggga tcatgtaact cgccttgatc gttgggaacc    2580
ggagctgaat gaagccatac caaacgacga gcgtgacacc acgatgcctg tagcaatggc    2640
aacaacgttg cgcaaactat taactggcga actacttact ctagcttccc ggcaacaatt    2700
aatagactgg atggaggcgg ataaagttgc aggaccactt ctgcgctcgg cccttccggc    2760
tggctggttt attgctgata atctggagc cggtgagcgt ggctctcgcg gtatcattgc    2820
agcactgggg ccagatggta agccctcccg tatcgtagtt atctacacga cggggagtca    2880
ggcaactatg gatgaacgaa atagacagat cgctgagata ggtgcctcac tgattaagca    2940
ttggtaactg tcagaccaag tttactcata tatactttag attgatttaa aacttcattt    3000
ttaatttaaa aggatctagg tgaagatcct ttttgataat ctcatgacca aaatccctta    3060
acgtgagttt tcgttccact gagcgtcaga ccccgtagaa aagatcaaag gatcttcttg    3120
agatcctttt tttctgcgcg taatctgctg cttgcaaaca aaaaaaccac cgctaccagc    3180
ggtggtttgt ttgccggatc aagagctacc aactcttttt ccgaaggtaa ctggcttcag    3240
cagagcgcag ataccaaata ctgttcttct agtgtagccg tagttaggcc accacttcaa    3300
```

```
gaactctgta gcaccgccta catacctcgc tctgctaatc ctgttaccag tggctgctgc    3360
cagtggcgat aagtcgtgtc ttaccgggtt ggactcaaga cgatagttac cggataaggc    3420
gcagcggtcg ggctgaacgg ggggttcgtg cacacagccc agcttggagc gaacgaccta    3480
caccgaactg agatacctac agcgtgagct atgagaaagc gccacgcttc ccgaagggag    3540
aaaggcggac aggtatccgg taagcggcag ggtcggaaca ggagagcgca cgagggagct    3600
tccaggggga aacgcctggt atctttatag tcctgtcggg tttcgccacc tctgacttga    3660
gcgtcgattt ttgtgatgct cgtcaggggg gcggagccta tggaaaaacg ccagcaacgc    3720
ggccttttta cggttcctgg ccttttgctg gccttttgct cacatgttct ttcctgcgtt    3780
atcccctgat tctgtggata accgtattac cgcctttgag tgagctgata ccgctcgccg    3840
cagccgaacg accgagcgca gcgagtcagt gagcgaggaa gcggaagagc gcccaatacg    3900
caaaccgcct ctccccgcgc gttggccgat tcattaatgc agctggcacg acaggtttcc    3960
cgactggaaa gcgggcagtg agcgcaacgc aattaatgtg agttagctca ctcattaggc    4020
accccaggct ttacacttta tgcttccggc tcgtatgttg tgtggaattg tgagcggata    4080
acaatttcac acaggaaaca gctatgacca tgattacgcc aagcgcgcaa ttaaccctca    4140
ctaaagggaa caaaagctgg agctgcaagc ttaatgtagt cttatgcaat actcttgtag    4200
tcttgcaaca tggtaacgat gagttagcaa catgccttac aaggagagaa aaagcaccgt    4260
gcatgccgat tggtggaagt aaggtggtac gatcgtgcct tattaggaag caacagacg    4320 ggtctgacat ggattggacg aaccactgaa ttgccgcatt gcagagatat tgtatttaag    4380
tgcctagctc gatacataaa cggctctctc tggttagacc agatctgagc ctgggagctc    4440
tctggctaac tagggaaccc actgcttaag cctcaataaa gcttgccttg agtgcttcaa    4500
gtagtgtgtg cccgtctgtt gtgtgactct ggtaactaga gatccctcag ccccttttag    4560
tcagtgtgga aaatctctag cagtggcgcc cgaacaggga cttgaaagcg aaagggaaac    4620
cagaggagct ctctcgacgc aggactcggc ttgctgaagc gcgcacggca agaggcgagg    4680
ggcggcgact ggtgagtacg ccaaaaattt tgactagcgg aggctagaag gagagagatg    4740
ggtgcgagag cgtcagtatt aagcggggga gaattagatc gcgatgggaa aaaattcggt    4800
taaggccagg gggaagaaa aaatataaat taaaacatat agtatgggca agcagggagc    4860
tagaacgatt cgcagttaat cctggcctgt tagaaacatc agaaggctgt agacaaatac    4920
tgggacagct acaaccatcc cttcagacag gatcagaaga acttagatca ttatataata    4980
cagtagcaac cctctattgt gtgcatcaaa ggatagagat aaaagacacc aaggaagctt    5040
tagacaagat agaggaagag caaaacaaaa gtaagaccac cgcacagcaa gcggccgctg    5100
atcttcagac ctggaggagg agatatgagg gacaattgga gaagtgaatt atataaatat    5160
aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tgggcgcagc gtcaatgacg ctgacggtac aggccagaca attattgtct    5340
ggtatagtgc agcagcagaa caatttgctg agggctattg aggcgcaaca gcatctgttg    5400
caactcacag tctgggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg gaatcacacg    5580
acctggatgg agtgggacag agaaattaac aattacacaa gcttaataca ctccttaatt    5640
gaagaatcgc aaaaccagca agaaaagaat gaacaagaat tattggaatt agataaatgg    5700
```

-continued

```
gcaagtttgt ggaattggtt taacataaca aattggctgt ggtatataaa attattcata    5760
atgatagtag gaggcttggt aggtttaaga atagttttg ctgtactttc tatagtgaat    5820
agagttaggc agggatattc accattatcg tttcagaccc acctcccaac cccgagggga    5880
cccgacaggc ccgaaggaat agaagaagaa ggtggagaga gagacagaga cagatccatt    5940
cgattagtga acggatctcg acggtatcga tcacgagact agcctcgaca caaatggcag    6000
tattcatcca caatttaaa agaaaagggg ggattggggg gtacagtgca ggggaaagaa    6060
tagtagacat aatagcaaca gacatacaaa ctaagaatt acaaaaacaa attacaaaaa    6120
ttcaaaattt tcgggtttat tacagggaca gcagaaatcc actttggctc gagaagcttg    6180
atatcggctc cggtgcccgt cagtgggcag agcgcacatc gcccacagtc cccgagaagt    6240
tgggggagg ggtcggcaat tgaaccggtg cctagagaag gtggcgcggg gtaaactggg    6300
aaagtgatgt cgtgtactgg ctccgccttt tccgaggg tggggagaa ccgtatataa    6360
gtgcagtagt cgccgtgaac gttcttttc gcaacgggtt tgccgccaga acacaggatc    6420
cgccaccatg gccttaccag tgaccgcctt gctcctgccg ctggccttgc tgctccacgc    6480
cgccaggccg gatatccaga tgacccagag cccaagctcc ctgtccgcct ctgtgggcga    6540
cagggtgacc atcacatgcc gcgccagcca gacaatctgg tcctacctga actggtatca    6600
gcagagaccc ggcaaggcc ctaatctgct gatctacgca gcatctagcc tgcagtctgg    6660
agtgccctcc cggttctctg gaagaggatc cggaaccgac ttcaccctga caatctcctc    6720
tctgcaggcc gaggacttcg ccacatacta ttgccagcag agctattcca tccctcagac    6780
ctttggccag ggcacaaagc tggagatcaa gggcggcggc ggctctggag gaggaggaag    6840
cggaggagga ggatcccagg tgcagctgca gcagagcgga ccaggactgg tgaagccctc    6900
ccagaccctg tctctgacat gtgccatcag cggcgattcc gtgagctcca acagcgccgc    6960
ctggaattgg atccggcagt ctcccagcag aggactggag tggctgggaa ggacctacta    7020
tcgctccaag tggtacaacg attatgccgt gtctgtgaag agccggatca ccatcaaccc    7080
tgacacatct aagaatcagt tcagcctgca gctgaattcc gtgacccag aggacacagc    7140
cgtgtactat tgtgcaaggg aggtgaccgg cgacctggag gatgcctttg acatctgggg    7200
ccagggcacc atggtgacag tgtctagcac cacgacgcca gcgccgcgac caccaacacc    7260
ggcgcccacc atcgcgtcgc agcccctgtc cctgcgccca gaggcgtgcc ggccagcgg    7320
ggggggcgca gtgcacacga gggggctgga cttcgcctgt gatatctaca tctgggcgcc    7380
cttggccggg acttgtgggg tccttctcct gtcactggtt atcacccttt actgcaaacg    7440
gggcagaaag aaactcctgt atatattcaa acaaccattt atgagaccag tacaaactac    7500
tcaagaggaa gatggctgta gctgccgatt tccagaagaa gaagaaggag gatgtgaact    7560
gagagtgaag ttcagcagga gcgcagacgc ccccgcgtac aagcagggcc agaaccagct    7620
ctataacgag ctcaatctag gacgaagaga ggagtacgat gtttggaca agaggcgtgg    7680
ccgggaccct gagatggggg gaaagccgag aaggaagaac cctcaggaag gcctgtacaa    7740
tgaactgcag aaagataaga tggcggaggc ctacagtgag attgggatga aggcgagcg    7800
ccggaggggc aaggggcacg atggccttta ccagggtctc agtacagcca ccaaggacac    7860
ctacgacgcc cttcacatgc aggccctgcc ccctcgctaa tctagaggcg cgcc           7914
```

<210> SEQ ID NO 20
<211> LENGTH: 7899
<212> TYPE: DNA

<213> ORGANISM: Artificial Sequence
<220> FEATURE:
<223> OTHER INFORMATION: synthesis

<400> SEQUENCE: 20

```
gtcgacacta gtaatcaacc tctggattac aaaatttgtg aaagattgac tggtattctt      60
aactatgttg ctcctttac gctatgtgga tacgctgctt taatgccttt gtatcatgct     120
attgcttccc gtatggcttt cattttctcc tccttgtata aatcctggtt gctgtctctt     180
tatgaggagt tgtggcccgt tgtcaggcaa cgtggcgtgg tgtgcactgt gtttgctgac     240
gcaaccccca ctggttgggg cattgccacc acctgtcagc tcctttccgg gactttcgct     300
ttccccctcc ctattgccac ggcggaactc atcgccgcct gccttgcccg ctgctggaca     360
ggggctcggc tgttgggcac tgacaattcc gtggtgttgt cggggaagct gacgtccttt     420
ccatggctgc tcgcctgtgt tgccacctgg attctgcgcg ggacgtcctt ctgctacgtc     480
ccttcggccc tcaatccagc ggaccttcct cccgcggcc tgctgccggc tctgcggcct     540
cttccgcgtc ttcgccttcg ccctcagacg agtcggatcc ccctttgggc cgcctccccg     600
cctgccgcgg aattcgagct cggtaccttt aagaccaatg acttacaagg cagctgtaga     660
tcttagccac ttttaaaag aaaagggggg actggaaggg ctaattcact cccaacgaag     720
acaagatctg cttttgctt gtactgagtc tctctggtta gaccagatct gagcctggga     780
gctctctggc taactaggga acccactgct taagcctcaa taaagcttgc cttgagtgct     840
tcaagtagtg tgtgcccgtc tgttgtgtga ctctggtaac tagagatccc tcagaccctt     900
ttagtcagtg tggaaaatct ctagcagtag tagttcatgt catcttatta ttcagtattt     960
ataacttgca aagaaatgaa tatcagagag tgagaggaac ttgtttattg cagcttataa    1020
tggttacaaa taaagcaata gcatcacaaa tttcacaaat aaagcatttt ttcactgca    1080
ttctagttgt ggtttgtcca aactcatcaa tgtatcttat catgtctggc tctagctatc    1140
ccgcccctaa ctccgcccat cccgcccta actccgccca gttccgccca ttctccgccc    1200
catggctgac taatttttt tatttatgca gaggccgagg ccgcctcggc ctctgagcta    1260
ttccagaagt agtgaggagg cttttttgga ggcctaggga cgtacccaat tcgccctata    1320
gtgagtcgta ttacgcgcgc tcactggccg tcgttttaca acgtcgtgac tgggaaaacc    1380
ctggcgttac ccaacttaat cgccttgcag cacatccccc tttcgccagc tggcgtaata    1440
gcgaagaggc ccgcaccgat cgcccttccc aacagttgcg cagcctgaat ggcgaatggg    1500
acgcgcctg tagcggcgca ttaagcgcgg cgggtgtggt ggttacgcgc agcgtgaccg    1560
ctacacttgc cagcgcccta gcgcccgctc ctttcgcttt cttcccttcc tttctcgcca    1620
cgttcgccgg ctttccccgt caagctctaa atcgggggct ccctttaggg ttccgattta    1680
gtgctttacg gcacctcgac cccaaaaaac ttgattaggg tgatggttca cgtagtgggc    1740
catcgccctg atagacggtt tttcgccctt tgacgttgga gtccacgttc tttaatagtg    1800
gactcttgtt ccaaactgga acaacactca accctatctc ggtctattct tttgatttat    1860
aagggatttt gccgatttcg gcctattggt taaaaaatga gctgatttaa caaaaattta    1920
acgcgaattt taacaaaata ttaacgctta caatttaggt ggcactttc ggggaaatgt    1980
gcgcggaacc cctatttgtt tatttttcta aatacattca aatatgtatc cgctcatgag    2040
acaataaccc tgataaatgc ttcaataata ttgaaaaagg aagagtatga gtattcaaca    2100
tttccgtgtc gcccttattc ccttttttgc ggcattttgc cttcctgttt ttgctcaccc    2160
agaaacgctg gtgaaagtaa aagatgctga agatcagttg ggtgcacgag tgggttacat    2220
```

```
cgaactggat ctcaacagcg gtaagatcct tgagagtttt cgccccgaag aacgttttcc    2280
aatgatgagc acttttaaag ttctgctatg tggcgcggta ttatcccgta ttgacgccgg    2340
gcaagagcaa ctcggtcgcc gcatacacta ttctcagaat gacttggttg agtactcacc    2400
agtcacagaa aagcatctta cggatggcat gacagtaaga gaattatgca gtgctgccat    2460
aaccatgagt gataacactg cggccaactt acttctgaca acgatcggag gaccgaagga    2520
gctaaccgct tttttgcaca acatggggga tcatgtaact cgccttgatc gttgggaacc    2580
ggagctgaat gaagccatac caaacgacga gcgtgacacc acgatgcctg tagcaatggc    2640
aacaacgttg cgcaaactat taactggcga actacttact ctagcttccc ggcaacaatt    2700
aatagactgg atggaggcgg ataaagttgc aggaccactt ctgcgctcgg ccttccggc    2760 tggctggttt attgctgata atctggagcc ggtgagcgt ggctctcgcg gtatcattgc    2820
agcactgggg ccagatggta agccctcccg tatcgtagtt atctacacga cggggagtca    2880
ggcaactatg gatgaacgaa atagacagat cgctgagata ggtgcctcac tgattaagca    2940
ttggtaactg tcagaccaag tttactcata tatactttag attgatttaa aacttcattt    3000
ttaatttaaa aggatctagg tgaagatcct tttgataat ctcatgacca aaatccctta    3060
acgtgagttt tcgttccact gagcgtcaga ccccgtagaa aagatcaaag gatcttcttg    3120
agatcctttt tttctgcgcg taatctgctg cttgcaaaca aaaaaaccac cgctaccagc    3180
ggtggtttgt ttgccggatc aagagctacc aactcttttt ccgaaggtaa ctggcttcag    3240
cagagcgcag ataccaaata ctgttcttct agtgtagccg tagttaggcc accacttcaa    3300
gaactctgta gcaccgccta catacctcgc tctgctaatc ctgttaccag tggctgctgc    3360
cagtggcgat aagtcgtgtc ttaccgggtt ggactcaaga cgatagttac cggataaggc    3420
gcagcggtcg ggctgaacgg ggggttcgtg cacacagccc agcttggagc gaacgaccta    3480
caccgaactg agatacctac agcgtgagct atgagaaagc gccacgcttc ccgaagggag    3540
aaaggcggac aggtatccgg taagcggcag ggtcggaaca ggagagcgca cgagggagct    3600
tccaggggga aacgcctggt atctttatag tcctgtcggg tttcgccacc tctgacttga    3660
gcgtcgattt ttgtgatgct cgtcaggggg gcggagccta tggaaaaacg ccagcaacgc    3720 ggcctttta cggttcctgg ccttttgctg gccttttgct cacatgttct ttcctgcgtt    3780 atccctgat tctgtggata accgtattac cgcctttgag tgagctgata ccgctcgccg    3840
cagccgaacg accgagcgca gcgagtcagt gagcgaggaa gcggaagagc gcccaatacg    3900
caaaccgcct ctccccgcgc gttggccgat tcattaatgc agctggcacg acaggtttcc    3960
cgactggaaa gcgggcagtg agcgcaacgc aattaatgtg agttagctca ctcattaggc    4020
accccaggct ttacacttta tgcttccggc tcgtatgttg tgtggaattg tgagcggata    4080
acaatttcac acaggaaaca gctatgacca tgattacgcc aagcgcgcaa ttaaccctca    4140
ctaaagggaa caaagctggg agctgcaagc ttaatgtagt cttatgcaat actcttgtag    4200
tcttgcaaca tggtaacgat gagttagcaa catgccttac aaggagagaa aaagcaccgt    4260
gcatgccgat tggtggaagt aaggtggtac gatcgtgcct tattaggaag gcaacagacg    4320
ggtctgacat ggattggacg aaccactgaa ttgccgcatt gcagagatat tgtatttaag    4380
tgcctagctc gatacataaa cggctctctc tggttagacc agatctgagc ctgggagctc    4440
tctggctaac tagggaaccc actgcttaag cctcaataaa gcttgccttg agtgcttcaa    4500
gtagtgtgtg cccgtctgtt gtgtgactct ggtaactaga gatccctcag acccttttag    4560
```

```
tcagtgtgga aaatctctag cagtggcgcc cgaacaggga cttgaaagcg aaagggaaac    4620
cagaggagct ctctcgacgc aggactcggc ttgctgaagc gcgcacggca agaggcgagg    4680
ggcggcgact ggtgagtacg ccaaaaattt tgactagcgg aggctagaag gagagagatg    4740
ggtgcgagag cgtcagtatt aagcggggga gaattagatc gcgatgggaa aaaattcggt    4800
taaggccagg gggaagaaaa aaatataaat taaaacatat agtatgggca agcagggagc    4860
tagaacgatt cgcagttaat cctggcctgt tagaaacatc agaaggctgt agacaaatac    4920
tgggacagct acaaccatcc cttcagacag gatcagaaga acttagatca ttatataata    4980
cagtagcaac cctctattgt gtgcatcaaa ggatagagat aaaagacacc aaggaagctt    5040
tagacaagat agaggaagag caaaacaaaa gtaagaccac cgcacagcaa gcggccgctg    5100
atcttcagac ctggaggagg agatatgagg gacaattgga gaagtgaatt atataaatat    5160
aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tgggcgcagc gtcaatgacg ctgacggtac aggccagaca attattgtct    5340
ggtatagtgc agcagcagaa caatttgctg agggctattg aggcgcaaca gcatctgttg    5400
caactcacag tctggggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg gaatcacacg    5580
acctggatgg agtgggacag agaaattaac aattacacaa gcttaataca ctccttaatt    5640
gaagaatcgc aaaaccagca agaaaagaat gaacaagaat tattggaatt agataaatgg    5700
gcaagtttgt ggaattggtt taacataaca aattggctgt ggtatataaa attattcata    5760
atgatagtag gaggcttggt aggtttaaga atagttttg ctgtactttc tatagtgaat    5820
agagttaggc agggatattc accattatcg tttcagaccc acctcccaac cccgagggga    5880
cccgacaggc ccgaaggaat agaagaagaa ggtggagaga gagacagaga cagatccatt    5940
cgattagtga acggatctcg acggtatcga tcacgagact agcctcgaca caaatggcag    6000
tattcatcca caattttaaa agaaaagggg ggattggggg gtacagtgca ggggaaagaa    6060
tagtagacat aatagcaaca gacatacaaa ctaaagaatt acaaaaacaa attacaaaaa    6120
ttcaaaattt tcgggtttat tacagggaca gcagaaatcc actttggctc gagaagcttg    6180
atatcggctc cggtgcccgt cagtgggcag agcgcacatc gcccacagtc cccgagaagt    6240
tggggggagg ggtcggcaat tgaaccggtg cctagaaaag gtggcgcggg gtaaactggg    6300
aaagtgatgt cgtgtactgg ctccgccttt ttcccgaggg tgggggagaa ccgtatataa    6360
gtgcagtagt cgccgtgaac gttctttttc gcaacgggtt tgccgccaga acacaggatc    6420
cgccaccatg gccttaccag tgaccgcctt gctcctgccg ctggccttgc tgctccacgc    6480
cgccaggccg cggatcgtga tgacccagtc tccaggcaca ctgtctgtga gcccaggaga    6540
gaccgccaca ctgtcctgcc gggcctccca gtctttcagc aacatgctgg cctggtacca    6600
gcagaagtcc ggccagcccc ctagactgct gatctatggc gtgtctacca gggcagcagg    6660
agtgccagca agattctccg gatctggaag cggcacagag tttaccctga caatctccaa    6720
tctgcagtct gaggacttcg ccgtgtacta ttgccagcag tacggcgatt ggcctaggta    6780
tacctttggc cagggcacaa aggtggagcg caagggagga ggaggaagcg gaggaggagg    6840
atccggcggc ggcggctctg aggtgcagct ggtgcagagc ggaggaggag tggtgaggcc    6900
tggaggatct ctgcgcctgc catgtgcagc aagcggcttc acctttgacg attacggaat    6960
```

```
gagctgggtg aggcaggcac caggcaaggg actggagtgg gtgtccggca tcaactggaa      7020
tggaggaagc accggatacg cagactccgt gaagggccgg ttcacaatct ctagagataa      7080
cgccaagaat agcctgtatc tgcagatgaa ctccctgatc gccgaggaca ccgccctgta      7140
ccactgtgca aggggaggcg actatgatgc ctttgatatc tggggccagg gcaccatggt      7200
gacagtgagc tccaccacga cgccagcgcc gcgaccacca acaccggcgc ccaccatcgc      7260
gtcgcagccc ctgtccctgc gcccagaggc gtgccggcca gcggcggggg gcgcagtgca      7320
cacgaggggg ctggacttcg cctgtgatat ctacatctgg gcgcccttgg ccgggacttg      7380
tggggtcctt ctcctgtcac tggttatcac cctttactgc aaacggggca gaaagaaact      7440
cctgtatata ttcaaacaac catttatgag accagtacaa actactcaag aggaagatgg      7500
ctgtagctgc cgatttccag aagaagaaga aggaggatgt gaactgagag tgaagttcag      7560
caggagcgca gacgcccccg cgtacaagca gggccagaac cagctctata cgagctcaa       7620 tctaggacga agagaggagt acgatgtttt ggacaagagg cgtggccggg accctgagat      7680 gggggggaaag ccgagaagga agaaccctca ggaaggcctg tacaatgaac tgcagaaaga      7740
taagatggcg gaggcctaca gtgagattgg gatgaaaggc gagcgccgga ggggcaaggg      7800
gcacgatggc ctttaccagg gtctcagtac agccaccaag gacacctacg acgcccttca      7860
catgcaggcc ctgccccctc gctaatctag aggcgcgcc                             7899
```

<210> SEQ ID NO 21
<211> LENGTH: 242
<212> TYPE: PRT
<213> ORGANISM: Artificial Sequence
<220> FEATURE:
<223> OTHER INFORMATION: Synthesized

<400> SEQUENCE: 21

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190
```

```
Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 22
<211> LENGTH: 270
<212> TYPE: PRT
<213> ORGANISM: Artificial Sequence
<220> FEATURE:
<223> OTHER INFORMATION: Synthesized

<400> SEQUENCE: 22

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
            85                  90                  95

Glu Gly Ser Gly Glu Leu Phe Arg Trp Asn Val Ser Asp Leu Gly Gly
        100                 105                 110

Leu Gly Cys Gly Leu Lys Asn Arg Ser Ser Glu Gly Pro Ser Ser Pro
    115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
            165                 170                 175

Leu Trp Leu Ser Cys Gly Val Pro Pro Asp Ser Val Ser Arg Gly Pro
        180                 185                 190

Leu Ser Trp Thr His Val His Pro Lys Gly Pro Lys Ser Leu Leu Ser
    195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
            245                 250                 255

Ala Arg Pro Val Leu Trp His Trp Leu Leu Arg Thr Gly Gly
        260                 265                 270

<210> SEQ ID NO 23
<211> LENGTH: 196
<212> TYPE: PRT
<213> ORGANISM: Artificial Sequence
<220> FEATURE:
<223> OTHER INFORMATION: Synthesized
```

<400> SEQUENCE: 23

```
Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195
```

<210> SEQ ID NO 24
<211> LENGTH: 196
<212> TYPE: PRT
<213> ORGANISM: Artificial Sequence
<220> FEATURE:
<223> OTHER INFORMATION: Synthesized

<400> SEQUENCE: 24

```
Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
130                 135                 140
```

```
Tyr Lys Ala Gln Leu Thr Arg Leu Asn His Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 25
<211> LENGTH: 7
<212> TYPE: PRT
<213> ORGANISM: Artificial Sequence
<220> FEATURE:
<223> OTHER INFORMATION: Synthesized

<400> SEQUENCE: 25

Trp Arg Ser Ser Leu Ala Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Synthesized

<400> SEQUENCE: 26

Gln Ser Gly Asp Leu Thr Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Synthesized

<400> SEQUENCE: 27

His Lys Trp Val Leu Arg Gln
1               5

<210> SEQ ID NO 28
<211> LENGTH: 7
<212> TYPE: PRT
<213> ORGANISM: Artificial Sequence
<220> FEATURE:
<223> OTHER INFORMATION: Synthesized

<400> SEQUENCE: 28

Cys Pro Ser Asn Leu Arg Arg
1               5

<210> SEQ ID NO 29
<211> LENGTH: 15
<212> TYPE: DNA
<213> ORGANISM: Artificial Sequence
<220> FEATURE:
<223> OTHER INFORMATION: Synthesized

<400> SEQUENCE: 29
gactttgcat gtgca                                                15

<210> SEQ ID NO 30
<211> LENGTH: 7
```

```
<212> TYPE: PRT
<213> ORGANISM: Artificial Sequence
<220> FEATURE:
<223> OTHER INFORMATION: Synthesized

<400> SEQUENCE: 30

Glu Arg Gly Thr Leu Ala Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Synthesized

<400> SEQUENCE: 31

Arg Ser Asp Asn Leu Arg Glu
1               5

<210> SEQ ID NO 32
<211> LENGTH: 7
<212> TYPE: PRT
<213> ORGANISM: Artificial Sequence
<220> FEATURE:
<223> OTHER INFORMATION: Synthesized

<400> SEQUENCE: 32

Thr Ser Gly Ala Leu Thr Arg
1               5

<210> SEQ ID NO 33
<211> LENGTH: 13
<212> TYPE: DNA
<213> ORGANISM: Artificial Sequence
<220> FEATURE:
<223> OTHER INFORMATION: Synthesized

<400> SEQUENCE: 33
gttgctccag gcc                                                          13

<210> SEQ ID NO 34
<211> LENGTH: 380
<212> TYPE: PRT
<213> ORGANISM: Artificial Sequence
<220> FEATURE:
<223> OTHER INFORMATION: Synthesized

<400> SEQUENCE: 34

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
                20                  25                  30

Gln Glu Glu Asp Phe Arg Val Thr Cys Lys Asp Ile Gln Arg Ile Pro
            35                  40                  45

Ser Leu Pro Pro Ser Thr Gln Thr Leu Lys Leu Ile Glu Thr His Leu
        50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110
```

-continued

```
Asn Leu Thr Tyr Ile Asp Pro Asp Ala Leu Lys Glu Leu Pro Leu Leu
            115                 120                 125
Lys Phe Leu Gly Ile Phe Asn Thr Gly Leu Lys Met Phe Pro Asp Leu
    130                 135                 140
Thr Lys Val Tyr Ser Thr Asp Ile Phe Phe Ile Leu Glu Ile Thr Asp
145                 150                 155                 160
Asn Pro Tyr Met Thr Ser Ile Pro Val Asn Ala Phe Gln Gly Leu Cys
                165                 170                 175
Asn Glu Thr Leu Thr Leu Lys Leu Tyr Asn Asn Gly Phe Thr Ser Val
            180                 185                 190
Gln Gly Tyr Ala Phe Asn Gly Thr Lys Leu Asp Ala Val Tyr Leu Asn
        195                 200                 205
Lys Asn Lys Tyr Leu Thr Val Ile Asp Lys Asp Ala Phe Gly Gly Val
    210                 215                 220
Tyr Ser Gly Pro Ser Leu Leu Asp Val Ser Gln Thr Ser Val Thr Ala
225                 230                 235                 240
Leu Pro Ser Lys Gly Leu Glu His Leu Lys Glu Leu Ile Ala Arg Asn
                245                 250                 255
Thr Trp Thr Leu Lys Lys Leu Pro Leu Ser Leu Ser Phe Leu His Leu
            260                 265                 270
Thr Arg Ala Asp Leu Ser Tyr Pro Ser His Cys Cys Ala Phe Lys Asn
        275                 280                 285
Gln Lys Lys Ile Arg Gly Ile Leu Glu Ser Leu Met Cys Asn Glu Ser
    290                 295                 300
Ser Met Gln Ser Leu Arg Gln Arg Lys Ser Val Asn Ala Leu Asn Ser
305                 310                 315                 320
Pro Leu His Gln Glu Tyr Glu Glu Asn Leu Gly Asp Ser Ile Val Gly
                325                 330                 335
Tyr Lys Glu Lys Ser Lys Phe Gln Asp Thr His Asn Asn Ala His Tyr
            340                 345                 350
Tyr Val Phe Phe Glu Glu Gln Glu Asp Glu Ile Ile Gly Phe Gly Gln
        355                 360                 365
Glu Leu Lys Asn Pro Gln Glu Glu Thr Leu Gln Ala
    370                 375                 380

<210> SEQ ID NO 35
<211> LENGTH: 69
<212> TYPE: PRT
<213> ORGANISM: Artificial Sequence
<220> FEATURE:
<223> OTHER INFORMATION: Synthesized

<400> SEQUENCE: 35

Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp Ile Tyr Ile
        35                  40                  45
Trp Ala Pro Leu Ala Gly Thr Cys Gly Val Leu Leu Leu Ser Leu Val
    50                  55                  60
Ile Thr Leu Tyr Cys
65

<210> SEQ ID NO 36
<211> LENGTH: 47
```

<212> TYPE: PRT
<213> ORGANISM: Artificial Sequence
<220> FEATURE:
<223> OTHER INFORMATION: Synthesized

<400> SEQUENCE: 36

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 37
<211> LENGTH: 22
<212> TYPE: PRT
<213> ORGANISM: Artificial Sequence
<220> FEATURE:
<223> OTHER INFORMATION: Synthesized

<400> SEQUENCE: 37

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 38
<211> LENGTH: 21
<212> TYPE: PRT
<213> ORGANISM: Artificial Sequence
<220> FEATURE:
<223> OTHER INFORMATION: Synthesized

<400> SEQUENCE: 38

Met Ala Leu Pro Val Thr Ala Leu Leu Leu Pro Leu Ala Leu Leu Leu
1               5                   10                  15

His Ala Ala Arg Pro
            20

<210> SEQ ID NO 39
<211> LENGTH: 42
<212> TYPE: PRT
<213> ORGANISM: Artificial Sequence
<220> FEATURE:
<223> OTHER INFORMATION: Synthesized

<400> SEQUENCE: 39

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 40
<211> LENGTH: 112
<212> TYPE: PRT
<213> ORGANISM: Artificial Sequence
<220> FEATURE:
<223> OTHER INFORMATION: Synthesized

<400> SEQUENCE: 40

Arg Val Lys Phe Ser Arg Ser Ala Asp Ala Pro Ala Tyr Lys Gln Gly
1               5                   10                  15

```
Gln Asn Gln Leu Tyr Asn Glu Leu Asn Leu Gly Arg Arg Glu Glu Tyr
             20                  25                  30

Asp Val Leu Asp Lys Arg Arg Gly Arg Asp Pro Glu Met Gly Gly Lys
         35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110

<210> SEQ ID NO 41
<211> LENGTH: 272
<212> TYPE: PRT
<213> ORGANISM: Homo sapiens

<400> SEQUENCE: 41

Pro Glu Glu Pro Leu Val Val Lys Val Glu Glu Gly Asp Asn Ala Val
 1               5                  10                  15

Leu Gln Cys Leu Lys Gly Thr Ser Asp Gly Pro Thr Gln Gln Leu Thr
             20                  25                  30

Trp Ser Arg Glu Ser Pro Leu Lys Pro Phe Leu Lys Leu Ser Leu Gly
         35                  40                  45

Leu Pro Gly Leu Gly Ile His Met Arg Pro Leu Ala Ile Trp Leu Phe
     50                  55                  60

Ile Phe Asn Val Ser Gln Gln Met Gly Gly Phe Tyr Leu Cys Gln Pro
 65                  70                  75                  80

Gly Pro Pro Ser Glu Lys Ala Trp Gln Pro Gly Trp Thr Val Asn Val
                 85                  90                  95

Glu Gly Ser Gly Glu Leu Phe Arg Trp Asn Val Ser Asp Leu Gly Gly
                100                 105                 110

Leu Gly Cys Gly Leu Lys Asn Arg Ser Ser Glu Gly Pro Ser Ser Pro
                115                 120                 125

Ser Gly Lys Leu Met Ser Pro Lys Leu Tyr Val Trp Ala Lys Asp Arg
            130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270
```

```
<210> SEQ ID NO 42
<211> LENGTH: 205
<212> TYPE: PRT
<213> ORGANISM: Homo sapiens

<400> SEQUENCE: 42

Ile Ser Ser Met Asp Met Glu Arg Pro Gly Asp Gly Lys Cys Gln Pro
1               5                   10                  15

Ile Glu Ile Pro Met Cys Lys Asp Ile Gly Tyr Asn Met Thr Arg Met
            20                  25                  30

Pro Asn Leu Met Gly His Glu Asn Gln Arg Glu Ala Ala Ile Gln Leu
        35                  40                  45

His Glu Phe Ala Pro Leu Val Glu Tyr Gly Cys His Gly His Leu Arg
    50                  55                  60

Phe Phe Leu Cys Ser Leu Tyr Ala Pro Met Cys Thr Glu Gln Val Ser
65                  70                  75                  80

Thr Pro Ile Pro Ala Cys Arg Val Met Cys Glu Gln Ala Arg Leu Lys
                85                  90                  95

Cys Ser Pro Ile Met Glu Gln Phe Asn Phe Lys Trp Pro Asp Ser Leu
            100                 105                 110

Asp Cys Arg Lys Leu Pro Asn Lys Asn Asp Pro Asn Tyr Leu Cys Met
        115                 120                 125

Glu Ala Pro Asn Asn Gly Ser Asp Glu Pro Thr Arg Gly Ser Gly Leu
    130                 135                 140

Phe Pro Pro Leu Phe Arg Pro Gln Arg Pro His Ser Ala Gln Glu His
145                 150                 155                 160

Pro Leu Lys Asp Gly Gly Pro Gly Arg Gly Gly Cys Asp Asn Pro Gly
                165                 170                 175

Lys Phe His His Val Glu Lys Ser Ala Ser Cys Ala Pro Leu Cys Thr
            180                 185                 190

Pro Gly Val Asp Val Tyr Trp Ser Arg Glu Asp Lys Arg
        195                 200                 205

<210> SEQ ID NO 43
<211> LENGTH: 393
<212> TYPE: PRT
<213> ORGANISM: Homo sapiens

<400> SEQUENCE: 43

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
```

```
                130                 135                 140
Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
                195                 200                 205

Ser Leu Leu Asp Val Ser Gln Thr Ser Val Thr Ala Leu Pro Ser Lys
            210                 215                 220

Gly Leu Glu His Leu Lys Glu Leu Ile Ala Arg Asn Thr Trp Thr Leu
225                 230                 235                 240

Lys Lys Leu Pro Leu Ser Leu Ser Phe Leu His Leu Thr Arg Ala Asp
                245                 250                 255

Leu Ser Tyr Pro Ser His Cys Cys Ala Phe Lys Asn Gln Lys Lys Ile
            260                 265                 270

Arg Gly Ile Leu Glu Ser Leu Met Cys Asn Glu Ser Ser Met Gln Ser
                275                 280                 285

Leu Arg Gln Arg Lys Ser Val Asn Ala Leu Asn Ser Pro Leu His Gln
            290                 295                 300

Glu Tyr Glu Glu Asn Leu Gly Asp Ser Ile Val Gly Tyr Lys Glu Lys
305                 310                 315                 320

Ser Lys Phe Gln Asp Thr His Asn Asn Ala His Tyr Tyr Val Phe Phe
                325                 330                 335

Glu Glu Gln Glu Asp Glu Ile Ile Gly Phe Gly Gln Glu Leu Lys Asn
            340                 345                 350

Pro Gln Glu Glu Thr Leu Gln Ala Phe Asp Ser His Tyr Asp Tyr Thr
                355                 360                 365

Ile Cys Gly Asp Ser Glu Asp Met Val Cys Thr Pro Lys Ser Asp Glu
            370                 375                 380

Phe Asn Pro Cys Glu Asp Ile Met Gly
385                 390

<210> SEQ ID NO 44
<211> LENGTH: 210
<212> TYPE: PRT
<213> ORGANISM: Homo sapiens

<400> SEQUENCE: 44

Gln Leu Pro Pro Gly Lys Pro Glu Ile Phe Lys Cys Arg Ser Pro Asn
1               5                   10                  15

Lys Glu Thr Phe Thr Cys Trp Trp Arg Pro Gly Thr Asp Gly Gly Leu
                20                  25                  30

Pro Thr Asn Tyr Ser Leu Thr Tyr His Arg Glu Gly Glu Thr Leu Met
            35                  40                  45

His Glu Cys Pro Asp Tyr Ile Thr Gly Gly Pro Asn Ser Cys His Phe
        50                  55                  60

Gly Lys Gln Tyr Thr Ser Met Trp Arg Thr Tyr Ile Met Met Val Asn
65                  70                  75                  80

Ala Thr Asn Gln Met Gly Ser Ser Phe Ser Asp Glu Leu Tyr Val Asp
                85                  90                  95

Val Thr Tyr Ile Val Gln Pro Asp Pro Pro Leu Glu Leu Ala Val Glu
            100                 105                 110
```

```
Val Lys Gln Pro Glu Asp Arg Lys Pro Tyr Leu Trp Ile Lys Trp Ser
            115                 120                 125

Pro Pro Thr Leu Ile Asp Leu Lys Thr Gly Trp Phe Thr Leu Leu Tyr
130                 135                 140

Glu Ile Arg Leu Lys Pro Glu Lys Ala Ala Glu Trp Glu Ile His Phe
145                 150                 155                 160

Ala Gly Gln Gln Thr Glu Phe Lys Ile Leu Ser Leu His Pro Gly Gln
                165                 170                 175

Lys Tyr Leu Val Gln Val Arg Cys Lys Pro Asp His Gly Tyr Trp Ser
            180                 185                 190

Ala Trp Ser Pro Ala Thr Phe Ile Gln Ile Pro Ser Asp Phe Thr Met
            195                 200                 205

Asn Asp
    210

<210> SEQ ID NO 45
<211> LENGTH: 660
<212> TYPE: PRT
<213> ORGANISM: Homo sapiens

<400> SEQUENCE: 45

Glu Gln Asp Leu Ser Val Asn Arg Ala Val Trp Asp Gly Gly Gly Cys
1               5                   10                  15

Ile Ser Gln Gly Asp Val Leu Asn Arg Gln Cys Gln Gln Leu Ser Gln
            20                  25                  30

His Val Arg Thr Gly Ser Ala Ala Asn Thr Ala Thr Gly Thr Thr Ser
        35                  40                  45

Thr Asn Val Val Glu Pro Arg Met Tyr Leu Ser Cys Ser Thr Asn Pro
50                  55                  60

Glu Met Thr Ser Ile Glu Ser Ser Val Thr Ser Asp Thr Pro Gly Val
65                  70                  75                  80

Ser Ser Thr Arg Met Thr Pro Thr Glu Ser Arg Thr Thr Ser Glu Ser
            85                  90                  95

Thr Ser Asp Ser Thr Thr Leu Phe Pro Ser Ser Thr Glu Asp Thr Ser
                100                 105                 110

Ser Pro Thr Thr Pro Glu Gly Thr Asp Val Pro Met Ser Thr Pro Ser
            115                 120                 125

Glu Glu Ser Ile Ser Ser Thr Met Ala Phe Val Ser Thr Ala Pro Leu
130                 135                 140

Pro Ser Phe Glu Ala Tyr Thr Ser Leu Thr Tyr Lys Val Asp Met Ser
145                 150                 155                 160

Thr Pro Leu Thr Thr Ser Thr Gln Ala Ser Ser Ser Pro Thr Thr Pro
                165                 170                 175

Glu Ser Thr Thr Ile Pro Lys Ser Thr Asn Ser Glu Gly Ser Thr Pro
            180                 185                 190

Leu Thr Ser Met Pro Ala Ser Thr Met Lys Val Ala Ser Ser Glu Ala
            195                 200                 205

Ile Thr Leu Leu Thr Thr Pro Val Glu Ile Ser Thr Pro Val Thr Ile
        210                 215                 220

Ser Ala Gln Ala Ser Ser Pro Thr Thr Ala Glu Gly Pro Ser Leu
225                 230                 235                 240

Ser Asn Ser Ala Pro Ser Gly Gly Ser Thr Pro Leu Thr Arg Met Pro
                245                 250                 255

Leu Ser Val Met Leu Val Val Ser Glu Ala Ser Thr Leu Ser Thr
            260                 265                 270
```

```
Thr Pro Ala Ala Thr Asn Ile Pro Val Ile Thr Ser Thr Glu Ala Ser
            275                 280                 285

Ser Ser Pro Thr Thr Ala Glu Gly Thr Ser Ile Pro Thr Ser Thr Tyr
    290                 295                 300

Thr Glu Gly Ser Thr Pro Leu Thr Ser Thr Pro Ala Ser Thr Met Pro
305                 310                 315                 320

Val Ala Thr Ser Glu Met Ser Thr Leu Ser Ile Thr Pro Val Asp Thr
                325                 330                 335

Ser Thr Leu Val Thr Thr Ser Thr Glu Pro Ser Ser Leu Pro Thr Thr
            340                 345                 350

Ala Glu Ala Thr Ser Met Leu Thr Ser Thr Leu Ser Glu Gly Ser Thr
            355                 360                 365

Pro Leu Thr Asn Met Pro Val Ser Thr Ile Leu Val Ala Ser Ser Glu
    370                 375                 380

Ala Ser Thr Thr Ser Thr Ile Pro Val Asp Ser Lys Thr Phe Val Thr
385                 390                 395                 400

Thr Ala Ser Glu Ala Ser Ser Pro Thr Thr Ala Glu Asp Thr Ser
                405                 410                 415

Ile Ala Thr Ser Thr Pro Ser Glu Gly Ser Thr Pro Leu Thr Ser Met
            420                 425                 430

Pro Val Ser Thr Thr Pro Val Ala Ser Ser Glu Ala Ser Asn Leu Ser
            435                 440                 445

Thr Thr Pro Val Asp Ser Lys Thr Gln Val Thr Thr Ser Thr Glu Ala
            450                 455                 460

Ser Ser Ser Pro Pro Thr Ala Glu Val Asn Ser Met Pro Thr Ser Thr
465                 470                 475                 480

Pro Ser Glu Gly Ser Thr Pro Leu Thr Ser Met Ser Val Ser Thr Met
                485                 490                 495

Pro Val Ala Ser Ser Glu Ala Ser Thr Leu Ser Thr Thr Pro Val Asp
                500                 505                 510

Thr Ser Thr Pro Val Thr Thr Ser Ser Glu Ala Ser Ser Ser Ser Thr
            515                 520                 525

Thr Pro Glu Gly Thr Ser Ile Pro Thr Ser Thr Pro Ser Glu Gly Ser
    530                 535                 540

Thr Pro Leu Thr Asn Met Pro Val Ser Thr Arg Leu Val Val Ser Ser
545                 550                 555                 560

Glu Ala Ser Thr Thr Ser Thr Thr Pro Ala Asp Ser Asn Thr Phe Val
                565                 570                 575

Thr Thr Ser Ser Glu Ala Ser Ser Ser Thr Thr Ala Glu Gly Thr
                580                 585                 590

Ser Met Pro Thr Ser Thr Tyr Ser Glu Arg Gly Thr Thr Ile Thr Ser
            595                 600                 605

Met Ser Val Ser Thr Thr Leu Val Ala Ser Ser Glu Ala Ser Thr Leu
    610                 615                 620

Ser Thr Thr Pro Val Asp Ser Asn Thr Pro Val Thr Thr Ser Thr Glu
625                 630                 635                 640

Ala Thr Ser Ser Ser Thr Thr Ala Glu Gly Thr Ser Met Pro Thr Ser
                645                 650                 655

Thr Tyr Thr Glu
            660

<210> SEQ ID NO 46
<211> LENGTH: 407
```

```
<212> TYPE: PRT
<213> ORGANISM: Homo sapiens

<400> SEQUENCE: 46

Ser Gln Val Ser Gln Asn Cys His Asn Gly Ser Tyr Glu Ile Ser Val
1               5                   10                  15

Leu Met Met Gly Asn Ser Ala Phe Ala Glu Pro Leu Lys Asn Leu Glu
            20                  25                  30

Asp Ala Val Asn Glu Gly Leu Glu Ile Val Arg Gly Arg Leu Gln Asn
        35                  40                  45

Ala Gly Leu Asn Val Thr Val Asn Ala Thr Phe Met Tyr Ser Asp Gly
    50                  55                  60

Leu Ile His Asn Ser Gly Asp Cys Arg Ser Ser Thr Cys Glu Gly Leu
65                  70                  75                  80

Asp Leu Leu Arg Lys Ile Ser Asn Ala Gln Arg Met Gly Cys Val Leu
                85                  90                  95

Ile Gly Pro Ser Cys Thr Tyr Ser Thr Phe Gln Met Tyr Leu Asp Thr
            100                 105                 110

Glu Leu Ser Tyr Pro Met Ile Ser Ala Gly Ser Phe Gly Leu Ser Cys
        115                 120                 125

Asp Tyr Lys Glu Thr Leu Thr Arg Leu Met Ser Pro Ala Arg Lys Leu
    130                 135                 140

Met Tyr Phe Leu Val Asn Phe Trp Lys Thr Asn Asp Leu Pro Phe Lys
145                 150                 155                 160

Thr Tyr Ser Trp Ser Thr Ser Tyr Val Tyr Lys Asn Gly Thr Glu Thr
                165                 170                 175

Glu Asp Cys Phe Trp Tyr Leu Asn Ala Leu Glu Ala Ser Val Ser Tyr
            180                 185                 190

Phe Ser His Glu Leu Gly Phe Lys Val Val Leu Arg Gln Asp Lys Glu
        195                 200                 205

Phe Gln Asp Ile Leu Met Asp His Asn Arg Lys Ser Asn Val Ile Ile
    210                 215                 220

Met Cys Gly Gly Pro Glu Phe Leu Tyr Lys Leu Lys Gly Asp Arg Ala
225                 230                 235                 240

Val Ala Glu Asp Ile Val Ile Leu Val Asp Leu Phe Asn Asp Gln
                245                 250                 255

Tyr Phe Glu Asp Asn Val Thr Ala Pro Asp Tyr Met Lys Asn Val Leu
            260                 265                 270

Val Leu Thr Leu Ser Pro Gly Asn Ser Leu Leu Asn Ser Ser Phe Ser
        275                 280                 285

Arg Asn Leu Ser Pro Thr Lys Arg Asp Phe Ala Leu Ala Tyr Leu Asn
    290                 295                 300

Gly Ile Leu Leu Phe Gly His Met Leu Lys Ile Phe Leu Glu Asn Gly
305                 310                 315                 320

Glu Asn Ile Thr Thr Pro Lys Phe Ala His Ala Phe Arg Asn Leu Thr
                325                 330                 335

Phe Glu Gly Tyr Asp Gly Pro Val Thr Leu Asp Asp Trp Gly Asp Val
            340                 345                 350

Asp Ser Thr Met Val Leu Leu Tyr Thr Ser Val Asp Thr Lys Lys Tyr
        355                 360                 365

Lys Val Leu Leu Thr Tyr Asp Thr His Val Asn Lys Thr Tyr Pro Val
    370                 375                 380

Asp Met Ser Pro Thr Phe Thr Trp Lys Asn Ser Lys Leu Pro Asn Asp
385                 390                 395                 400
```

<210> SEQ ID NO 47
<211> LENGTH: 264
<212> TYPE: PRT
<213> ORGANISM: Homo sapiens

<400> SEQUENCE: 47

```
Ile Thr Gly Arg Gly Pro Gln
                405
```

```
Pro Arg Phe Met Gly Thr Ile Ser Asp Val Lys Thr Asn Val Gln Leu
1               5                   10                  15
Leu Lys Gly Arg Val Asp Asn Ile Ser Thr Leu Asp Ser Glu Ile Lys
            20                  25                  30
Lys Asn Ser Asp Gly Met Glu Ala Ala Gly Val Gln Ile Gln Met Val
        35                  40                  45
Asn Glu Ser Leu Gly Tyr Val Arg Ser Gln Phe Leu Lys Leu Lys Thr
    50                  55                  60
Ser Val Glu Lys Ala Asn Ala Gln Ile Gln Ile Leu Thr Arg Ser Trp
65                  70                  75                  80
Glu Glu Val Ser Thr Leu Asn Ala Gln Ile Pro Glu Leu Lys Ser Asp
                85                  90                  95
Leu Glu Lys Ala Ser Ala Leu Asn Thr Lys Ile Arg Ala Leu Gln Gly
            100                 105                 110
Ser Leu Glu Asn Met Ser Lys Leu Leu Lys Arg Gln Asn Asp Ile Leu
        115                 120                 125
Gln Val Val Ser Gln Gly Trp Lys Tyr Phe Lys Gly Asn Phe Tyr Tyr
    130                 135                 140
Phe Ser Leu Ile Pro Lys Thr Trp Tyr Ser Ala Glu Gln Phe Cys Val
145                 150                 155                 160
Ser Arg Asn Ser His Leu Thr Ser Val Thr Ser Glu Ser Glu Gln Glu
                165                 170                 175
Phe Leu Tyr Lys Thr Ala Gly Gly Leu Ile Tyr Trp Ile Gly Leu Thr
            180                 185                 190
Lys Ala Gly Met Glu Gly Asp Trp Ser Trp Val Asp Asp Thr Pro Phe
        195                 200                 205
Asn Lys Val Gln Ser Val Arg Phe Trp Ile Pro Gly Glu Pro Asn Asn
    210                 215                 220
Ala Gly Asn Asn Glu His Cys Gly Asn Ile Lys Ala Pro Ser Leu Gln
225                 230                 235                 240
Ala Trp Asn Asp Ala Pro Cys Asp Lys Thr Phe Leu Phe Ile Cys Lys
                245                 250                 255
Arg Pro Tyr Val Pro Ser Glu Pro
            260
```

<210> SEQ ID NO 48
<211> LENGTH: 237
<212> TYPE: PRT
<213> ORGANISM: Artificial Sequence
<220> FEATURE:
<223> OTHER INFORMATION: Synthesized

<400> SEQUENCE: 48

```
Asp Ile Gln Met Thr Gln Ser Pro Ala Ser Leu Ser Val Ser Val Gly
1               5                   10                  15
Glu Thr Val Thr Ile Thr Cys Arg Ala Ser Glu Asn Ile Tyr Ser Asn
            20                  25                  30
```

```
Leu Ala Trp Tyr Gln Gln Lys Gln Gly Lys Ser Pro Gln Leu Leu Val
            35                  40                  45

Tyr Val Ala Thr Asn Leu Ala Asp Gly Val Pro Ser Arg Phe Ser Gly
 50                  55                  60

Ser Gly Ser Gly Thr Gln Tyr Ser Leu Lys Ile Asn Ser Leu Gln Ser
 65                  70                  75                  80

Glu Asp Phe Gly Ser Tyr Tyr Cys Gln His Phe Trp Gly Thr Pro Tyr
                 85                  90                  95

Thr Phe Gly Gly Gly Thr Lys Leu Gly Gly Gly Ser Gly Gly Gly
                100                 105                 110

Gly Ser Gly Gly Gly Gly Ser Glu Val Gln Leu Gln Gln Ser Gly Ala
            115                 120                 125

Glu Leu Val Lys Pro Gly Ala Ser Val Lys Leu Ser Cys Thr Ala Ser
130                 135                 140

Gly Phe Asn Ile Asn Asp Thr Tyr Met His Trp Val Lys Gln Arg Pro
145                 150                 155                 160

Glu Gln Gly Leu Glu Trp Ile Gly Arg Ile Asp Pro Ala Asn Gly Asn
                165                 170                 175

Thr Lys Tyr Asp Pro Lys Phe Gln Gly Lys Ala Thr Ile Thr Ala Asp
            180                 185                 190

Thr Ser Ser Asn Thr Ala Tyr Leu Gln Leu Ser Ser Leu Thr Ser Glu
        195                 200                 205

Asp Thr Ala Val Tyr Tyr Cys Ala Arg Gly Ala Arg Gly Ser Arg Phe
210                 215                 220

Ala Tyr Trp Gly Gln Gly Thr Leu Val Thr Val Ser Ala
225                 230                 235

<210> SEQ ID NO 49
<211> LENGTH: 244
<212> TYPE: PRT
<213> ORGANISM: Artificial Sequence
<220> FEATURE:
<223> OTHER INFORMATION: Synthesized

<400> SEQUENCE: 49

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
            35                  40                  45

Ile Tyr Asp Asn Asn Lys Arg Pro Ser Ala Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Arg Leu
                 85                  90                  95

Gly Ile Ala Val Phe Gly Gly Gly Thr Gln Leu Thr Val Leu Gly Gly
                100                 105                 110

Gly Gly Ser Gly Gly Gly Gly Ser Gly Gly Gly Ser Glu Val Gln
            115                 120                 125

Leu Val Gln Ser Gly Ala Glu Val Lys Lys Pro Gly Gln Ser Leu Lys
130                 135                 140

Ile Ser Cys Lys Ala Ser Gly Tyr Ser Leu Thr Asp Asn Trp Ile Gly
145                 150                 155                 160
```

```
Trp Val Arg Gln Lys Pro Gly Lys Gly Leu Glu Trp Met Gly Ile Ile
                165                 170                 175

Tyr Pro Gly Asp Ser Asp Thr Arg Tyr Ser Pro Ser Phe Gln Gly Gln
            180                 185                 190

Val Thr Ile Ser Ala Asp Lys Ser Ile Asn Thr Ala Tyr Leu Gln Trp
        195                 200                 205

Ser Ser Leu Lys Ala Ser Asp Thr Ala Ile Tyr Tyr Cys Val Gly Leu
    210                 215                 220

Asp Trp Asn Tyr Asn Pro Leu Arg Tyr Trp Gly Pro Gly Thr Leu Val
225                 230                 235                 240

Thr Val Ser Ser

<210> SEQ ID NO 50
<211> LENGTH: 252
<212> TYPE: PRT
<213> ORGANISM: Artificial Sequence
<220> FEATURE:
<223> OTHER INFORMATION: Synthesized

<400> SEQUENCE: 50

Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Pro Ser Phe Gly Gly Gly Thr Lys Leu Glu Ile Lys Arg
            100                 105                 110

Ala Gly Gly Gly Gly Ser Gly Gly Gly Gly Ser Gly Gly Gly Gly Ser
        115                 120                 125

Glu Val Gln Leu Val Glu Ser Gly Gly Asp Leu Val Lys Pro Gly Gly
    130                 135                 140

Ser Leu Lys Leu Ser Cys Ala Val Ser Gly Phe Thr Phe Ser Ser Tyr
145                 150                 155                 160

Gly Met Ser Trp Val Arg Gln Thr Pro Asp Lys Arg Leu Glu Trp Val
                165                 170                 175

Ala Thr Val Ser Ser Gly Gly Thr Tyr Thr Tyr Tyr Pro Asp Ser Val
            180                 185                 190

Lys Gly Arg Phe Thr Ile Ser Arg Asp Asn Ala Lys Asn Thr Leu Tyr
        195                 200                 205

Leu Gln Met Ser Ser Leu Lys Ser Glu Asp Ser Ala Met Tyr Tyr Cys
    210                 215                 220

Ala Arg His Arg Gly Asn Tyr Tyr Ala Thr Tyr Tyr Ala Met Asp
225                 230                 235                 240

Tyr Trp Gly Gln Gly Thr Ser Val Thr Val Ser Ser
                245                 250

<210> SEQ ID NO 51
<211> LENGTH: 243
<212> TYPE: PRT
```

<213> ORGANISM: Artificial Sequence
<220> FEATURE:
<223> OTHER INFORMATION: Synthesized

<400> SEQUENCE: 51

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His His Glu Tyr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Gln Val Gln Leu Gln Gln
        115                 120                 125

Pro Gly Ala Glu Leu Val Arg Pro Gly Ala Ser Val Lys Leu Ser Cys
130                 135                 140

Lys Ala Ser Gly Tyr Thr Phe Thr Thr Tyr Trp Met Asn Trp Val Lys
145                 150                 155                 160

Gln Arg Pro Glu Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
            180                 185                 190

Thr Val Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Gly Pro Tyr Tyr
    210                 215                 220

Gly Thr Asn Pro Trp Phe Pro Tyr Trp Gly Gln Gly Thr Leu Val Thr
225                 230                 235                 240

Val Ser Ser

<210> SEQ ID NO 52
<211> LENGTH: 241
<212> TYPE: PRT
<213> ORGANISM: Artificial Sequence
<220> FEATURE:
<223> OTHER INFORMATION: Synthesized

<400> SEQUENCE: 52

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg

```
                    85                  90                  95
Thr Phe Gly Gln Gly Thr Asn Val Glu Ile Lys Gly Gly Gly Ser
                100                 105                 110
Gly Gly Gly Gly Ser Gly Gly Gly Ser Gln Val Gln Leu Gln Gln
                115                 120                 125
Trp Gly Ala Gly Leu Leu Lys Pro Ser Glu Thr Leu Ser Leu Thr Cys
        130                 135                 140
Ala Val Phe Gly Gly Ser Phe Ser Gly Tyr Tyr Trp Ser Trp Ile Arg
145                 150                 155                 160
Gln Pro Pro Gly Lys Gly Leu Glu Trp Ile Gly Glu Ile Asn His Arg
                165                 170                 175
Gly Asn Thr Asn Asp Asn Pro Ser Leu Lys Ser Arg Val Thr Ile Ser
                180                 185                 190
Val Asp Thr Ser Lys Asn Gln Phe Ala Leu Lys Leu Ser Ser Val Thr
            195                 200                 205
Ala Ala Asp Thr Ala Val Tyr Tyr Cys Ala Arg Glu Arg Gly Tyr Thr
        210                 215                 220
Tyr Gly Asn Phe Asp His Trp Gly Gln Gly Thr Leu Val Thr Val Ser
225                 230                 235                 240
Ser

<210> SEQ ID NO 53
<211> LENGTH: 246
<212> TYPE: PRT
<213> ORGANISM: Artificial Sequence
<220> FEATURE:
<223> OTHER INFORMATION: Synthesized

<400> SEQUENCE: 53

Asp Val Val Met Thr Gln Thr Pro Leu Ser Leu Pro Val Arg Leu Gly
1               5                   10                  15
Asp Gln Ala Ser Ile Ser Cys Arg Ser Ser Gln Ser Leu Val His Ser
            20                  25                  30
Asn Gly Asn Thr Tyr Leu His Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asn Phe Thr Leu Lys Ile
65                  70                  75                  80
Ser Arg Val Glu Ala Glu Asp Leu Gly Leu Tyr Phe Cys Ser Gln Ser
                85                  90                  95
Thr His Val Pro Tyr Thr Phe Gly Gly Gly Thr Lys Leu Glu Ile Lys
                100                 105                 110
Arg Ala Gly Gly Gly Gly Ser Gly Gly Gly Gly Ser Gly Gly Gly Gly
            115                 120                 125
Ser Gln Val Gln Leu Arg Gln Ser Gly Pro Glu Leu Val Lys Pro Gly
        130                 135                 140
Ala Ser Val Lys Met Ser Cys Lys Ala Ser Gly Tyr Thr Phe Thr Asp
145                 150                 155                 160
Tyr Val Ile Ser Trp Val Lys Gln Arg Thr Gly Gln Gly Leu Glu Trp
                165                 170                 175
Ile Gly Asp Ile Tyr Pro Gly Ser Gly Tyr Ser Phe Tyr Asn Glu Asn
            180                 185                 190
Phe Lys Gly Lys Ala Thr Leu Thr Ala Asp Lys Ser Ser Thr Thr Ala
        195                 200                 205
```

Tyr Met Gln Leu Ser Ser Leu Thr Ser Glu Asp Ser Ala Val Tyr Phe
            210                 215                 220

Cys Ala Thr Tyr Tyr Asn Tyr Pro Phe Ala Tyr Trp Gly Gln Gly Thr
225                 230                 235                 240

Leu Val Thr Val Ser Ala
                245

<210> SEQ ID NO 54
<211> LENGTH: 196
<212> TYPE: PRT
<213> ORGANISM: Artificial Sequence
<220> FEATURE:
<223> OTHER INFORMATION: Synthesized

<400> SEQUENCE: 54

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asn Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 55
<211> LENGTH: 242
<212> TYPE: PRT
<213> ORGANISM: Artificial Sequence
<220> FEATURE:
<223> OTHER INFORMATION: Synthesized

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Tyr
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
            130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
                165                 170                 175

Glu Thr Thr Tyr Tyr Asn Ser Ala Leu Lys Ser Arg Phe Thr Ile Ser
                180                 185                 190

Arg Asp Asn Ala Lys Asn Ser Leu Tyr Leu Gln Met Asn Ser Leu Arg
            195                 200                 205

Ala Glu Asp Thr Ala Val Tyr Tyr Cys Ala Lys His Tyr Tyr Tyr Gly
            210                 215                 220

Gly Ser Tyr Ala Met Asp Tyr Trp Gly Gln Gly Thr Leu Val Thr Val
225                 230                 235                 240

Ser Ser

<210> SEQ ID NO 56
<211> LENGTH: 199
<212> TYPE: PRT
<213> ORGANISM: Artificial Sequence
<220> FEATURE:
<223> OTHER INFORMATION: Synthesized

<400> SEQUENCE: 56

Leu Pro Ile Cys Pro Gly Gly Ala Ala Arg Cys Gln Val Thr Leu Arg
 1               5                  10                  15

Asp Leu Phe Asp Arg Ala Val Val Leu Ser His Tyr Ile His Asn Leu
                 20                  25                  30

Ser Ser Glu Met Phe Ser Glu Phe Asp Lys Arg Tyr Thr His Gly Arg
             35                  40                  45

Gly Phe Ile Thr Lys Ala Ile Asn Ser Cys His Thr Ser Ser Leu Ala
         50                  55                  60

Thr Pro Glu Asp Lys Glu Gln Ala Gln Gln Met Asn Gln Lys Asp Phe
 65                  70                  75                  80

Leu Ser Leu Ile Val Ser Ile Leu Arg Ser Trp Asn Glu Pro Leu Tyr
                 85                  90                  95

His Leu Val Thr Glu Val Arg Gly Met Gln Glu Ala Pro Glu Ala Ile
                100                 105                 110

Leu Ser Lys Ala Val Glu Ile Glu Glu Gln Thr Lys Arg Leu Leu Glu
            115                 120                 125

Gly Met Glu Leu Ile Val Ser Gln Val His Pro Glu Thr Lys Glu Asn
            130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175
```

-continued

Arg Asp Ser His Lys Ile Asp Asn Tyr Leu Lys Leu Leu Lys Cys Arg
            180                 185                 190

Ile Ile His Asn Asn Cys
            195

<210> SEQ ID NO 57
<211> LENGTH: 240
<212> TYPE: PRT
<213> ORGANISM: Artificial Sequence
<220> FEATURE:
<223> OTHER INFORMATION: Synthesized

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Gly Gly Gly Gly Ser Gly Gly Gly Ser Gly Gly Gly Gly Ser
        115                 120                 125

Asp Ile Val Met Thr Gln Ser Pro Asp Ser Leu Ala Val Ser Leu Gly
        130                 135                 140

Glu Arg Ala Thr Ile Asn Cys Lys Ser Ser Gln Ser Leu Leu Asn Ser
145                 150                 155                 160

Arg Thr Arg Lys Asn Tyr Leu Ala Trp Tyr Gln Gln Lys Pro Gly Gln
                165                 170                 175

Pro Pro Lys Leu Leu Ile Tyr Trp Ala Ser Thr Arg Glu Ser Gly Val
            180                 185                 190

Pro Asp Arg Phe Ser Gly Ser Gly Ser Gly Thr Asp Phe Thr Leu Thr
        195                 200                 205

Ile Ser Ser Leu Gln Ala Glu Asp Val Ala Val Tyr Tyr Cys Thr Gln
    210                 215                 220

Ser Phe Ile Leu Arg Thr Phe Gly Gln Gly Thr Lys Val Glu Ile Lys
225                 230                 235                 240

<210> SEQ ID NO 58
<211> LENGTH: 281
<212> TYPE: PRT
<213> ORGANISM: Artificial Sequence
<220> FEATURE:
<223> OTHER INFORMATION: Synthesized

<400> SEQUENCE: 58

Met Asn Val Pro Thr Gln Leu Leu Gly Leu Leu Leu Leu Trp Leu Thr
1               5                   10                  15

Gly Gly Lys Cys Asp Ile Gln Met Thr Gln Ser Pro Ala Ser Leu Ser
            20                  25                  30

Ala Ser Leu Glu Glu Ile Val Thr Ile Thr Cys Lys Ala Ser Gln Ala

```
            35                  40                  45
Ile Asp Ala Tyr Leu Ser Trp Tyr Gln Gln Lys Pro Gly Lys Ser Pro
 50                  55                  60
Gln Leu Leu Ile Tyr Asp Ala Thr Ser Leu Ala Asp Gly Val Pro Ser
65                  70                  75                  80
Arg Phe Ser Gly Ser Arg Ser Gly Thr Gln Tyr Ser Leu Lys Ile Ser
                85                  90                  95
Arg Pro Gln Val Asp Asp Ser Gly Ile Tyr Tyr Cys Leu Gln Ser Tyr
                100                 105                 110
Ser Thr Pro Phe Thr Phe Gly Ser Gly Thr Lys Leu Glu Ile Lys Gly
            115                 120                 125
Gly Gly Gly Gly Ser Gly Gly Gly Ser Gly Gly Gly Ser Met
    130                 135                 140
Ala Val Leu Val Leu Leu Leu Cys Leu Leu Ile Phe Pro Ser Cys Val
145                 150                 155                 160
Leu Ser Gln Val Gln Leu Lys Glu Ser Gly Pro Gly Leu Val Gln Pro
                165                 170                 175
Ser Gln Thr Leu Ser Leu Thr Cys Thr Val Ser Gly Ser Ser Leu Thr
            180                 185                 190
Ser Asn Ser Val Ser Trp Ile Arg Gln Pro Pro Gly Lys Gly Leu Glu
            195                 200                 205
Trp Met Gly Val Ile Trp Ser Asn Gly Asp Ala Asp Tyr Asn Ser Ala
    210                 215                 220
Ile Lys Ser Arg Leu Ser Ile Ser Arg Asp Thr Ser Lys Ser Gln Val
225                 230                 235                 240
Phe Leu Lys Met Asn Ser Leu Gln Thr Glu Asp Thr Ala Met Tyr Phe
                245                 250                 255
Cys Ala Ser Pro Tyr Tyr Gly Tyr Tyr Phe Pro Phe Asp Tyr Trp Gly
                260                 265                 270
Gln Gly Val Met Val Thr Val Ser Ser
            275                 280

<210> SEQ ID NO 59
<211> LENGTH: 285
<212> TYPE: PRT
<213> ORGANISM: Artificial Sequence
<220> FEATURE:
<223> OTHER INFORMATION: Synthesized

<400> SEQUENCE: 59

Met Glu Thr Asp Thr Leu Leu Leu Trp Val Leu Leu Leu Trp Val Pro
1               5                   10                  15
Gly Ser Thr Gly Asp Ile Val Leu Thr Gln Ser Pro Ala Leu Ala Val
                20                  25                  30
Ser Leu Gly Gln Arg Ala Thr Ile Ser Cys Arg Ala Ser Gln Ser Val
            35                  40                  45
Ser Ile Ser Ser His Asp Leu Met Gln Trp Tyr Gln Gln Lys Pro Gly
        50                  55                  60
Gln Gln Pro Lys Leu Leu Ile Tyr Asp Ala Phe Asn Leu Ala Ser Gly
65                  70                  75                  80
Ile Pro Val Arg Phe Ser Gly Ser Gly Ser Gly Thr Asp Phe Thr Leu
                85                  90                  95
Thr Ile Asp Pro Val Gln Ala Asp Asp Ile Ala Thr Tyr Tyr Cys Gln
                100                 105                 110
Gln Ser Lys Asp Asp Pro Tyr Thr Phe Gly Ala Gly Thr Lys Leu Glu
```

```
            115                 120                 125
Leu Lys Gly Gly Gly Gly Ser Gly Gly Gly Ser Gly Gly
    130                 135                 140

Gly Ser Met Asp Ile Arg Leu Ser Leu Ala Phe Leu Val Leu Phe Ile
145                 150                 155                 160

Lys Gly Val Gln Cys Glu Val Gln Leu Val Glu Ser Gly Gly Gly Leu
                165                 170                 175

Val Gln Pro Gly Arg Ser Met Lys Leu Ser Cys Ala Ala Ser Gly Phe
            180                 185                 190

Thr Phe Ser Asn Tyr Gly Met Ala Trp Val Arg Gln Ala Pro Thr Lys
        195                 200                 205

Gly Leu Glu Trp Val Ala Thr Ile Ser Tyr Asp Gly Ser Ile Thr Tyr
    210                 215                 220

Tyr Arg Asp Ser Val Lys Gly Arg Phe Thr Ile Ser Arg Asp His Ala
225                 230                 235                 240

Lys Ser Thr Leu Tyr Leu Gln Met Asn Ser Leu Arg Ser Glu Asp Thr
                245                 250                 255

Ala Thr Tyr Tyr Cys Thr Arg Glu Glu Gln Tyr Ser Ser Trp Tyr Phe
            260                 265                 270

Asp Phe Trp Gly Pro Gly Ile Met Val Thr Val Ser Ser
        275                 280                 285

<210> SEQ ID NO 60
<211> LENGTH: 100
<212> TYPE: PRT
<213> ORGANISM: Homo sapiens

<400> SEQUENCE: 60

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
                20                  25                  30

Ser Glu Ile Leu Trp Gln His Asn Asp Lys Asn Ile Gly Gly Asp Glu
            35                  40                  45

Asp Asp Lys Asn Ile Gly Ser Asp Glu Asp His Leu Ser Leu Lys Glu
        50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys
            100

<210> SEQ ID NO 61
<211> LENGTH: 371
<212> TYPE: PRT
<213> ORGANISM: Homo sapiens

<400> SEQUENCE: 61

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
```

```
                50                  55                  60
Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Val Gln Leu Leu
                 85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
                115                 120                 125

Gln Cys Arg Ser Pro Arg Gly Lys Asn Ile Gln Gly Gly Lys Thr Leu
                130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
                180                 185                 190

Gln Val Glu Phe Ser Phe Pro Leu Ala Phe Thr Val Glu Lys Leu Thr
                195                 200                 205

Gly Ser Gly Glu Leu Trp Trp Gln Ala Glu Arg Ala Ser Ser Ser Lys
                210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
                260                 265                 270

Thr Leu Ala Leu Glu Ala Lys Thr Gly Lys Leu His Gln Glu Val Asn
                275                 280                 285

Leu Val Val Met Arg Ala Thr Gln Leu Gln Lys Asn Leu Thr Cys Glu
                290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
                340                 345                 350

Val Leu Leu Glu Ser Asn Ile Lys Val Leu Pro Thr Trp Ser Thr Pro
                355                 360                 365

Val Gln Pro
    370

<210> SEQ ID NO 62
<211> LENGTH: 348
<212> TYPE: PRT
<213> ORGANISM: Homo sapiens

<400> SEQUENCE: 62

Arg Leu Ser Trp Tyr Asp Pro Asp Phe Gln Ala Arg Leu Thr Arg Ser
 1               5                  10                  15

Asn Ser Lys Cys Gln Gly Gln Leu Glu Val Tyr Leu Lys Asp Gly Trp
                20                  25                  30

His Met Val Cys Ser Gln Ser Trp Gly Arg Ser Ser Lys Gln Trp Glu
                35                  40                  45
```

Asp Pro Ser Gln Ala Ser Lys Val Cys Gln Arg Leu Asn Cys Gly Val
    50              55                  60

Pro Leu Ser Leu Gly Pro Phe Leu Val Thr Tyr Thr Pro Gln Ser Ser
65                  70                  75                  80

Ile Ile Cys Tyr Gly Gln Leu Gly Ser Phe Ser Asn Cys Ser His Ser
                85                  90                  95

Arg Asn Asp Met Cys His Ser Leu Gly Leu Thr Cys Leu Glu Pro Gln
            100                 105                 110

Lys Thr Thr Pro Pro Thr Thr Arg Pro Pro Thr Thr Pro Glu
        115                 120                 125

Pro Thr Ala Pro Pro Arg Leu Gln Leu Val Ala Gln Ser Gly Gly Gln
130                 135                 140

His Cys Ala Gly Val Val Glu Phe Tyr Ser Gly Ser Leu Gly Gly Thr
145                 150                 155                 160

Ile Ser Tyr Glu Ala Gln Asp Lys Thr Gln Asp Leu Glu Asn Phe Leu
                165                 170                 175

Cys Asn Asn Leu Gln Cys Gly Ser Phe Leu Lys His Leu Pro Glu Thr
            180                 185                 190

Glu Ala Gly Arg Ala Gln Asp Pro Gly Glu Pro Arg Glu His Gln Pro
        195                 200                 205

Leu Pro Ile Gln Trp Lys Ile Gln Asn Ser Ser Cys Thr Ser Leu Glu
210                 215                 220

His Cys Phe Arg Lys Ile Lys Pro Gln Lys Ser Gly Arg Val Leu Ala
225                 230                 235                 240

Leu Leu Cys Ser Gly Phe Gln Pro Lys Val Gln Ser Arg Leu Val Gly
                245                 250                 255

Gly Ser Ser Ile Cys Glu Gly Thr Val Glu Val Arg Gln Gly Ala Gln
            260                 265                 270

Trp Ala Ala Leu Cys Asp Ser Ser Ala Arg Ser Ser Leu Arg Trp
        275                 280                 285

Glu Glu Val Cys Arg Glu Gln Gln Cys Gly Ser Val Asn Ser Tyr Arg
290                 295                 300

Val Leu Asp Ala Gly Asp Pro Thr Ser Arg Gly Leu Phe Cys Pro His
305                 310                 315                 320

Gln Lys Leu Ser Gln Cys His Glu Leu Trp Glu Arg Asn Ser Tyr Cys
                325                 330                 335

Lys Lys Val Phe Val Thr Cys Gln Asp Pro Asn Pro
            340                 345

<210> SEQ ID NO 63
<211> LENGTH: 7902
<212> TYPE: DNA
<213> ORGANISM: Artificial Sequence
<220> FEATURE:
<223> OTHER INFORMATION: Synthesized

<400> SEQUENCE: 63
gtcgacacta gtaatcaacc tctggattac aaaatttgtg aaagattgac tggtattctt    60
aactatgttg ctccttttac gctatgtgga tacgctgctt taatgccttt gtatcatgct   120
attgcttccc gtatggcttt cattttctcc tccttgtata aatcctggtt gctgtctctt   180
tatgaggagt tgtggcccgt tgtcaggcaa cgtggcgtgg tgtgcactgt gtttgctgac   240
gcaaccccca ctggttgggg cattgccacc acctgtcagc tcctttccgg gactttcgct   300
ttccccctcc ctattgccac ggcggaactc atcgccgcct gccttgcccg ctgctggaca   360

```
ggggctcggc tgttgggcac tgacaattcc gtggtgttgt cggggaagct gacgtccttt    420
ccatggctgc tcgcctgtgt tgccacctgg attctgcgcg ggacgtcctt ctgctacgtc    480
ccttcggccc tcaatccagc ggaccttcct tcccgcggcc tgctgccggc tctgcggcct    540
cttccgcgtc ttcgccttcg ccctcagacg agtcggatct ccctttgggc cgcctccccg    600
cctgccgcgg aattcgagct cggtaccttt aagaccaatg acttacaagg cagctgtaga    660
tcttagccac tttttaaaag aaaagggggg actggaaggg ctaattcact cccaacgaag    720
acaagatctg cttttgtctt gtactgagtc tctctggtta gaccagatct gagcctggga    780
gctctctggc taactaggga acccactgct taagcctcaa taaagcttgc cttgagtgct    840
tcaagtagtg tgtgcccgtc tgttgtgtga ctctggtaac tagagatccc tcagaccctt    900
ttagtcagtg tggaaaatct ctagcagtag tagttcatgt catcttatta ttcagtattt    960
ataacttgca aagaaatgaa tatcagagag tgagaggaac ttgtttattg cagcttataa   1020
tggttacaaa taaagcaata gcatcacaaa tttcacaaat aaagcatttt tttcactgca   1080
ttctagttgt ggtttgtcca aactcatcaa tgtatcttat catgtctggc tctagctatc   1140
ccgcccctaa ctccgcccat cccgccccta actccgccca gttccgccca ttctccgccc   1200
catggctgac taatttttt tatttatgca gaggccgagg ccgcctcggc ctctgagcta   1260
ttccagaagt agtgaggagg cttttttgga ggcctaggga cgtacccaat tcgccctata   1320
gtgagtcgta ttacgcgcgc tcactggccg tcgttttaca acgtcgtgac tgggaaaacc   1380
ctggcgttac ccaacttaat cgccttgcag cacatccccc tttcgccagc tggcgtaata   1440
gcgaagaggc ccgcaccgat cgcccttccc aacagttgcg cagcctgaat ggcgaatggg   1500
acgcgccctg tagcggcgca ttaagcgcgg cgggtgtggt ggttacgcgc agcgtgaccg   1560
ctacacttgc cagcgcccta gcgcccgctc ctttcgcttt cttcccttcc tttctcgcca   1620
cgttcgccgg ctttccccgt caagctctaa atcgggggct ccctttaggg ttccgattta   1680
gtgctttacg gcacctcgac cccaaaaaac ttgattaggg tgatggttca cgtagtgggc   1740
catcgccctg atagacggtt tttcgccctt tgacgttgga gtccacgttc tttaatagtg   1800
gactcttgtt ccaaactgga acaacactca accctatctc ggtctattct tttgatttat   1860
aagggatttt gccgatttcg gcctattggt taaaaaatga gctgatttaa caaaaattta   1920
acgcgaattt taacaaaata ttaacgctta caatttaggt ggcactttc ggggaaatgt   1980
gcgcggaacc cctatttgtt tatttttcta aatacattca aatatgtatc cgctcatgag   2040
acaataaccc tgataaatgc ttcaataata ttgaaaaagg aagagtatga gtattcaaca   2100
tttccgtgtc gcccttattc ccttttttgc ggcattttgc cttcctgttt ttgctcaccc   2160
agaaacgctg gtgaaagtaa aagatgctga agatcagttg ggtgcacgag tgggttacat   2220
cgaactggat ctcaacagcg gtaagatcct tgagagtttt cgccccgaag aacgttttcc   2280
aatgatgagc acttttaaag ttctgctatg tggcgcggta ttatcccgta ttgacgccgg   2340
gcaagagcaa ctcggtcgcc gcatacacta ttctcagaat gacttggttg agtactcacc   2400
agtcacagaa aagcatctta cggatggcat gacagtaaga gaattatgca gtgctgccat   2460
aaccatgagt gataacactg cggccaactt acttctgaca acgatcggag gaccgaagga   2520
gctaaccgct ttttgcaca acatggggga tcatgtaact cgccttgatc gttgggaacc   2580
ggagctgaat gaagccatac caaacgacga gcgtgacacc acgatgcctg tagcaatggc   2640
aacaacgttg cgcaaactat taactggcga actacttact ctagcttccc ggcaacaatt   2700
aatagactgg atggaggcgg ataaagttgc aggaccactt ctgcgctcgg cccttccggc   2760
```

```
tggctggttt attgctgata aatctggagc cggtgagcgt ggctctcgcg gtatcattgc   2820
agcactgggg ccagatggta agccctcccg tatcgtagtt atctacacga cggggagtca   2880
ggcaactatg gatgaacgaa atagacagat cgctgagata ggtgcctcac tgattaagca   2940
ttggtaactg tcagaccaag tttactcata tatactttag attgatttaa aacttcattt   3000
ttaatttaaa aggatctagg tgaagatcct tttgataat ctcatgacca aaatccctta    3060
acgtgagttt cgttccact gagcgtcaga ccccgtagaa aagatcaaag gatcttcttg    3120
agatcctttt tttctgcgcg taatctgctg cttgcaaaca aaaaaaccac cgctaccagc   3180
ggtggtttgt ttgccggatc aagagctacc aactctttt ccgaaggtaa ctggcttcag    3240
cagagcgcag ataccaaata ctgttcttct agtgtagccg tagttaggcc accacttcaa   3300
gaactctgta gcaccgccta catacctcgc tctgctaatc ctgttaccag tggctgctgc   3360
cagtggcgat aagtcgtgtc ttaccgggtt ggactcaaga cgatagttac cggataaggc   3420
gcagcggtcg ggctgaacgg ggggttcgtg cacacagccc agcttggagc gaacgaccta   3480
caccgaactg agatacctac agcgtgagct atgagaaagc gccacgcttc ccgaagggag   3540
aaaggcggac aggtatccgg taagcggcag ggtcggaaca ggagagcgca cgagggagct   3600
tccaggggga aacgcctggt atctttatag tcctgtcggg tttcgccacc tctgacttga   3660
gcgtcgattt tgtgatgct cgtcaggggg gcggagccta tggaaaaacg ccagcaacgc    3720
ggccttttta cggttcctgg ccttttgctg gccttttgct cacatgttct ttcctgcgtt   3780 atccctgat tctgtggata accgtattac cgcctttgag tgagctgata ccgctcgccg    3840
cagccgaacg accgagcgca gcgagtcagt gagcgaggaa gcggaagagc gcccaatacg   3900
caaaccgcct ctccccgcgc gttggccgat tcattaatgc agctggcacg acaggtttcc   3960
cgactggaaa gcgggcagtg agcgcaacgc aattaatgtg agttagctca ctcattaggc   4020
accccaggct ttacacttta tgcttccggc tcgtatgttg tgtggaattg tgagcggata   4080
acaatttcac acaggaaaca gctatgacca tgattacgcc aagcgcgcaa ttaaccctca   4140
ctaaagggaa caaaagctgg agctgcaagc ttaatgtagt cttatgcaat actcttgtag   4200
tcttgcaaca tggtaacgat gagttagcaa catgccttac aaggagagaa aaagcaccgt   4260
gcatgccgat tggtggaagt aaggtggtac gatcgtgcct tattaggaag caacagacg    4320 ggtctgacat ggattggacg aaccactgaa ttgccgcatt gcagagatat tgtatttaag   4380
tgcctagctc gatacataaa cggctctctc tggttagacc agatctgagc ctgggagctc   4440
tctggctaac tagggaaccc actgcttaag cctcaataaa gcttgccttg agtgcttcaa   4500
gtagtgtgtg cccgtctgtt gtgtgactct ggtaactaga gatccctcag acccttttag   4560
tcagtgtgga aaatctctag cagtggcgcc cgaacaggga cttgaaagcg aaagggaaac   4620
cagaggagct ctctcgacgc aggactcggc ttgctgaagc gcgcacggca agaggcgagg   4680
ggcggcgact ggtgagtacg ccaaaaattt tgactagcgg aggctagaag gagagagatg   4740
ggtgcgagag cgtcagtatt aagcggggga gaattagatc gcgatgggaa aaaattcggt   4800
taaggccagg gggaaagaaa aaatataaat taaaacatat agtatgggca agcagggagc   4860
tagaacgatt cgcagttaat cctggcctgt tagaaacatc agaaggctgt agacaaatac   4920
tgggacagct acaaccatcc cttcagacag gatcagaaga acttagatca ttatataata   4980
cagtagcaac cctctattgt gtgcatcaaa ggatagagat aaaagacacc aaggaagctt   5040
tagacaagat agaggaagag caaaacaaaa gtaagaccac cgcacagcaa gcggccgctg   5100
```

```
atcttcagac ctggaggagg agatatgagg gacaattgga gaagtgaatt atataaatat    5160
aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tggcgcagc gtcaatgacg ctgacggtac aggccagaca attattgtct    5340
ggtatagtgc agcagcagaa caatttgctg agggctattg aggcgcaaca gcatctgttg    5400
caactcacag tctggggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg gaatcacacg    5580
acctggatgg agtgggacag agaaattaac aattacacaa gcttaataca ctccttaatt    5640
gaagaatcgc aaaaccagca agaaaagaat gaacaagaat tattggaatt agataaatgg    5700
gcaagtttgt ggaattggtt taacataaca aattggctgt ggtatataaa attattcata    5760
atgatagtag gaggcttggt aggtttaaga atagttttg ctgtactttc tatagtgaat    5820
agagttaggc agggatattc accattatcg tttcagaccc acctcccaac cccgagggga    5880
cccgacaggc ccgaaggaat agaagaagaa ggtggagaga gacagaga cagatccatt    5940 cgattagtga acggatctcg acggtatcga tcacgagact agcctcgaca caaatggcag    6000
tattcatcca caattttaaa agaaaagggg ggattggggg gtacagtgca ggggaaagaa    6060
tagtagacat aatagcaaca gacatacaaa ctaagaatt acaaaaacaa attacaaaaa    6120
ttcaaaattt tcgggtttat tacagggaca gcagaaatcc actttggctc gagaagcttg    6180
atatcggctc cggtgcccgt cagtgggcag agcgcacatc gcccacagtc cccgagaagt    6240
tggggggagg ggtcggcaat tgaaccggtg cctagagaag gtggcgcggg gtaaactggg    6300
aaagtgatgt cgtgtactgg ctccgccttt ttcccgaggg tggggagaa ccgtatataa    6360 gtgcagtagt cgccgtgaac gttcttttc gcaacgggtt tgccgccaga acacaggatc    6420
cgccaccatg gccttaccag tgaccgcctt gctcctgccg ctggccttgc tgctccacgc    6480
cgccaggccg gatatccaga tgacccagag cccgagcagc ctgagcgcga gcgtgggtga    6540
tcgcgtgacc attacctgca gggcaagtca ggacattagt aaatatttaa attggtatca    6600
gcagaaaccg ggtaaagcgc cgaaactgtt aatttatcat acatcaagat tacactcagg    6660
cgtgccgtcg cgttttagcg gctcgggttc gggcaccgat tttaccctga ccatctcgag    6720
cttgcagccg gaggacttcg ccacctacta ttgccaacag ggtaatacgc ttccgtacac    6780
gttcggtcag ggcaccaaag tggagatcaa aggtggcggt ggctcgggcg gtggtgggtc    6840
gggtggcggc ggatctgagg tgcagctggt ggagtctggg ggaggcttgg tacagcctgg    6900
ggggtccctg agactctcct gtgcagcctc tggagtgtcc ctgcctgatt atggcgtgtc    6960
ctgggtccgc caggctccag ggaaggggct ggagtgggtt tcagtgatct ggggcagcga    7020
gacaacctac tacaacagcg ccctgaagtc ccgattcacc atctccagag acaatgccaa    7080
gaactcactg tatctgcaaa tgaacagcct gagagccgag gacacggctg tgtattactg    7140
tgcgaagcac tactactacg gcggcagcta cgctatggac tactggggcc aaggaaccct    7200
ggtcaccgtg tcctcaacca cgacgccagc gccgcgacca ccaacaccgg cgcccaccat    7260
cgcgtcgcag cccctgtccc tgcgcccaga ggcgtgccgg ccagcggcgg ggggcgcagt    7320
gcacacgagg gggctggact cgcctgtga tatctacatc tgggcgccct tggccgggac    7380
ttgtggggtc cttctcctgt cactggttat cacccttac tgcaaacggg gcagaaagaa    7440
actcctgtat atattcaaac aaccatttat gagaccagta caaactactc aagaggaaga    7500
```

```
tggctgtagc tgccgatttc cagaagaaga agaaggagga tgtgaactga gagtgaagtt    7560
cagcaggagc gcagacgccc ccgcgtacaa gcagggccag aaccagctct ataacgagct    7620
caatctagga cgaagagagg agtacgatgt tttggacaag aggcgtggcc gggaccctga    7680
gatgggggga aagccgagaa ggaagaaccc tcaggaaggc ctgtacaatg aactgcagaa    7740
agataagatg gcggaggcct acagtgagat tgggatgaaa ggcgagcgcc ggaggggcaa    7800
ggggcacgat ggcctttacc agggtctcag tacagccacc aaggacacct acgacgccct    7860
tcacatgcag gccctgcccc ctcgctaatc tagaggcgcg cc                       7902
```

<210> SEQ ID NO 64
<211> LENGTH: 66
<212> TYPE: PRT
<213> ORGANISM: Artificial Sequence
<220> FEATURE:
<223> OTHER INFORMATION: Synthesized

<400> SEQUENCE: 64

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr
65

<210> SEQ ID NO 65
<211> LENGTH: 69
<212> TYPE: PRT
<213> ORGANISM: Artificial Sequence
<220> FEATURE:
<223> OTHER INFORMATION: Synthesized

<400> SEQUENCE: 65

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 66
<211> LENGTH: 72
<212> TYPE: PRT
<213> ORGANISM: Artificial Sequence
<220> FEATURE:
<223> OTHER INFORMATION: Synthesized

<400> SEQUENCE: 66

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro

```
                    20                  25                  30

Ala Ala Gly Gly Ala Val His Thr Arg Gly Leu Asp Phe Ala Cys Asp
            35                  40                  45

Ile Tyr Ile Trp Ala Pro Leu Ala Gly Thr Cys Gly Val Leu Leu Leu
        50                  55                  60

Ser Leu Val Ile Thr Leu Tyr Cys
 65                  70

<210> SEQ ID NO 67
<211> LENGTH: 69
<212> TYPE: PRT
<213> ORGANISM: Artificial Sequence
<220> FEATURE:
<223> OTHER INFORMATION: Synthesized

<400> SEQUENCE: 67

Ala Lys Pro Thr Thr Thr Pro Ala Pro Arg Pro Pro Thr Pro Ala Pro
 1               5                  10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
            35                  40                  45

Ile Tyr Ile Trp Ala Pro Leu Ala Gly Thr Cys Gly Val Leu Leu Leu
        50                  55                  60

Ser Leu Val Ile Thr
 65

<210> SEQ ID NO 68
<211> LENGTH: 50
<212> TYPE: PRT
<213> ORGANISM: Artificial Sequence
<220> FEATURE:
<223> OTHER INFORMATION: Synthesized

<400> SEQUENCE: 68

Ala Lys Pro Thr Thr Thr Pro Ala Pro Arg Pro Pro Thr Pro Ala Pro
 1               5                  10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
            35                  40                  45

Ile Tyr
    50

<210> SEQ ID NO 69
<211> LENGTH: 50
<212> TYPE: PRT
<213> ORGANISM: Artificial Sequence
<220> FEATURE:
<223> OTHER INFORMATION: Synthesized

<400> SEQUENCE: 69

Ala Lys Pro Thr Thr Thr Pro Ala Pro Arg Pro Pro Thr Pro Ala Pro
 1               5                  10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
            35                  40                  45

Ile Tyr
    50
```

<210> SEQ ID NO 70
<211> LENGTH: 47
<212> TYPE: PRT
<213> ORGANISM: Artificial Sequence
<220> FEATURE:
<223> OTHER INFORMATION: Synthesized

<400> SEQUENCE: 70

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

<210> SEQ ID NO 71
<211> LENGTH: 47
<212> TYPE: PRT
<213> ORGANISM: Artificial Sequence
<220> FEATURE:
<223> OTHER INFORMATION: Synthesized

<400> SEQUENCE: 71

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

<210> SEQ ID NO 72
<211> LENGTH: 22
<212> TYPE: PRT
<213> ORGANISM: Artificial Sequence
<220> FEATURE:
<223> OTHER INFORMATION: Synthesized

<400> SEQUENCE: 72

```
Ile Trp Ala Pro Leu Ala Gly Thr Cys Gly Val Leu Leu Leu Ser Leu
1               5                   10                  15

Val Ile Thr Leu Tyr Cys
            20
```

<210> SEQ ID NO 73
<211> LENGTH: 19
<212> TYPE: PRT
<213> ORGANISM: Artificial Sequence
<220> FEATURE:
<223> OTHER INFORMATION: Synthesized

<400> SEQUENCE: 73

```
Ile Trp Ala Pro Leu Ala Gly Thr Cys Gly Val Leu Leu Leu Ser Leu
1               5                   10                  15

Val Ile Thr
```

<210> SEQ ID NO 74
<211> LENGTH: 19
<212> TYPE: PRT
<213> ORGANISM: Artificial Sequence
<220> FEATURE:
<223> OTHER INFORMATION: Synthesized

<400> SEQUENCE: 74

```
Ile Trp Ala Pro Leu Ala Gly Thr Cys Gly Val Leu Leu Ser Leu
1               5                   10                  15

Val Ile Thr
```

<210> SEQ ID NO 75
<211> LENGTH: 22
<212> TYPE: PRT
<213> ORGANISM: Artificial Sequence
<220> FEATURE:
<223> OTHER INFORMATION: Synthesized

<400> SEQUENCE: 75

```
Ile Trp Ala Pro Leu Ala Gly Thr Cys Gly Val Leu Leu Ser Leu
1               5                   10                  15

Val Ile Thr Leu Tyr Cys
            20
```

<210> SEQ ID NO 76
<211> LENGTH: 15
<212> TYPE: PRT
<213> ORGANISM: Artificial Sequence
<220> FEATURE:
<223> OTHER INFORMATION: Synthesized

<400> SEQUENCE: 76

```
Gly Gly Gly Gly Ser Gly Gly Gly Ser Gly Gly Gly Ser
1               5                   10                  15
```

<210> SEQ ID NO 77
<211> LENGTH: 7
<212> TYPE: PRT
<213> ORGANISM: Artificial Sequence
<220> FEATURE:
<223> OTHER INFORMATION: Synthesized

<400> SEQUENCE: 77

```
Gln Trp Gly Thr Arg Tyr Arg
1               5
```

<210> SEQ ID NO 78
<211> LENGTH: 7
<212> TYPE: PRT
<213> ORGANISM: Artificial Sequence
<220> FEATURE:
<223> OTHER INFORMATION: Synthesized

<400> SEQUENCE: 78

```
Gln Ser Gly Asp Leu Thr Arg
1               5
```

<210> SEQ ID NO 79
<211> LENGTH: 7
<212> TYPE: PRT
<213> ORGANISM: Artificial Sequence
<220> FEATURE:
<223> OTHER INFORMATION: Synthesized

<400> SEQUENCE: 79

```
Arg Ser Asp Asn Leu Arg Glu
1               5
```

<210> SEQ ID NO 80
<211> LENGTH: 7
<212> TYPE: PRT
<213> ORGANISM: Artificial Sequence

```
<220> FEATURE:
<223> OTHER INFORMATION: Synthesized

<400> SEQUENCE: 80

Glu Arg Gly Thr Leu Ala Arg
1               5

<210> SEQ ID NO 81
<211> LENGTH: 19
<212> TYPE: DNA
<213> ORGANISM: Homo sapiens

<400> SEQUENCE: 81
gttgctccag gccacagca                                                    19

<210> SEQ ID NO 82
<211> LENGTH: 7
<212> TYPE: PRT
<213> ORGANISM: Artificial Sequence
<220> FEATURE:
<223> OTHER INFORMATION: Synthesized

<400> SEQUENCE: 82

Trp Arg Ser Ser Leu Ala Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Synthesized

<400> SEQUENCE: 83

Gln Ser Gly Ser Leu Thr Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Synthesized

<400> SEQUENCE: 84

Asp Arg Ser Asn Leu Thr Arg
1               5

<210> SEQ ID NO 85
<211> LENGTH: 12
<212> TYPE: DNA
<213> ORGANISM: Homo sapiens

<400> SEQUENCE: 85
gactttgcat gt                                                           12

<210> SEQ ID NO 86
<211> LENGTH: 7
<212> TYPE: PRT
<213> ORGANISM: Artificial Sequence
<220> FEATURE:
<223> OTHER INFORMATION: Synthesized

<400> SEQUENCE: 86

His Lys Trp Val Leu Arg Gln
1               5
```

<210> SEQ ID NO 87
<211> LENGTH: 7
<212> TYPE: PRT
<213> ORGANISM: Artificial Sequence
<220> FEATURE:
<223> OTHER INFORMATION: Synthesized

<400> SEQUENCE: 87

Thr Ser Gly Ala Leu Thr Arg
1               5

<210> SEQ ID NO 88
<211> LENGTH: 112
<212> TYPE: PRT
<213> ORGANISM: Artificial Sequence
<220> FEATURE:
<223> OTHER INFORMATION: Synthesized

<400> SEQUENCE: 88

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 89
<211> LENGTH: 119
<212> TYPE: PRT
<213> ORGANISM: Artificial Sequence
<220> FEATURE:
<223> OTHER INFORMATION: Synthesized

<400> SEQUENCE: 89

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
            115

```
<210> SEQ ID NO 90
<211> LENGTH: 127
<212> TYPE: PRT
<213> ORGANISM: Artificial Sequence
<220> FEATURE:
<223> OTHER INFORMATION: Synthesized

<400> SEQUENCE: 90

Met Asn Val Pro Thr Gln Leu Leu Gly Leu Leu Leu Trp Leu Thr
1               5                   10                  15

Gly Gly Lys Cys Asp Ile Gln Met Thr Gln Ser Pro Ala Ser Leu Ser
            20                  25                  30

Ala Ser Leu Glu Glu Ile Val Thr Ile Thr Cys Lys Ala Ser Gln Ala
        35                  40                  45

Ile Asp Ala Tyr Leu Ser Trp Tyr Gln Gln Lys Pro Gly Lys Ser Pro
    50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110

Ser Thr Pro Phe Thr Phe Gly Ser Gly Thr Lys Leu Glu Ile Lys
        115                 120                 125

<210> SEQ ID NO 91
<211> LENGTH: 138
<212> TYPE: PRT
<213> ORGANISM: Artificial Sequence
<220> FEATURE:
<223> OTHER INFORMATION: Synthesized

<400> SEQUENCE: 91

Met Ala Val Leu Val Leu Leu Leu Cys Leu Leu Ile Phe Pro Ser Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Ser Ser Leu
        35                  40                  45

Thr Ser Asn Ser Val Ser Trp Ile Arg Gln Pro Pro Gly Lys Gly Leu
    50                  55                  60

Glu Trp Met Gly Val Ile Trp Ser Asn Gly Asp Ala Asp Tyr Asn Ser
65                  70                  75                  80

Ala Ile Lys Ser Arg Leu Ser Ile Ser Arg Asp Thr Ser Lys Ser Gln
                85                  90                  95

Val Phe Leu Lys Met Asn Ser Leu Gln Thr Glu Asp Thr Ala Met Tyr
            100                 105                 110

Phe Cys Ala Ser Pro Tyr Tyr Gly Tyr Tyr Phe Pro Phe Asp Tyr Trp
        115                 120                 125

Gly Gln Gly Val Met Val Thr Val Ser Ser
    130                 135

<210> SEQ ID NO 92
<211> LENGTH: 130
<212> TYPE: PRT
<213> ORGANISM: Artificial Sequence
<220> FEATURE:
<223> OTHER INFORMATION: Synthesized
```

-continued

<400> SEQUENCE: 92

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Ser His Asp Leu Met Gln Trp Tyr Gln Gln Lys Pro Gly
    50                  55                  60

Gln Gln Pro Lys Leu Leu Ile Tyr Asp Ala Phe Asn Leu Ala Ser Gly
65                  70                  75                  80

Ile Pro Val Arg Phe Ser Gly Ser Gly Ser Gly Thr Asp Phe Thr Leu
                85                  90                  95

Thr Ile Asp Pro Val Gln Ala Asp Ile Ala Thr Tyr Tyr Cys Gln
            100                 105                 110

Gln Ser Lys Asp Asp Pro Tyr Thr Phe Gly Ala Gly Thr Lys Leu Glu
        115                 120                 125

Leu Lys
    130

<210> SEQ ID NO 93
<211> LENGTH: 139
<212> TYPE: PRT
<213> ORGANISM: Artificial Sequence
<220> FEATURE:
<223> OTHER INFORMATION: Synthesized

<400> SEQUENCE: 93

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Met Lys Leu Ser Cys Ala Ala Ser Gly Phe Thr Phe
        35                  40                  45

Ser Asn Tyr Gly Met Ala Trp Val Arg Gln Ala Pro Thr Lys Gly Leu
    50                  55                  60

Glu Trp Val Ala Thr Ile Ser Tyr Asp Gly Ser Ile Thr Tyr Tyr Arg
65                  70                  75                  80

Asp Ser Val Lys Gly Arg Phe Thr Ile Ser Arg Asp His Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Glu Glu Gln Tyr Ser Ser Trp Tyr Phe Asp Phe
        115                 120                 125

Trp Gly Pro Gly Ile Met Val Thr Val Ser Ser
    130                 135

<210> SEQ ID NO 94
<211> LENGTH: 242
<212> TYPE: PRT
<213> ORGANISM: Artificial Sequence
<220> FEATURE:
<223> OTHER INFORMATION: Synthesized

<400> SEQUENCE: 94

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys Gly Gly Gly Gly Ser
            100                 105                 110

Gly Gly Gly Gly Ser Gly Gly Gly Ser Gln Val Thr Leu Lys Glu
        115                 120                 125

Ser Gly Pro Val Leu Val Lys Pro Thr Glu Thr Leu Thr Leu Thr Cys
130                 135                 140

Thr Phe Ser Gly Phe Ser Leu Ser Thr Ser Gly Met Gly Val Gly Trp
145                 150                 155                 160

Ile Arg Gln Ala Pro Gly Lys Gly Leu Glu Trp Val Ala His Ile Trp
                165                 170                 175

Trp Asp Asp Val Tyr Tyr Asn Pro Ser Leu Lys Ser Arg Leu Thr
            180                 185                 190

Ile Thr Lys Asp Ala Ser Lys Asp Gln Val Ser Leu Lys Leu Ser Ser
        195                 200                 205

Val Thr Ala Ala Asp Thr Ala Val Tyr Tyr Cys Val Arg Arg Arg Ala
210                 215                 220

Thr Gly Thr Gly Phe Asp Tyr Trp Gly Gln Gly Thr Leu Val Thr Val
225                 230                 235                 240

Ser Ser

<210> SEQ ID NO 95
<211> LENGTH: 106
<212> TYPE: PRT
<213> ORGANISM: Artificial Sequence
<220> FEATURE:
<223> OTHER INFORMATION: Synthesized

<400> SEQUENCE: 95

Asn Ile Val Met Thr Gln Ser Pro Ser Ser Leu Ser Ala Ser Val Gly
 1               5                  10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys
            100                 105

<210> SEQ ID NO 96
<211> LENGTH: 120
<212> TYPE: PRT

```
<213> ORGANISM: Artificial Sequence
<220> FEATURE:
<223> OTHER INFORMATION: Synthesized

<400> SEQUENCE: 96

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Ala Pro Gly Lys Gly Leu Glu
        35                  40                  45

Trp Val Ala His Ile Trp Trp Asp Asp Asp Val Tyr Tyr Asn Pro Ser
    50                  55                  60

Leu Lys Ser Arg Leu Thr Ile Thr Lys Asp Ala Ser Lys Asp Gln Val
65                  70                  75                  80

Ser Leu Lys Leu Ser Ser Val Thr Ala Ala Asp Thr Ala Val Tyr Tyr
                85                  90                  95

Cys Val Arg Arg Arg Ala Thr Gly Thr Gly Phe Asp Tyr Trp Gly Gln
            100                 105                 110

Gly Thr Leu Val Thr Val Ser Ser
            115                 120
```